United States Patent
Hasick et al.

(10) Patent No.: US 12,163,182 B2
(45) Date of Patent: Dec. 10, 2024

(54) MULTIPLEX DETECTION OF NUCLEIC ACIDS

(71) Applicant: SPEEDX PTY LTD, Eveleigh (AU)

(72) Inventors: Nicole Jane Hasick, Randwick (AU); Ryung Rae Kim, Rhodes (AU); Andrea Lee Lawrence, Berkeley (AU); Alison Velyian Todd, Glebe (AU)

(73) Assignee: SPEEDX PTY LTD, Eveleigh (AU)

( * ) Notice: Subject to any disclaimer, the term of this patent is extended or adjusted under 35 U.S.C. 154(b) by 960 days.

(21) Appl. No.: 17/266,951

(22) PCT Filed: Aug. 9, 2019

(86) PCT No.: PCT/IB2019/056811
§ 371 (c)(1),
(2) Date: Feb. 8, 2021

(87) PCT Pub. No.: WO2020/031156
PCT Pub. Date: Feb. 13, 2020

(65) Prior Publication Data
US 2022/0056507 A1 Feb. 24, 2022

(30) Foreign Application Priority Data
Aug. 9, 2018 (AU) ................................ 2018902915

(51) Int. Cl.
*C12Q 1/6818* (2018.01)
*C12Q 1/6816* (2018.01)
*G01N 21/64* (2006.01)

(52) U.S. Cl.
CPC ......... *C12Q 1/6818* (2013.01); *C12Q 1/6816* (2013.01); *C12Q 2521/345* (2013.01); *C12Q 2525/30* (2013.01); *C12Q 2525/301* (2013.01); *C12Q 2527/101* (2013.01); *C12Q 2537/143* (2013.01); *C12Q 2563/107* (2013.01); *C12Q 2565/1015* (2013.01); *G01N 2021/6432* (2013.01); *G01N 2021/6439* (2013.01)

(58) Field of Classification Search
None
See application file for complete search history.

(56) References Cited

U.S. PATENT DOCUMENTS 5,514,546 A * 5/1996 Kool .................... C12Q 1/6839
435/5

FOREIGN PATENT DOCUMENTS

| EP | 3150726 A1 * | 4/2017 | ........... C12Q 1/6851 |
| WO | WO 2016/025452 A1 | 2/2016 | |
| WO | WO 2020/031156 A1 | 2/2020 | |

OTHER PUBLICATIONS

PCT/IB2019/056811 International Preliminary Report on Patentability mailed Feb. 9, 2021.
PCT/IB2019/056811 International Search Report and Written Opinion mailed Oct. 28, 2019.
(Continued)

*Primary Examiner* — Carla J Myers
(74) *Attorney, Agent, or Firm* — Alston & Bird LLP

(57) ABSTRACT

The present invention provides oligonucleotides and methods for their use in the detection and/or differentiation of target nucleic acids. The oligonucleotides and methods find particular application in amplifying, detecting, and/or discriminating multiple targets simultaneously.

25 Claims, 32 Drawing Sheets
Specification includes a Sequence Listing.

(56) References Cited

OTHER PUBLICATIONS

Mokany, et al., "MNAzymes, a versatile new class of nucleic acid enzymes that can function as biosensors and molecular switches," Journal of the American Chemical Society, vol. 132, pp. 1051-1059, (2009).

Wood, et al., "A real-time assay for CpG-specific cytosine-C5 methyltransferase activity," Nucleic acids research, vol. 38, pp. 1-11, e107, (2010).

* cited by examiner

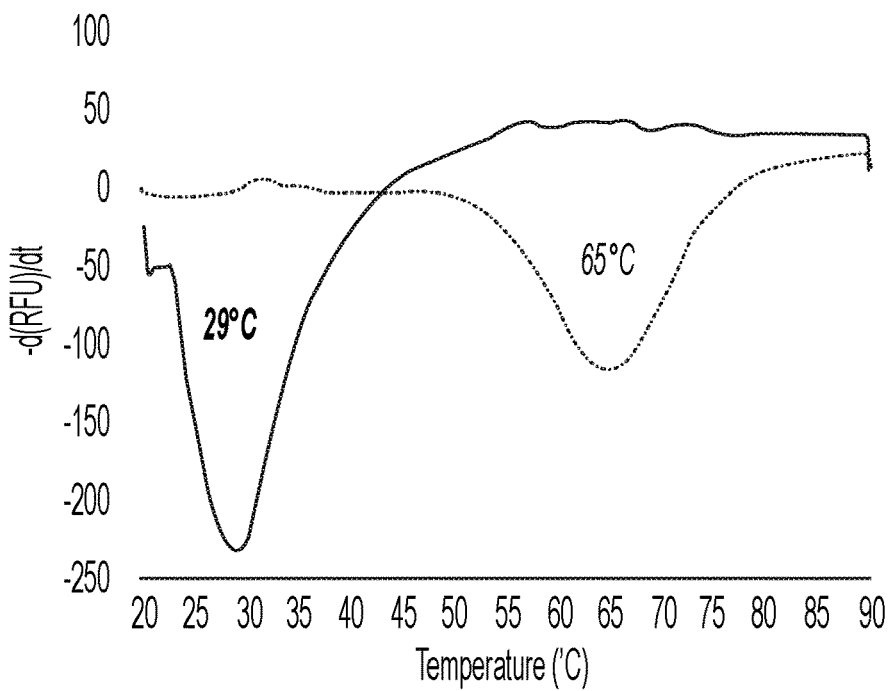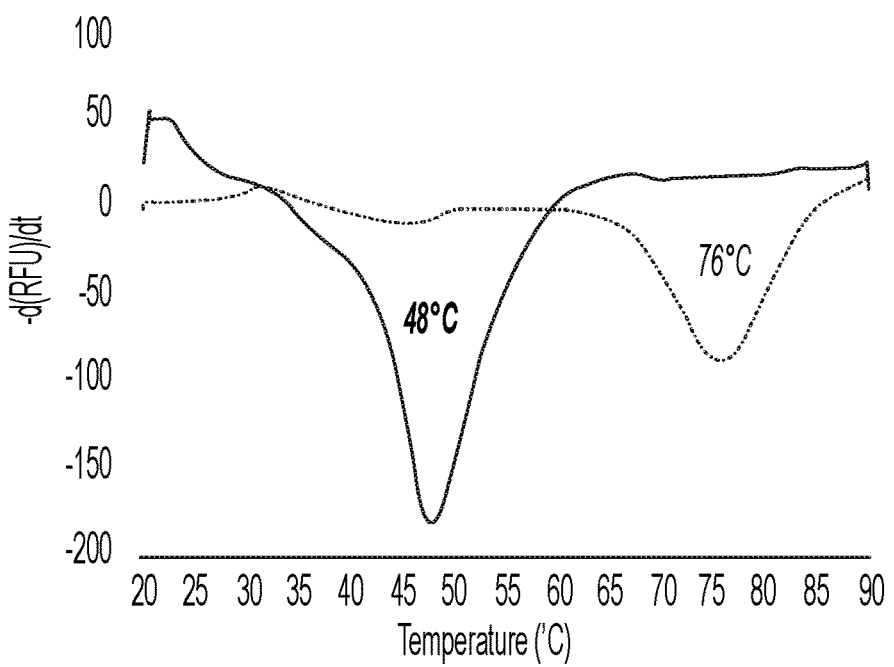
Figure 15

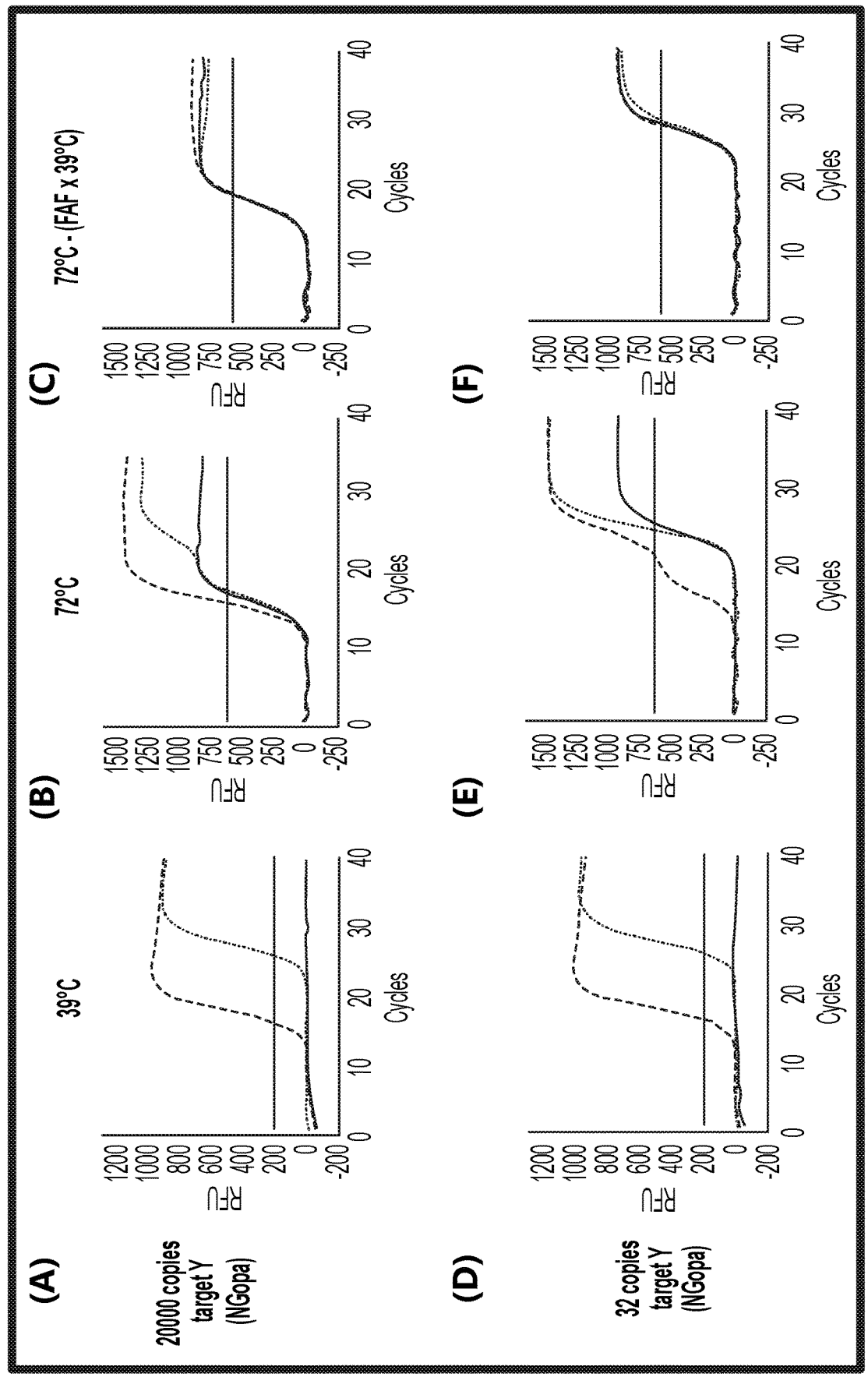
Figures 18A-F

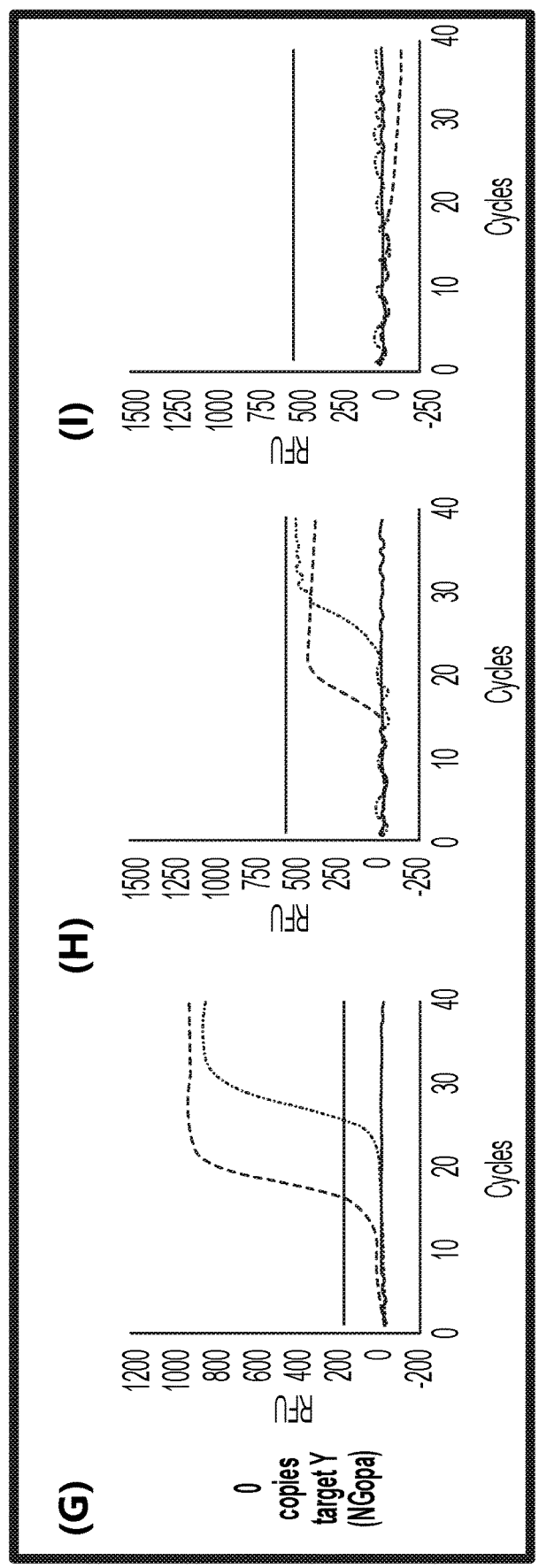
Figures 18G-I

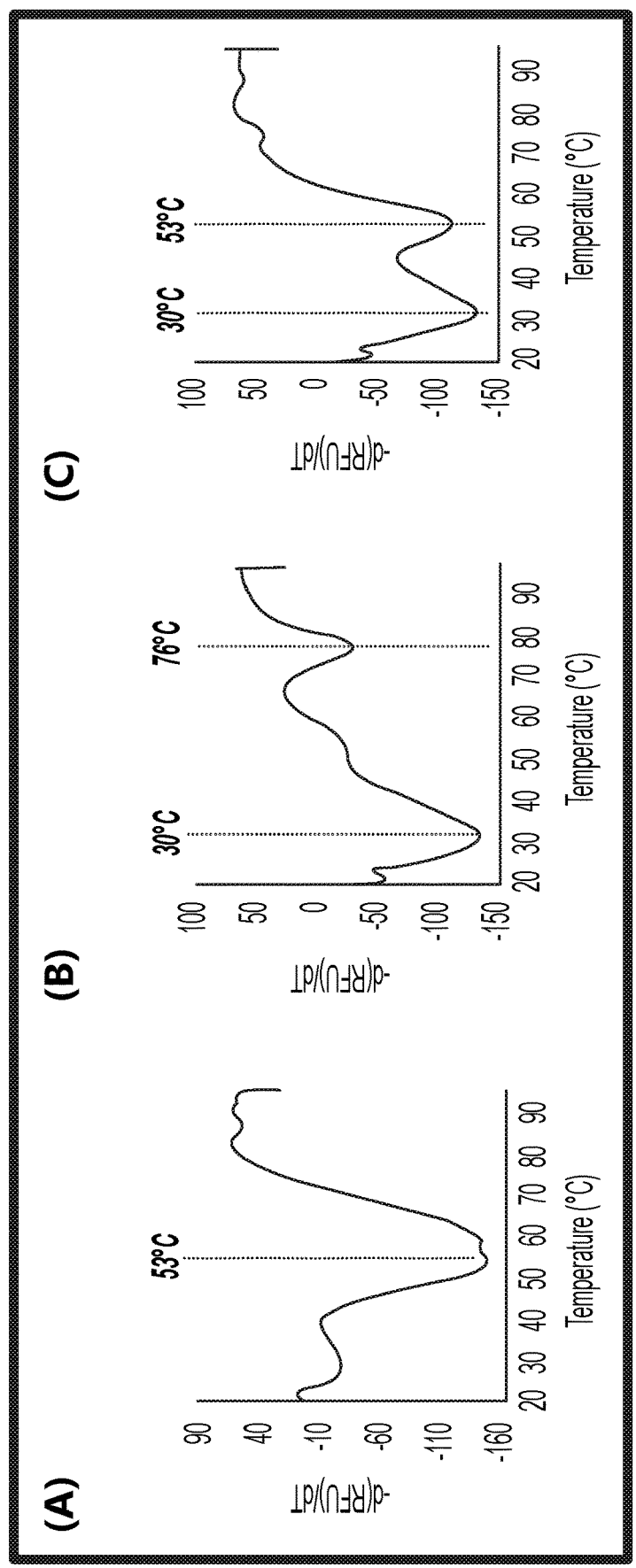
Figures 23A-C

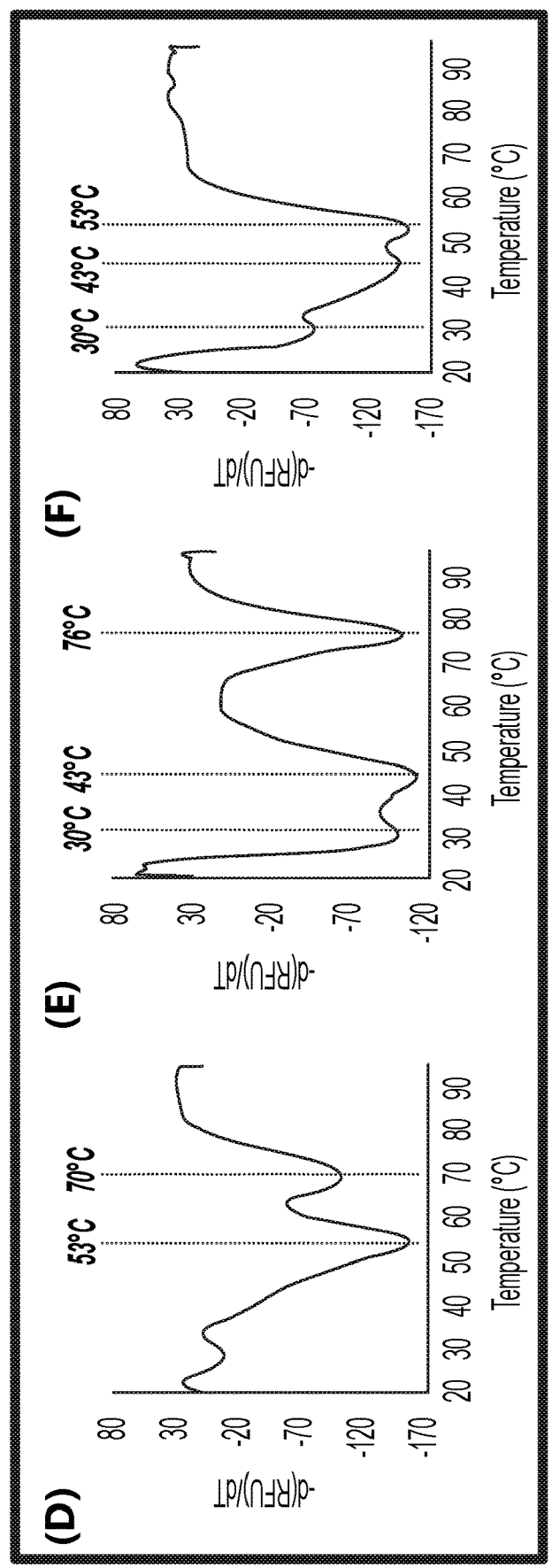
Figures 23D-F

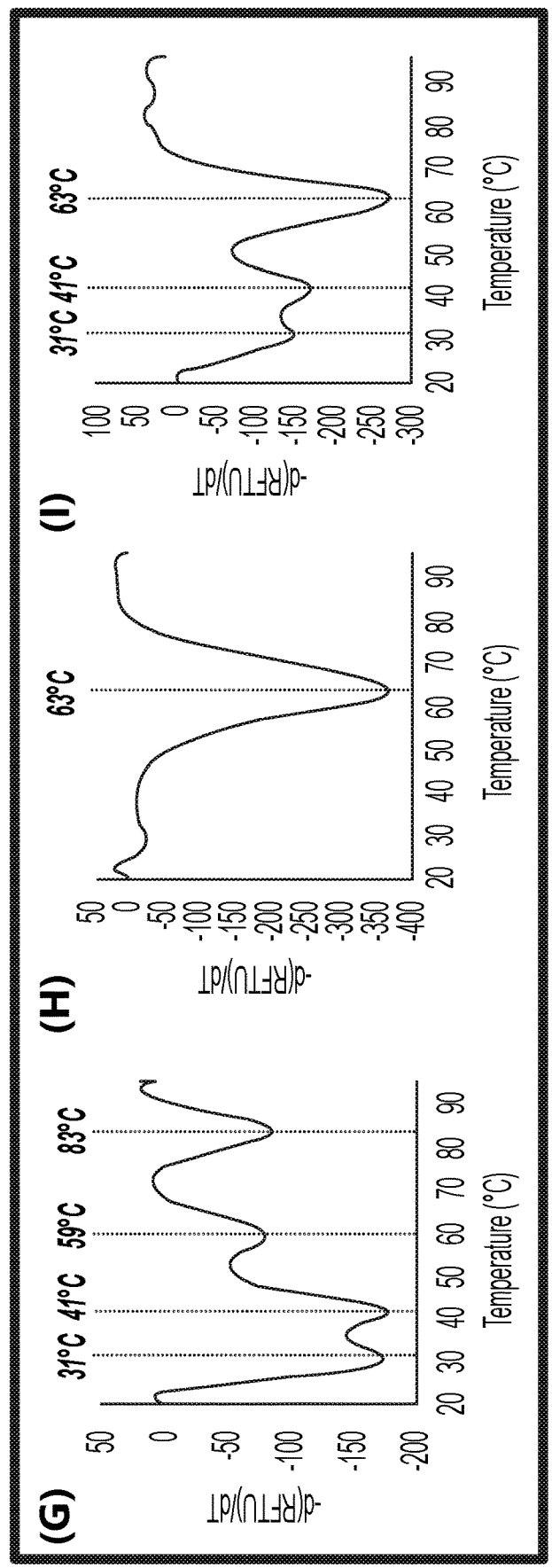
Figures 23G-I

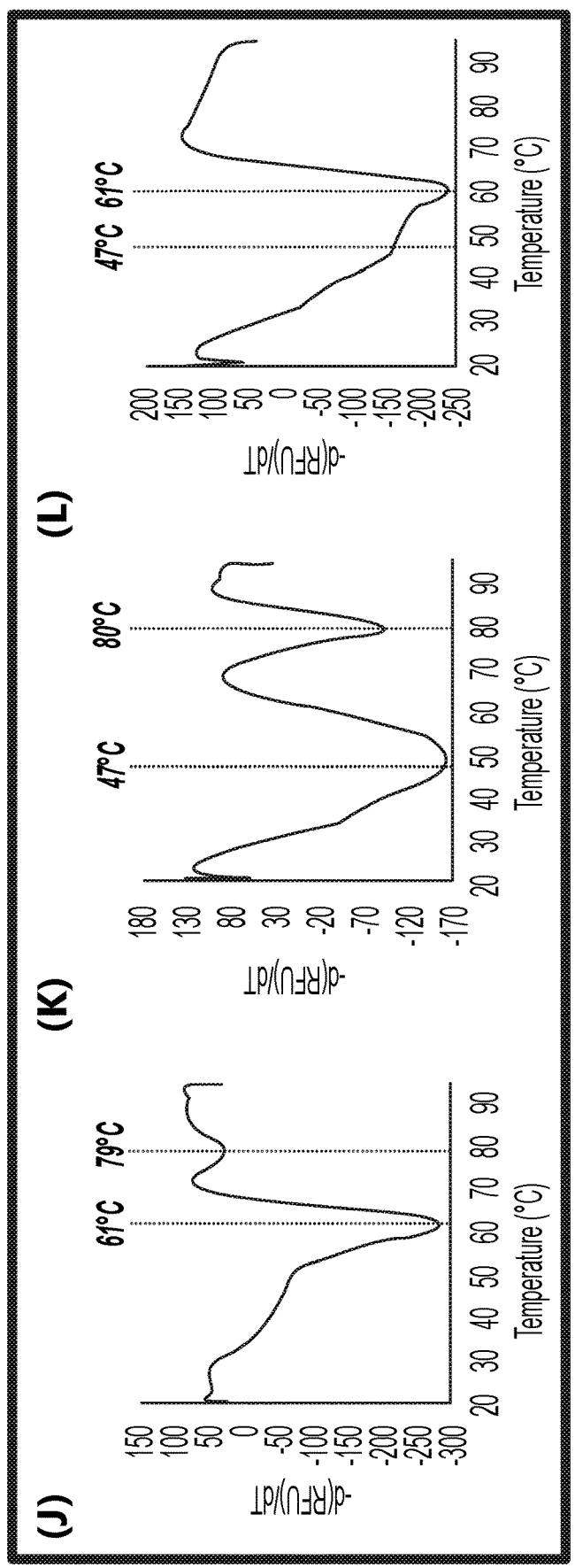
Figures 23J-K

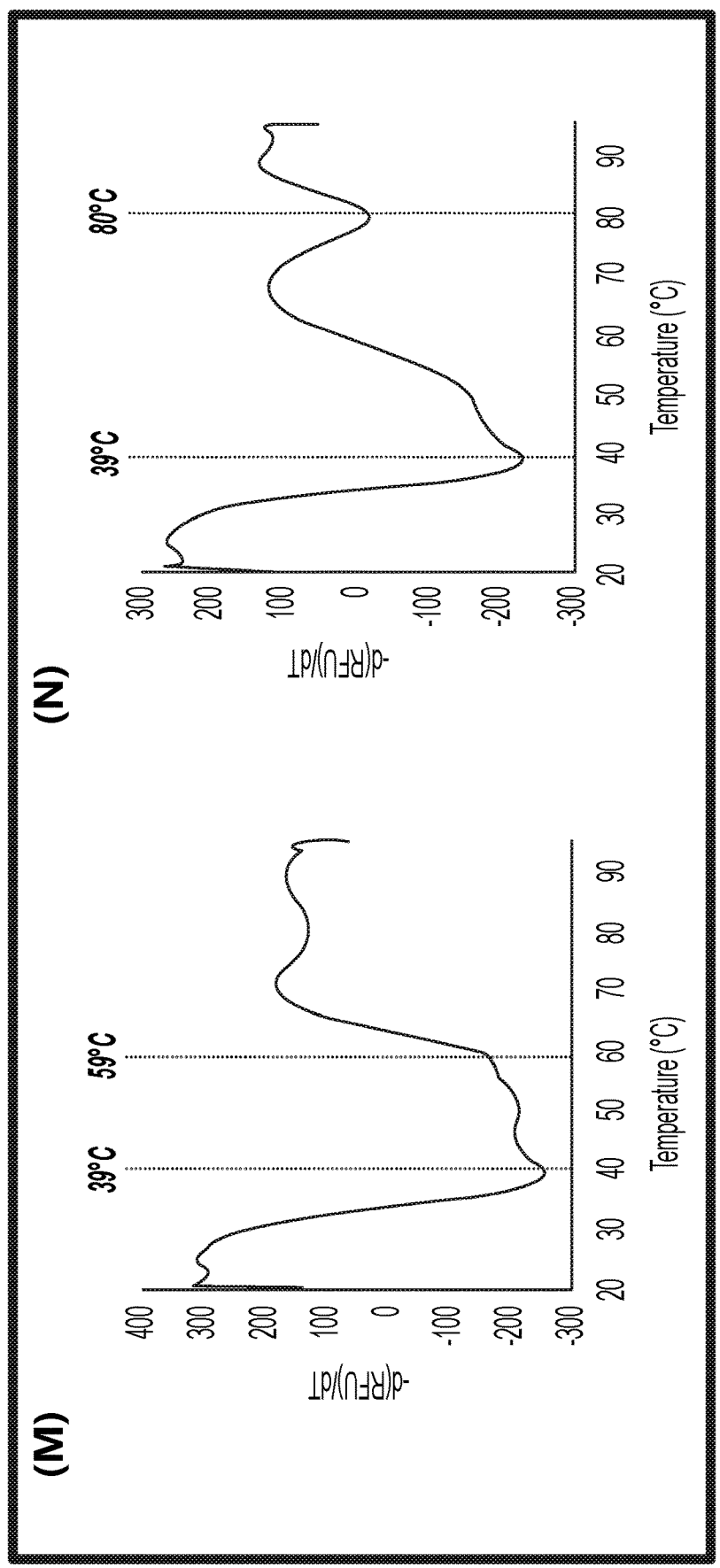
Figures 23M-N

SEQUENCE LISTING

<160> NUMBER OF SEQ ID NOS: 131

<210> SEQ ID NO 1
<211> LENGTH: 48
<212> TYPE: DNA
<213> ORGANISM: Artificial Sequence
<220> FEATURE:
<223> OTHER INFORMATION: Synthetic LOCS sequence

<400> SEQUENCE: 1
tatgccgact ttttcgacgt cccguccuct accgcttttc tcggcata                48

<210> SEQ ID NO 2
<211> LENGTH: 48
<212> TYPE: DNA
<213> ORGANISM: Artificial Sequence
<220> FEATURE:
<223> OTHER INFORMATION: Synthetic LOCS sequence

<400> SEQUENCE: 2
cgcactggct tttatcacgc ctcguctcct cccagttttg ccagtgcg                48

<210> SEQ ID NO 3
<211> LENGTH: 40
<212> TYPE: DNA
<213> ORGANISM: Artificial Sequence
<220> FEATURE:
<223> OTHER INFORMATION: Synthetic partzyme sequence

<400> SEQUENCE: 3
atcagaaggt atgataacaa cggacaacga gggacgtcga                         40

<210> SEQ ID NO 4
<211> LENGTH: 44
<212> TYPE: DNA
<213> ORGANISM: Artificial Sequence
<220> FEATURE:
<223> OTHER INFORMATION: Synthetic partzyme seqeunce

<400> SEQUENCE: 4
cggtagagga ggctagctta gagctttata tgatattaac ttag                    44

<210> SEQ ID NO 5
<211> LENGTH: 39
<212> TYPE: DNA
<213> ORGANISM: Artificial Sequence
<220> FEATURE:
<223> OTHER INFORMATION: Synthetic partzyme sequence

<400> SEQUENCE: 5
aagctcacaa caccaacata cgacaacgag aggcgtgat                          39

<210> SEQ ID NO 6
<211> LENGTH: 41
<212> TYPE: DNA
<213> ORGANISM: Artificial Sequence
<220> FEATURE:
<223> OTHER INFORMATION: Synthetic partzyme sequence

<400> SEQUENCE: 6
ctgggaggag aggctagctg cgatcttaac caccttgttt c                       41

<210> SEQ ID NO 7
<211> LENGTH: 30
<212> TYPE: DNA
<213> ORGANISM: Artificial Sequence

```
<220> FEATURE:
<223> OTHER INFORMATION: Synthetic primer sequence

<400> SEQUENCE: 7
gttgagaaat accttgatgg tcagcaaaac                              30

<210> SEQ ID NO 8
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 8
acccctttgc accgttgagg                                         20

<210> SEQ ID NO 9
<211> LENGTH: 26
<212> TYPE: DNA
<213> ORGANISM: Artificial Sequence
<220> FEATURE:
<223> OTHER INFORMATION: Synthetic primer sequence

<400> SEQUENCE: 9
cgaagctctt tatgatattt gcttcc                                  26

<210> SEQ ID NO 10
<211> LENGTH: 25
<212> TYPE: DNA
<213> ORGANISM: Artificial Sequence
<220> FEATURE:
<223> OTHER INFORMATION: Synthetic primer sequence

<400> SEQUENCE: 10
aacatgttgt tccggacata accat                                   25

<210> SEQ ID NO 11
<211> LENGTH: 37
<212> TYPE: DNA
<213> ORGANISM: Artificial Sequence
<220> FEATURE:
<223> OTHER INFORMATION: Synthetic partzyme sequence

<400> SEQUENCE: 11
cagaggcctt cagcaccaga acaacgaggg acgtcga                      37

<210> SEQ ID NO 12
<211> LENGTH: 48
<212> TYPE: DNA
<213> ORGANISM: Artificial Sequence
<220> FEATURE:
<223> OTHER INFORMATION: Synthetic partzyme sequence

<400> SEQUENCE: 12
cggtagagga ggctagctca cacctataat tttattatgt gtaggtgc          48

<210> SEQ ID NO 13
<211> LENGTH: 37
<212> TYPE: DNA
<213> ORGANISM: Artificial Sequence
<220> FEATURE:
<223> OTHER INFORMATION: Artificial partzyme sequence

<400> SEQUENCE: 13
ttgcaccact tggtgtgacg acaacgaggg acgtcga                      37
```

<210> SEQ ID NO 14
<211> LENGTH: 39
<212> TYPE: DNA
<213> ORGANISM: Artificial Sequence
<220> FEATURE:
<223> OTHER INFORMATION: Artificial partzyme sequence

<400> SEQUENCE: 14
cggtagagga ggctagctct atcagcatgc gtgtgggtt                        39

<210> SEQ ID NO 15
<211> LENGTH: 32
<212> TYPE: DNA
<213> ORGANISM: Artificial Sequence
<220> FEATURE:
<223> OTHER INFORMATION: Synthetic primer sequence

<400> SEQUENCE: 15
acaatggtaa ctttgcttaa ggaatcatca gg                              32

<210> SEQ ID NO 16
<211> LENGTH: 33
<212> TYPE: DNA
<213> ORGANISM: Artificial Sequence
<220> FEATURE:
<223> OTHER INFORMATION: Synthetic primer sequence

<400> SEQUENCE: 16
tcaacaagtc tctagtccca cttctattgt tga                             33

<210> SEQ ID NO 17
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 17
tttcggcgga gatccttgcg atcc                                       24

<210> SEQ ID NO 18
<211> LENGTH: 25
<212> TYPE: DNA
<213> ORGANISM: Artificial Sequence
<220> FEATURE:
<223> OTHER INFORMATION: Synthetic primer sequence

<400> SEQUENCE: 18
cgaaaacaaa gtcaccgtag taacc                                      25

<210> SEQ ID NO 19
<211> LENGTH: 39
<212> TYPE: DNA
<213> ORGANISM: Artificial Sequence
<220> FEATURE:
<223> OTHER INFORMATION: Synthetic partzyme sequence

<400> SEQUENCE: 19
caacagttct acaagtttgc ggacaacgag aggcgtgat                       39

<210> SEQ ID NO 20
<211> LENGTH: 43
<212> TYPE: DNA
<213> ORGANISM: Artificial Sequence
<220> FEATURE:
<223> OTHER INFORMATION: Synthetic partzyme sequence

```
<400> SEQUENCE: 20
ctgggaggag aggctagctg cataatcgtt aataaattga cag                    43

<210> SEQ ID NO 21
<211> LENGTH: 38
<212> TYPE: DNA
<213> ORGANISM: Artificial Sequence
<220> FEATURE:
<223> OTHER INFORMATION: Synthetic partzyme sequence

<400> SEQUENCE: 21
tacctgtctg ctatcgaaga aacaacgaga ggcgtgat                          38

<210> SEQ ID NO 22
<211> LENGTH: 39
<212> TYPE: DNA
<213> ORGANISM: Artificial Sequence
<220> FEATURE:
<223> OTHER INFORMATION: Synthetic partzyme sequence

<400> SEQUENCE: 22
ctgggaggag aggctagctg gcaactacgt tatcgctca                         39

<210> SEQ ID NO 23
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 23
ctaacggtgt cgtcatataa caac                                         24

<210> SEQ ID NO 24
<211> LENGTH: 25
<212> TYPE: DNA
<213> ORGANISM: Artificial Sequence
<220> FEATURE:
<223> OTHER INFORMATION: Synthetic primer sequence

<400> SEQUENCE: 24
cagaaggttt taatgaaggg agtcg                                        25

<210> SEQ ID NO 25
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 25
caacggtgtg gttactgacg                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 26
tctacgaagt ggccgttttc                                              20

<210> SEQ ID NO 27
```

```
<211> LENGTH: 50
<212> TYPE: DNA
<213> ORGANISM: Artificial Sequence
<220> FEATURE:
<223> OTHER INFORMATION: Synthetic LOCS sequence

<400> SEQUENCE: 27
ctatgccgac tttttcgacg tcccguccte taccgctttt ctcggcatag          50

<210> SEQ ID NO 28
<211> LENGTH: 44
<212> TYPE: DNA
<213> ORGANISM: Artificial Sequence
<220> FEATURE:
<223> OTHER INFORMATION: Synthetic LOCS sequence

<400> SEQUENCE: 28
cactggcttt tatcacgcct cguctcctcc cagttttgcc agtg               44

<210> SEQ ID NO 29
<211> LENGTH: 35
<212> TYPE: DNA
<213> ORGANISM: Artificial Sequence
<220> FEATURE:
<223> OTHER INFORMATION: Artificial partzyme sequence

<400> SEQUENCE: 29
tgctcgaagc acgtgcggac aacgagggac gtcga                        35

<210> SEQ ID NO 30
<211> LENGTH: 39
<212> TYPE: DNA
<213> ORGANISM: Artificial Sequence
<220> FEATURE:
<223> OTHER INFORMATION: Artificial partzyme sequence

<400> SEQUENCE: 30
gcggtagagg aggctagctg gttatcttaa aagggattg                    39

<210> SEQ ID NO 31
<211> LENGTH: 38
<212> TYPE: DNA
<213> ORGANISM: Artificial Sequence
<220> FEATURE:
<223> OTHER INFORMATION: Artificial partzyme sequence

<400> SEQUENCE: 31
ggaatatgga aggagactgt cacaacgaga ggcgtgat                     38

<210> SEQ ID NO 32
<211> LENGTH: 40
<212> TYPE: DNA
<213> ORGANISM: Artificial Sequence
<220> FEATURE:
<223> OTHER INFORMATION: Artificial partzyme sequence

<400> SEQUENCE: 32
ctgggaggag aggctagctc ctctgactgg aaaacagact                   40

<210> SEQ ID NO 33
<211> LENGTH: 92
<212> TYPE: DNA
<213> ORGANISM: Artificial Sequence
<220> FEATURE:
<223> OTHER INFORMATION: Synthetic AF-CT-Cds sequence
```

<400> SEQUENCE: 33
actacaagct gcaatcccttt ttaagataac cccgcacgtg cttcgagcaa ccgctgtgac    60
ggagtacaaa cgcctagggt gctcagactc cg                                   92

<210> SEQ ID NO 34
<211> LENGTH: 42
<212> TYPE: DNA
<213> ORGANISM: Artificial Sequence
<220> FEATURE:
<223> OTHER INFORMATION: Synthetic AF-TFRC sequence

<400> SEQUENCE: 34 agtctgttttt ccagtcagag ggacagtctc cttccatatt cc                       42

<210> SEQ ID NO 35
<211> LENGTH: 48
<212> TYPE: DNA
<213> ORGANISM: Artificial Sequence
<220> FEATURE:
<223> OTHER INFORMATION: Synthetic LOCS sequence

<400> SEQUENCE: 35
tatgccgact ttttcgacgt cccgucctct accgcttttc tcggcata                  48

<210> SEQ ID NO 36
<211> LENGTH: 48
<212> TYPE: DNA
<213> ORGANISM: Artificial Sequence
<220> FEATURE:
<223> OTHER INFORMATION: Synthetic LOCS sequence

<400> SEQUENCE: 36
cgcactggct tttatcacgc ctcguctcct cccagttttg ccagtgcg                  48

<210> SEQ ID NO 37
<211> LENGTH: 48
<212> TYPE: DNA
<213> ORGANISM: Artificial Sequence
<220> FEATURE:
<223> OTHER INFORMATION: Synthetic LOCS sequence

<400> SEQUENCE: 37
tatgccgact ttttcgacgt cccgucctct accgcttttc tcggcata                  48

<210> SEQ ID NO 38
<211> LENGTH: 48
<212> TYPE: DNA
<213> ORGANISM: Artificial Sequence
<220> FEATURE:
<223> OTHER INFORMATION: Synthetic LOCS sequence

<400> SEQUENCE: 38
cgcactggct tttatcacgc ctcguctcct cccagttttg ccagtgcg                  48

<210> SEQ ID NO 39
<211> LENGTH: 48
<212> TYPE: DNA
<213> ORGANISM: Artificial Sequence
<220> FEATURE:
<223> OTHER INFORMATION: Synthetic LOCS sequence

<400> SEQUENCE: 39
tatgccgact ttttcgacgt cccgucctct accgcttttc tcggcata                  48

<210> SEQ ID NO 40
<211> LENGTH: 48
<212> TYPE: DNA
<213> ORGANISM: Artificial Sequence
<220> FEATURE:
<223> OTHER INFORMATION: Synthetic LOCS sequence

<400> SEQUENCE: 40
cgcactggct tttatcacgc ctcguctcct cccagttttg ccagtgcg         48

<210> SEQ ID NO 41
<211> LENGTH: 26
<212> TYPE: DNA
<213> ORGANISM: Artificial Sequence
<220> FEATURE:
<223> OTHER INFORMATION: Synthetic primer sequence

<400> SEQUENCE: 41
aatatcatct ttgcggttgc gtgtcc                                 26

<210> SEQ ID NO 42
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 42
gctgtgacgg agtacaaacg cc                                     22

<210> SEQ ID NO 43
<211> LENGTH: 40
<212> TYPE: DNA
<213> ORGANISM: Artificial Sequence
<220> FEATURE:
<223> OTHER INFORMATION: Synthetic partzyme sequence

<400> SEQUENCE: 43
tcctgtgacc ttcattatgt cgacaacgag aggaaacctt                  40

<210> SEQ ID NO 44
<211> LENGTH: 37
<212> TYPE: DNA
<213> ORGANISM: Artificial Sequence
<220> FEATURE:
<223> OTHER INFORMATION: Synthetic partzyme sequence

<400> SEQUENCE: 44
tgcccaggga ggctagctga gtctgagcac cctaggc                     37

<210> SEQ ID NO 45
<211> LENGTH: 50
<212> TYPE: DNA
<213> ORGANISM: Artificial Sequence
<220> FEATURE:
<223> OTHER INFORMATION: Synthetic LOCS sequence

<400> SEQUENCE: 45
tatggcctat ttttaaggtt tcctcguccc tgggcatttt ataggccata       50

<210> SEQ ID NO 46
<211> LENGTH: 47
<212> TYPE: DNA
<213> ORGANISM: Artificial Sequence
<220> FEATURE:
<223> OTHER INFORMATION: Synthetic LOCS sequence -continued

<400> SEQUENCE: 46
tatgccgact tttctcgacc ctcgucccctc gtccttttct cggcata         47

<210> SEQ ID NO 47
<211> LENGTH: 47
<212> TYPE: DNA
<213> ORGANISM: Artificial Sequence
<220> FEATURE:
<223> OTHER INFORMATION: Synthetic LOCS sequence

<400> SEQUENCE: 47
cgcactggct tttaccgcac ctcguccca gctcttttgc cagtgcg           47

<210> SEQ ID NO 48
<211> LENGTH: 36
<212> TYPE: DNA
<213> ORGANISM: Artificial Sequence
<220> FEATURE:
<223> OTHER INFORMATION: Synthetic partzyme sequence

<400> SEQUENCE: 48
ggaacccgat ataatccgca caacgagagg gtcgag                      36

<210> SEQ ID NO 49
<211> LENGTH: 39
<212> TYPE: DNA
<213> ORGANISM: Artificial Sequence
<220> FEATURE:
<223> OTHER INFORMATION: Synthetic partzyme sequence

<400> SEQUENCE: 49
ggacgaggga ggctagctcc ttcaacatca gtgaaaatc                   39

<210> SEQ ID NO 50
<211> LENGTH: 37
<212> TYPE: DNA
<213> ORGANISM: Artificial Sequence
<220> FEATURE:
<223> OTHER INFORMATION: Synthetic partzyme sequence

<400> SEQUENCE: 50
agacccctcg cttaagatgg acaacgagag gtgcggt                     37

<210> SEQ ID NO 51
<211> LENGTH: 38
<212> TYPE: DNA
<213> ORGANISM: Artificial Sequence
<220> FEATURE:
<223> OTHER INFORMATION: Synthetic partzyme sequence

<400> SEQUENCE: 51
gagctgggga ggctagctcc gatcccaatc gatttcgc                    38

<210> SEQ ID NO 52
<211> LENGTH: 19
<212> TYPE: DNA
<213> ORGANISM: Artificial Sequence
<220> FEATURE:
<223> OTHER INFORMATION: Synthetic primer sequence

<400> SEQUENCE: 52
gtgttgaaac accgcccgg                                         19

<210> SEQ ID NO 53

```
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 53
cggctcctta ttcggtttga cc                                              22

<210> SEQ ID NO 54
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 54
ctaccaaata cgccttagca gacc                                            24

<210> SEQ ID NO 55
<211> LENGTH: 26
<212> TYPE: DNA
<213> ORGANISM: Artificial Sequence
<220> FEATURE:
<223> OTHER INFORMATION: Synthetic primer sequence

<400> SEQUENCE: 55
caggctgaat gtggtaaaca cgcttc                                          26

<210> SEQ ID NO 56
<211> LENGTH: 10
<212> TYPE: DNA
<213> ORGANISM: Artificial Sequence
<220> FEATURE:
<223> OTHER INFORMATION: Synthetic DSO sequence

<400> SEQUENCE: 56
ttttagtgcg                                                            10

<210> SEQ ID NO 57
<211> LENGTH: 10
<212> TYPE: DNA
<213> ORGANISM: Artificial Sequence
<220> FEATURE:
<223> OTHER INFORMATION: Synthetic DSO sequence

<400> SEQUENCE: 57
cgcactttt                                                             10

<210> SEQ ID NO 58
<211> LENGTH: 11
<212> TYPE: DNA
<213> ORGANISM: Artificial Sequence
<220> FEATURE:
<223> OTHER INFORMATION: Synthetic DSO sequence

<400> SEQUENCE: 58
ttttaagtgc g                                                          11

<210> SEQ ID NO 59
<211> LENGTH: 10
<212> TYPE: DNA
<213> ORGANISM: Artificial Sequence
<220> FEATURE:
<223> OTHER INFORMATION: Synthetic DSO sequence
```

```
<400> SEQUENCE: 59
cgcactttt                                                          10

<210> SEQ ID NO 60
<211> LENGTH: 11
<212> TYPE: DNA
<213> ORGANISM: Artificial Sequence
<220> FEATURE:
<223> OTHER INFORMATION: Synthetic DSO sequence

<400> SEQUENCE: 60
ttttcagtgc g                                                       11

<210> SEQ ID NO 61
<211> LENGTH: 11
<212> TYPE: DNA
<213> ORGANISM: Artificial Sequence
<220> FEATURE:
<223> OTHER INFORMATION: Synthetic DSO sequence

<400> SEQUENCE: 61
cgcactgttt t                                                       11

<210> SEQ ID NO 62
<211> LENGTH: 12
<212> TYPE: DNA
<213> ORGANISM: Artificial Sequence
<220> FEATURE:
<223> OTHER INFORMATION: Synthetic DSO sequence

<400> SEQUENCE: 62
ttttacagtg cg                                                      12

<210> SEQ ID NO 63
<211> LENGTH: 12
<212> TYPE: DNA
<213> ORGANISM: Artificial Sequence
<220> FEATURE:
<223> OTHER INFORMATION: Synthetic DSO sequence

<400> SEQUENCE: 63
cgcactgttt tt                                                      12

<210> SEQ ID NO 64
<211> LENGTH: 12
<212> TYPE: DNA
<213> ORGANISM: Artificial Sequence
<220> FEATURE:
<223> OTHER INFORMATION: Synthetic DSO sequence

<400> SEQUENCE: 64
ttttccagtg cg                                                      12

<210> SEQ ID NO 65
<211> LENGTH: 12
<212> TYPE: DNA
<213> ORGANISM: Artificial Sequence
<220> FEATURE:
<223> OTHER INFORMATION: Synthetic DSO sequence

<400> SEQUENCE: 65
cgcactggtt tt                                                      12

<210> SEQ ID NO 66
```

```
<211> LENGTH: 12
<212> TYPE: DNA
<213> ORGANISM: Artificial Sequence
<220> FEATURE:
<223> OTHER INFORMATION: Synthetic DSO sequence

<400> SEQUENCE: 66
cgcactggtt tt                                                        12

<210> SEQ ID NO 67
<211> LENGTH: 13
<212> TYPE: DNA
<213> ORGANISM: Artificial Sequence
<220> FEATURE:
<223> OTHER INFORMATION: Synthetic DSO sequence

<400> SEQUENCE: 67
cgcactggtt ttt                                                       13

<210> SEQ ID NO 68
<211> LENGTH: 13
<212> TYPE: DNA
<213> ORGANISM: Artificial Sequence
<220> FEATURE:
<223> OTHER INFORMATION: Synthetic DSO sequence

<400> SEQUENCE: 68
ttttgccagt gcg                                                       13

<210> SEQ ID NO 69
<211> LENGTH: 13
<212> TYPE: DNA
<213> ORGANISM: Artificial Sequence
<220> FEATURE:
<223> OTHER INFORMATION: Synthetic DSO sequence

<400> SEQUENCE: 69
cgcactggct ttt                                                       13

<210> SEQ ID NO 70
<211> LENGTH: 14
<212> TYPE: DNA
<213> ORGANISM: Artificial Sequence
<220> FEATURE:
<223> OTHER INFORMATION: Synthetic DSO sequence

<400> SEQUENCE: 70
tttttgccag tgcg                                                      14

<210> SEQ ID NO 71
<211> LENGTH: 14
<212> TYPE: DNA
<213> ORGANISM: Artificial Sequence
<220> FEATURE:
<223> OTHER INFORMATION: Synthetic DSO sequence

<400> SEQUENCE: 71
cgcactggca tttt                                                      14

<210> SEQ ID NO 72
<211> LENGTH: 26
<212> TYPE: DNA
<213> ORGANISM: Artificial Sequence
<220> FEATURE:
<223> OTHER INFORMATION: Synthetic primer sequence
```

```
<400> SEQUENCE: 72
gctaaaacaa taactcagaa cttacg                                              26

<210> SEQ ID NO 73
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 73
cagctttctg aggttaccat ccta                                                24

<210> SEQ ID NO 74
<211> LENGTH: 38
<212> TYPE: DNA
<213> ORGANISM: Artificial Sequence
<220> FEATURE:
<223> OTHER INFORMATION: Synthetic partzyme sequence

<400> SEQUENCE: 74
ggaatatgga aggagactgt cacaacgagg gacgtcga                                 38

<210> SEQ ID NO 75
<211> LENGTH: 40
<212> TYPE: DNA
<213> ORGANISM: Artificial Sequence
<220> FEATURE:
<223> OTHER INFORMATION: Synthetic partzyme sequence

<400> SEQUENCE: 75
gcggtagagg aggctagctc ctctgactgg aaaacagact                               40

<210> SEQ ID NO 76
<211> LENGTH: 38
<212> TYPE: DNA
<213> ORGANISM: Artificial Sequence
<220> FEATURE:
<223> OTHER INFORMATION: Synthetic partzyme sequence

<400> SEQUENCE: 76
ggaatatgga aggagactgt cacaacgaga gggtcgag                                 38

<210> SEQ ID NO 77
<211> LENGTH: 39
<212> TYPE: DNA
<213> ORGANISM: Artificial Sequence
<220> FEATURE:
<223> OTHER INFORMATION: Synthetic partzyme sequence

<400> SEQUENCE: 77
ggacgaggga ggctagctcc tctgactgga aaacagact                                39

<210> SEQ ID NO 78
<211> LENGTH: 50
<212> TYPE: DNA
<213> ORGANISM: Artificial Sequence
<220> FEATURE:
<223> OTHER INFORMATION: Synthetic LOCS sequence

<400> SEQUENCE: 78
cgcactggct ttttcgacgt cccrgrucct ctaccgcttt tgccagtgcg                    50

<210> SEQ ID NO 79
```

```
<211> LENGTH: 47
<212> TYPE: DNA
<213> ORGANISM: Artificial Sequence
<220> FEATURE:
<223> OTHER INFORMATION: Synthetic LOCS sequence

<400> SEQUENCE: 79
cgcactggct tttctcgacc ctcguccctc gtccttttgc cagtgcg                    47

<210> SEQ ID NO 80
<211> LENGTH: 48
<212> TYPE: DNA
<213> ORGANISM: Artificial Sequence
<220> FEATURE:
<223> OTHER INFORMATION: Synthetic LOCS sequence

<400> SEQUENCE: 80
tatgccgact tttcacggcg tggatcgcaa gcagcttttc tcggcata                   48

<210> SEQ ID NO 81
<211> LENGTH: 52
<212> TYPE: DNA
<213> ORGANISM: Artificial Sequence
<220> FEATURE:
<223> OTHER INFORMATION: Synthetic LOCS sequence

<400> SEQUENCE: 81
cgcactggct tttataagag gatcgataca taagacgagt tttgccagtg cg              52

<210> SEQ ID NO 82
<211> LENGTH: 22
<212> TYPE: DNA
<213> ORGANISM: Artificial Sequence
<220> FEATURE:
<223> OTHER INFORMATION: Synthetic AF-NE-TV1 sequence

<400> SEQUENCE: 82
gctgcttgcg atccacgccg tg                                               22

<210> SEQ ID NO 83
<211> LENGTH: 26
<212> TYPE: DNA
<213> ORGANISM: Artificial Sequence
<220> FEATURE:
<223> OTHER INFORMATION: Synthetic AF-NE-R5b sequence

<400> SEQUENCE: 83
ctcgtcttat gtatcgatcc tcttat                                           26

<210> SEQ ID NO 84
<211> LENGTH: 49
<212> TYPE: DNA
<213> ORGANISM: Artificial Sequence
<220> FEATURE:
<223> OTHER INFORMATION: Synthetic LOCS sequence

<400> SEQUENCE: 84
tatgccgact tttcaccaac atacggcgat cttaactttt ctcggcata                  49

<210> SEQ ID NO 85
<211> LENGTH: 22
<212> TYPE: DNA
<213> ORGANISM: Artificial Sequence
<220> FEATURE:
<223> OTHER INFORMATION: Synthetic primer sequence
```

```
<400> SEQUENCE: 85
gctccttatt cggtttgacc gg                                          22

<210> SEQ ID NO 86
<211> LENGTH: 44
<212> TYPE: DNA
<213> ORGANISM: Artificial Sequence
<220> FEATURE:
<223> OTHER INFORMATION: Synthetic LOCS sequence

<400> SEQUENCE: 86
cgtgcagttt taaggtttcc tcguccctgg gcattttctg cacg                  44

<210> SEQ ID NO 87
<211> LENGTH: 55
<212> TYPE: DNA
<213> ORGANISM: Artificial Sequence
<220> FEATURE:
<223> OTHER INFORMATION: Synthetic LOCS sequence

<400> SEQUENCE: 87
aacgacaatg gccttttctc gaccctcguc cctcgtcctt ttggccattg tcgtt      55

<210> SEQ ID NO 88
<211> LENGTH: 51
<212> TYPE: DNA
<213> ORGANISM: Artificial Sequence
<220> FEATURE:
<223> OTHER INFORMATION: Synthetic LOCS sequence

<400> SEQUENCE: 88
tcgggtagct ttttctcga ccccguctcc acgccatttt aagctacccg a           51

<210> SEQ ID NO 89
<211> LENGTH: 46
<212> TYPE: DNA
<213> ORGANISM: Artificial Sequence
<220> FEATURE:
<223> OTHER INFORMATION: Synthetic LOCS sequence

<400> SEQUENCE: 89
acagtgcatt ttcctagtcc tcguccctcac gtccttttg cactgt                46

<210> SEQ ID NO 90
<211> LENGTH: 55
<212> TYPE: DNA
<213> ORGANISM: Artificial Sequence
<220> FEATURE:
<223> OTHER INFORMATION: Synthetic LOCS sequence

<400> SEQUENCE: 90
gcgtgaccgg tccttttacc gcacctcguc cccagctctt ttggaccggt cacgc      55

<210> SEQ ID NO 91
<211> LENGTH: 46
<212> TYPE: DNA
<213> ORGANISM: Artificial Sequence
<220> FEATURE:
<223> OTHER INFORMATION: Synthetic LOCS sequence

<400> SEQUENCE: 91
tcaaggactt ttcctctcc ccguccccctt caacttttgt ccttga                46

<210> SEQ ID NO 92
```

```
<211> LENGTH: 48
<212> TYPE: DNA
<213> ORGANISM: Artificial Sequence
<220> FEATURE:
<223> OTHER INFORMATION: Synthetic LOCS sequence

<400> SEQUENCE: 92
tctacgccac ttttaccgcc ctcgucccgt gaactttgt ggcgtaga                    48

<210> SEQ ID NO 93
<211> LENGTH: 60
<212> TYPE: DNA
<213> ORGANISM: Artificial Sequence
<220> FEATURE:
<223> OTHER INFORMATION: Synthetic LOCS sequence

<400> SEQUENCE: 93
gctgtcgatc cgttatttta tcacgcctcg uctcctccca gttttaacg gatcgacagc      60

<210> SEQ ID NO 94
<211> LENGTH: 38
<212> TYPE: DNA
<213> ORGANISM: Artificial Sequence
<220> FEATURE:
<223> OTHER INFORMATION: Synthetic partzyme sequence

<400> SEQUENCE: 94
ccgatcatca gttatcctta agacaacgag gggtcgag                              38

<210> SEQ ID NO 95
<211> LENGTH: 40
<212> TYPE: DNA
<213> ORGANISM: Artificial Sequence
<220> FEATURE:
<223> OTHER INFORMATION: Synthetic partzyme sequence

<400> SEQUENCE: 95
tggcgtggag aggctagctg tctcttttgt gtggtgcgtt                            40

<210> SEQ ID NO 96
<211> LENGTH: 37
<212> TYPE: DNA
<213> ORGANISM: Artificial Sequence
<220> FEATURE:
<223> OTHER INFORMATION: Synthetic partzyme sequence

<400> SEQUENCE: 96 agaccctcg cttaagatgg acaacgagag gactagg                                37

<210> SEQ ID NO 97
<211> LENGTH: 38
<212> TYPE: DNA
<213> ORGANISM: Artificial Sequence
<220> FEATURE:
<223> OTHER INFORMATION: Synthetic partzyme sequence

<400> SEQUENCE: 97
gacgtgagga ggctagctcc gatcccaatc gatttcgc                              38

<210> SEQ ID NO 98
<211> LENGTH: 36
<212> TYPE: DNA
<213> ORGANISM: Artificial Sequence
<220> FEATURE:
<223> OTHER INFORMATION: Synthetic partzyme sequence
```

<400> SEQUENCE: 98
aagtccgcct atacgcctga caacgagagg tgcggt                36

<210> SEQ ID NO 99
<211> LENGTH: 38
<212> TYPE: DNA
<213> ORGANISM: Artificial Sequence
<220> FEATURE:
<223> OTHER INFORMATION: Synthetic partzyme sequence

<400> SEQUENCE: 99
agctggggag gctagctcta ctttcacgct ggaaagta              38

<210> SEQ ID NO 100
<211> LENGTH: 40
<212> TYPE: DNA
<213> ORGANISM: Artificial Sequence
<220> FEATURE:
<223> OTHER INFORMATION: Synthetic partzyme sequence

<400> SEQUENCE: 100
ccgtacactc aagctcacaa cacacaacga ggggagagga            40

<210> SEQ ID NO 101
<211> LENGTH: 41
<212> TYPE: DNA
<213> ORGANISM: Artificial Sequence
<220> FEATURE:
<223> OTHER INFORMATION: Synthetic partzyme sequence

<400> SEQUENCE: 101
ttgaagggga ggctagctca acatacggcg atcttaacca c          41

<210> SEQ ID NO 102
<211> LENGTH: 40
<212> TYPE: DNA
<213> ORGANISM: Artificial Sequence
<220> FEATURE:
<223> OTHER INFORMATION: Synthetic partzyme sequence

<400> SEQUENCE: 102
atcagaaggt atgataacaa cggacaacga gagggcggtt            40

<210> SEQ ID NO 103
<211> LENGTH: 45
<212> TYPE: DNA
<213> ORGANISM: Artificial Sequence
<220> FEATURE:
<223> OTHER INFORMATION: Synthetic partzyme sequence

<400> SEQUENCE: 103
ggttcacggg aggctagctt agagctttat atgatattaa cttag      45

<210> SEQ ID NO 104
<211> LENGTH: 37
<212> TYPE: DNA
<213> ORGANISM: Artificial Sequence
<220> FEATURE:
<223> OTHER INFORMATION: Synthetic partzyme sequence

<400> SEQUENCE: 104
ccgagcatca ctaactgttg acaacgagag gcgtgat               37

<210> SEQ ID NO 105

```
<211> LENGTH: 38
<212> TYPE: DNA
<213> ORGANISM: Artificial Sequence
<220> FEATURE:
<223> OTHER INFORMATION: Synthetic partzyme sequence

<400> SEQUENCE: 105
tgggaggaga ggctagctga gcaggcggag ttgatgat                          38

<210> SEQ ID NO 106
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 106
ctaacagcgc gaacgaccaa ctac                                        24

<210> SEQ ID NO 107
<211> LENGTH: 20
<212> TYPE: DNA
<213> ORGANISM: Artificial Sequence
<220> FEATURE:
<223> OTHER INFORMATION: Synthetic primer sequence

<400> SEQUENCE: 107
cagcccccat accggaacgc                                             20

<210> SEQ ID NO 108
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 108
agcattcaat ttgttccgag tc                                          22

<210> SEQ ID NO 109
<211> LENGTH: 22
<212> TYPE: DNA
<213> ORGANISM: Artificial Sequence
<220> FEATURE:
<223> OTHER INFORMATION: Synthetic primer sequence

<400> SEQUENCE: 109
caacagccgg aactggtttc at                                          22

<210> SEQ ID NO 110
<211> LENGTH: 33
<212> TYPE: DNA
<213> ORGANISM: Artificial Sequence
<220> FEATURE:
<223> OTHER INFORMATION: Synthetic primer sequence

<400> SEQUENCE: 110
tgcattgata acgaagctct ttatgatatt tgc                              33

<210> SEQ ID NO 111
<211> LENGTH: 23
<212> TYPE: DNA
<213> ORGANISM: Artificial Sequence
<220> FEATURE:
<223> OTHER INFORMATION: Synthetic primer sequence
```

```
<400> SEQUENCE: 111
tacagaaaaa atagacccett tcc                                          23

<210> SEQ ID NO 112
<211> LENGTH: 23
<212> TYPE: DNA
<213> ORGANISM: Artificial Sequence
<220> FEATURE:
<223> OTHER INFORMATION: Synthetic primer sequence

<400> SEQUENCE: 112
gtattctcct ttatctactg tgc                                           23

<210> SEQ ID NO 113
<211> LENGTH: 47
<212> TYPE: DNA
<213> ORGANISM: Artificial Sequence
<220> FEATURE:
<223> OTHER INFORMATION: Synthetic LOCS sequence

<400> SEQUENCE: 113
tatgccgact tttaccgcac ctcguccca gctcttttct cggcata                  47

<210> SEQ ID NO 114
<211> LENGTH: 54
<212> TYPE: DNA
<213> ORGANISM: Artificial Sequence
<220> FEATURE:
<223> OTHER INFORMATION: Synthetic LOCS sequence

<400> SEQUENCE: 114
tctacgccac cagttttacc gccctcgucc cgtgaacttt tctggtggcg taga          54

<210> SEQ ID NO 115
<211> LENGTH: 60
<212> TYPE: DNA
<213> ORGANISM: Artificial Sequence
<220> FEATURE:
<223> OTHER INFORMATION: Synthetic LOCS sequence

<400> SEQUENCE: 115
cacggtctag agctctttta aggtttcctc gucectgggc attttgagct ctagaccgtg    60

<210> SEQ ID NO 116
<211> LENGTH: 56
<212> TYPE: DNA
<213> ORGANISM: Artificial Sequence
<220> FEATURE:
<223> OTHER INFORMATION: Synthetic LOCS sequence

<400> SEQUENCE: 116
aacgacaatg gccttttcg acgtcccguc ctctaccgct tttggccatt gtcgtt        56

<210> SEQ ID NO 117
<211> LENGTH: 49
<212> TYPE: DNA
<213> ORGANISM: Artificial Sequence
<220> FEATURE:
<223> OTHER INFORMATION: Synthetic LOCS sequence

<400> SEQUENCE: 117
cgcactggct tttccacggt cccguccctcc tgtacctttt gccagtgcg              49

<210> SEQ ID NO 118
```

```
<211> LENGTH: 39
<212> TYPE: DNA
<213> ORGANISM: Artificial Sequence
<220> FEATURE:
<223> OTHER INFORMATION: Synthetic partzyme sequence

<400> SEQUENCE: 118
ttgaagtcgg agttgaagac gaacaacgag ggacgtcga                           39

<210> SEQ ID NO 119
<211> LENGTH: 38
<212> TYPE: DNA
<213> ORGANISM: Artificial Sequence
<220> FEATURE:
<223> OTHER INFORMATION: Synthetic partzyme sequence

<400> SEQUENCE: 119
cggtagagga ggctagctgt gctgtgtctg gcgccata                            38

<210> SEQ ID NO 120
<211> LENGTH: 38
<212> TYPE: DNA
<213> ORGANISM: Artificial Sequence
<220> FEATURE:
<223> OTHER INFORMATION: Synthetic partzyme sequence

<400> SEQUENCE: 120
ggaatatgga aggagactgt cacaacgagg gaccgtgg                            38

<210> SEQ ID NO 121
<211> LENGTH: 41
<212> TYPE: DNA
<213> ORGANISM: Artificial Sequence
<220> FEATURE:
<223> OTHER INFORMATION: Synthetic partzyme sequence

<400> SEQUENCE: 121
ggtacaggag gaggctagct cctctgactg gaaaacagac t                        41

<210> SEQ ID NO 122
<211> LENGTH: 19
<212> TYPE: DNA
<213> ORGANISM: Artificial Sequence
<220> FEATURE:
<223> OTHER INFORMATION: Synthetic primer sequence

<400> SEQUENCE: 122
agggctagta caccggagg                                                 19

<210> SEQ ID NO 123
<211> LENGTH: 24
<212> TYPE: DNA
<213> ORGANISM: Artificial Sequence
<220> FEATURE:
<223> OTHER INFORMATION: Synthetic primer sequence

<400> SEQUENCE: 123
cctaagatct ctattttcta tagg                                           24

<210> SEQ ID NO 124
<211> LENGTH: 38
<212> TYPE: DNA
<213> ORGANISM: Artificial Sequence
<220> FEATURE:
<223> OTHER INFORMATION: Synthetic partzyme sequence
```

```
<400> SEQUENCE: 124
ggaatatgga aggagactgt cacaacgaga ggactagg                                    38

<210> SEQ ID NO 125
<211> LENGTH: 39
<212> TYPE: DNA
<213> ORGANISM: Artificial Sequence
<220> FEATURE:
<223> OTHER INFORMATION: Synthetic partzyme sequence

<400> SEQUENCE: 125
gacgtgagga ggctagctcc tctgactgga aaacagact                                   39

<210> SEQ ID NO 126
<211> LENGTH: 37
<212> TYPE: DNA
<213> ORGANISM: Artificial Sequence
<220> FEATURE:
<223> OTHER INFORMATION: Synthetic partzyme sequence

<400> SEQUENCE: 126
tacctgtctg ctatcgaaga aacaacgagg ggtcgag                                     37

<210> SEQ ID NO 127
<211> LENGTH: 39
<212> TYPE: DNA
<213> ORGANISM: Artificial Sequence
<220> FEATURE:
<223> OTHER INFORMATION: Synthetic partzyme sequence

<400> SEQUENCE: 127
tggcgtggag aggctagctg gcaactacgt tatcgctca                                   39

<210> SEQ ID NO 128
<211> LENGTH: 23
<212> TYPE: DNA
<213> ORGANISM: Artificial Sequence
<220> FEATURE:
<223> OTHER INFORMATION: Synthetic primer sequence

<400> SEQUENCE: 128
ctaagtagcc accataagat gcc                                                    23

<210> SEQ ID NO 129
<211> LENGTH: 25
<212> TYPE: DNA
<213> ORGANISM: Artificial Sequence
<220> FEATURE:
<223> OTHER INFORMATION: Synthetic primer sequence

<400> SEQUENCE: 129
cagttccttt atatcaggtg tcctt                                                  25

<210> SEQ ID NO 130
<211> LENGTH: 36
<212> TYPE: DNA
<213> ORGANISM: Artificial Sequence
<220> FEATURE:
<223> OTHER INFORMATION: Synthetic partzyme sequence

<400> SEQUENCE: 130
agatgccaaa tcgagaagga caacgagagg tgcggt                                      36

<210> SEQ ID NO 131
```

```
<211> LENGTH: 37
<212> TYPE: DNA
<213> ORGANISM: Artificial Sequence
<220> FEATURE:
<223> OTHER INFORMATION: Synthetic partzyme sequence

<400> SEQUENCE: 131
gagctgggga ggctagctgc cacacaaaga gctccta                               37
```

MULTIPLEX DETECTION OF NUCLEIC ACIDS

CROSS-REFERENCE TO RELATED APPLICATIONS

This application is a national stage entry of PCT/IB2019/056811 filed Aug. 9, 2019, which claims priority from Australian provisional application number 2018902915 filed Aug. 9, 2018, the entire contents of which are incorporated herein by reference.

TECHNICAL FIELD

The present invention relates generally to the field of molecular biology. More specifically, the present invention provides oligonucleotides and methods for their use in the detection and/or differentiation of target nucleic acids. The oligonucleotides and methods find particular application in amplifying, detecting, and/or discriminating multiple targets simultaneously.

CROSS-REFERENCE TO RELATED APPLICATIONS

The present application is a national stage entry of PCT/IB2019/056811 filed Aug. 9, 2019, which claims priority from Australian provisional application number 2018902915 filed on 9 Aug. 2018, the entire contents of which are incorporated herein by cross-reference.

REFERENCE TO SEQUENCE LISTING

This application includes an electronic sequence listing in a file named 555283SEQLST.TXT, created on Oct. 25, 2021 and containing 26,386 bytes, which is hereby incorporated by reference.

BACKGROUND

Genetic analysis is becoming routine in the clinic for assessing disease risk, diagnosis of disease, predicting a patient's prognosis or response to therapy, and for monitoring a patient's progress. The introduction of such genetic tests depends on the development of simple, inexpensive, and rapid assays for discriminating genetic variations.

Methods of in vitro nucleic acid amplification have widespread applications in genetics and disease diagnosis. Such methods include polymerase chain reaction (PCR), strand displacement amplification (SDA), helicase dependent amplification (HDA), Recombinase Polymerase Amplification (RPA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR). Each of these target amplification strategies requires the use of oligonucleotide primers. The process of amplification results in the exponential amplification of amplicons which incorporate the oligonucleotide primers at their 5' termini and which contain newly synthesized copies of the sequences located between the primers.

Commonly used methods for monitoring the accumulation of amplicons in real time, or at the conclusion of amplification, include detection using MNAzymes with universal substrate probes; the use of target-specific Molecular Beacons, TaqMan Probes or Hydrolysis probes; Scorpion primer/probes; and/or the use of intercalating dyes such as SybGreen. High Resolution Melt curve analysis can be performed during or at the conclusion of several of these protocols to obtain additional information since amplicons with different sequences denature at different temperatures, known as the melting temperature or Tm. Such protocols measure melting curves which result from either a) the separation of the two strands of double stranded amplicons in the presence of an intercalating dye, or b) the separation of one strand of the amplicon and a complementary target-specific probe labelled with a fluorophore and quencher. Melt curve analysis provides information about the dissociation kinetics of two DNA strands during heating. The melting temperature (Tm) is the temperature at which 50% of the DNA is dissociated. The Tin is dependent on the length, sequence composition and G-C content of the paired nucleotides. Elucidation of information about the target DNA from melt curve analysis conventionally involves a series of fluorescence measurements acquired at small intervals typically over a broad temperature range. Melting temperature does not only depend upon on the base sequence. The melting temperature can be influenced by the concentrations of oligonucleotides, cations in the buffer (both monovalent (Na+) and divalent (Mg2+) salts), and the presence or absence of destabilizing agents such as urea or formamide.

In general, the number of available fluorescent channels, capable of monitoring discreet wavelengths, limits the number of targets which can be detected and specifically identified in a single reaction on a real time instrument. Recently, a protocol known as "Tagging Oligonucleotide Cleavage and Extension" (TOCE) expands this capacity allowing multiple targets to be analysed at a single wavelength. TOCE technology uses Pitcher and Catcher oligonucleotides. Pitchers have two regions, the Targeting Portion, which is complementary to the target, and the Tagging portion which is non-complementary and located at the 5' end. The Capture oligonucleotide is dual labelled and has a region at its 3' end which is complementary to the tagging portion of the Pitcher. During amplification, the Pitcher binds to the amplicons and when the primers extend the exonuclease activity of the polymerase can cleave the Tagging portion from the Pitcher. The released Tagging portion then binds to the Catcher Oligonucleotide and functions as a primer to synthesise a complementary strand. The melting temperature of the double stranded Catcher molecule (Catcher-Tm) then acts as a surrogate marker for the original template. Since it is possible to incorporate multiple Catchers with different sequences and lengths, all of which melt at different temperatures, it is possible to obtain a series of Catcher-Tm values indicative of a series of targets whilst still measuring at a single wavelength. Limitations with this approach include inherent complexity as it requires the released fragment to initiate and complete a second extension on an artificial target.

Hairpin probes or Stem-Loop probes have also proven useful tools for detection of nucleic acids and/or monitoring target amplification. Hairpin probes, which are dual labelled with a fluorophore and quencher dye pair, are commonly known in the art as Molecular Beacons. In general, these molecules have three features; 1) a Stem structure formed by hybridization of complementary 5' and 3' ends of the oligonucleotide; 2) a loop region which is complementary to the target, or target amplicon, to be detected; and 3) a fluorophore quencher dye pair attached at the termini of the Molecular Beacon. During PCR, the loop region binds to the amplicons due to complementarity and this causes the stem to open thus separating the fluorophore quencher dye pair. The separation of the dye pair attached on the termini of an intact, open Molecular Beacon causes a change in fluorescence which is indicative of the presence of target. The method is commonly used for multiplex analysis of multiple targets in a single PCR test. In multiplex reactions, each Molecular Beacon has a different target-specific loop region and a unique fluorophore such that hybridization of each different Molecular Beacons to each amplicon species can be monitored in a separate channel i.e. at a separate wavelength.

The concept of Molecular Beacons has been extended in a strategy known as Sloppy Beacons. In this protocol the loop region of a single Beacon is long enough such that it can tolerate mismatched bases and hence bind to a number of closely related targets differing by one or more nucleotides. Following amplification, melt curve analysis is performed and different target species can be differentiated based on the temperature at which the target species and loop region of the Beacon separate (melt). In this way multiple closely related species can be detected at a single wavelength and discriminated simultaneously by characterising the melting profile of specific targets with the single Sloppy Beacon. Standard Molecular Beacons and Sloppy Beacons differ from TaqMan and Hydrolysis probes in that they are not intended to be degraded or cleaved during amplification. A disadvantage of DNA hybridisation-based technologies such as sloppy beacons and TOCE is that they may produce false positive results due to non-specific hybridisation between probes and non-target nucleic acid sequences.

Many nucleic acid detection assays utilise melt curve analyses to identify the presence of specific target sequences in a given sample. Melt curve analysis protocols entail measuring fluorescence at various temperatures over an incrementally increasing temperature range. The change in slope of this curve is then plotted as a function of temperature to obtain the melt curve. This process is often slow and typically takes anywhere between 30-60 mins to complete. Furthermore, melt curve analyses can require interpretation by skilled personel and/or use of specialised software for results interpretation. Hence, there is a high demand for faster and/or simpler alternatives to melt curve analyses.

A need exists for improved compositions and methods for the simultaneous detection, differentiation, and/or quantification of multiple unrelated amplicons generated by PCR or by alternative target amplification protocols.

SUMMARY OF THE INVENTION

The present invention addresses one or more deficiencies existing in current multiplex detection assays.

Provided herein are methods and compositions which extend the capacity to multiplex during amplification protocols by using oligonucleotide structures referred to herein as LOCS (Loops Connected to Stems). A series of LOCS, labelled with a single fluorophore and quencher pair can be individually discriminated within a single reaction by virtue of the temperature at which the stem portion melts following opening of the LOCS by cleavage or degradation in response to the presence of target. The melting temperature of the stem region thus acts as a surrogate marker for the specific target which opened the LOCS. While other methods incorporating stem-loop structures have exploited the change in fluorescence following either a) hybridization of the loop region to the target amplicons (Molecular Beacons & Sloppy Beacons) which increases the distance between dye pairs, or b) by cleavage allowing physical separation of the dyes (Cleavable Molecular Beacons), the present invention provides improvements over existing multiplex detection assays. These improvements arise, at least in part, through manipulating the melting temperature of the stem portion of stem-loop oligonucleotides by changing the length and/or sequence composition of the stem such that each stem melts at a different temperature.

As described herein, multiple LOCS labelled with the same fluorophore may contain a) different loop sequences which allow direct or indirect detection of multiple targets simultaneously and b) different stem sequences that melt at discreet temperatures and which can be used to identify the specific target(s) present within the multiple targets under investigation. The methods of the present invention provide one or more advantages over art-known methods such as, for example, the TOCE protocol in that separate catcher molecules are not required thus reducing the number of components in the reaction mix and reducing costs. Furthermore, the TOCE method is inherently more complex than the methods of the present invention as it requires the released fragment to initiate and complete a second extension on a synthetic target. Furthermore, in some embodiments, the LOCS probes may be universal (independent of target sequence) and/or may be combined with a range of detection technologies, thus delivering wide applicability in the field of molecular diagnostics. Additionally, the melting temperature used inconventional amplification and detection techniques is based on hybridisation and melting of a probe with a target nucleic acid. This suffers from the disadvantage of increased false-positives due to non-specific hybridisation between pobes and non-target nucleic acid sequences. The methods of the present invention overcome this limitation because the LOCS reporter probes containing universal substrates do not bind with target sequence. Finally, it is well-known known in the art that intramolecular bonds are stronger than intermolecular bonds and thus, the probability of these un-cleaved (closed) LOCS hybrising with non-specific target and producing false-positive signal is significantly lower.

As a result of intramolecular bonds being stronger than intermolecular bonds, a dual labelled LOCS will melt at one temperature when intact (closed) but will melt at a lower temperature following opening of the loop region by target-dependent cleavage or degradation. This property of nucleic acids is exploited in the current invention to extend the capacity of instruments to differentiate multiple targets using a single type of detector such as one fluorescence channel.

The temperature dependent fluorescence signals produced by LOCS reporters of the present invention are well-defined and independent of the target DNA. Thus, it is possible to elucidate information about target DNA from measurements of fluorescence signal generated at selected temperatures, rather than a complete temperature gradient, providing an advantage in reduction of the run time on thermal cycling devices (e.g. PCR devices). By way of non-limiting example, on a Bio-Rad CFX96 PCR system, conducting a traditional melt analysis with settings for the temperature between 20° C. and 90° C. with 0.5° C. increments and 5 seconds hold time requires 141 fluorescence measurement cycles and require approximately 50 minutes of run time. With the use of LOCS probes, the information about target DNA may be obtained from the same device with 2-6 fluorescence measurements and require approximately 2-5 minutes of run time. Without any specific limitation, the reduction of run time can be advantageous in numerous applications including, for example, diagnostics.

LOCS probes of the present invention can also be used to simultaneously detect, differentiate, and/or quantify multiple targets in a single fluorescent channel. In the conventional qPCR, quantification of the target DNA is determined using the cycle quantification (Cq) value from an amplification curve obtained by measuring fluorescence at a single temperature at each amplification cycle. Cq value is proportional to negative logarithmic value of the concentration of the target DNA, and therefore it is possible to ma determine the concentration from the experimentally determined Cq value. However, it is difficult to correctly and specifically quantify each target where there is more than one target-specific probe in a single channel, because it is difficult to identify if the signal originated from a specific probe. Addressing this problem, LOCS enable correct and specific quantification of more than one target in a single channel, provided that the amplification curve is obtained by measuring fluorescence at more than one temperature during amplification. This is possible because different LOCS may produce significantly different amount of fluorescence at different temperatures.

In some embodiments where analysis only requires fluorescent acquisition at a limited number of time points within PCR, for example post-PCR, using LOCS structures eliminates the need for acquisition at each cycle. As such, these embodiments are well suited to very rapid cycling protocols which can reduce the time to result.

As noted above, melt curve analysis protocols entail measuring fluorescence at various temperatures over an incrementally increasing temperature range (e.g. between 30° C. and 90° C.). The change in slope of this curve is then plotted as a function of temperature to obtain the melt curve. This process is often slow and can take, for example, anywhere between 30-60 mins to complete. Increasing the speed of melt curve analysis requires access to highly specialised instrumentation and cannot be accomplished using standard PCR devices. Thus, there is a high demand for faster alternatives to melt curve analysis that can provide simultaneous detection of multiple targets in a single fluorescence channel using standard instrumentation. The melting temperature (Tm) the LOCS structures of the present invention are pre-determined and constant (i.e. unaffected by target sequence or concentration) and therefore do not require ramping through the entire temperature gradient. Each LOCS structure only requires a single fluorescent measurement at its specific Tm, negating the need to run a full temperature gradient, facilitating a faster time to result and therefore overcoming the above limitations.

Furthermore, melt curve analysis typically requires interpretation by skilled personal or use of specialised software for results interpretation.

In some embodiments of the present invention, the use of single temperature fluorescence measurements following completion of PCR eliminates the need for subjective interpretation of melt curves and facilitates objective determination of the presence or absence of targets.

In other embodiments of the present invention, analysis may only require fluorescent acquisition at a limited number of points within PCR, for example post-PCR, which eliminates the need for acquisition at each cycle. As such, these embodiments are well suited to very rapid cycling protocols which can reduce the time to result.

Several methods have been described which involve fluorescence acquisition at multiple temperatures during PCR, including two temperature acquisition to facilitate distinction between fully matched and mismatched probes. Additionally, some protocols use multiple acquisition temperatures after each PCR cycle to quantify the concentration of each target when two targets are present and detected from a single channel. Other methods for simultaneous quantification of two targets are achieved by performing a complete melt curve at the end of each PCR cycle.

LOCS structures of the present invention may be compatible with most and potentially all of these existing methods of analysis.

The present invention relates at least in part to the following embodiments 1-59:

Embodiment 1. A method for determining the presence or absence of first and second targets in a sample, the method comprising:
preparing a reaction mixture by contacting the sample or a derivative thereof putatively comprising the first and/or second targets or amplicons thereof with:
first and second closed stem-loop oligonucleotides, wherein each of the closed stem-loop oligonucleotides comprise a double-stranded stem portion of hybridised nucleotides connected to a closed single-stranded loop portion of unhybridised nucleotides, wherein:
the number of hybridised nucleotides and/or the sequence of hybridised nucleotides in the stem portion of the first and second closed stem-loop oligonucleotide differs, and
each of the double-stranded stem portions comprise a fluorophore molecule connected to one strand and a quencher molecule connected to an opposing strand; and
enzymes capable of cleaving or degrading the single-stranded loop portion of the first and second closed stem-loop oligonucleotides only when in contact with the target or an amplicon thereof;
treating the reaction mixture:
under conditions suitable for the enzymes to induce cleavage or degradation of the loop portion of the first and second closed stem-loop oligonucleotides to thereby produce first and second open stem-loop oligonucleotides;
detecting the presence or absence of said first and second open oligonucleotides by treating the reaction mixture or a derivative thereof at: a first temperature at which strands of the double-stranded stein portion of the first open stein-loop oligonucleotide disassociate to thereby facilitate spatial separation of the fluorophore and quencher molecules of the stem portion of the first open stem-loop oligonucleotide and provide a first detectable signal, and
a second temperature at which strands of the double-stranded stem portion of the second open stem-loop oligonucleotide disassociate to thereby facilitate spatial separation of the fluorophore and quencher molecules of the stem portion of the second open stem-loop oligonucleotide and provide a second detectable signal,
wherein:
the first temperature differs from the second temperature,
the fluorophore of the first open stem-loop oligonucleotide and the fluorophore of the second open stem-loop oligonucleotide emit in the same colour region of the visible spectrum, and
detection of a signal at the first temperature is indicative of the presence of the first target in the sample, and failure to detect a signal at the first temperature is indicative of the absence of the first target in the sample; and
detection of a signal at the second temperature is indicative of the presence of the second target in the sample, and failure to detect a signal at the second temperature is indicative of the absence of the second target in the sample.

Embodiment 2. The method of embodiment 1, wherein the enzymes comprise multi-component nucleic acid enzymes (MNAzymes), and said treating of the reaction mixture comprises treating the reaction mixture under conditions suitable for:

binding of a first multi-component nucleic acid enzyme (MNAzyme) to the first target or amplicon thereof and hybridisation of substrate arms of said first MNAzyme to the loop portion of the first closed stem-loop oligonucleotide, to thereby facilitate said cleavage of the loop portion of the first closed stem-loop oligonucleotide by the first MNAzyme forming the first open stem-loop oligonucleotide.

Embodiment 3. The method of embodiment 2, wherein the target is a nucleic acid sequence or amplicon thereof capable of hybridising to the sensor arms of the first MNAzyme to thereby facilitate assembly of the first MNAzyme.

Embodiment 4. The method of embodiment 1, wherein:
    the target is an analyte, protein, compound or molecule;
    the enzymes comprise enzymes with an aptamer capable of binding to the first target; and
    binding of the first target to the aptamer is capable of rendering the enzymes with an aptamer catalytically active.

Embodiment 5. The method of embodiment 4, wherein the enzymes with an aptamer comprise any one or more of: apta-DNAzymes, apta-ribozymes, apta-MNAzymes.

Embodiment 6. The method of any one of embodiments 2, 4, or 5, wherein:
    the target is an analyte, protein, compound or molecule;
    the reaction mixture further comprises an oligonucleotide sequence capable of hybridising to the sensor arms of the first MNAzyme to thereby facilitate assembly of the first MNAzyme;
    the first MNAzyme comprises an aptamer sequence capable of binding to the first target; and
    binding of the target to the aptamer is capable of rendering the first MNAzyme catalytically active.

Embodiment 7. The method of any one of embodiments 1 to 6, wherein the enzymes comprise restriction endonucleases, and said treating of the reaction mixture comprises:
    treating the reaction mixture under conditions suitable for hybridisation of a first target or amplicon thereof to the loop portion of the first closed stem-loop oligonucleotide to form a double-stranded sequence for a first restriction endonuclease to associate with and thereby facilitate said cleavage of the loop portion of the first closed stem-loop oligonucleotide forming the first open stem-loop oligonucleotide.

Embodiment 8. The method of embodiment 7, wherein the restriction endonuclease is a nicking endonuclease capable of associating with and cleaving a loop strand of said double-stranded sequence for the first restriction endonuclease.

Embodiment 9. The method of any one of embodiments 1 to 8, wherein the enzymes comprise exonuclease activity (e.g. polymerase enzymes, exonucleases), and said treating of the reaction mixture comprises:
    treating the reaction mixture under conditions suitable for:
        hybridisation of a first target or amplicon thereof to the loop portion of the first closed stem-loop oligonucleotide to form a first double-stranded sequence comprising the first target or amplicon thereof,
        hybridisation of a first primer oligonucleotide to the first target or amplicon thereof to form a second double-stranded sequence located upstream (5') relative to the first double-stranded sequence comprising the first target or amplicon thereof association of a first enzyme comprising exonuclease activity with a loop portion of the first closed stem-loop oligonucleotide at or adjacent to a terminus of the first primer oligonucleotide, and
        catalytic activity of the first enzyme comprising exonuclease activity to thereby facilitate degradation of the loop portion of the first double-stranded sequence comprising the first target or amplicon and form the first open stem-loop oligonucleotide.

Embodiment 10. The method of any one of embodiments 1 to 9, wherein the enzymes comprise exonuclease activity, and said treating of the reaction mixture comprises: treating the reaction mixture under conditions suitable for:
    hybridisation of a first target or amplicon thereof to the loop portion of the first closed stem-loop oligonucleotide to form a first double-stranded sequence comprising the first target or amplicon thereof,
    association of a first enzyme comprising exonuclease activity with the first double-stranded sequence comprising the first target or amplicon thereof, and
    catalytic activity of the first enzyme comprising exonuclease activity to thereby facilitate degradation of the loop portion of the first double-stranded sequence comprising the first target or amplicon and form the first open stem-loop oligonucleotide.

Embodiment 11. The method of any one of embodiments 1 to 10, wherein the enzymes comprise DNAzymes and/or ribozymes requiring a first co-factor for catalytic activity, and said treating of the reaction mixture comprises treating the reaction mixture under conditions suitable for:
    binding of a said first cofactor to the DNAzyme and/or binding of a said first cofactor to the ribozyme to render the DNAzyme and/or ribozyme catalytically active,
    hybridisation of DNAzyme and/or ribozyme to the loop portion of a first closed stem-loop oligonucleotide,
    catalytic activity of the DNAzyme and/or ribozyme to thereby facilitate cleavage of the loop portion of the first closed stem-loop oligonucleotide and form the first open stem-loop oligonucleotide.
    wherein:
    the first target is the first co-factor.

Embodiment 12. The method of embodiment 11, wherein the first co-factor is a metal ion (e.g. $Mg^{2+}$, $Mn^{2+}$, $Ca^{2+}$, $Pb^{2+}$).

Embodiment 13. The method of any one of embodiments 1 to 12, wherein said treating further comprises treating the reaction mixture under conditions suitable for any one or more of:
    binding of a second MNAzyme to the second target or amplicon thereof and hybridisation of substrate arms of said second MNAzyme to the loop portion of the second closed stem-loop oligonucleotide, to thereby facilitate said cleavage of the loop portion of the second closed stem-loop oligonucleotide by the second MNAzyme forming the second open stem-loop oligonucleotide;
    hybridisation of a second target or amplicon thereof to the loop portion of the second closed stem-loop oligonucleotide to form a double-stranded sequence for a second restriction endonuclease to associate with the double-stranded sequence and thereby facilitate said cleavage of the loop portion of the second closed stem-loop oligonucleotide forming the second open stem-loop oligonucleotide;
    hybridisation of a second target or amplicon thereof to the loop portion of the second closed stein-loop oligonucleotide to form a second double-stranded sequence comprising the second target or amplicon thereof, hybridisation of a second primer oligonucleotide to the second target or amplicon thereof to form a second double-stranded sequence located upstream (5') relative to the second double-stranded sequence comprising the second target or amplicon thereof, association of a second enzyme comprising exonuclease activity with a loop portion of the second closed stem-loop oligonucleotide at or adjacent to a terminus of the second primer oligonucleotide, and catalytic activity of the second enzyme comprising exonuclease activity to thereby facilitate degradation of the loop portion of the second double-stranded sequence comprising the second target or amplicon and form the second open stem-loop oligonucleotide;

hybridisation of a second target or amplicon thereof to the loop portion of the second closed stem-loop oligonucleotide to form a second double-stranded sequence comprising the second target or amplicon thereof, association of a second enzyme comprising exonuclease activity with the second double-stranded sequence comprising the second target or amplicon thereof, and catalytic activity of the second enzyme comprising exonuclease activity to thereby facilitate degradation of the loop portion of the second double-stranded sequence comprising the second target or amplicon and form the second open stem-loop oligonucleotide;

binding of a second cofactor to a DNAzyme and/or binding of a second cofactor to a ribozyme to render the DNAzyme and/or ribozyme catalytically active, hybridisation of DNAzyme and/or ribozyme to the loop portion of a second closed stem-loop oligonucleotide, catalytic activity of the DNAzyme and/or ribozyme to thereby facilitate cleavage of the loop portion of the second closed stem-loop oligonucleotide and form the second open stem-loop oligonucleotide.

wherein:

the second target is the second co-factor.

Embodiment 14. The method of embodiment 13, wherein the second co-factor is a metal ion (e.g. $Mg^{2+}$, $Mn^{2+}$, $Ca^{2+}$, $Pb^{2+}$).

Embodiment 15. The method of embodiment 13, wherein the second restriction endonuclease is a nicking endonuclease capable of associating with and cleaving a loop strand of said double-stranded sequence comprising the second target or amplicon thereof.

Embodiment 16. The method of embodiment 15, wherein the first and second restriction endonucleases are a different type of restriction endonuclease.

Embodiment 17. The method of embodiment 15, wherein the first and second restriction endonucleases are the same type of restriction endonuclease.

Embodiment 18. The method of embodiment 13, wherein the second target is a nucleic acid sequence or amplicon thereof capable of hybridising to the sensor arms of the second MNAzyme to thereby facilitate assembly of the second MNAzyme.

Embodiment 19. The method of embodiment 13, wherein:
the second target is an analyte, protein, compound or molecule;
the enzymes comprise enzymes with an aptamer capable of binding to the second target; and
binding of the second target to the aptamer is capable of rendering the enzymes with an aptamer catalytically active.

Embodiment 20. The method of embodiment 19, wherein the enzymes with an aptamer comprise any one or more of: apta-DNAzymes, apta-ribozymes, apta-MNAzymes.

Embodiment 21. The method of embodiment 13, 19 or 20, wherein:
the second target is an analyte, protein, compound or molecule;
the reaction mixture further comprises an oligonucleotide sequence capable of hybridising to the sensor arms of the second MNAzyme to thereby facilitate assembly of the second MNAzyme:
the second MNAzyme comprises an aptamer sequence capable of binding to the second target; and
binding of the second target to the aptamer sequence of the second MNAzyme is capable of rendering the second MNAzyme catalytically active by facilitating removal of an inhibitory molecule bound to the aptamer of the second MNAzyme.

Embodiment 22. The method of any one of embodiments 1 to 21 wherein the fluorophore of the first closed and open stem-loop oligonucleotides is the same as the fluorophore of the second closed and open stem-loop oligonucleotides.

Embodiment 23. The method of any one of embodiments 13 to 22, wherein:
the reaction mixture comprises said first and second MNAzymes; and
the sequence of the loop portion of the first closed stem-loop oligonucleotide capable of hybridising to the substrate arms of the first MNAzyme is different from the sequence of the loop portion of the second closed stem-loop oligonucleotide capable of hybridising to the substrate arms of the second MNAzyme.

Embodiment 24. The method of any one of embodiments 1 to 23, wherein the fluorophore of the first closed and open stem-loop oligonucleotides and the fluorophore of the second closed and open stem-loop oligonucleotides are detectable in a single fluorescence emission channel of a device.

Embodiment 25. The method of any one of embodiments 1 to 24, further comprising determining the presence or absence of a third target or amplicon thereof in a sample by:
contacting the reaction mixture comprising the sample or a derivative thereof with:
a third closed stem-loop oligonucleotide, wherein the third closed stem-loop oligonucleotide comprises a double-stranded stem portion of hybridised nucleotides connected to a closed single-stranded loop portion of unhybridised nucleotides, wherein:
the number of hybridised nucleotides and/or the sequence of hybridised nucleotides in the stem portion of the third closed stem-loop oligonucleotide differs from that of the stem portions of the first and second closed stem-loop oligonucleotide;
the double-stranded stem portion comprises a fluorophore molecule connected to one strand and a quencher molecule connected to an opposing strand; and
enzymes capable of cleaving or degrading the single-stranded loop portion of the third closed stem-loop oligonucleotide only when in contact with the target or amplicon thereof:
treating the reaction mixture under conditions suitable for the enzymes to induce cleavage or degradation of the loop portion of the third closed stem-loop oligonucleotide to thereby produce a third open stem-loop oligonucleotide:
detecting the presence or absence of the third oligonucleotide by treating the reaction mixture or a derivative thereof at:

a third temperature at which strands of the double-stranded stem portion of the third open stem-loop oligonucleotide disassociate to thereby facilitate spatial separation of the fluorophore and quencher molecules of the stem portion of the third open stem-loop oligonucleotide and provide a third detectable signal,
wherein:
the third temperature differs from the first and second temperatures, and
detection of a signal at the third temperature is indicative of the presence of the third target in the sample, and failure to detect a signal at the third temperature is indicative of the absence of the third target in the sample.

Embodiment 26. The method of any one of embodiments 1 to 24, further comprising determining the presence or absence of a third target or amplicon thereof in a sample by:
contacting the reaction mixture comprising the sample or a derivative thereof with:
a third closed stem-loop oligonucleotide, wherein the third closed stem-loop oligonucleotide comprises a double-stranded stem portion of hybridised nucleotides connected to a closed single-stranded loop portion of unhybridised nucleotides, wherein:
the number of hybridised nucleotides and/or the sequence of hybridised nucleotides in the stem portion of the third closed stem-loop oligonucleotide is the same as that of the stem portions of the first or second closed stem-loop oligonucleotide;
the double-stranded stem portion comprises a fluorophore molecule connected to one strand and a quencher molecule connected to an opposing strand, wherein the fluorophore molecule connected to the third open stem-loop oligonucleotide emits in a different colour region of the visible spectrum than the fluorophore of the first and/or second closed stem-loop oligonucleotides; and
enzymes capable of cleaving or degrading the single-stranded loop portion of the third closed stem-loop oligonucleotide only when in contact with the target or amplicon thereof;
treating the reaction mixture under conditions suitable for the enzymes to induce cleavage or degradation of the loop portion of the third closed stem-loop oligonucleotide to thereby produce a third open stem-loop oligonucleotide;
detecting the presence or absence of the third oligonucleotide by treating the reaction mixture or a derivative thereof at:
a third temperature at which strands of the double-stranded stem portion of the third open stem-loop oligonucleotide disassociate to thereby facilitate spatial separation of the fluorophore and quencher molecules of the stem portion of the third open stem-loop oligonucleotide and provide a third detectable signal,
wherein:
detection of a signal at the third temperature is indicative of the presence of the third target in the sample, and failure to detect a signal at the third temperature is indicative of the absence of the third target in the sample.

Embodiment 27. The method of embodiment 26, wherein the third temperature differs from the first and/or second temperatures.

Embodiment 28. The method of any one of embodiments 25 to 27, wherein the method comprises treating the reaction mixture under conditions suitable for any one or more of:
binding of a third MNAzyme to the third target or amplicon thereof and hybridisation of substrate arms of said third MNAzyme to the loop portion of the third closed stem-loop oligonucleotide, to thereby facilitate said cleavage of the loop portion of the third closed stem-loop oligonucleotide by the third MNAzyme forming the third open stem-loop oligonucleotide;
hybridisation of the third target or amplicon thereof to the loop portion of the third closed stem-loop oligonucleotide to form a double-stranded sequence for a third restriction endonuclease to associate with the double-stranded sequence and thereby facilitate said cleavage of the loop portion of the third closed stem-loop oligonucleotide forming the third open stem-loop oligonucleotide;
hybridisation of a third target or amplicon thereof to the loop portion of the third closed stem-loop oligonucleotide to form a third double-stranded sequence comprising the third target or amplicon thereof,
hybridisation of a third primer oligonucleotide to the third target or amplicon thereof to form a third double-stranded sequence located upstream (5') relative to the third double-stranded sequence comprising the third target or amplicon thereof, association of a third enzyme comprising exonuclease activity with a loop portion of the third closed stem-loop oligonucleotide at or adjacent to a terminus of the third primer oligonucleotide, and
catalytic activity of the third enzyme comprising exonuclease activity to thereby facilitate degradation of the loop portion of the third double-stranded sequence comprising the third target or amplicon and form the third open stem-loop oligonucleotide;
hybridisation of a third target or amplicon thereof to the loop portion of the third closed stem-loop oligonucleotide to form a third double-stranded sequence comprising the third target or amplicon thereof,
association of a third enzyme comprising exonuclease activity with the third double-stranded sequence comprising the third target or amplicon thereof, and
catalytic activity of the third enzyme comprising exonuclease activity to thereby facilitate degradation of the loop portion of the third double-stranded sequence comprising the third target or amplicon and form the third open stem-loop oligonucleotide;
binding of a third cofactor to a DNAzyme and/or binding of a third cofactor to a ribozyme to render the DNAzyme and/or ribozyme catalytically active,
hybridisation of DNAzyme and/or ribozyme to the loop portion of a third closed stem-loop oligonucleotide,
catalytic activity of the DNAzyme and/or ribozyme to thereby facilitate cleavage of the loop portion of the third closed stem-loop oligonucleotide and form the third open stem-loop oligonucleotide.
wherein:
the third target is the third co-factor.

Embodiment 29. The method of embodiment 28, wherein the co-factor is a metal ion (e.g. $Mg^{2+}$, $Mn^{2+}$, $Ca^{2+}$, $Pb^{2+}$).

Embodiment 30. The method of embodiment 28, wherein the restriction endonuclease is a nicking endonuclease capable of associating with and cleaving a loop strand of said double-stranded sequence comprising the third target or amplicon thereof.

Embodiment 31. The method of embodiment 28, wherein the third target is a nucleic acid sequence or amplicon thereof capable of hybridising to the sensor arms of the third MNAzyme to thereby facilitate assembly of the third MNAzyme.

Embodiment 32. The method of embodiment 28, wherein:
the target is an analyte, protein, compound or molecule;
the enzymes comprise enzymes with an aptamer capable of binding to the third target; and
binding of the third target to the aptamer is capable of rendering the enzymes with an aptamer catalytically active Embodiment 33. The method of embodiment 32, wherein the enzymes with an aptamer comprise any one or more of: apta-DNAzymes, apta-ribozymes, apta-MNAzymes.

Embodiment 34. The method of embodiment 28, wherein:
the third target is an analyte, protein, compound or molecule;
the reaction mixture further comprises an oligonucleotide sequence capable of hybridising to the sensor arms of the third MNAzyme to thereby facilitate assembly of the third MNAzyme;
the third MNAzyme comprises an aptamer sequence capable of binding to the third target; and
binding of the third target to the aptamer sequence of the third MNAzyme is capable of rendering the third MNAzyme catalytically active by facilitating removal of an inhibitory molecule bound to the aptamer of the third MNAzyme.

Embodiment 35. The method of any one of embodiments 28, or 30 to 34, wherein:
the reaction mixture comprises said third MNAzyme and either of both of said first and second MNAzymes; and
the sequence of the loop portion of the third closed stein-loop oligonucleotide capable of hybridising to the substrate arms of the third MNAzyme is different from:
the sequence of the loop portion of the first closed stem-loop oligonucleotide capable of hybridising to the substrate arms of the first MNAzyme, and/or
the sequence of the loop portion of the second closed stem-loop oligonucleotide capable of hybridising to the substrate arms of the first MNAzyme.

Embodiment 36. The method of any one of embodiments 25 or embodiments 28 to 35, wherein:
the number of hybridised nucleotides and/or the sequence of hybridised nucleotides in the stem portion of the third closed stem-loop oligonucleotide differs from that of the stem portions of the first and second closed stem-loop oligonucleotides;
the third temperature differs from the first and second temperatures; and
the fluorophore of the third closed and open stem-loop oligonucleotides emits in the same colour region of the visible spectrum as the fluorophores of the first and second closed and open stem-loop oligonucleotides.

Embodiment 37. The method of any one of embodiments 25 or embodiments 28 to 36, wherein the fluorophore of the third closed and open stem-loop oligonucleotides is the same as the fluorophore of the first and/or second closed and open stem-loop oligonucleotides.

Embodiment 38. The method of embodiment 37, wherein the fluorophore of the third closed and open stem-loop oligonucleotides and the fluorophore of the first closed and open stem-loop oligonucleotides and/or the fluorophore of the second closed and open oligonucleotides are detectable using the same emission channel of a device.

Embodiment 39. The method of any one of embodiments 25 to 35 or 36, wherein:
the fluorophore of the first closed and open stein-loop oligonucleotides emits in the same colour region of the visible spectrum as the fluorophore of the second closed and open stem-loop oligonucleotides; and
the fluorophore of the third closed and open stem-loop oligonucleotides emits in a different colour region of the visible spectrum than the fluorophore of the first and second closed and open stem-loop oligonucleotides.

Embodiment 40. The method of any one of embodiments 25 to 39, wherein the third temperature differs from the first temperature and/or the second temperature by more than: 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 25° C., 30° C., 35° C., 40° C., 45° C., 50° C., 55° C., 60° C., 65° C., 70° C., 75° C., 80° C.

Embodiment 41. The method of any one of embodiments 1 to 40, wherein a melt curve analysis is used to for any said detection of a signal or any said failure to detect a signal.

Embodiment 42. The method of any one of embodiments 1 to 41, wherein the first temperature differs from the second temperature by more than: 1° C., 2° C., 3° C., 4° C., 5° C. 6° C., 7° C., 8° C., 9° C., 10° C., 11° C., 12° C., 13° C., 14° C., 15° C., 16° C., 17° C., 18° C., 19° C., 20° C., 25° C., 30° C., 35° C., 40° C., 45° C., 50° C., 55° C., 60° C., 65° C., 70° C., 75° C., 80° C.

Embodiment 43. The method of any one of embodiments 1 to 42, wherein any said amplicon thereof is produced by any one of more of polymerase chain reaction (PCR), strand displacement amplification (SDA), helicase dependent amplification (HDA), Recombinase Polymerase Amplification (RPA), loop-mediated isothermal amplification (LAMP), rolling circle amplification (RCA), transcription-mediated amplification (TMA), self-sustained sequence replication (3SR), nucleic acid sequence based amplification (NASBA), and/or reverse transcription polymerase chain reaction (RT-PCR).

Embodiment 44. The method of any one of embodiments 1 to 43, wherein the sample is a biological sample obtained from a subject.

Embodiment 45. The method of any one of embodiments 1 to 43, wherein the method is performed in vitro.

Embodiment 46. The method of any one of embodiments 1 to 43, wherein the method is performed ex vivo.

Embodiment 47. A composition comprising:
first and second closed stem-loop oligonucleotides, wherein each of the closed stem-loop oligonucleotides comprise a double-stranded stem portion of hybridised nucleotides connected to a single-stranded loop portion of unhybridised nucleotides, wherein:
the number of hybridised nucleotides and/or the sequence of hybridised nucleotides in the stem portion of the first and second closed stem-loop oligonucleotide differs, and
each of the double-stranded stem portions comprise a fluorophore molecule connected to one strand and a quencher molecule connected to an opposing strand,
wherein the fluorophore molecules emit in the same colour region of the visible spectrum, and the melting temperature (Tm) of the double-stranded stem portion of the first closed stein-loop oligonucleotide differs from the Tm of the double-stranded stem portion of the second closed stem-loop oligonucleotide.

Embodiment 48. The composition of embodiment 47, wherein the single-stranded loop portion of the first closed stem-loop oligonucleotide differs from the sequence of the single-stranded loop portion of the second closed stem-loop oligonucleotide.

Embodiment 49. The composition of embodiment 47 or embodiment 48, further comprising:
  a first MNAzyme comprising substrate arms capable of hybridising to the closed single-stranded loop portion of the first closed stem-loop oligonucleotide; and
  a second MNAzyme comprising substrate arms capable of hybridising to the single-stranded loop portion of the second closed stem-loop oligonucleotide.

Embodiment 50. The composition of embodiment 49, wherein:
  the substrate arms of the first MNAzyme are hybridised to the single-stranded loop portion of the first closed stem-loop oligonucleotide; and
  the substrate arms of the second MNAzyme are hybridised to the single-stranded loop portion of the second closed stem-loop oligonucleotide.

Embodiment 51. The composition of embodiment 50, wherein:
  the first and/or second MNAzymes comprise an aptamer sequence bound to a target analyte, protein, compound or molecule and sensor arms hybridised to an oligonucleotide sequence; and
  the first MNAzyme is designed to detect a different target than the second MNAzyme.

Embodiment 52. The composition of embodiment 50, wherein:
  the first and/or second MNAzymes comprise sensor arms hybridised to a target sequence, and the first MNAzyme is designed to detect a different target than the second MNAzyme.

Embodiment 53. The composition of any one of embodiments 47 to 52, further comprising:
  a first oligonucleotide sequence hybridised to said single-stranded loop portion of the first closed stem-loop oligonucleotide that differs from the sequence of the single-stranded loop portion of the second closed stem-loop oligonucleotide, thereby forming a double stranded sequence comprising said first oligonucleotide;
  a second oligonucleotide sequence hybridised to said single-stranded loop portion of the second closed stem-loop oligonucleotide that differs from the sequence of the single-stranded loop portion of the first closed stem-loop oligonucleotide, thereby forming a double stranded sequence comprising said second oligonucleotide;
  a restriction endonuclease associated with and capable of cleaving the double stranded sequence comprising said first oligonucleotide; and/or
  a restriction endonuclease associated with and capable of cleaving the double stranded sequence comprising said second oligonucleotide.

Embodiment 54. The composition of any one of embodiments 47 to 53, further comprising:
  a first double-stranded sequence comprising a first target oligonucleotide sequence hybridised to said single-stranded loop portion of the first closed stem-loop oligonucleotide that differs from the sequence of the single-stranded loop portion of the second closed stem-loop oligonucleotide, thereby forming a first double stranded sequence comprising said first target oligonucleotide;
  a second double-stranded sequence comprising a second target oligonucleotide sequence hybridised to said single-stranded loop portion of the second closed stem-loop oligonucleotide that differs from the sequence of the single-stranded loop portion of the first closed stem-loop oligonucleotide, thereby forming a double stranded sequence comprising said second target oligonucleotide;
  a first primer oligonucleotide hybridised to the first target oligonucleotide upstream (5') relative to said first double-stranded sequence and a first enzyme comprising exonuclease activity (e.g. a polymerase, an exonuclease) associated with a loop portion of the first closed stem-loop oligonucleotide at or adjacent to a terminus of the first primer oligonucleotide; and/or
  a second primer oligonucleotide hybridised to the second target oligonucleotide upstream (5') relative to said second double-stranded sequence second and a second enzyme comprising exonuclease activity (e.g. a polymerase, an exonuclease) associated with a loop portion of the second closed stem-loop oligonucleotide at or adjacent to a terminus of the second primer oligonucleotide Embodiment 55. The composition of any one of embodiments 47 to 54, further comprising:
  a first double-stranded sequence comprising a first target oligonucleotide sequence hybridised to said single-stranded loop portion of the closed first stem-loop oligonucleotide that differs from the sequence of the single-stranded loop portion of the second closed stem-loop oligonucleotide, thereby forming a first double-stranded sequence comprising said first target oligonucleotide;
  a second double-stranded sequence comprising a second target oligonucleotide sequence hybridised to said single-stranded loop portion of the second closed stem-loop oligonucleotide that differs from the sequence of the single-stranded loop portion of the first closed stem-loop oligonucleotide, thereby forming a second double stranded sequence comprising said second target oligonucleotide;
  wherein a first enzyme comprising exonuclease activity is associated with the first double-stranded sequence and a second enzyme comprising exonuclease activity is associated with the second double-stranded sequence.

Embodiment 56. The composition of any one of embodiments 47 to 55, further comprising:
  a first DNAzyme and/or a first ribozyme hybridised to a loop portion of the first closed stein-loop oligonucleotide that differs from the sequence of the single-stranded loop portion of the second closed stem-loop oligonucleotide,
  a second DNAzyme and/or a second ribozyme hybridised to a loop portion of the second closed stem-loop oligonucleotide that differs from the sequence of the single-stranded loop portion of the first closed stem-loop oligonucleotide,
  cofactors for each said DNAzyme capable of rendering each said DNAzyme catalytically active, and thus induce cleavage activity of any said DNAzyme hybridised to the loop portion,
  cofactors for each said ribozyme capable of rendering each said ribozyme catalytically active, and thus induce cleavage activity of any said ribozyme hybridised to the loop portion.

Embodiment 57. The composition of any one of embodiments 47 to 56, further comprising:
  third closed stem-loop oligonucleotides, wherein the third closed stem-loop oligonucleotides comprise a double-stranded stem portion of hybridised nucleotides connected to a single-stranded loop portion of unhybridised nucleotides, wherein:
the number of hybridised nucleotides and/or the sequence of hybridised nucleotides in the stem portion of the third closed stem-loop oligonucleotides differs from those of the first and second closed stem-loop oligonucleotides, and
the double-stranded stem portion of the third closed stem-loop oligonucleotides comprises a fluorophore molecule connected to one strand and a quencher molecule connected to an opposing strand, wherein the fluorophore molecule of the third closed stem-loop oligonucleotide emits in a different colour region of the visible spectrum compared to the fluorophore molecules of the first and second closed stem-loop oligonucleotides.

Embodiment 58. The composition of any one of embodiments 47 to 56, further comprising:
third closed stem-loop oligonucleotides, wherein the third closed stem-loop oligonucleotides comprise a double-stranded stem portion of hybridised nucleotides connected to a single-stranded loop portion of unhybridised nucleotides, wherein:
the number of hybridised nucleotides and/or the sequence of hybridised nucleotides in the stem portion of the third closed stem-loop oligonucleotides differs from those of the first and second closed stem-loop oligonucleotides, and
the double-stranded stem portion of the third closed stem-loop oligonucleotides comprises a fluorophore molecule connected to one strand and a quencher molecule connected to an opposing strand, wherein the fluorophore molecule of the third closed stem-loop oligonucleotide emits in a same colour region of the visible spectrum compared to the fluorophore molecules of the first and second closed stem-loop oligonucleotides.

Embodiment 59. The composition of any one of embodiments 47 to 56, further comprising:
third closed stein-loop oligonucleotides, wherein the third closed stem-loop oligonucleotides comprise a double-stranded stem portion of hybridised nucleotides connected to a single-stranded loop portion of unhybridised nucleotides, wherein:
the number of hybridised nucleotides and/or the sequence of hybridised nucleotides in the stem portion of the third closed stem-loop oligonucleotides is the same those of the first or second closed stem-loop oligonucleotides, and
the double-stranded stem portion of the third closed stem-loop oligonucleotides comprises a fluorophore molecule connected to one strand and a quencher molecule connected to an opposing strand, wherein the fluorophore molecule of the third closed stem-loop oligonucleotide emits in a different colour region of the visible spectrum compared to the fluorophore molecules of the first and second closed stem-loop oligonucleotides.

The present invention also relates to embodiments 1-81 listed below:

Embodiment 1. A method for determining the presence or absence of first and second targets in a sample, the method comprising:
(a) preparing a reaction mixture by contacting the sample or a derivative thereof putatively comprising the first and/or second targets or amplicons thereof with:
first and second closed stem-loop oligonucleotides, wherein each of the closed stem-loop oligonucleotides comprise a double-stranded stem portion of hybridised nucleotides connected to a closed single-stranded loop portion of unhybridised nucleotides, wherein:
the number of hybridised nucleotides and/or the sequence of hybridised nucleotides in the stem portion of the first and second closed stem-loop oligonucleotide differs, and
enzymes capable of cleaving or degrading the single-stranded loop portion of the first and second closed stem-loop oligonucleotides only when in contact with the target or an amplicon thereof;
(b) treating the reaction mixture:
under conditions suitable for the enzymes to induce cleavage or degradation of the loop portion of the first and second closed stem-loop oligonucleotides to thereby produce first and second open stem-loop oligonucleotides:
at a first temperature at or above which strands of the double-stranded stem portion of the first open stem-loop oligonucleotide disassociate to thereby facilitate spatial separation of the fluorophore and quencher molecules of the stem portion of the first open stem-loop oligonucleotide and provide a first detectable fluorescent signal, and
at a second temperature at or above which strands of the double-stranded stem portion of the second open stem-loop oligonucleotide disassociate to thereby facilitate spatial separation of the fluorophore and quencher molecules of the stem portion of the second open stem-loop oligonucleotide and provide a second detectable fluorescent signal;
wherein:
the first temperature is lower than the second temperature, and
the fluorophore of the first open stem-loop oligonucleotide and the fluorophore of the second open stem-loop oligonucleotide emit in the same colour region of the visible spectrum; and
(c) detecting levels of said first and second fluorescent signals at one or more temperatures comprising or consisting of a temperature equal to or above the second temperature, to thereby determine the presence or absence of said targets in the sample.

Embodiment 2. The method of embodiment 1, wherein the enzymes comprise multi-component nucleic acid enzymes (MNAzymes), and said treating of the reaction mixture comprises treating the reaction mixture under conditions suitable for:
binding of a first multi-component nucleic acid enzyme (MNAzyme) to the first target or amplicon thereof and hybridisation of substrate arms of said first MNAzyme to the loop portion of the first closed stem-loop oligonucleotide, to thereby facilitate said cleavage of the loop portion of the first closed stem-loop oligonucleotide by the first MNAzyme forming the first open stem-loop oligonucleotide.

Embodiment 3. The method of embodiment 2, wherein the first target is a nucleic acid sequence or amplicon thereof capable of hybridising to the sensor arms of the first MNAzyme to thereby facilitate assembly of the first MNAzyme.

Embodiment 4. The method of embodiment 1, wherein:
the first target is an analyte, protein, compound or molecule;

the enzymes comprise enzymes with an aptamer capable of binding to the first target; and binding of the first target to the aptamer is capable of rendering the enzymes with an aptamer catalytically active.

Embodiment 5. The method of embodiment 4, wherein the enzymes with an aptamer comprise any one or more of: apta-DNAzymes, apta-ribozymes, apta-MNAzymes.

Embodiment 6. The method of any one of embodiments 2, 4, or 5, wherein:

the first target is an analyte, protein, compound or molecule;

the reaction mixture further comprises an oligonucleotide sequence capable of hybridising to the sensor arms of the first MNAzyme to thereby facilitate assembly of the first MNAzyme;

the first MNAzyme comprises an aptamer sequence capable of binding to the first target; and binding of the target to the aptamer is capable of rendering the first MNAzyme catalytically active.

Embodiment 7. The method of any one of embodiments 1 to 6, wherein said closed stem-loop oligonucleotides are not hybridised to said target or amplicon thereof during said cleavage or degradation by the enzymes.

Embodiment 8. The method of any one of embodiments 1 to 6, wherein the enzymes comprise restriction endonucleases, and said treating of the reaction mixture comprises:

treating the reaction mixture under conditions suitable for hybridisation of a first target or amplicon thereof to the loop portion of the first closed stem-loop oligonucleotide to form a double-stranded sequence for a first restriction endonuclease to associate with and thereby facilitate said cleavage of the loop portion of the first closed stem-loop oligonucleotide forming the first open stem-loop oligonucleotide.

Embodiment 9. The method of embodiment 8, wherein the restriction endonuclease is a nicking endonuclease capable of associating with and cleaving a loop strand of said double-stranded sequence for the first restriction endonuclease.

Embodiment 10. The method of any one of embodiments 1 to 6, wherein the enzymes comprise exonuclease activity (e.g. polymerase enzymes, exonucleases), and said treating of the reaction mixture comprises:

treating the reaction mixture under conditions suitable for:
hybridisation of a first target or amplicon thereof to the loop portion of the first closed stem-loop oligonucleotide to form a first double-stranded sequence comprising the first target or amplicon thereof, hybridisation of a first primer oligonucleotide to the first target or amplicon thereof to form a second double-stranded sequence located upstream (5') relative to the first double-stranded sequence comprising the first target or amplicon thereof association of a first enzyme comprising exonuclease activity with a loop portion of the first closed stem-loop oligonucleotide at or adjacent to a terminus of the first primer oligonucleotide, and catalytic activity of the first enzyme comprising exonuclease activity to thereby facilitate degradation of the loop portion of the first double-stranded sequence comprising the first target or amplicon and form the first open stem-loop oligonucleotide.

Embodiment 11. The method of any one of embodiments 1 to 6, wherein the enzymes comprise exonuclease activity, and said treating of the reaction mixture comprises:

treating the reaction mixture under conditions suitable for:
hybridisation of a first target or amplicon thereof to the loop portion of the first closed stem-loop oligonucleotide to form a first double-stranded sequence comprising the first target or amplicon thereof, association of a first enzyme comprising exonuclease activity with the first double-stranded sequence comprising the first target or amplicon thereof, and catalytic activity of the first enzyme comprising exonuclease activity to thereby facilitate degradation of the loop portion of the first double-stranded sequence comprising the first target or amplicon and form the first open stem-loop oligonucleotide.

Embodiment 12. The method of any one of embodiments 1 to 11, wherein the enzymes comprise DNAzymes and/or ribozymes requiring a first co-factor for catalytic activity, and said treating of the reaction mixture comprises treating the reaction mixture under conditions suitable for:

binding of a said first cofactor to the DNAzyme and/or binding of a said first cofactor to the ribozyme to render the DNAzyme and/or ribozyme catalytically active, hybridisation of DNAzyme and/or ribozyme to the loop portion of a first closed stem-loop oligonucleotide, catalytic activity of the DNAzyme and/or ribozyme to thereby facilitate cleavage of the loop portion of the first closed stem-loop oligonucleotide and form the first open stem-loop oligonucleotide.

wherein:
the first target is the first co-factor.

Embodiment 13. The method of embodiment 12, wherein the first co-factor is a metal ion (e.g. $Mg^{2+}$, $Mn^{2+}$, $Ca^{2+}$. $Pb^{2+}$).

Embodiment 14. The method of any one of embodiments 1 to 13, wherein said treating further comprises treating the reaction mixture under conditions suitable for any one or more of:

binding of a second MNAzyme to the second target or amplicon thereof and hybridisation of substrate arms of said second MNAzyme to the loop portion of the second closed stem-loop oligonucleotide, to thereby facilitate said cleavage of the loop portion of the second closed stem-loop oligonucleotide by the second MNAzyme forming the second open stem-loop oligonucleotide;

hybridisation of a second target or amplicon thereof to the loop portion of the second closed stem-loop oligonucleotide to form a double-stranded sequence for a second restriction endonuclease to associate with the double-stranded sequence and thereby facilitate said cleavage of the loop portion of the second closed stem-loop oligonucleotide forming the second open stem-loop oligonucleotide;

hybridisation of a second target or amplicon thereof to the loop portion of the second closed stem-loop oligonucleotide to form a second double-stranded sequence comprising the second target or amplicon thereof, hybridisation of a second primer oligonucleotide to the second target or amplicon thereof to form a second double-stranded sequence located upstream (5') relative to the second double-stranded sequence comprising the second target or amplicon thereof, association of a second enzyme comprising exonuclease activity with a loop portion of the second closed stem-loop oligonucleotide at or adjacent to a terminus of the second primer oligonucleotide, and catalytic activity of the second enzyme comprising exonuclease activity to thereby facilitate degradation of the loop portion of the second double-stranded sequence comprising the second target or amplicon and form the second open stem-loop oligonucleotide;

hybridisation of a second target or amplicon thereof to the loop portion of the second closed stem-loop oligonucleotide to form a second double-stranded sequence comprising the second target or amplicon thereof, association of a second enzyme comprising exonuclease activity with the second double-stranded sequence comprising the second target or amplicon thereof, and catalytic activity of the second enzyme comprising exonuclease activity to thereby facilitate degradation of the loop portion of the second double-stranded sequence comprising the second target or amplicon and form the second open stem-loop oligonucleotide;

binding of a second cofactor to a DNAzyme and/or binding of a second cofactor to a ribozyme to render the DNAzyme and/or ribozyme catalytically active, hybridisation of DNAzyme and/or ribozyme to the loop portion of a second closed stem-loop oligonucleotide, catalytic activity of the DNAzyme and/or ribozyme to thereby facilitate cleavage of the loop portion of the second closed stem-loop oligonucleotide and form the second open stein-loop oligonucleotide.

wherein:

the second target is the second co-factor.

Embodiment 15. The method of embodiment 14, wherein the second co-factor is a metal ion (e.g. $Mg^{2+}$, $Mn^{2+}$, $Ca^{2+}$, $Pb^{2+}$).

Embodiment 16. The method of embodiment 14, wherein the second restriction endonuclease is a nicking endonuclease capable of associating with and cleaving a loop strand of said double-stranded sequence comprising the second target or amplicon thereof.

Embodiment 17. The method of embodiment 16, wherein the first and second restriction endonucleases are a different type of restriction endonuclease.

Embodiment 18. The method of embodiment 16, wherein the first and second restriction endonucleases are the same type of restriction endonuclease.

Embodiment 19. The method of embodiment 14, wherein the second target is a nucleic acid sequence or amplicon thereof capable of hybridising to the sensor arms of the second MNAzyme to thereby facilitate assembly of the second MNAzyme.

Embodiment 20. The method of embodiment 14, wherein:

the second target is an analyte, protein, compound or molecule;

the enzymes comprise enzymes with an aptamer capable of binding to the second target; and binding of the second target to the aptamer is capable of rendering the enzymes with an aptamer catalytically active.

Embodiment 21. The method of embodiment 20, wherein the enzymes with an aptamer comprise any one or more of: apta-DNAzymes, apta-ribozymes, apta-MNAzymes.

Embodiment 22. The method of embodiment 14, 20 or 21, wherein:

the second target is an analyte, protein, compound or molecule;

the reaction mixture further comprises an oligonucleotide sequence capable of hybridising to the sensor arms of the second MNAzyme to thereby facilitate assembly of the second MNAzyme;

the second MNAzyme comprises an aptamer sequence capable of binding to the second target; and binding of the second target to the aptamer sequence of the second MNAzyme is capable of rendering the second MNAzyme catalytically active by facilitating removal of an inhibitory molecule bound to the aptamer of the second MNAzyme.

Embodiment 23. The method of any one of embodiments 1 to 22 wherein the fluorophore of the first closed and open stem-loop oligonucleotides is the same as the fluorophore of the second closed and open stem-loop oligonucleotides.

Embodiment 24. The method of any one of embodiments 14 to 23, wherein:

the reaction mixture comprises said first and second MNAzymes; and the sequence of the loop portion of the first closed stem-loop oligonucleotide capable of hybridising to the substrate arms of the first MNAzyme is different from the sequence of the loop portion of the second closed stem-loop oligonucleotide capable of hybridising to the substrate arms of the second MNAzyme.

Embodiment 25. The method of any one of embodiments 1 to 24, wherein the fluorophore of the first closed and open stem-loop oligonucleotides and the fluorophore of the second closed and open stem-loop oligonucleotides are detectable in a single fluorescence emission channel of a device.

Embodiment 26. The method of any one of embodiments 1 to 25, wherein said enzymes do not induce cleavage or degradation of any said target or amplicon thereof.

Embodiment 27. The method of any one of embodiments 1 to 26, wherein the first and second closed stem-loop oligonucleotides each consist of said double-stranded stem portion and said single-stranded loop portion.

Embodiment 28. The method of any one of embodiments 1 to 27, further comprising determining the presence or absence of a third target or amplicon thereof in a sample by:

(d) contacting the reaction mixture comprising the sample or a derivative thereof with:

a third closed stem-loop oligonucleotide, wherein the third closed stem-loop oligonucleotide comprises a double-stranded stem portion of hybridised nucleotides connected to a closed single-stranded loop portion of unhybridised nucleotides, wherein:

the number of hybridised nucleotides and/or the sequence of hybridised nucleotides in the stem portion of the third closed stem-loop oligonucleotide differs from that of the stem portions of the first and second closed stem-loop oligonucleotide;

the double-stranded stem portion comprises a fluorophore molecule connected to one strand and a quencher molecule connected to an opposing strand; and enzymes capable of cleaving or degrading the single-stranded loop portion of the third closed stem-loop oligonucleotide only when in contact with the target or amplicon thereof;

(e) treating the reaction mixture:

under conditions suitable for the enzymes to induce cleavage or degradation of the loop portion of the third closed stem-loop oligonucleotide to thereby produce a third open stem-loop oligonucleotide;

at a third temperature at or above which strands of the double-stranded stem portion of the third open stem-loop oligonucleotide disassociate to thereby facilitate spatial separation of the fluorophore and quencher molecules of the stein portion of the third open stem-loop oligonucleotide and provide a third detectable fluorescent signal;

wherein:
the third temperature is higher than the first and second temperatures, and
(f) detecting levels of said first, second and third fluorescent signals at one or more temperatures comprising or consisting of a temperature equal to or above the third temperature, to thereby determine the presence or absence of said targets in the sample.

Embodiment 29. The method of any one of embodiments 1 to 27, further comprising determining the presence or absence of a third target or amplicon thereof in a sample by:
(d) contacting the reaction mixture comprising the sample or a derivative thereof with:
a third closed stem-loop oligonucleotide, wherein the third closed stem-loop oligonucleotide comprises a double-stranded stem portion of hybridised nucleotides connected to a closed single-stranded loop portion of unhybridised nucleotides, wherein:
the number of hybridised nucleotides and/or the sequence of hybridised nucleotides in the stem portion of the third closed stem-loop oligonucleotide is the same as that of the stem portions of the first or second closed stem-loop oligonucleotide;
the double-stranded stem portion comprises a fluorophore molecule connected to one strand and a quencher molecule connected to an opposing strand, wherein the fluorophore molecule connected to the third open stem-loop oligonucleotide emits in a different colour region of the visible spectrum than the fluorophore of the first and/or second closed stem-loop oligonucleotides; and
enzymes capable of cleaving or degrading the single-stranded loop portion of the third closed stem-loop oligonucleotide only when in contact with the target or amplicon thereof;
(e) treating the reaction mixture:
under conditions suitable for the enzymes to induce cleavage or degradation of the loop portion of the third closed stem-loop oligonucleotide to thereby produce a third open stem-loop oligonucleotide;
at a third temperature at which strands of the double-stranded stem portion of the third open stem-loop oligonucleotide disassociate to thereby facilitate spatial separation of the fluorophore and quencher molecules of the stem portion of the third open stem-loop oligonucleotide and provide a third detectable fluorescent signal
(f) detecting levels of said first, second and third fluorescent signals at one or more temperatures comprising or consisting of a temperature equal to or above the third temperature, to thereby determine the presence or absence of said targets in the sample.

Embodiment 30. The method of embodiment 29, wherein the third temperature differs from the first and/or second temperatures.

Embodiment 31. The method of any one of embodiments 28 to 30, wherein the method comprises treating the reaction mixture under conditions suitable for any one or more of:
binding of a third MNAzyme to the third target or amplicon thereof and hybridisation of substrate arms of said third MNAzyme to the loop portion of the third closed stem-loop oligonucleotide, to thereby facilitate said cleavage of the loop portion of the third closed stem-loop oligonucleotide by the third MNAzyme forming the third open stem-loop oligonucleotide;
hybridisation of the third target or amplicon thereof to the loop portion of the third closed stem-loop oligonucleotide to form a double-stranded sequence for a third restriction endonuclease to associate with the double-stranded sequence and thereby facilitate said cleavage of the loop portion of the third closed stem-loop oligonucleotide forming the third open stem-loop oligonucleotide;
hybridisation of a third target or amplicon thereof to the loop portion of the third closed stem-loop oligonucleotide to form a third double-stranded sequence comprising the third target or amplicon thereof,
hybridisation of a third primer oligonucleotide to the third target or amplicon thereof to form a third double-stranded sequence located upstream (5') relative to the third double-stranded sequence comprising the third target or amplicon thereof, association of a third enzyme comprising exonuclease activity with a loop portion of the third closed stem-loop oligonucleotide at or adjacent to a terminus of the third primer oligonucleotide, and
catalytic activity of the third enzyme comprising exonuclease activity to thereby facilitate degradation of the loop portion of the third double-stranded sequence comprising the third target or amplicon and form the third open stein-loop oligonucleotide;
hybridisation of a third target or amplicon thereof to the loop portion of the third closed stem-loop oligonucleotide to form a third double-stranded sequence comprising the third target or amplicon thereof,
association of a third enzyme comprising exonuclease activity with the third double-stranded sequence comprising the third target or amplicon thereof, and
catalytic activity of the third enzyme comprising exonuclease activity to thereby facilitate degradation of the loop portion of the third double-stranded sequence comprising the third target or amplicon and form the third open stem-loop oligonucleotide;
binding of a third cofactor to a DNAzyme and/or binding of a third cofactor to a ribozyme to render the DNAzyme and/or ribozyme catalytically active,
hybridisation of DNAzyme and/or ribozyme to the loop portion of a third closed stem-loop oligonucleotide,
catalytic activity of the DNAzyme and/or ribozyme to thereby facilitate cleavage of the loop portion of the third closed stem-loop oligonucleotide and form the third open stem-loop oligonucleotide.
wherein:
the third target is the third co-factor.

Embodiment 32. The method of embodiment 31, wherein the co-factor is a metal ion (e.g. $Mg^{2+}$, $Mn^{2+}$, $Ca^{2+}$. $Pb^{2+}$).

Embodiment 33. The method of embodiment 31, wherein the restriction endonuclease is a nicking endonuclease capable of associating with and cleaving a loop strand of said double-stranded sequence comprising the third target or amplicon thereof.

Embodiment 34. The method of embodiment 31, wherein the third target is a nucleic acid sequence or amplicon thereof capable of hybridising to the sensor arms of the third MNAzyme to thereby facilitate assembly of the third MNAzyme.

Embodiment 35. The method of embodiment 31, wherein:
the target is an analyte, protein, compound or molecule;
the enzymes comprise enzymes with an aptamer capable of binding to the third target; and
binding of the third target to the aptamer is capable of rendering the enzymes with an aptamer catalytically active Embodiment 36. The method of embodiment 35, wherein the enzymes with an aptamer comprise any one or more of apta-DNAzymes, apta-ribozymes, apta-MNAzymes.

Embodiment 37. The method of embodiment 31, wherein:
the third target is an analyte, protein, compound or molecule;
the reaction mixture further comprises an oligonucleotide sequence capable of hybridising to the sensor arms of the third MNAzyme to thereby facilitate assembly of the third MNAzyme;
the third MNAzyme comprises an aptamer sequence capable of binding to the third target; and
binding of the third target to the aptamer sequence of the third MNAzyme is capable of rendering the third MNAzyme catalytically active by facilitating removal of an inhibitory molecule bound to the aptamer of the third MNAzyme.

Embodiment 38. The method of any one of embodiments 31, or 33 to 37, wherein:
the reaction mixture comprises said third MNAzyme and either of both of said first and second MNAzymes; and
the sequence of the loop portion of the third closed stem-loop oligonucleotide capable of hybridising to the substrate arms of the third MNAzyme is different from:
the sequence of the loop portion of the first closed stem-loop oligonucleotide capable of hybridising to the substrate arms of the first MNAzyme, and/or
the sequence of the loop portion of the second closed stem-loop oligonucleotide capable of hybridising to the substrate arms of the first MNAzyme.

Embodiment 3. The method of any one of embodiments 28 or embodiments 31 to 38, wherein:
the number of hybridised nucleotides and/or the sequence of hybridised nucleotides in the stem portion of the third closed stem-loop oligonucleotide differs from that of the stem portions of the first and second closed stem-loop oligonucleotides;
the third temperature differs from the first and second temperatures; and
the fluorophore of the third closed and open stem-loop oligonucleotides emits in the same colour region of the visible spectrum as the fluorophores of the first and second closed and open stem-loop oligonucleotides.

Embodiment 40. The method of any one of embodiments 28 or embodiments 31 to 39, wherein the fluorophore of the third closed and open stem-loop oligonucleotides is the same as the fluorophore of the first and/or second closed and open stem-loop oligonucleotides.

Embodiment 41. The method of embodiment 40, wherein the fluorophore of the third closed and open stem-loop oligonucleotides and the fluorophore of the first closed and open stem-loop oligonucleotides and/or the fluorophore of the second closed and open stem-loop oligonucleotides are detectable using the same fluorescence emission channel of a device.

Embodiment 42. The method of any one of embodiments 28 to 38 or 39, wherein:
the fluorophore of the first closed and open stem-loop oligonucleotides emits in the same colour region of the visible spectrum as the fluorophore of the second closed and open stem-loop oligonucleotides; and
the fluorophore of the third closed and open stem-loop oligonucleotides emits in a different colour region of the visible spectrum than the fluorophore of the first and second closed and open stem-loop oligonucleotides.

Embodiment 43. The method of any one of embodiments 28 to 42, wherein the third temperature differs from the first temperature and/or the second temperature by more than: 1° C., 2° C., 3° C., 4° C., 5° C., 6° C., 7° C., 8° C., 9C, 10° C., 11° C., 12° C., 13° C., 14° C., 15° C., 16° C., 17° C., 18° C., 19° C., 20° C., 25° C., 30° C., 35° C., 40° C., 45° C., 50° C., 55° C., 60° C., 65° C. 70° C., 75° C., 80° C.

Embodiment 44. The method of any one of embodiments 28 to 43, wherein detection of a third fluorescent signal at the third temperature is indicative of the presence of the third target in the sample, and failure to detect a third fluorescent signal at the third temperature is indicative of the absence of the third target in the sample.

Embodiment 45. The method of any one of embodiments 1 to 44, wherein:
(i) determining a presence of the first fluorescent signal at the first temperature is indicative of the presence of the first target in the sample, and determining an absence of the first fluorescent signal is indicative of the absence of the first target in the sample; and
(ii) determining a presence of the second fluorescent signal at the second temperature is indicative of the presence of the second target in the sample, and determining an absence of the second fluorescent signal is indicative of the absence of the second target in the sample.

Embodiment 46. The method of any one of embodiments 1 to 44, wherein said determining the presence or absence of the first and second targets comprises a melt curve analysis using said first and second fluorescent signals.

Embodiment 47. The method of any one of embodiments 1 to 44, wherein part (c) comprises detecting levels of said first and second fluorescent signals at:
a temperature equal to or above the second temperature; and
a temperature equal to or above the first temperature and below the second temperature.

Embodiment 48. The method of embodiment 47, wherein part (c) further comprises detecting levels of said first and second fluorescent signals at a temperature below the second temperature.

Embodiment 49. The method of embodiment 47 or embodiment 48 wherein part (c) comprises detecting levels of said first and second fluorescent signals during and/or upon completion of a nucleic acid amplification reaction.

Embodiment 50. The method of any one of embodiments 47 to 49 further comprising generating a first target positive control fluorescent signal using a known concentration of the first target and/or a known concentration the first closed stem-loop oligonucleotide.

Embodiment 51. The method of any one of embodiments 47 to 50, further comprising generating a first target positive control fluorescent signal by repeating said method on a separate control sample comprising said first target.

Embodiment 52. The method of embodiment 51, wherein the control sample comprising the first target comprises a known concentration of the first target.

Embodiment 53. The method of embodiment 51 or embodiment 52, wherein the control sample comprising the first target further comprises said second target.

Embodiment 54. The method of any one of embodiments 46 to 53, further comprising generating a second target positive control fluorescent signal by repeating said method on a separate control sample comprising said second target.

Embodiment 55. The method of embodiment 54, wherein the control sample comprising the second target comprises a known concentration of the second target.

Embodiment 56. The method of embodiment 54 or embodiment 55, wherein said control sample further comprises said first target.

Embodiment 57. The method of any one of embodiments 46 to 53, further comprising generating a combined positive control fluorescent signal by repeating said method on a separate control sample comprising said first and said second targets.

Embodiment 58. The method of embodiment 57, wherein the combined control sample comprises a known concentration of the first target and/or a known concentration of the second target.

Embodiment 59. The method of any one of embodiments 50 to 58, further comprising normalising said first fluorescent signal and/or said second fluorescent signal using any said positive control fluorescent signal.

Embodiment 60. The method of any one of embodiments 46 to 59, further comprising generating a negative control fluorescent signal by repeating the method of any one of embodiments 1 to 3 on a separate negative control sample that does not contain:
  (i) said first target; or
  (ii) said second target; or
  (iii) said first target or said second target.

Embodiment 61. The method of embodiment 60, further comprising normalising said first fluorescent signal and/or said second fluorescent signal using said negative control fluorescent signal.

Embodiment 62. The method of any one of embodiments 46 to 61, further comprising comparing said first and/or second fluorescent signals to a threshold value wherein:
  the threshold value is generated using fluorescent signals derived from a series of samples tested according to the method of any one of embodiments 1 to 3, and comprising any one or more of:
    (i) a no template control and the first target
    (ii) a no template control and the second target
    (iii) a no template control, the first target, and the second target to thereby determine said presence or absence of the first and second targets in the sample.

Embodiment 63. The method of embodiment 62, wherein the series of samples is tested using a known concentration of said first closed stem-loop oligonucleotide and/or a known concentration of said second closed stem-loop oligonucleotide.

Embodiment 64. The method of any one of embodiments 1 to 63, wherein the first temperature differs from the second temperature by more than: 1° C., 2° C., 3° C., 4° C., 5° C., 6° C., 7° C., 8° C., 9° C., 10° C., 11° C., 12° C., 13° C., 14° C., 15° C., 16° C., 17° C. 18° C., 19° C., 20° C., 25° C., 30° C., 35° C., 40° C., 45° C., 50° C., 55° C., 60° C., 65° C., 70° C., 75° C. 80° C.

Embodiment 65. The method of any one of embodiments 1 to 64, wherein any said amplicon thereof is produced by any one of more of polymerase chain reaction (PCR), strand displacement amplification (SDA), helicase dependent amplification (HDA), Recombinase Polymerase Amplification (RPA), loop-mediated isothermal amplification (LAMP), rolling circle amplification (RCA), transcription-mediated amplification (TMA), self-sustained sequence replication (3SR), nucleic acid sequence based amplification (NASBA), and/or reverse transcription polymerase chain reaction (RT-PCR).

Embodiment 66. The method of any one of embodiments 1 to 65, wherein the sample is a biological sample obtained from a subject.

Embodiment 67. The method of any one of embodiments 1 to 65, wherein the method is performed in vitro.

Embodiment 68. The method of any one of embodiments 1 to 65, wherein the method is performed ex vivo.

Embodiment 69. A composition comprising:
  first and second closed stem-loop oligonucleotides, wherein each of the closed stem-loop oligonucleotides comprise a double-stranded stem portion of hybridised nucleotides connected to a single-stranded loop portion of unhybridised nucleotides, wherein:
    the number of hybridised nucleotides and/or the sequence of hybridised nucleotides in the stem portion of the first and second closed stein-loop oligonucleotide differs, and
    each of the double-stranded stem portions comprise a fluorophore molecule connected to one strand and a quencher molecule connected to an opposing strand, wherein the fluorophore molecules emit in the same colour region of the visible spectrum, and the melting temperature (Tm) of the double-stranded stem portion of the first closed stem-loop oligonucleotide differs from the Tm of the double-stranded stem portion of the second closed stem-loop oligonucleotide.

Embodiment 70. The composition of embodiment 69, wherein the single-stranded loop portion of the first closed stem-loop oligonucleotide differs from the sequence of the single-stranded loop portion of the second closed stem-loop oligonucleotide.

Embodiment 71. The composition of embodiment 69 or embodiment 70, further comprising:
  a first MNAzyme comprising substrate arms capable of hybridising to the closed single-stranded loop portion of the first closed stem-loop oligonucleotide; and
  a second MNAzyme comprising substrate arms capable of hybridising to the single-stranded loop portion of the second closed stem-loop oligonucleotide.

Embodiment 72. The composition of embodiment 71, wherein:
  the substrate arms of the first MNAzyme are hybridised to the single-stranded loop portion of the first closed stem-loop oligonucleotide; and
  the substrate arms of the second MNAzyme are hybridised to the single-stranded loop portion of the second closed stem-loop oligonucleotide.

Embodiment 73. The composition of embodiment 72, wherein: the first and/or second MNAzymes comprise an aptamer sequence bound to a target analyte, protein, compound or molecule and sensor arms hybridised to an oligonucleotide sequence; and
  the first MNAzyme is designed to detect a different target than the second MNAzyme.

Embodiment 74. The composition of embodiment 72, wherein:
  the first and/or second MNAzymes comprise sensor arms hybridised to a target sequence, and the first MNAzyme is designed to detect a different target than the second MNAzyme.

Embodiment 75. The composition of any one of embodiments 69 to 74, further comprising:
  a first oligonucleotide sequence hybridised to said single-stranded loop portion of the first closed stem-loop oligonucleotide that differs from the sequence of the single-stranded loop portion of the second closed stem-loop oligonucleotide, thereby forming a double stranded sequence comprising said first oligonucleotide;

a second oligonucleotide sequence hybridised to said single-stranded loop portion of the second closed stem-loop oligonucleotide that differs from the sequence of the single-stranded loop portion of the first closed stem-loop oligonucleotide, thereby forming a double stranded sequence comprising said second oligonucleotide;

a restriction endonuclease associated with and capable of cleaving the double stranded sequence comprising said first oligonucleotide; and/or a restriction endonuclease associated with and capable of cleaving the double stranded sequence comprising said second oligonucleotide.

Embodiment 76. The composition of any one of embodiments 69 to 75, further comprising:

a first double-stranded sequence comprising a first target oligonucleotide sequence hybridised to said single-stranded loop portion of the first closed stem-loop oligonucleotide that differs from the sequence of the single-stranded loop portion of the second closed stem-loop oligonucleotide, thereby forming a first double stranded sequence comprising said first target oligonucleotide;

a second double-stranded sequence comprising a second target oligonucleotide sequence hybridised to said single-stranded loop portion of the second closed stem-loop oligonucleotide that differs from the sequence of the single-stranded loop portion of the first closed stem-loop oligonucleotide, thereby forming a double stranded sequence comprising said second target oligonucleotide;

a first primer oligonucleotide hybridised to the first target oligonucleotide upstream (5') relative to said first double-stranded sequence and a first enzyme comprising exonuclease activity (e.g. a polymerase, an exonuclease) associated with a loop portion of the first closed stem-loop oligonucleotide at or adjacent to a terminus of the first primer oligonucleotide; and/or a second primer oligonucleotide hybridised to the second target oligonucleotide upstream (5') relative to said second double-stranded sequence second and a second enzyme comprising exonuclease activity (e.g. a polymerase, an exonuclease) associated with a loop portion of the second closed stem-loop oligonucleotide at or adjacent to a terminus of the second primer oligonucleotide Embodiment 77. The composition of any one of embodiments 69 to 76, further comprising:

a first double-stranded sequence comprising a first target oligonucleotide sequence hybridised to said single-stranded loop portion of the closed first stem-loop oligonucleotide that differs from the sequence of the single-stranded loop portion of the second closed stem-loop oligonucleotide, thereby forming a first double-stranded sequence comprising said first target oligonucleotide;

a second double-stranded sequence comprising a second target oligonucleotide sequence hybridised to said single-stranded loop portion of the second closed stem-loop oligonucleotide that differs from the sequence of the single-stranded loop portion of the first closed stem-loop oligonucleotide, thereby forming a second double stranded sequence comprising said second target oligonucleotide;

wherein a first enzyme comprising exonuclease activity is associated with the first double-stranded sequence and a second enzyme comprising exonuclease activity is associated with the second double-stranded sequence.

Embodiment 78. The composition of any one of embodiments 69 to 77, further comprising:

a first DNAzyme and/or a first ribozyme hybridised to a loop portion of the first closed stem-loop oligonucleotide that differs from the sequence of the single-stranded loop portion of the second closed stem-loop oligonucleotide, a second DNAzyme and/or a second ribozyme hybridised to a loop portion of the second closed stem-loop oligonucleotide that differs from the sequence of the single-stranded loop portion of the first closed stem-loop oligonucleotide, cofactors for each said DNAzyme capable of rendering each said DNAzyme catalytically active, and thus induce cleavage activity of any said DNAzyme hybridised to the loop portion.

cofactors for each said ribozyme capable of rendering each said ribozyme catalytically active, and thus induce cleavage activity of any said ribozyme hybridised to the loop portion.

Embodiment 79. The composition of any one of embodiments 69 to 78, further comprising:

third closed stein-loop oligonucleotides, wherein the third closed stem-loop oligonucleotides comprise a double-stranded stem portion of hybridised nucleotides connected to a single-stranded loop portion of unhybridised nucleotides, wherein:

the number of hybridised nucleotides and/or the sequence of hybridised nucleotides in the stem portion of the third closed stem-loop oligonucleotides differs from those of the first and second closed stem-loop oligonucleotides, and the double-stranded stem portion of the third closed stem-loop oligonucleotides comprises a fluorophore molecule connected to one strand and a quencher molecule connected to an opposing strand, wherein the fluorophore molecule of the third closed stem-loop oligonucleotide emits in a different colour region of the visible spectrum compared to the fluorophore molecules of the first and second closed stem-loop oligonucleotides.

Embodiment 80. The composition of any one of embodiments 69 to 78, further comprising:

third closed stem-loop oligonucleotides, wherein the third closed stem-loop oligonucleotides comprise a double-stranded stem portion of hybridised nucleotides connected to a single-stranded loop portion of unhybridised nucleotides, wherein:

the number of hybridised nucleotides and/or the sequence of hybridised nucleotides in the stem portion of the third closed stem-loop oligonucleotides differs from those of the first and second closed stem-loop oligonucleotides, and the double-stranded stem portion of the third closed stem-loop oligonucleotides comprises a fluorophore molecule connected to one strand and a quencher molecule connected to an opposing strand, wherein the fluorophore molecule of the third closed stem-loop oligonucleotide emits in a same colour region of the visible spectrum compared to the fluorophore molecules of the first and second closed stem-loop oligonucleotides.

Embodiment 81. The composition of any one of embodiments 69 to 78, further comprising:
- third closed stem-loop oligonucleotides, wherein the third closed stem-loop oligonucleotides comprise a double-stranded stem portion of hybridised nucleotides connected to a single-stranded loop portion of unhybridised nucleotides, wherein:
  - the number of hybridised nucleotides and/or the sequence of hybridised nucleotides in the stem portion of the third closed stem-loop oligonucleotides is the same those of the first or second closed stem-loop oligonucleotides, and
    - the double-stranded stem portion of the third closed stem-loop oligonucleotides comprises a fluorophore molecule connected to one strand and a quencher molecule connected to an opposing strand, wherein the fluorophore molecule of the third closed stem-loop oligonucleotide emits in a different colour region of the visible spectrum compared to the fluorophore molecules of the first and second closed stem-loop oligonucleotides.

BRIEF DESCRIPTION OF THE DRAWINGS

Preferred embodiments of the present invention will now be described, by way of example only, with reference to the accompanying FIGS. 1-8 as set out below.

Figure 6:
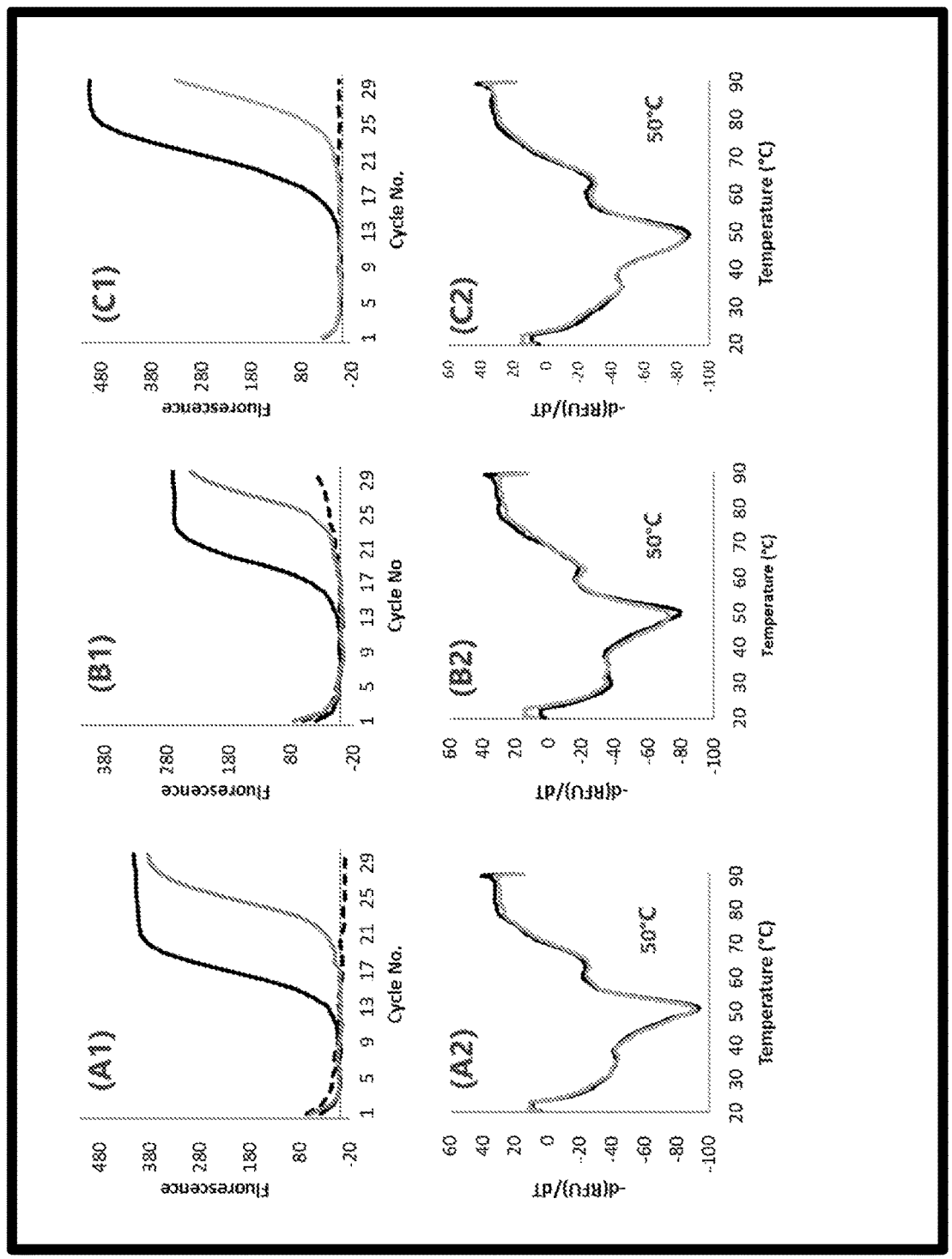

FIG. 6 (top panel) illustrates PCR amplification plots obtained from reactions containing 10,000 copies (black line), 40 copies (grey line) or 0 copies (dotted line) of the TV-Btub (FIG. 6A1), VZV (FIG. 6B1), and rpoB (FIG. 6C1) targets. The results shown in the bottom panel are melt curve signatures obtained from reactions containing 10,000 copies (black line) or 40 copies (grey line) of TV-Btub (FIG. 6A2), VZV (FIG. 6B2), and rpoB (FIG. 6C2) targets. The three targets were specifically detected by three different MNAzymes; each of which had identical substrate binding arms and differed only by the target binding arms. Each MNAzyme opened the same Universal LOCS-2 comprising a universal substrate and a universal stem. Each target produced a melt curve signature with a peak at 50° C. which corresponds to Tm of the universal stem within LOCS-2.

Figure 7:
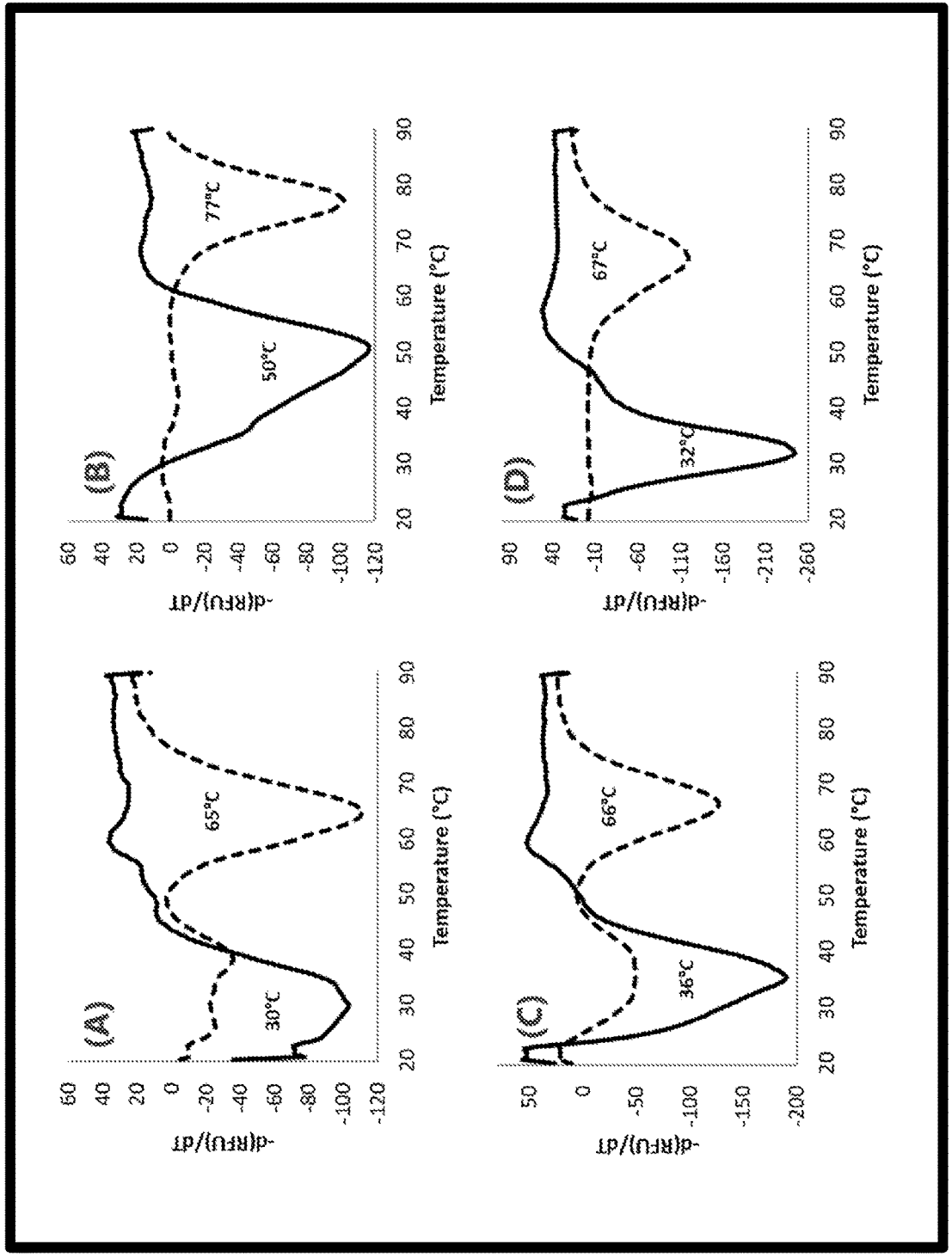

FIG. 7 shows melt curve signatures obtained when LOCS-1 (FIG. 7A), LOCS-2, (FIG. 7B), LOCS-3 (FIG. 7C) and LOCS-4 (FIG. 7D) were used to monitor amplification of the targets CT-Cds (FIGS. 7A and 7C) or TFRC (FIGS. 7B and 7D). The melt curve signatures obtained in the absence of target (dotted line) had peaks at Tms of 65° C., 77° C., 66° C. and 67° C. corresponding to the melting temperatures of closed, intact LOCS-1, LOCS-2, LOCS-3 and LOCS-4 respectively. In the presence of CT-Cds target (black line; FIGS. 7A and 7C), the open LOCS-1 and LOC-3 structures resulted in melting temperature of 30° C. and 36° C. respectively. In the presence of TFRC target (black line; FIGS. 7B and 7D), the open LOCS-2 and LOC-4 structures resulted in melting temperatures of 50° C. and 32° C. respectively.

Figure 8:
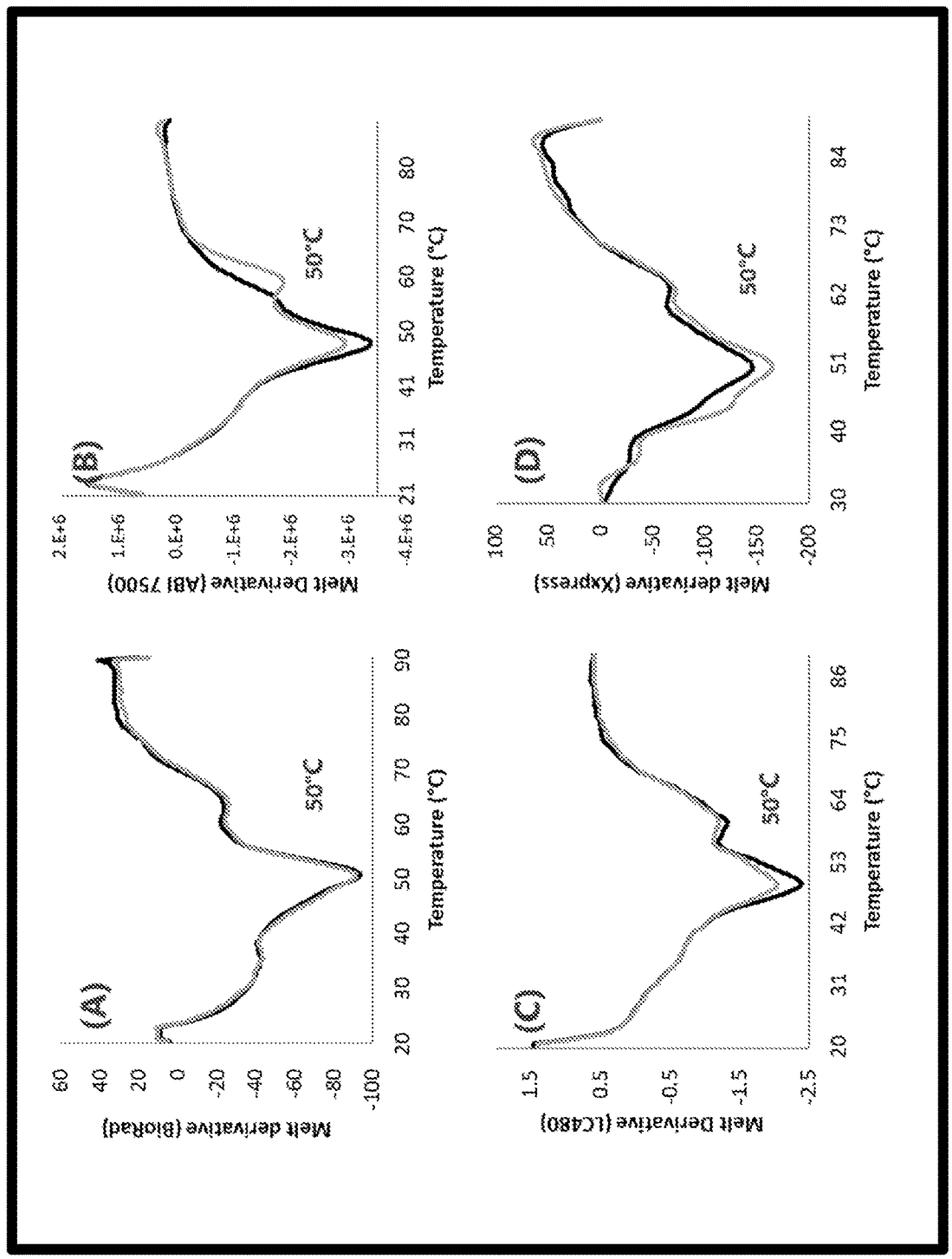

FIG. 8 shows the melting curves obtained for amplification of the MgPa target when performed on the BioRad® CFX96 thermocycler (FIG. 8A) or an ABI 7500 (FIG. 8B), or a Light Cycler 480 (Panel C), or the XXpress PCR (FIG. 8D). Both targets were monitored in the FAM channel on all machines.

Figure 9:
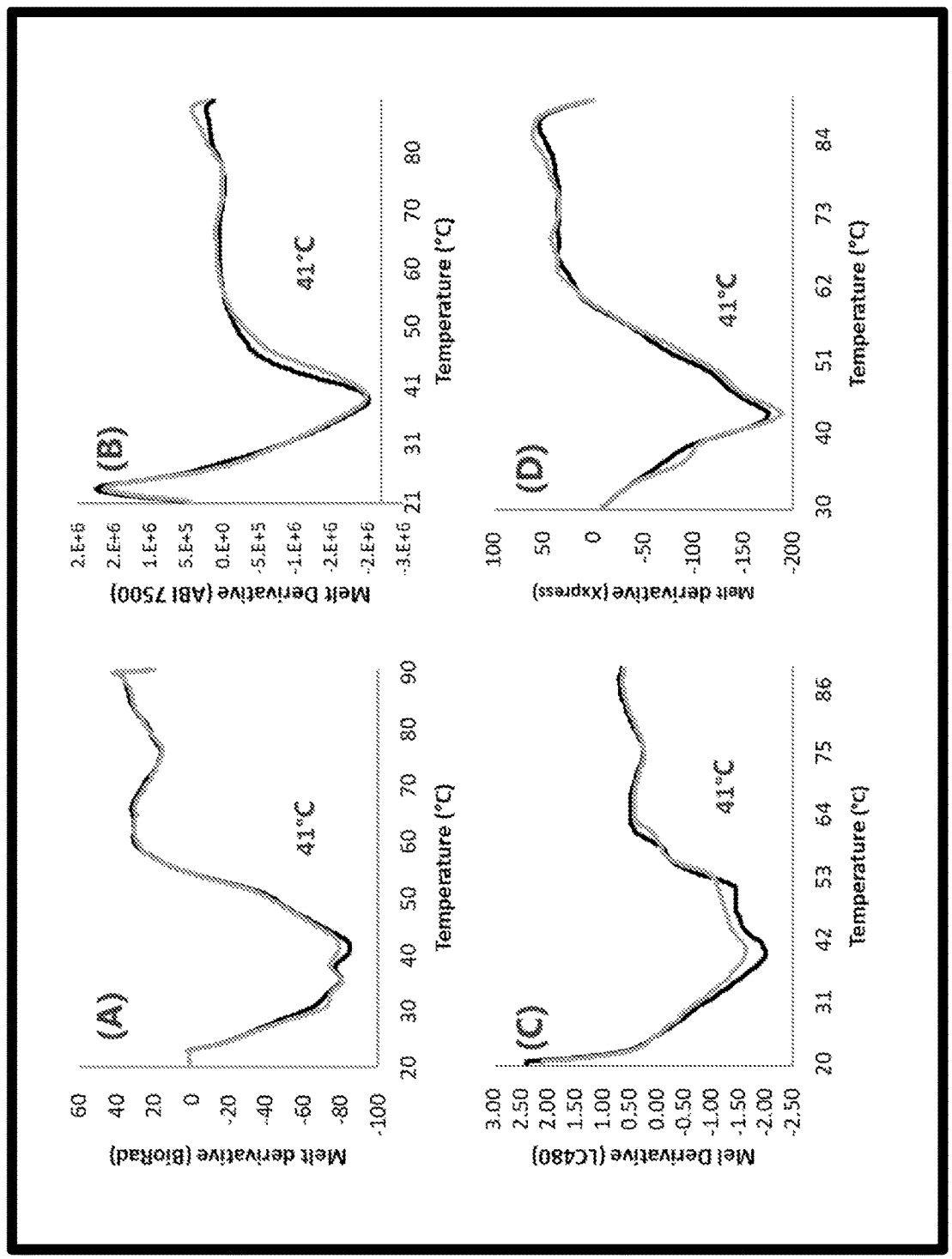
Figure 10:
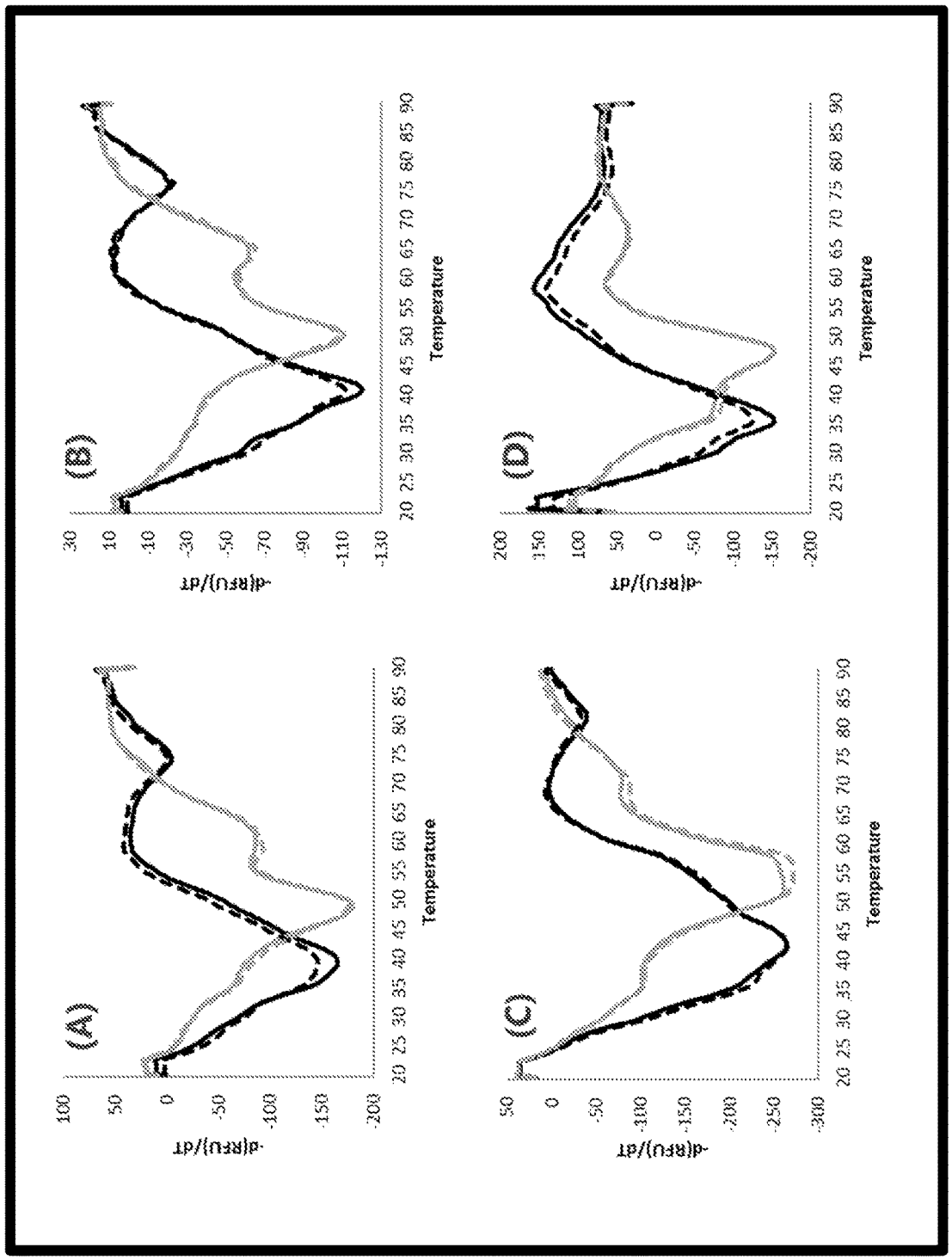

FIG. 9 shows the melting curves obtained for amplification of the TV-Btub target when performed on the BioRad® CFX96 thermocycler (FIG. 9A) or an ABI 7500 (FIG. 9B), or a Lightcycler 480 (FIG. 9C), or the XXpress PCR (FIG. 9D). Both targets were monitored in the FAM channel on all machines, FIG. 10 shows melt curve signatures obtained from duplex PCR reactions where the targets MgPa (black curves) and TV-Btub (grey curves) were co-amplified and read in a single channel. The solid lines and dotted lines indicate target concentrations of 10,000 copies and 40 copies respectively. FIG. 10A illustrates melt curves obtained using LOCS-1 and LOCS-2 read in the FAM channel; FIG. 10B shows results using LOC-5 and LOCS-6 read in the HEX channel; FIG. 10C shows results using LOCS-7 and LOCS-8 read in the Texas Red channel and FIG. 10D shows results using LOCS-9 and LOCS-10 read in the Cy5 channel.

Figure 11:
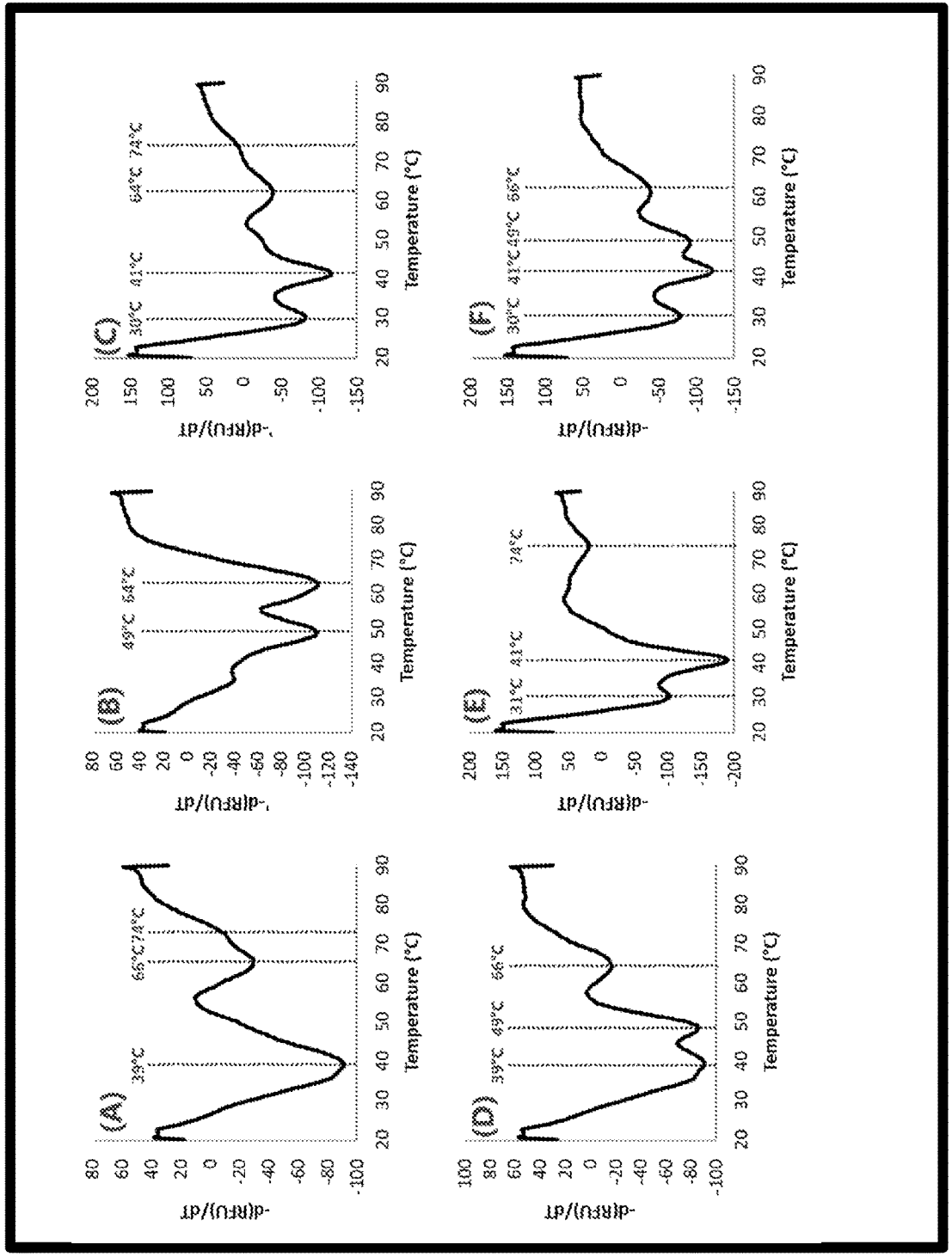

FIG. 11 illustrates the melt curve signatures obtained post PCR amplification from reactions containing 10,000 copies of MgPa (FIG. 11A), TV-Btub (FIG. 11B), CTcry (FIG. 11C), both MgPa and TV-Btub (FIG. 11D), both MgPa and CTcry (FIG. 1E) or both TV-Btub and CTcry (FIG. 11F) gene targets. The melt signatures produced by opening LOCS-1 and/or LOCS-2 and/or LOCS-11 produced peaks indicating these structures melted at Tms in the range between 30° C. and 50° C., whilst the intact closed LOCS melted at Tins ranging between 64° C. and 74° C. In each scenario, the LOCS melt signatures are unique and distinct from the other LOCS melt signatures.

Figure 12:
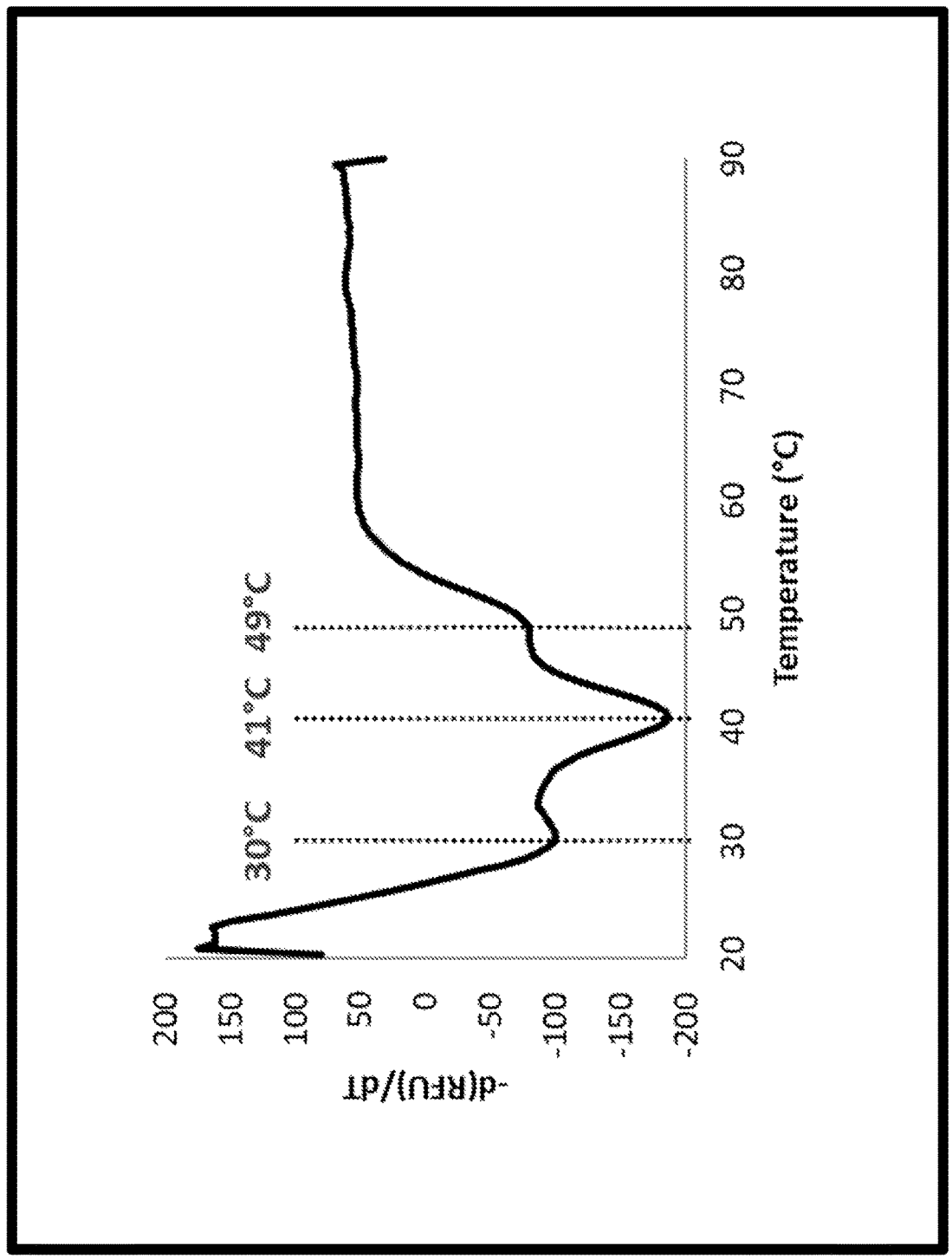

FIG. 12 illustrates the melt curve signatures obtained post PCR amplification from reactions containing 10,000 copies each of MgPa, TV-Btub and CTcry gene targets. The melt signatures produced by opening LOCS-1, LOCS-2 and LOCS-11 in the presence of MgPa, TV-Btub and CTcry gene targets included three peaks at melting temperatures of 30° C., 41° C. and 49° C. The reaction containing all three gene targets can be distinguished from those that only contain a single gene target (FIGS. 11A-11C) and those that contain two of the three gene targets (FIGS. 11D-11E). For example, the reaction containing all three gene targets can be distinguished from reaction containing only TV-Btub and CTcry (FIG. 11F) by the disappearance of the peak of the Tm of the Open LOCS 1 (~64° C.).

Figure 13:
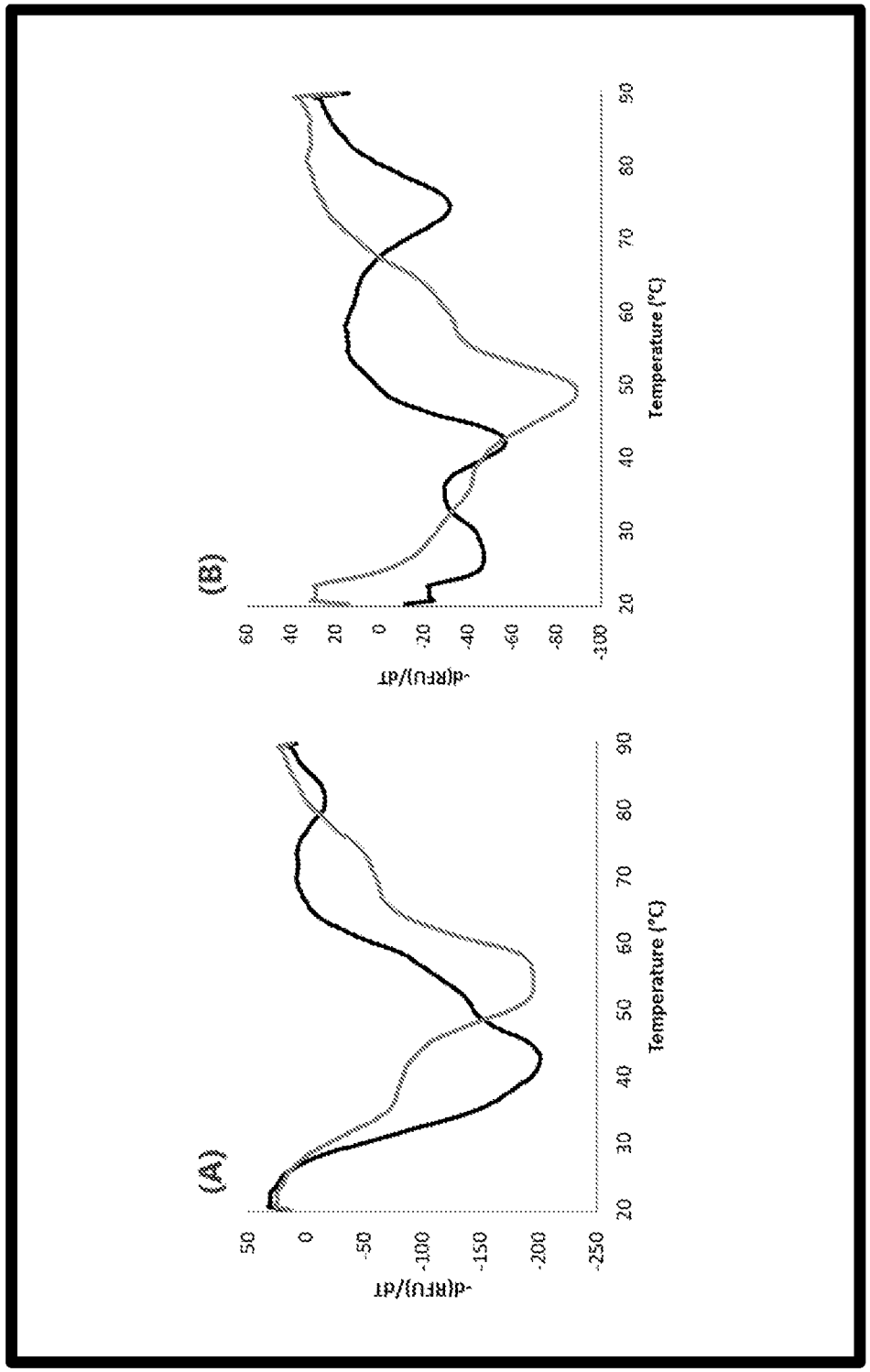

FIG. 13 illustrates the melt curve signatures obtained post PCR amplification from 4-plex reactions containing 10,000 copies of either MgPa, TV-Btub, NGopa or gpd gene targets. The four targets were specifically detected using 4 different MNAzymes, in turn these MNAzymes cleaved and opened 4 different LOCS reporters which were monitored in 2 fluorescent channels. Each LOCS reporter contains a different universal substrate, yet the same universal stems (Stem-1 and Stem-2) were used in both the FAM and Texas Red channels. The presence of either MgPa or TV-Btub genes was detected by an increase in signal in the Texas Red channel; and the presence of either NGopa or gpd genes were detected by an increase in signal in the FAM channel. The specific detection of MgPa or TV-Btub in the Texas Red channel and NGopa or gpd in the FAM channel, was determined based on the presence of a unique melt curve signature. The melt signatures produced in the Texas Red channel by opening LOCS-7 in the presence of MgPa and LOCS-8 in the presence of TV-Btub included peaks at melting temperatures of 43° C. and 53° C. respectively. The melt signatures produced in the FAM channel by opening LOCS-12 in the presence of NGopa and LOCS-13 in the presence of gpd included peaks at melting temperatures of 26'C and 42° C., and 53° C. respectively.

Figure 14:
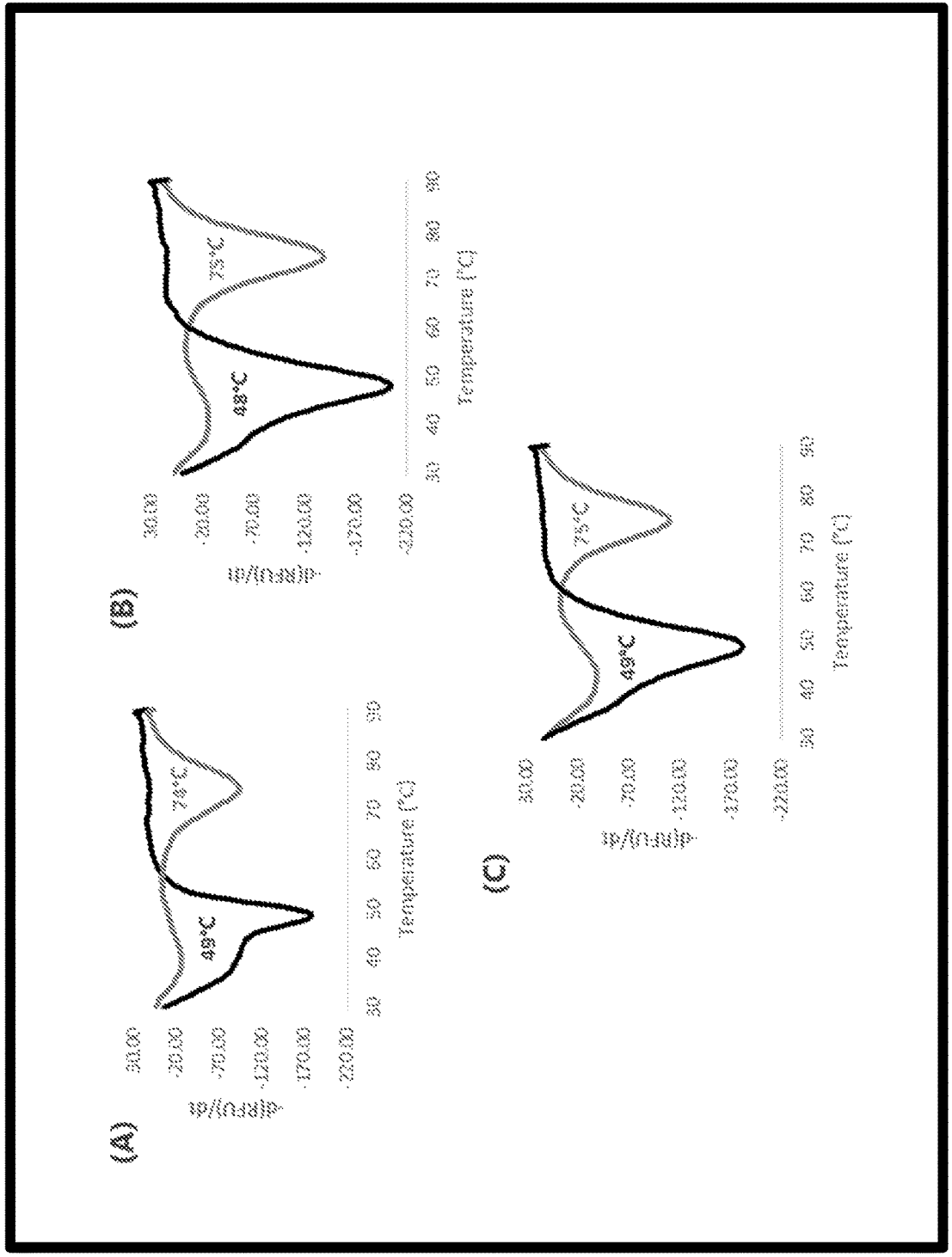

FIG. 14 shows melt curve signatures obtained from Singleplex PCR reactions where each of the loop regions of the three LOCS reporters contains a different substrate for a different MNAzyme, but all three contain the same stem sequence. The melt signatures obtained in the absence of target (grey lines) show melt peaks at 74° C. (FIG. 14A), 75° C. (FIG. 14B) and 75° C. (FIG. 14C) corresponding to the melting temperatures of closed, intact LOCS-2, LOCS-14 and LOCS-15 respectively. In the presence of TFRC target (black line; FIGS. 14A, 14B and 14C), the open LOCS-2, LOCS-14 and LOC-15 structures resulted in melting temperature of 49° C., 48° C. and 49° C. respectively.

FIG. 15 shows melt curve signatures obtained when LOCS-16 (FIG. 15A) and LOCS-17, (FIG. 15B) were used to detect and identify two different targets (AF-NE-TV1 and AF-NE-R5b) using a nicking endonuclease (Nt. AlwI) as an alternative method to MNAzyme cleavage. The melt curve signatures obtained in the absence of target (grey lines) had peaks at Tms of 65° C. and 76° C. corresponding to the melting temperatures of closed, intact LOCS-16 and LOCS-17 respectively. The melt curve signatures obtained in the presence of target (black line; AF-NE-TV] and AF-NE-R5b respectively) had peaks at Tms of 29° C. and 48° C.

corresponding to the melting temperatures of cleaved, open LOCS-16 and LOCS-17 respectively. The data from this example demonstrate that LOCS reporters can be used with alternative target detection methods such as those using nicking endonuclease enzymes.

Figure 16:
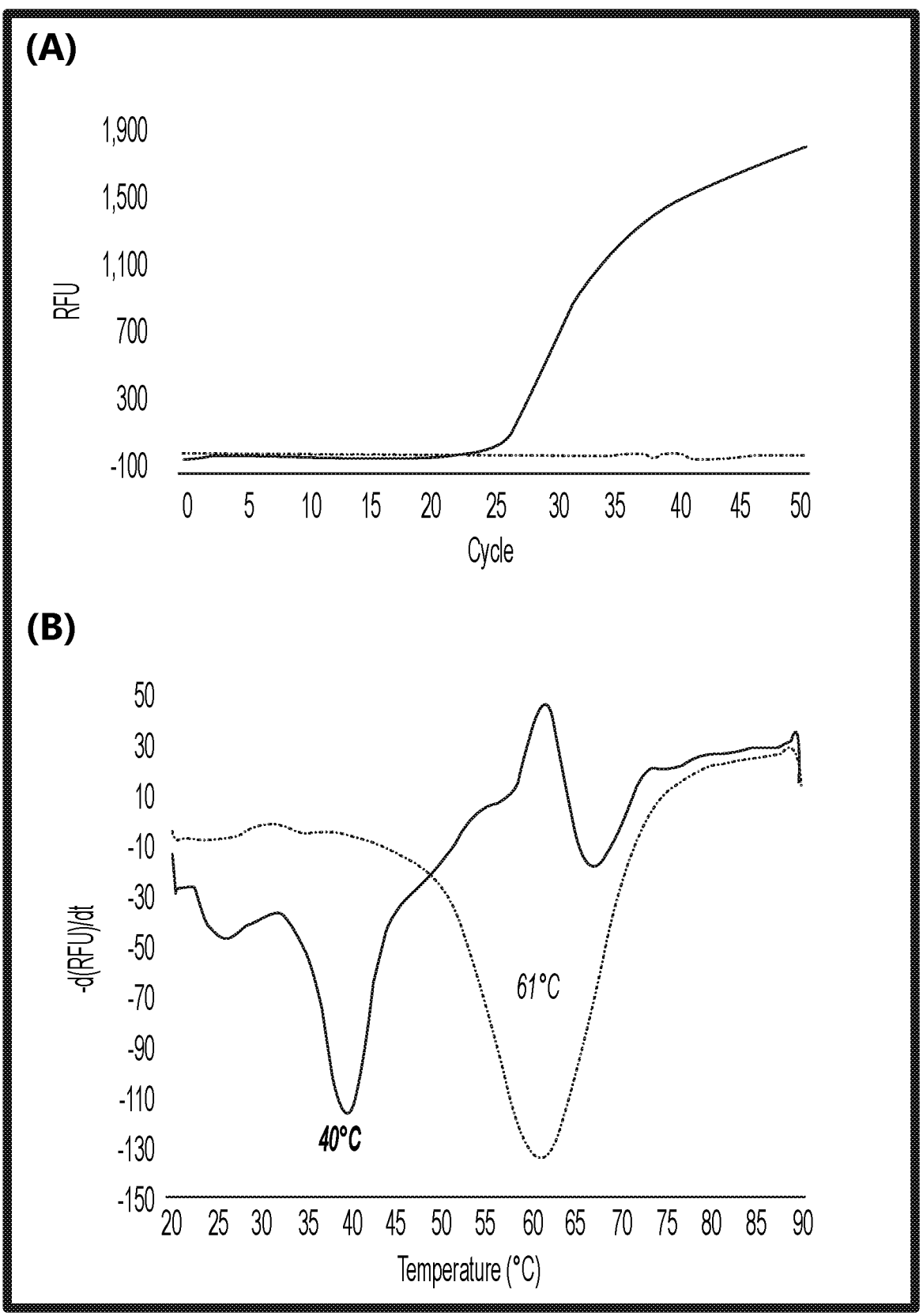

FIG. 16 shows the amplification curves (FIG. 16A) and melt curve signatures (FIG. 16B) obtained when a similar strategy to that mediating TaqMan/Hydrolysis signal generation is used to open LOCS probes, namely that target specific regions of probes (loops) are degraded during PCR by the exonuclease activity of the polymerase. PCR plots were obtained from reactions containing 10,000 copies (black line) or 0 copies (grey line) of TV-btub gene target (FIG. 16A). The melt curve signature obtained in the absence of target (grey line) had a melt peak at a Tm of 61° C. corresponding to the melting temperature of closed, intact LOCS-18 (FIG. 16B). The melt curve signature obtained in the presence of target (black line) had a melt peak at a Tm of 40° C., corresponding to the melting temperatures of cleaved, open LOCS-18 (FIG. 16B). The data from this example demonstrate that LOCS reporters can be used with alternative target detection methods such as TaqMan which uses enzymes with exonuclease activity to cleave probes which hybridize to amplicons.

Figure 17:
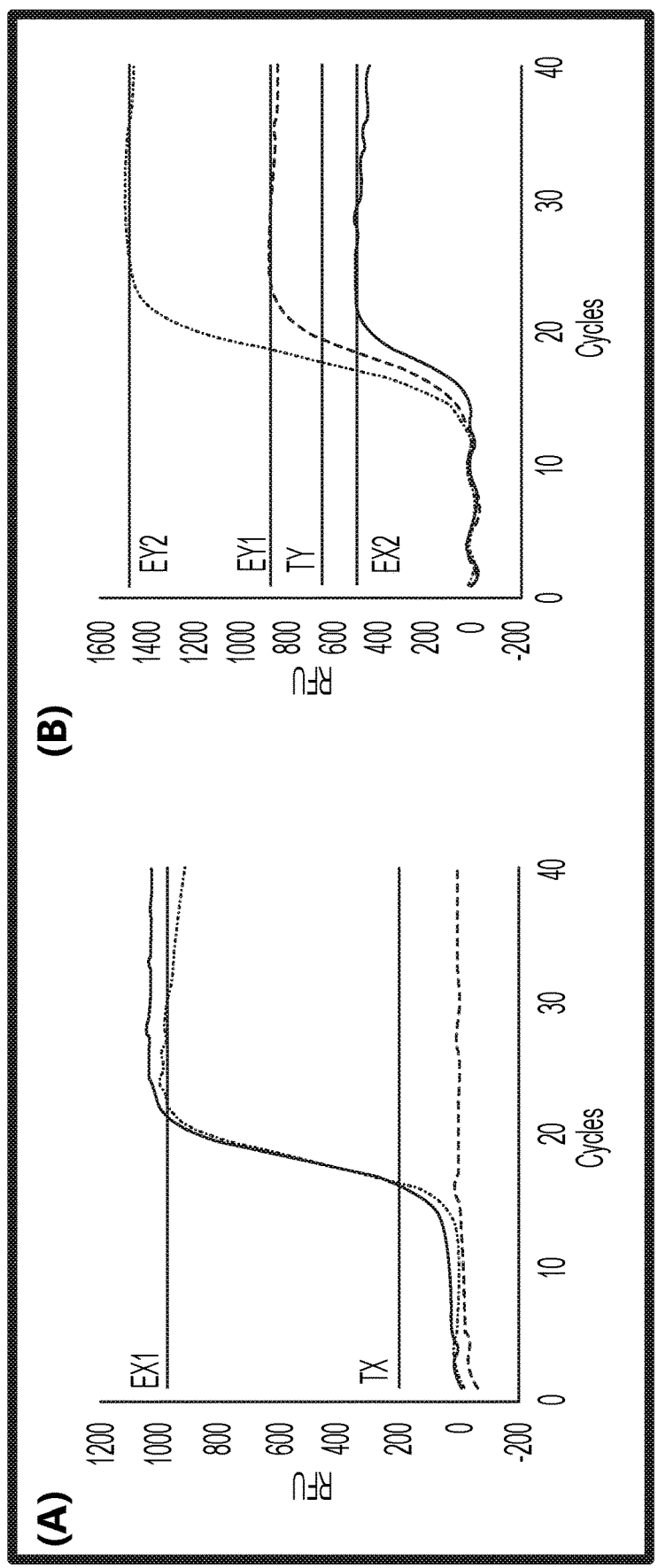

FIG. 17 illustrates PCR amplification plots obtained from reactions containing 20,000 copies of target X/CTcry (solid black line), 20,000 copies of target Y/NGopa (dotted black line) or 20,000 copies of both targets (grey line) at 39° C. (FIG. 17A) and 72° C. (FIG. 17B). Threshold values TX and TV are indicated for amplification plot obtained at 39° C. and 72° C. respectively. Endpoint fluorescence values designated EX1, EX2, EY1 and EY2 are indicated.

FIG. 18 illustrates PCR amplification plots obtained from reactions containing 0 copies of target X/CTcry (solid black line), 32 copies of target X/CTcry (grey line) or 20,000 copies of both target X/CTcry (dotted black line) at 39° C. with 20,000 copies of target Y/NGopa (FIG. 18A), at 72° C. with 20,000 copies of target Y/NGopa (FIG. 18B), at 72° C. with 20,000 copies of target Y/NGopa after normalisation with FAF (FIG. 18C), at 39° C. with 32 copies of target Y/NGopa (FIG. 18D), at 72° C. with 32 copies of target Y/NGopa (FIG. 18E), at 72° C. with 32 copies of target Y/NGopa after normalisation with FAF (FIG. 18F), at 39° C. with 0 copies of target Y/NGopa (FIG. 18G), at 72° C. with 0 copies of target Y/NGopa (FIG. 18H), at 72° C. with 0 copies of target Y/NGopa after normalisation with FAF (FIG. 18I).

Figure 19:
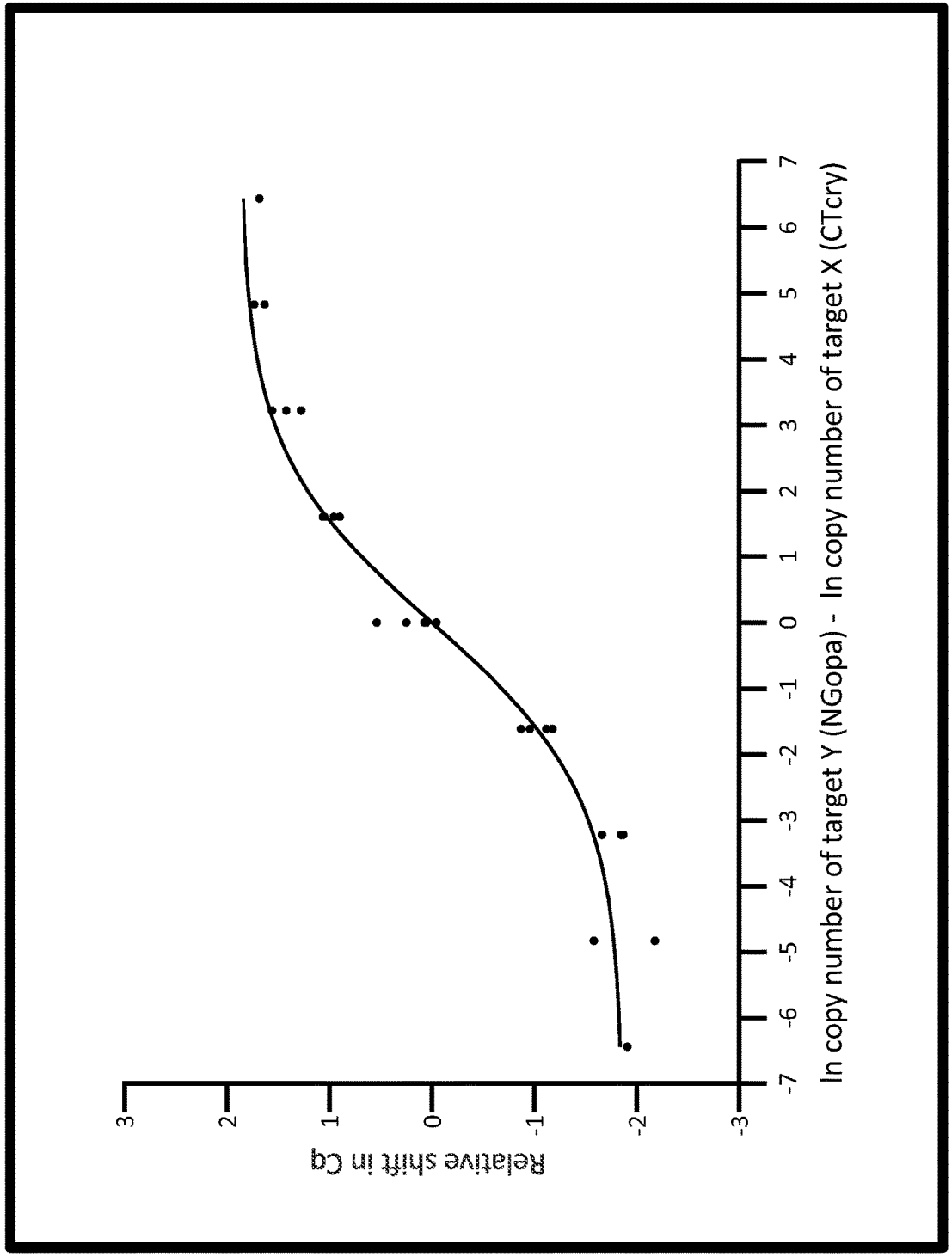

FIG. 19 illustrates the non-linear logistic regression for relative shift in Cq value plotted against ln copy number of target Y (NGopa)—ln copy number of target X (CTcry).

Figure 20:
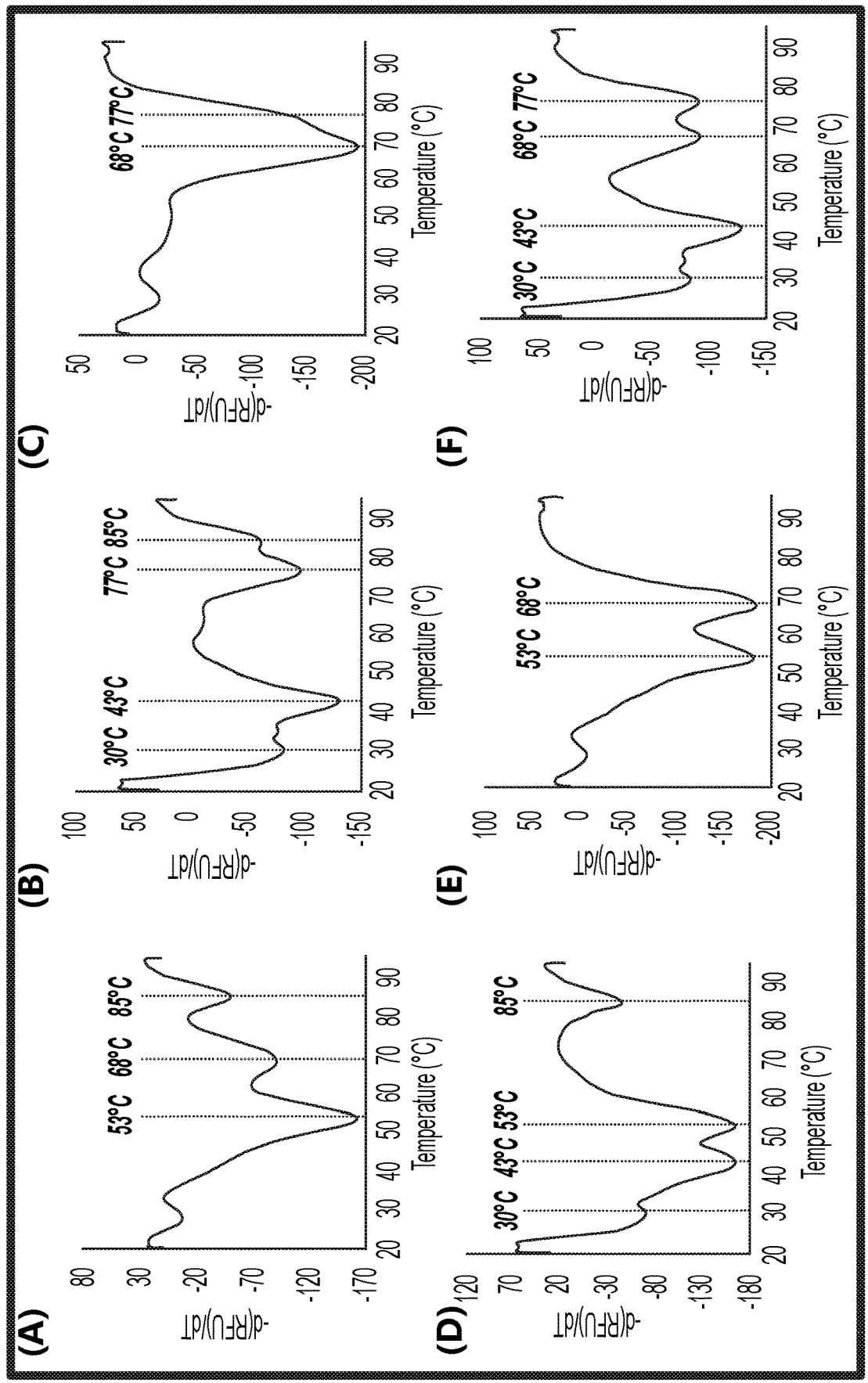

FIG. 20 illustrates the melt curve signatures obtained in the HEX channel from single-well, 6-plex reactions containing 10,000 copies of either gpd, gpd3 or porA gene targets. Using a single-well, six targets were specifically detected and differentiated using two fluorescent channels (three targets per channel). These targets were detected using six different MNAzymes which in turn cleaved and opened six different LOCS reporters. FIG. 20A: LOCS-21 in the presence of gpd (53° C., 68° C. and 85° C.), FIG. 20B: LOCS-22 in the presence of gpd3 (30° C., 43° C., 77° C. and 85° C.), FIG. 20C: LOCS-23 in the presence of porA (68° C. and 77° C.), FIG. 20D: LOCS-21 and LOCS-22 in the presence of gpd and gpd3 (30° C., 43° C., 53° C. and 85° C.), FIG. 20E: LOCS-21 and LOCS-23 in the presence of gpd and porA (53° C. and 68° C.), FIG. 20F: LOCS-22 and LOCS-23 in the presence of gpd3 and porA (30° C., 43° C., 68° C. and 77° C.).

Figure 21:
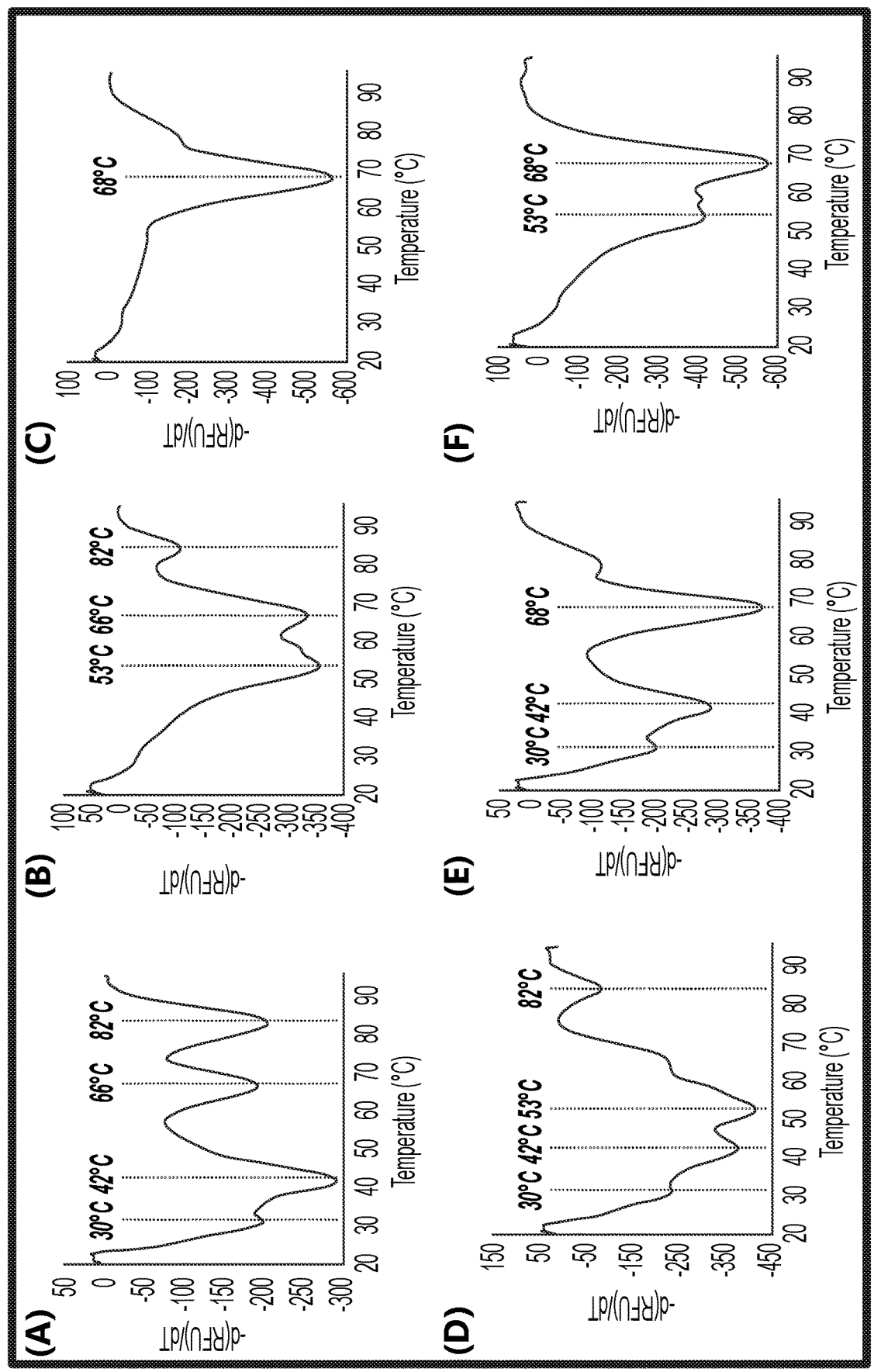

FIG. 21 illustrates the melt curve signatures obtained in the Texas Red channel from the same single-well, 6-plex reactions of FIG. 20 containing 10,000 copies of either TV-Btub, MgPa or LGV gene targets. In these reactions, six targets were specifically detected and differentiated using two fluorescent channels (three targets per channel). These targets were detected using six different MNAzymes which in turn cleaved and opened six different LOCS reporters monitored in HEX and Texas Red channels. FIG. 21A: melt curve signature produced by LOCS-24 in the presence of TV-Btub (30° C., 42° C., 66° C. and 82° C.), FIG. 21B: LOCS-25 in the presence of MgPa (53° C., 66° C. and 82° C.), FIG. 21C: LOCS-26 in the presence of LGV (68° C.), FIG. 21D: LOCS-24 and LOCS-25 in the presence of TV-Btub and MgPa (30° C., 42° C., 53° C. and 82° C.), FIG. 21E: LOCS-24 and LOCS-26 in the presence of TV-Btub and LGV (30° C., 42° C. and 68° C.), FIG. 21F: LOCS-25 and LOCS-26 in the presence of MgPa and LGV (30° C., 43° C., 53° C. and 68° C.).

Figure 22:
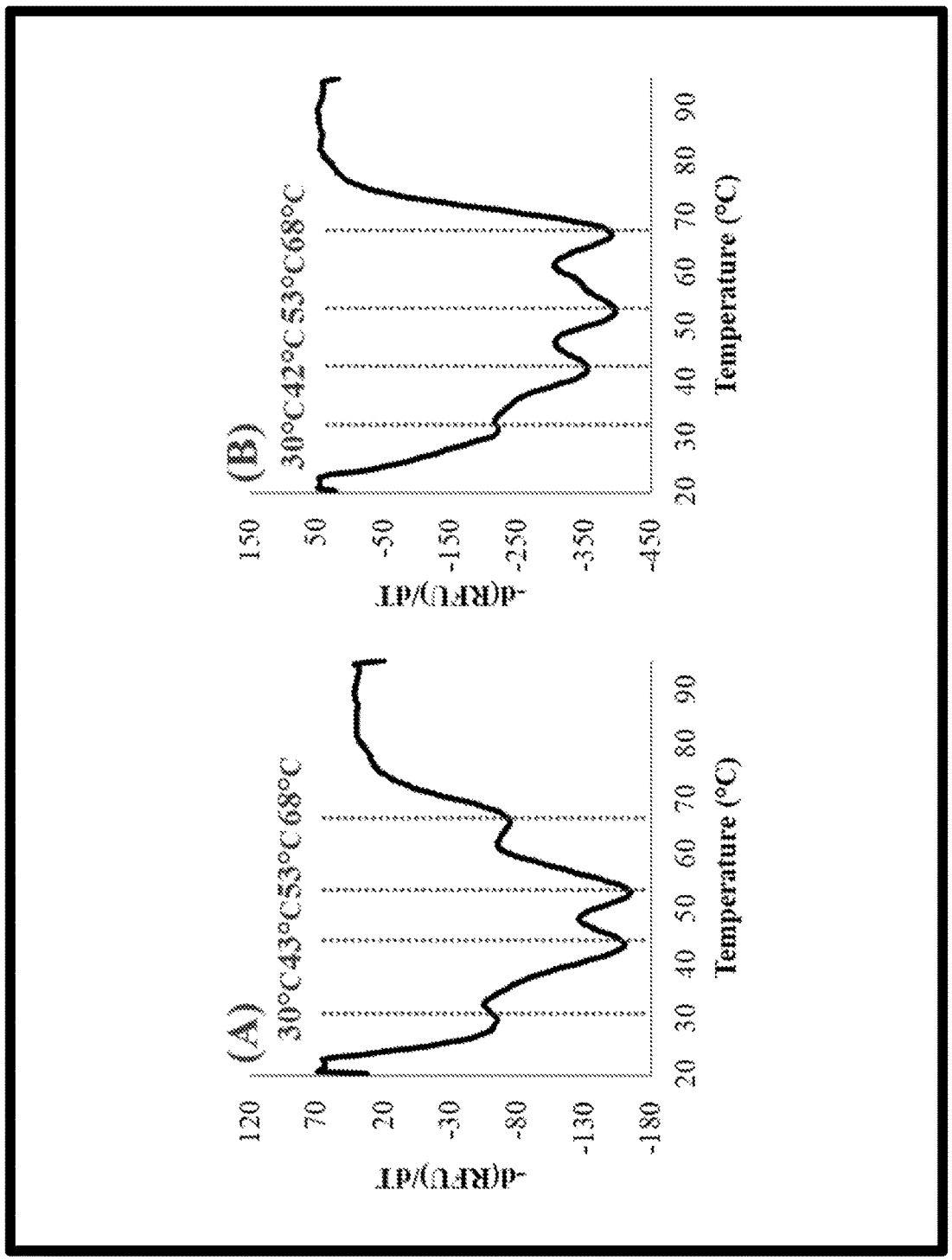

FIG. 22 illustrates the melt curve signatures obtained post PCR amplification from the same 6-plex reactions as FIGS. 20 and 21 containing 10,000 copies each of gpd, gpd3 and porA (FIG. 22A) or 10,000 copies each of TV-Btub, MgPa and LGV gene targets (FIG. 22B). These targets were detected using six MNAzymes, which in turn cleaved and opened six LOCS reporters, which were monitored in two fluorescent channels. FIG. 22A: Melt signature generated in the HEX channel by LOCS-21, LOCS-22 and LOCS-23 in the presence of gpd, gpd3 and porA gene targets (30° C., 43° C., 53° C. and 68° C.). FIG. 22B: Melt signature generated in the TEXAS RED channel by LOCS-24, LOCS-25 and LOCS-26 in the presence of TV-Btub, MgPa and LGV (30° C., 42° C., 53° C. and 68° C.).

FIG. 23 illustrates the melt curve signatures obtained post PCR amplification from 10-plex reactions containing 10,000 copies of either NGopa, porA, gpd, gpd3, TV-Btub, MgPa, CTcry, LGV, polA or TFRC gene targets. The ten gene targets were specifically detected using ten different MNAzymes, in turn these MNAzymes cleaved and opened ten different LOCS reporters which were monitored in five fluorescent channels (FAM, HEX, Texas Red, Cy5 and Cy5.5). Differentiation of targets within the FAM channel is shown by FIG. 23A: LOCS-15 in the presence of NGopa (53° C.), FIG. 23B: LOCS-27 in the presence of porA (30° C. and 76° C.) and FIG. 23C: LOCS-15 and LOCS-27 in the presence of both NGopa and porA (30° C. and 53° C.). Differentiation of targets within the HEX channel is shown by FIG. 23D: LOCS-21 in the presence of gpd (53° C. and 70° C.), FIG. 23E: LOCS-22 in the presence of gpd3 (30° C., 43° C. and 76° C.) and FIG. 23F: LOCS-21 and LOCS-22 in the presence of both gpd and gpd3 gene targets (30° C., 43° C. and 53° C.). Differentiation of targets within the Texas Red channel is shown by FIG. 23G: LOCS-24 in the presence of TV-Btub (31° C., 41° C., 59° C. and 83° C.), FIG. 23H: LOCS-28 in the presence of MgPa (63° C.) and FIG. 23I: LOCS-24 and LOCS-28 in the presence of both TV-Btub and MgPa (31° C., 41° C. and 63° C.). Differentiation of targets within the Cy5 channel is shown by FIG. 23J: LOCS-29 in the presence of CTcry (61° C. and 79° C.), FIG. 23K: LOCS-10 in the presence of LGV (47° C. and 80° C.) and FIG. 23L: LOCS-29 and LOCS-10 in the presence of both CTcry and LVG (47° C. and 61° C.). Differentiation of targets within the Cy5.5 channel is shown by FIG. 23M: LOCS-30 and LOCS-31 in the presence of both polA and TFRC gene targets (39° C. and 59'C) and FIG. 23N: LOCS-31 in the presence of TFRC gene (39° C. and 80° C.).

Figure 24:
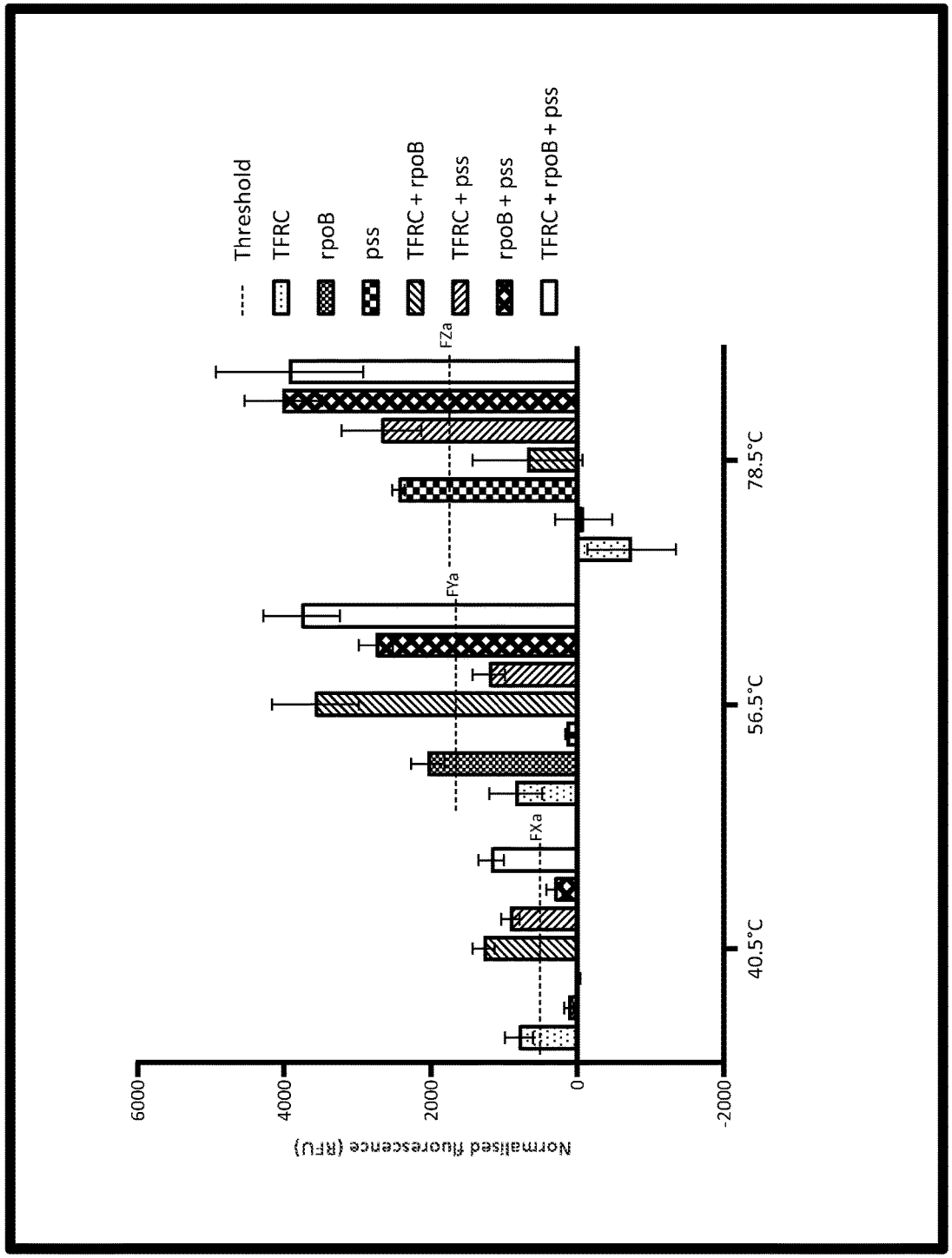

FIG. 24 illustrates the comparative analysis of the differential fluorescence level between pre- and post-amplification obtained in the JOE channel from reactions containing 10,000 copies of TFRC, rpoB, pss or all combinations of two or more gene targets, measured at 40.5° C., 56.5° C. and 78.5° C. expressed as averages of the fluorescence level from triplicate reactions subtracted by the average from triplicate reactions of the no template control. The error bar is the standard deviation of each triplicate.

Figure 25:
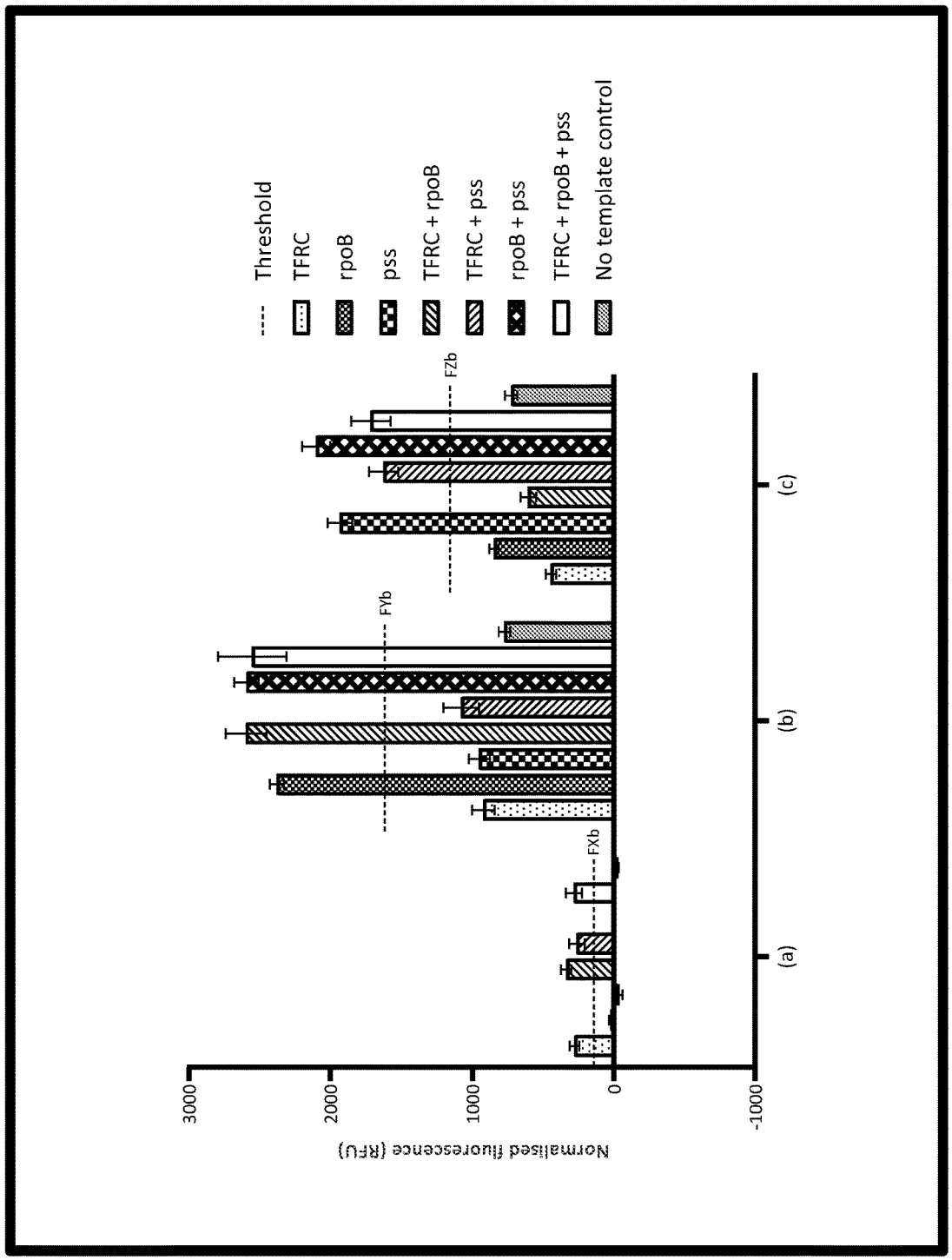

FIG. 25 illustrates the comparative differential post-amplification fluorescence level obtained in the JOE channel from reactions containing 10,000 copies of TFRC, rpoB, pss or all combinations of two or more gene targets, measured at 32° C., 40.5° C., 56.5° C. and 65.5° C. The values were expressed as the differential fluorescence level between (a) 32° C. and 40.5° C.; (b) 40.5° C. and 56.5° C.; and (c) 56.5° C. and 65° C., averaging from triplicate reactions. The error bar is the standard deviation of each triplicate.

Figure 26:
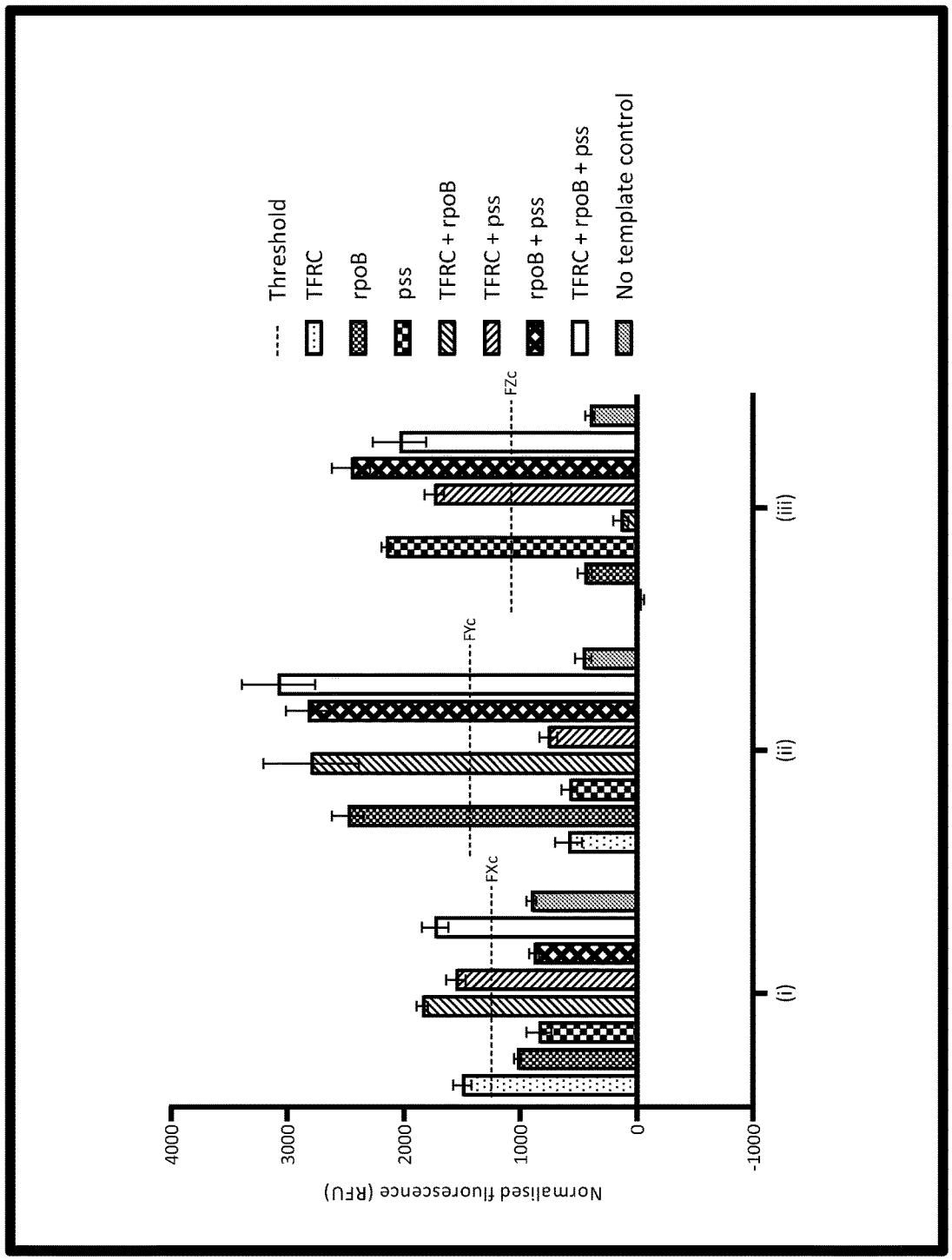

FIG. 26 illustrates the comparative analysis of differential pre- and post-amplification fluorescence level obtained in the JOE channel from reactions containing 10,000 copies of TFRC, rpoB, pss or all combinations of two or more gene targets, measured at 39.5° C., 56.5° C. and 65.5° C. The values were expressed as (i) the difference between pre- and post-amplification fluorescence level at 39.5° C. (ii) difference between the difference of pre- and post-amplification fluorescence level at 39.5° C. and the difference of pre- and post-amplification fluorescence level at 56.5° C. and (iii) difference between the difference of pre- and post-amplification fluorescence level at 56.5° C. and the difference of pre- and post-amplification fluorescence level at 65.5° C., averaging from triplicate reactions. The error bar is the standard deviation of each triplicate.

Figure 27:
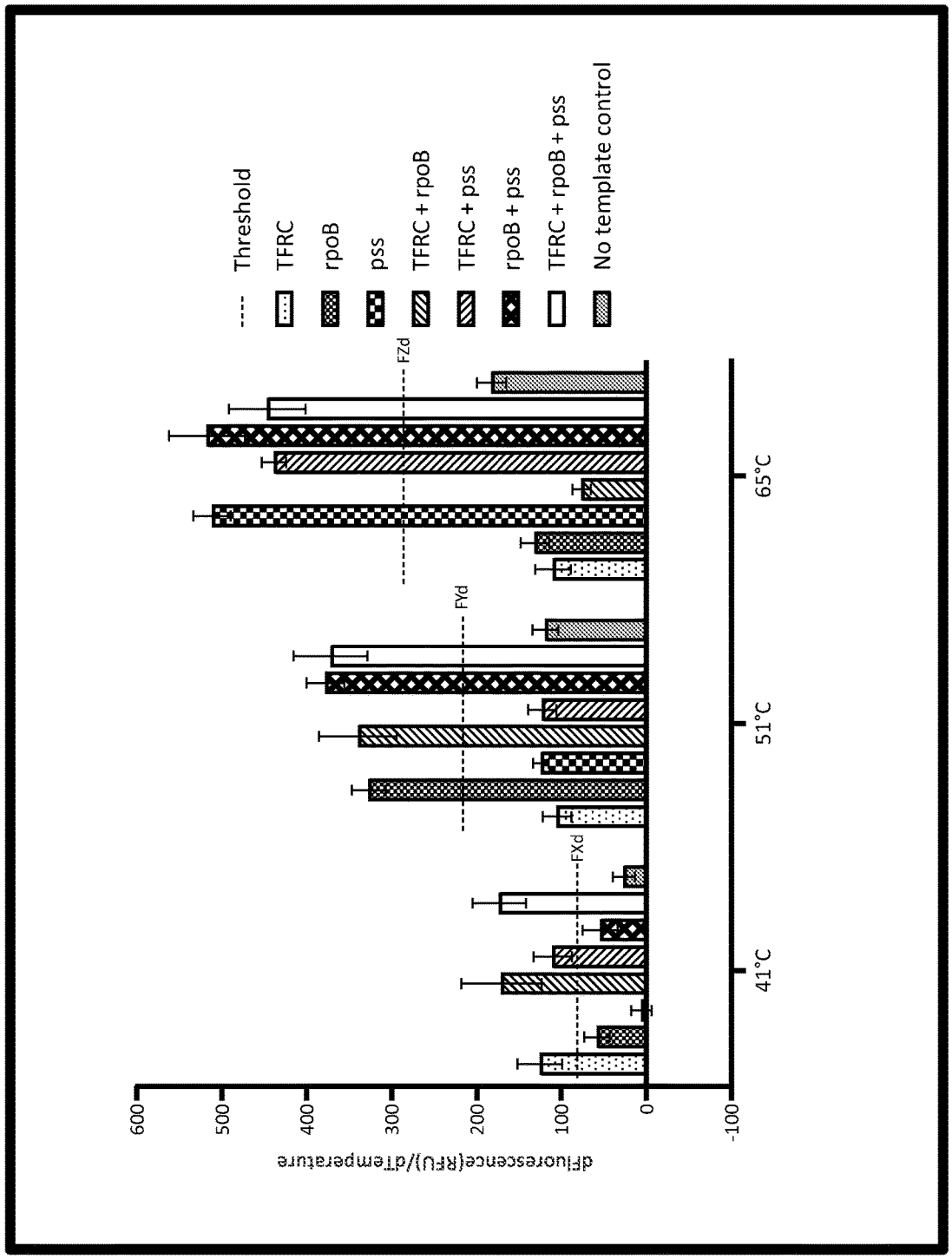

FIG. 27 illustrates the comparative melt peak height at 40° C., 51° C. and 65° C. obtained in the JOE channel from reactions containing 10,000 copies of TFRC, rpoB, pss or all combinations of two or more gene targets, averaging from triplicate reactions. The error bar is the standard deviation of each triplicate.

DEFINITIONS

As used in this application, the singular form "a", "an" and "the" include plural references unless the context clearly dictates otherwise. For example, the phrase "polynucleotide" also includes a plurality of polynucleotides.

As used herein, the term "comprising" means "including". Variations of the word "comprising", such as "comprise" and "comprises," have correspondingly varied meanings. Thus, for example, a polynucleotide "comprising" a sequence of nucleotides may consist exclusively of that sequence of nucleotides or may include one or more additional nucleotides.

As used herein the term "plurality" means more than one. In certain specific aspects or embodiments, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

As used herein, the term "subject" includes any animal of economic, social or research importance including bovine, equine, ovine, primate, avian and rodent species. Hence, a "subject" may be a mammal such as, for example, a human or a non-human mammal. Also encompassed are microorganism subjects including, but not limited to, bacteria, viruses, fungi/yeasts, protists and nematodes. A "subject" in accordance with the presence invention also includes infectious agents such as prions.

As used herein, the terms "polynucleotide" and "nucleic acid" may be used interchangeably and refer to a single- or double-stranded polymer of deoxyribonucleotide or ribonucleotide bases, or analogues, derivatives, variants, fragments or combinations thereof, including but not limited to DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof. By way of non-limiting example, the source of a nucleic acid may be selected from the group comprising synthetic, mammalian, human, animal, plant, fungal, bacterial, viral, archael or any combination thereof. The terms "polynucleotide" and M "nucleic acid" "oligonucleotide" include reference to any specified sequence as well as to the sequence complementary thereto, unless otherwise indicated.

As used herein, the term "target" refers to any molecule or analyte present in a sample that the methods of the present invention may be used to detect. The term "target" will be understood to include nucleic acid targets, and non-nucleic acid targets such as, for example proteins, peptides, analytes, ligands, and ions (e.g. metal ions).

As used herein, the term "oligonucleotide" refers to a segment of DNA or a DNA-containing nucleic acid molecule, or RNA or RNA-containing molecule, or a combination thereof. Examples of oligonucleotides include nucleic acid targets; substrates, for example, those which can be modified by an MNAzyme; primers such as those used for in vitro target amplification by methods such as PCR; and components of MNAzymes. The term "oligonucleotide" includes reference to any specified sequence as well as to the sequence complementary thereto, unless otherwise indicated. Oligonucleotides may comprise at least in one addition or substitution, including but not limited to the group comprising 4-acetylcytidine, 5-(carboxyhydroxylmethyl) uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta D-mannosylmethyluridine, 5-methoxycarbonylmethyluridine, 5-methoxyuridine, 2-methylthio-N6-isopentenyladenosine, N-((9-beta-ribofuranosyl-2-methylthiopurine-6-yl)carbamoyl)threonine, N-((9-beta-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl)threonine, 2'-O-methyl-5-methyluridine, 2'-O-methyluridine, wybutosine, 3-(3-amino-3-carboxypropyl)uridine, beta D-arabinosyl uridine, beta D-arabinosyl thymidine.

As used herein, the terms "complementary", "complementarity", "match" and "matched" refer to the capacity of nucleotides (e.g. deoxyribonucleotides, ribonucleotides or combinations thereof) to hybridise to each other via either Watson-Crick base-pairing or wobble base pairing. Bonds can be formed via Watson-Crick base-pairing between adenine (A) bases and uracil (U) bases, between adenine (A)

bases and thymine (T) bases, between cytosine (C) bases and guanine (G) bases. A wobble base pair is a non-Watson-Crick base pairing between two nucleotides in a polynucleotide duplex (e.g. guanine-uracil, inosine-uracil, inosine-adenine, and inosine-cytosine). Nucleotides referred to as "complementary" or that are the "complement" of each other are nucleotides which have the capacity to hybridise together by either Watson-Crick base pairing or by wobble base pairing between their respective bases.

As used herein, the terms "non-complementary", "not complementary", "mismatch" and "mismatched" refer to nucleotides (e.g. deoxyribonucleotides, ribonucleotides, and combinations thereof) that lack the capacity to hybridize together by either Watson-Crick base pairing or by wobble base pairing between their respective bases.

As used herein, an "enzyme" refers to any molecule which can catalyze a chemical reaction (e.g. amplification of a polynucleotide, cleavage of a polynucleotide etc.). Non-limiting examples of enzymes suitable for use in the present invention include nucleic acid enzymes and protein enzymes. Non-limiting examples of suitable nucleic acid enzymes include RNAzymes, MNAzymes and DNAzymes. Non-limiting examples of suitable protein enzymes include exonucleases and endonucleases. The enzymes will generally provide catalytic activity that assists in carrying out one or more of the methods described herein. By way of non-limiting example, the exonuclease activity may be an inherent catalytic activity of, for example, a polymerase. By way of non-limiting example, the endonuclease activity may be an inherent catalytic activity of, for example, a restriction enzyme including a Nicking endonuclease, a riboendonuclease or a duplex specific nuclease (DSN).

As used herein, an "amplicon" refers to nucleic acid (e.g. DNA or RNA, or a combination thereof) that is a product of natural or artificial nucleic acid amplification or replication events including, but not limited to, PCR, RT-PCR, SDA, HDA, RPA, LAMP, RCA, TMA, 3SR or NASBA.

As used herein, the term "stem-loop oligonucleotide" will be understood to mean a DNA or DNA-containing molecule, or an RNA or RNA-containing molecule, or a combination thereof (i.e. DNA-RNA hybrid molecule or complex), comprising or consisting of a double-stranded stem component joined to a single-stranded loop component. The double-stranded stem component comprises a forward strand hybridised by complementary base pairing to a complementary reverse strand, with the 3' nucleotide of the forward strand joined to the 5' nucleotide of the single-stranded loop component, and the 5' nucleotide of the reverse strand joined to the 3' nucleotide of the single-stranded loop component. The double-stranded stem component may further comprise one or more ituorophores on one strand (e.g. the forward strand), and one or more quenchers on the opposing strand (e.g. the reverse strand).

As used herein, the terms "stein-loop oligonucleotide" and "LOCS", also referred to herein as a "LOCS oligonucleotide", "LOCS structure" "LOCS reporter", "Intact LOCS", "Closed LOCS" and "LOCS probes", are used herein interchangeably and will be understood to mean a DNA or DNA-containing molecule, or an RNA or RNA-containing molecule, or a combination thereof (i.e. DNA-RNA hybrid molecule or complex), comprising or consisting of a double-stranded stem component (also referred to herein as "stem", "stem region" and "stem portion") joined to a single-stranded loop component (also referred to herein as "loop", "loop region" and "loop portion"). The double-stranded stem component comprises a forward strand hybridised by complementary base pairing to a complementary reverse strand, with the 3' nucleotide of the forward strand joined to the 5' nucleotide of the single-stranded loop component, and the 5' nucleotide of the reverse strand joined to the 3' nucleotide of the single-stranded loop component.

The double-stranded stem component may further comprise one or more fluorophores on one strand (e.g. the forward strand), and one or more quenchers on the opposing strand (e.g. the reverse strand). For example, the fluorophore(s) may be attached at or near the 5' terminus of the forward strand and the quencher(s) attached at or near the 3' terminus of the reverse strand, or vice versa. The single-stranded loop component may comprise a region capable of serving as a substrate for a catalytic nucleic acid such as, for example, an MNAzyme, a DNAzyme, a ribozyme, an apta-MNAzyme, or an aptazyme. Additionally or alternatively, the single-stranded loop component may comprise a region which is complementary to a target nucleic acid (e.g. a target for detection, quantification and the like), and/or amplicons derived therefrom, and which may further be capable of serving as a substrate for an exonuclease enzyme. By way of non-limiting example, the exonclease may be an inherent activity of a polymerase enzyme. Additionally or alternatively, the single-stranded loop component region may comprise a region which may: (i) be complementary to the target being detected, (ii) comprise one strand of a double stranded restriction enzyme recognition site; and (iii) be capable of serving as a substrate for a restriction enzyme.

As used herein, the terms "open stem-loop oligonucleotide", "open LOCS", "open LOCS oligonucleotide", "open LOCS structure" "open LOCS reporters", "open LOCS probes", "opened LOCS", "cleaved LOCS" and "degraded LOCS" are used herein interchangeably and will be understood to be a reference to a "stem-loop oligonucleotide" or "LOCS" in which the single-stranded loop component has been cleaved and/or degraded (e.g. by an enzyme as described herein) such that at least one bond between adjacent nucleotides within the loop is removed, thereby providing an open structure in the loop region. In open LOCS, the forward and reverse strands of the double-stranded stein portion may retain the ability to hybridise to each other to form a stem.

As used herein, the term "universal stem" refers to a double stranded sequence which can be incorporated into any LOCS structure. The same "universal stem" may be used in LOCS which contain Loops which comprise either catalytic nucleic acid substrates or sequence which is complementary to a target of interest. A single universal stem can be used as a surrogate marker for any target which is capable of facilitating the opening of a specific LOCS. A series of universal stems can be incorporated into a series of LOCS designed for analysis of any set of targets.

As used herein, the term "universal LOCS" refers to a LOCS structure which contains a "universal stem", and a "universal Loop" which comprises a universal catalytic nucleic acid substrate which can be cleaved by any MNAzyme with complementary substrate binding arms regardless of the sequences of the MNAzyme target sensing arms. A single universal LOCS can be used as a surrogate marker for any target which is capable of facilitating the opening of a specific LOCS. A series of universal LOCS can be incorporated into any multiplex assay designed to analyse any set of targets.

As used herein, the terms "nucleic acid enzyme", "catalytic nucleic acid", "nucleic acid with catalytic activity", and "catalytic nucleic acid enzyme" are used herein interchangeably and shall mean a DNA or DNA-containing molecule or complex, or an RNA or RNA-containing molecule or complex, or a combination thereof (i.e. DNA-RNA hybrid molecule or complex), which may recognize at least one substrate and catalyse a modification (such as cleavage) of the at least one substrate. The nucleotide residues in the catalytic nucleic acids may include the bases A, C, G, T, and U, as well as derivatives and analogues thereof. The terms above include uni-molecular nucleic acid enzymes which may comprise a single DNA or DNA-containing molecule (also known in the art as a "DNA enzyme", "deoxyribozyme" or "DNAzyme") or an RNA or RNA-containing molecule (also known in the art as a "ribozyme") or a combination thereof, being a DNA-RNA hybrid molecule which may recognize at least one substrate and catalyse a modification (such as cleavage) of the at least one substrate. The terms above include nucleic acid enzymes which comprise a DNA or DNA-containing complex or an RNA or RNA-containing complex or a combination thereof, being a DNA-RNA hybrid complex which may recognize at least one substrate and catalyse a modification (such as cleavage) of the at least one substrate. The terms "nucleic acid enzyme", "catalytic nucleic acid", "nucleic acid with catalytic activity", and "catalytic nucleic acid enzyme" include within their meaning MNAzymes.

As used herein, the terms "MNAzyme" and "multi-component nucleic acid enzyme" as used herein have the same meaning and refer to two or more oligonucleotide sequences (e.g. partzymes) which, only in the presence of an MNAzyme assembly facilitator (for example, a target), form an active nucleic acid enzyme that is capable of catalytically modifying a substrate. An "MNAzyme" is also known in the art as a "PlexZyme". MNAzymes can catalyse a range of reactions including cleavage of a substrate, and other enzymatic modifications of a substrate or substrates. MNAzymes with endonuclease or cleavage activity are also known as "MNAzyme cleavers". Component partzymes, partzymes A and B each of bind to an assembly facilitator (e.g. a target DNA or RNA sequence) through Watson-Crick base pairing. The MNAzyme only forms when the sensor arms of partzymes A and B hybridize adjacent to each other on the assembly facilitator. The substrate arms of the MNAzyme engage the substrate, the modification (e.g. cleavage) of which is catalyzed by the catalytic core of the MNAzyme, formed by the interaction of the catalytic domains of partzymes A and B. MNAzymes may cleave DNA/RNA chimeric reporter substrates. MNAzyme cleavage of a substrate between a fluorophore and a quencher dye pair may generate a fluorescent signal. The terms "multi-component nucleic acid enzyme" and "MNAzyme" comprise bipartite structures, composed of two molecules, or tripartite structures, composed of three nucleic acid molecules, or other multipartite structures, for example those formed by four or more nucleic acid molecules.

It will be understood that the terms "MNAzyme" and "multi-component nucleic acid enzyme" as used herein encompass all known MNAzymes and modified MNAzymes including those disclosed in any one or more of PCT patent publication numbers WO/2007/041774, WO/2008/040095, WO2008/122084, and related US patent publication numbers 2007-0231810, 2010-0136536, and 2011-0143338 (the contents of each of these documents are incorporated herein by reference in their entirety). Non-limiting examples of MNAzymes and modified MNAzymes encompassed by the terms "MNAzyme" and "multi-component nucleic acid enzyme" include MNAzymes with cleavage catalytic activity (as exemplified herein), disassembled or partially assembled MNAzymes comprising one or more assembly inhibitors, MNAzymes comprising one or more aptamers ("apta-MNAzymes"), MNAzymes comprising one or more truncated sensor arms and optionally one or more stabilizing oligonucleotides, MNAzymes comprising one or more activity inhibitors, multi-component nucleic acid inactive proenzymes (MNAi), each of which is described in detail in one or more of WO/2007/041774, WO/2008/040095, US 2007-0231810, US 2010-0 136536, and/or US 2011-0143338.

As used herein, the terms "partzyme", "component partzyme" and "partzyme component" refer to a DNA-containing or RNA-containing or DNA-RNA-containing oligonucleotide, two or more of which, only in the presence of an MNAzyme assembly facilitator as herein defined, can together form an "MNAzyme." In certain preferred embodiments, one or more component partzymes, and preferably at least two, may comprise three regions or domains: a "catalytic" domain, which forms part of the catalytic core that catalyzes a modification; a "sensor arm" domain, which may associate with and/or bind to an assembly facilitator; and a "substrate arm" domain, which may associate with and/or bind to a substrate. The terms "sensor arm", "target sensor arm" or "target sensing arm" or "target arm" may be used interchangeably to describe the domain of the partzymes which binds to the assembly facilitator, for example the target. Partzymes may comprise at least one additional component including but not limited to an aptamer, referred to herein as an "apta-partzyme." A partzyme may comprise multiple components, including but not limited to, a partzyme component with a truncated sensor arm and a stabilizing arm component which stabilises the MNAzyme structure by interacting with either an assembly facilitator or a substrate.

The terms "assembly facilitator molecule", "assembly facilitator", "MNAzyme assembly facilitator molecule", and "MNAzyme assembly facilitator" as used herein refer to entities that can facilitate the self-assembly of component partzymes to form a catalytically active MNAzyme by interaction with the sensor arms of the MNAzyme. As used herein, assembly facilitators may facilitate the assembly of MNAzymes which have cleavage or other enzymatic activities. In preferred embodiments an assembly facilitator is required for the self-assembly of an MNAzyme. An assembly facilitator may be comprised of one molecule, or may be comprised of two or more "assembly facilitator components" that may pair with, or bind to, the sensor arms of one or more oligonucleotide "partzymes". The assembly facilitator may comprise one or more nucleotide component/s which do not share sequence complementarity with sensor arm/s of the MNAzyme. The assembly facilitator may be a target. The target may be a nucleic acid selected from the group consisting of DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof. The nucleic acid may be amplified. The amplification may comprise one or more of: PCR, RT-PCR, SDA, HDA, RPA, LAMP, RCA, TMA, 3SR, or NASBA.

The term "detectable effect" as used herein is an effect that can be detected or quantified as an indication that cleavage of LOCS probe/s has occurred. The magnitude of the effect may be indicative of the quantity of an input such as an assembly facilitator (e.g. a target). The detectable effect may be detected by a variety of methods, including fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, electrochemical methods, V, visible light or infra-red spectroscopy, enzymatic methods or any combination thereof.

The terms "polynucleotide substrate" and "substrate" as used herein include any single- or double-stranded polymer of deoxyribonucleotide or ribonucleotide bases, or analogues, derivatives, variants, fragments or combinations thereof, which is capable of being recognized, acted upon or modified by an enzyme including a catalytic nucleic acid enzyme. A "polynucleotide substrate" or "substrate" may be modified by various enzymatic activities including but not limited to cleavage. Cleavage or degradation of a "polynucleotide substrate" or "substrate" may provide a "detectable effect" for monitoring the catalytic activity of an enzyme. The "polynucleotide substrate" or "substrate" may be capable of cleavage or degradation by one or more enzymes including, but not limited to, catalytic nucleic acid enzymes such as MNAzymes, AptaMNAzymes, DNAzymes, Aptazymes, ribozymes and/or protein enzymes such as exonucleases or endonucleases.

A "reporter substrate" as used herein is a substrate that is particularly adapted to facilitate measurement of either cleavage of a substrate or the appearance of a cleaved product in connection with a catalyzed reaction. Reporter substrates can be free in solution or bound (or "tethered"), for example, to a surface, or to another molecule. A reporter substrate can be labelled by any of a large variety of means including, for example, fluorophores (with or without one or more additional components, such as quenchers), radioactive labels, biotin (e.g. biotinylation) or chemiluminescent labels.

As used herein, a "universal substrate" is a substrate, for example, a reporter substrate, that is recognized by and acted on catalytically by a plurality of MNAzymes, each of which can recognize a different assembly facilitator. The use of such substrates facilitates development of separate assays for detection, identification or quantification of a wide variety of assembly facilitators using structurally related MNAzymes all of which recognize a universal substrate. These universal substrates can each be independently labelled with one or more labels. In preferred embodiments, independently detectable labels are used to label one or more universal substrates to allow the creation of a convenient system for independently or simultaneously detecting a variety of assembly facilitators using MNAzymes. In some embodiments the substrates may be capable of catalytic modification by DNAzymes which are catalytically active in the presence of a cofactor, for example a metal ion co-factor such as lead or mercury.

The terms "probe" as used herein refers to an oligonucleotide that is used for detection of a target nucleic acid. Non-limiting examples of probes include TaqMan probes; Molecular Beacon probes; and LOCS probes comprising nucleic acid enzyme substrates within the loop regions which are capable of catalytic cleavage by a nucleic acid enzyme.

The term "product" refers to the new molecule or molecules that are produced as a result of enzymatic modification of a substrate. As used herein the term "cleavage product" refers to a new molecule produced as a result of cleavage or endonuclease activity by an enzyme. In some embodiments, the products of enzymatic cleavage or degradation of an intact, closed LOCS structure comprise two oligonucleotide fragments capable of hybridization to form an open LOCS structure.

As used herein, use of the terms "melting temperature" and "Tm" in the context of a polynucleotide will be understood to be a reference to the melting temperature (Tm) as calculated using the Wallace rule, whereby Tm=2° C. (A+T)+4° C. (G+C) (see Wallace et al., (1979) Nucleic Acids Res. 6, 3543), unless specifically indicated otherwise. The effects of sequence composition on the melting temperature can be understood using the nearest neighbour method, which is governed by the following formula: Tm (° C.)=$\Delta H°/(\Delta S°+R \ln[\text{oligo}])-273.15$. In addition to stem length and sequence composition, other factors that are known to impact the melting temperature include ionic strength and oligonucleotide concentration. A higher oligonucleotide and/or ion concentration increases the chance of duplex formation which leads to an increase in melting temperature. In contrast, a lower oligonucleotide and/or ion concentration favours dissociation of the stem which leads to a decrease in melting temperature.

As used herein the term "quencher" includes any molecule that when in close proximity to a fluorophore, takes up emission energy generated by the fluorophore and either dissipates the energy as heat or emits light of a longer wavelength than the emission wavelength of the fluorophore. Non-limiting examples of quenchers include Dabcyl, TAMRA, graphene, FRET fluorophores, ZEN quenchers, ATTO quenchers, Black Hole Quenchers (BHQ) and Black Berry Quenchers (BBQ).

As used herein, the term "base" when used in the context of a nucleic acid will be understood to have the same meaning as the term "nucleotide".

As used herein, the term "kit" refers to any delivery system for delivering materials. Such delivery systems include systems that allow for the storage, transport, or delivery of reaction reagents (for example labels, reference samples, supporting material, etc. in the appropriate containers) and/or supporting materials (for example, buffers, written instructions for performing an assay etc.) from one location to another. For example, kits may include one or more enclosures, such as boxes, containing the relevant reaction reagents and/or supporting materials. The term "kit" includes both fragmented and combined kits.

As used herein, the term "fragmented kit" refers to a delivery system comprising two or more separate containers that each contains a subportion of the total kit components. The containers may be delivered to the intended recipient together or separately. Any delivery system comprising two or more separate containers that each contains a subportion of the total kit components are included within the meaning of the term "fragmented kit".

As used herein, a "combined kit" refers to a delivery system containing all of the components of a reaction assay in a single container (e.g. in a single box housing each of the desired components).

It will be understood that use the term "about" herein in reference to a recited numerical value includes the recited numerical value and numerical values within plus or minus ten percent of the recited value.

It will be understood that use of the term "between" herein when referring to a range of numerical values encompasses the numerical values at each endpoint of the range. For example, a polypeptide of between 10 residues and 20 residues in length is inclusive of a polypeptide of 10 residues in length and a polypeptide of 20 residues in length.

Any description of prior art documents herein, or statements herein derived from or based on those documents, is not an admission that the documents or derived statements are part of the common general knowledge of the relevant art.

For the purposes of description all documents referred to herein are hereby incorporated by reference in their entirety unless otherwise stated.

Abbreviations

The following abbreviations are used herein and throughout the specification:
LOCS: loop connected to stems
MNAzyme: multi-component nucleic acid enzyme, or multipartite nucleic acid enzyme;
Partzyme: Partial enzyme containing oligonucleotide;
PCR: polymerase chain reaction;
gDNA: genomic DNA
NTC: No template control
qPCR: Real-time quantitative PCR
Ct: Threshold cycle
$R^2$; Correlation coefficient
nM; Nanomolar
mM: Millimolar
μL; Microlitre
dNTP; Deoxyribonucleotide triphosphate
NF-$H_2O$: nuclease-free water;
LNA: locked nucleic acid;
F: fluorophore;
Q: quencher;
N=A, C, T, G, or any analogue thereof;
N'=any nucleotide complementary to N, or able to base pair with N;
$(N)_x$: any number of N;
$(N')_x$: any number of N';
W: A or T;
R: A, G, or AA;
rN: any ribonucleotide base;
$(rN)_x$: any number of rN;
rR: A or G;
rY: C or U;
M: A or C;
H: A, C, or T;
D: G, A, or T;
JOE or 6-JOE: 6-carboxy-4',5'-dichloro-2',7'-dimethoxyfluorescein;
FAM or 6-FAM: 6-Carboxyfluorescein.
BHQ1: Black Hole Quencher 1
BHQ2: Black Hole Quencher 2
RT-PCR: reverse transcription polymerase chain reaction
SDA: strand displacement amplification
HDA: helicase dependent amplification
RPA: Recombinase Polymerase Amplification
LAMP: loop-mediated isothermal amplification
RCA: rolling circle amplification
TMA: transcription-mediated amplification
3SR: self-sustained sequence replication
NASBA: nucleic acid sequence based amplification
IB: Iowa Black® FQ
IBR: Iowa Black® RQ
shRNA: short hairpin RNA
siRNA: short interfering RNA
mRNA: messenger RNA
tRNA: transfer RNA
snoRNA: small nucleolar RNA
stRNA: small temporal RNA
smRNA: small modulatory RNA
pre-microRNA: precursor microRNA
pri-microRNA: primary microRNA
LHS: Left hand side
RHS: Right hand side
DSO: double stranded oligonucleotide
Tm: Melting Temperature
RFU: Relative Fluorescence Units

DETAILED DESCRIPTION

The following detailed description conveys exemplary embodiments of the present invention in sufficient detail to enable those of ordinary skill in the art to practice the present invention. Features or limitations of the various embodiments described do not necessarily limit other embodiments of the present invention or the present invention as a whole. Hence, the following detailed description does not limit the scope of the present invention, which is defined only by the claims.

The present invention relates to methods and compositions for the improved multiplexed detection of targets (e.g. nucleic acids, proteins, analytes, compounds, molecules and the like). The methods and compositions each employ LOCS oligonucleotides, which may be used in combination with various other agent/s.

LOCS Oligonucleotides

Figure 1:
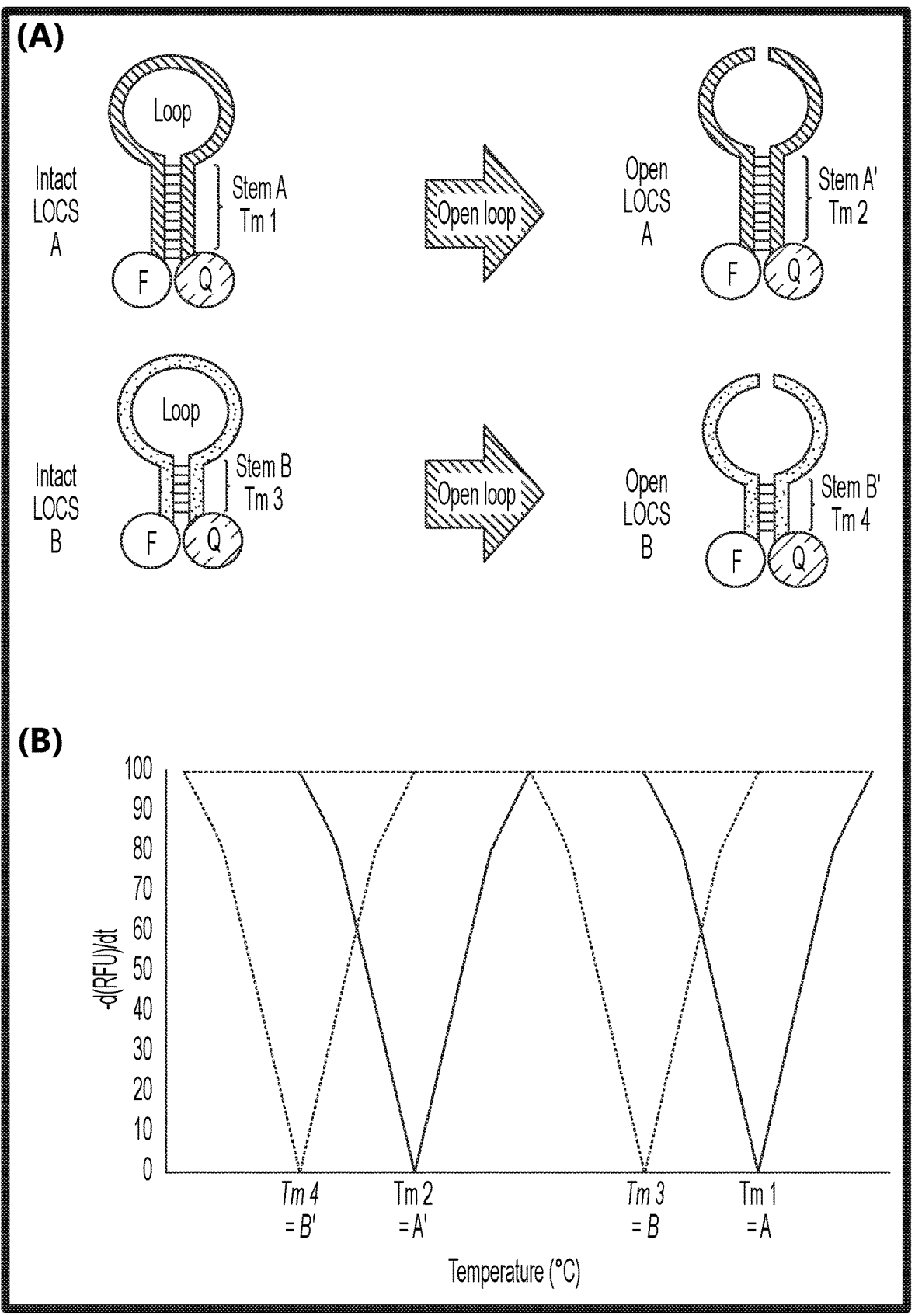
FIG. 1: Exemplary LOCS reporters and their melting temperatures (Tm) of intact closed, locked forms, and cleaved or degraded open forms are illustrated. Exemplary Intact (closed) LOCS (FIG. 1A, LHS) have a Loop region, a Stem region and fluorophore (F) quencher (Q) dye pair. Cleavage or degradation of the Loop region can produce Open LOCS reporter structures (FIG. 1A RHS). The melting temperatures (Tm) of the stem regions of Intact LOCS are higher than the Tm of the stein regions in Open LOCS structures. As such Stem A of LOCS A will separate or melt at Tm 1. This is higher than Tm 2, which is the temperature at which the Open LOCS stem A' melts (FIG. 1B). Similarly, the Tin of Stein B of Intact LOCS B will melt at Tm 3. This is higher than Tm 4 which is the temperature at which Open LOCS stem B' melts (FIG. 1B). The presence of a negative peak at the temperature which corresponds to the Tm of an open LOCS structure is indicative of the presence of the target which induces opening of the specific LOCS. Since each stem within each specific opened LOCS melts at a distinct temperature, multiple LOCS labelled with the same fluorophore can be analyzed simultaneously in a single reaction.

Exemplary LOCS oligonucleotides of the present invention are illustrated in FIG. 1. The exemplary intact (closed) LOCS oligonucleotides (FIG. 1A, LHS) have a Loop region, a Stem region and a fluorophore (F)/quencher (Q) dye pair. FIG. 1 illustrates two exemplary LOCS oligonucleotides denoted Intact LOCS A and Intact LOCS B. These LOCS oligonucleotides have different Loop sequences and different stem sequences. When used in combination two given LOCS oligonucleotides of the present invention will generally differ in the sequence and/or length of the stem. By way of non-limiting example only, Stem A of Intact LOCS A may be designed to melt at a first temperature denoted Tm 1; whilst Stem B of Intact LOCS B may be designed to melt at a different temperature denoted Tm 3. Cleavage or degradation of the Loop regions of the Intact LOCS oligonucleotides results in Open LOCS structures (FIG. 1A, RHS).

Since intramolecular bonds are stronger than intermolecular bonds, the stem regions of the intact LOCS structures will generally melt at higher temperatures than the stems of the open, cleaved or degraded LOCS oligonucleotide structures. For example, Stem A of intact LOCS A will melt at Tm 1 which is higher than Tm 2 which is the temperature at which Open LOCS stem A' melts (FIG. 1B). Similarly, the melting temperatures of Stem B of intact LOCS B will melt at Tm 3 which is higher than Tm 4 which is the temperature at which Open LOCS stem B' melts (FIG. 1B). The presence of a peak (as detected, for example, by means of an associated fluorescent marker) at a temperature corresponding to a specific open LOCS structure is indicative of the presence of target, or target amplicons, which directs the opening of this specific LOCS structure. Since the stem of open LOCS A melts at a distinct temperature from open LOCS B (FIG. 1B), multiple open LOCS structures labelled with the same fluorophore, can be detected and analyzed simultaneously in a single reaction. Further, multiple open LOCS structures labelled with different fluorophores, can also be detected and analyzed simultaneously in a single reaction.

Figure 2:
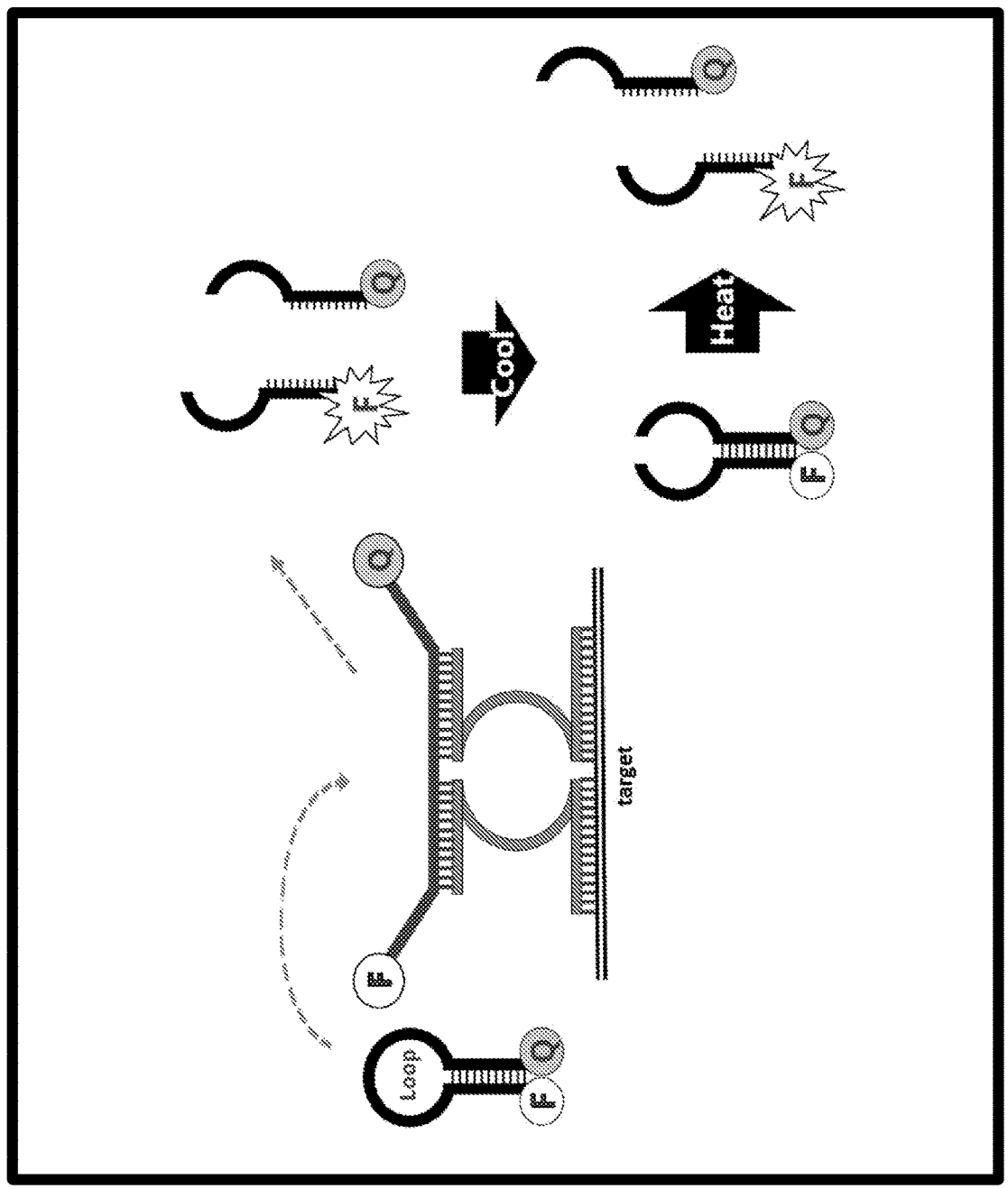
FIG. 2 illustrates an exemplary strategy for detection of a target using LOCS oligonucleotides which are universal and can be used to detect any target. In this scheme the LOCS oligonucleotide contains a stem region, a fluorophore quencher dye pair and a Loop region. The loop region comprises a universal substrate for a catalytic nucleic acid such as an MNAzyme, also known in the art as a PlexZyme. MNAzymes form when target sensor arms of component partzymes align adjacently on a target. The Loop region of the LOCS oligonucleotide binds to the substrate binding arms of the MNAzyme and the substrate within the Loop is cleaved by the MNAzyme and a fluorescent signal is generated. The reaction may be cooled allowing the stem region of the opened LOCS to re-anneal and the reaction may then be subjected to melt curve analysis whereby the fluorescence is monitored as the reaction is heated. The presence of a melt peak corresponding to the Tm of the open LOCS indicates the presence of the target which assembled the MNAzyme. The target can be directly detected, or target amplicons, produced by target amplification protocols, can be detected.

Referring now to the exemplary embodiment depicted in FIG. 2, the sequence of the Loop region of a LOCS oligonucleotide may be, for example, a substrate for a MNAzyme or other catalytic nucleic acid/s. In further embodiments, illustrated in FIG. 3A and FIG. 3B, the Loop region of a LOCS oligonucleotide may be a target-specific sequence which is fully or partially complementary to the target to be detected; and which, when double-stranded, may serve as substrate for degradation by an exonclease, for example, by exonuclease activity inherent to a polymerase. In yet a further exemplary embodiment, illustrated in FIG. 3B, the target specific sequence within the Loop may further comprise one strand of a double-stranded restriction enzyme recognition site. Hybridisation of the Loop sequence to the target sequence can result in a functional, cleavable restriction site. In preferred embodiments the restriction enzyme is a nicking enzyme which is capable of cleaving the Loop strand of the LOCS oligonucleotide while leaving the target intact.

In certain embodiments, LOCS oligonucleotides of the present invention may be used to detect target directly. In other exemplary embodiments LOCS may be used to detect target amplicons generated by target amplification technologies including, but not limited to, PCR, RT-PCR, SDA, HDA, RPA, LAMP, RCA, TMA, 3SR, or NASBA. Cleavage or degradation resulting in opening of LOCS may occur in real time during target amplification or may be performed following amplification, at the end point of the reaction. The Loop region may be opened by target-dependent cleavage or degradation mediated by the enzymatic activity of a catalytic nucleic acid including, but not limited to an MNAzyme, a DNAzyme, a ribozyme; or by the enzymatic activity of a protein enzyme including an exonuclease or an endonuclease. By way of non-limiting example, the exonuclease activity may be an inherent catalytic activity of, for example, a polymerase. By way of non-limiting example, the endonuclease activity may be an inherent catalytic activity of, for example, a restriction enzyme including a Nicking endonuclease, a riboendonuclease or a duplex specific nuclease (DSN).

An exemplary strategy, whereby the Loop region comprises a substrate for a catalytic nucleic acid is illustrated in FIG. 2. In this strategy LOCS oligonucleotides comprise universal substrates which can be used to detect any target. The LOCS oligonucleotide contains a stem region, a fluorophore quencher/dye pair and an intervening Loop region which comprises a universal substrate for a catalytic nucleic acid such as an MNAzyme. The MNAzyme may detect a target directly or may be used to detect amplicons generated during target amplification. MNAzymes forms when the target sensor arms of the partzymes align adjacently on a target, or on target amplicons, to form an active catalytic core. The Loop region of the LOCS oligonucleotide binds to the substrate binding arms of the MNAzyme and the substrate within the Loop is cleaved by the MNAzyme, which opens the LOCS and generates a fluorescent signal. The reaction may then be cooled so that stems of the open LOCS structure re-anneal. The reaction may then be heated and melt curve analysis performed to measure the temperature at which the open LOCS stem region melts. One skilled in the art would recognize that the targets could be detected in real time or at the end of the reaction.

Reactions designed to detect multiple targets simultaneously may contain multiple LOCS oligonucleotides; each of which comprises a different universal substrate within the Loops, and a different stem region capable of melting at a different temperature following cleavage of the substrate/Loop by different MNAzymes. The LOCS oligonucleotides may further comprise the same fluorophore/quencher dye pairs. By way of example, MNAzyme 1 may form in the presence of target 1 and cleave substrate 1 within LOCS oligonucleotide 1. This results in a cleaved, double-stranded, open LOCS structure 1 containing Stem 1 which melts at temperature 1. Concurrently, MNAzyme 2 may form in the presence of target 2 and cleave substrate 2 within LOCS oligonucleotide 2, resulting in a cleaved, double-stranded open LOCS structure 2 containing Stem 2 which melts at temperature 2. When the melting profile of the reaction is analysed the presence of a peak at temperature 1 indicates the presence of target 1; the presence of a peak at temperature 2 indicates the presence of target 2; and presence of two peaks at temperatures 1 and 2 indicates the presence of both target 1 and target 2. As such a single wavelength, read in a single channel on an instrument, allows detection and discrimination of two targets.

The reaction mix can farther contain additional LOCS labelled with different fluorophore and quencher pairs. By way of example, LOCS oligonucleotides 1 and 2 may be labelled with fluorophore A and LOCS oligonucleotides 3 and 4 may be labelled with fluorophore B. MNAzyme 1 may form in the presence of target 1 and cleave substrate 1 within LOCS oligonucleotide 1 resulting in a cleaved, double-stranded open LOCS structure 1 containing Stem 1 which melts at temperature 1. MNAzyme 2 may form in the presence of target 2 and cleave substrate 2 within LOCS oligonucleotide 2 resulting in a cleaved, double-stranded open LOCS structure 2 containing Stem 2 which melts at temperature 2. MNAzyme may form in the presence of target 3 and cleave substrate 3 within LOCS oligonucleotide 3 resulting in a cleaved, double-stranded open LOCS structure 3 containing Stem 3 which melts at temperature 3. MNAzyme 4 may form in the presence of target 4 and cleave substrate 4 within LOCS oligonucleotide 4 resulting in a cleaved, double-stranded open LOCS structure 4 containing Stem 4 which melts at temperature 4. When the melting profile of the reaction is analysed at the excitation wavelength of Fluorophore A, the presence of a peak at temperature 1 indicates the presence of target 1; the presence of a peak at temperature 2 indicates the presence of target 2; and presence of two peaks at temperatures 1 and 2 indicates the presence of both target 1 and target 2. When the melting profile of the reaction is analysed at the excitation wavelength of Fluorophore B, the presence of a peak at temperature 3 indicates the presence of target 3; the presence of a peak at temperature 4 indicates the presence of target 4; and the presence of two peaks at temperatures 3 and 4 indicates the presence of both target 3 and target 4. As such analysis at two wavelengths, read in two channels on an instrument, allows detection and discrimination of four targets. The skilled person will recognise that the strategy can be extended to monitor cleavage of more than two targets at one specific wavelength and further the number of fluorophores analysed can be increased to that determined by the maximum capacity of the available instrument to discriminate individual wavelengths.

Figure 3:
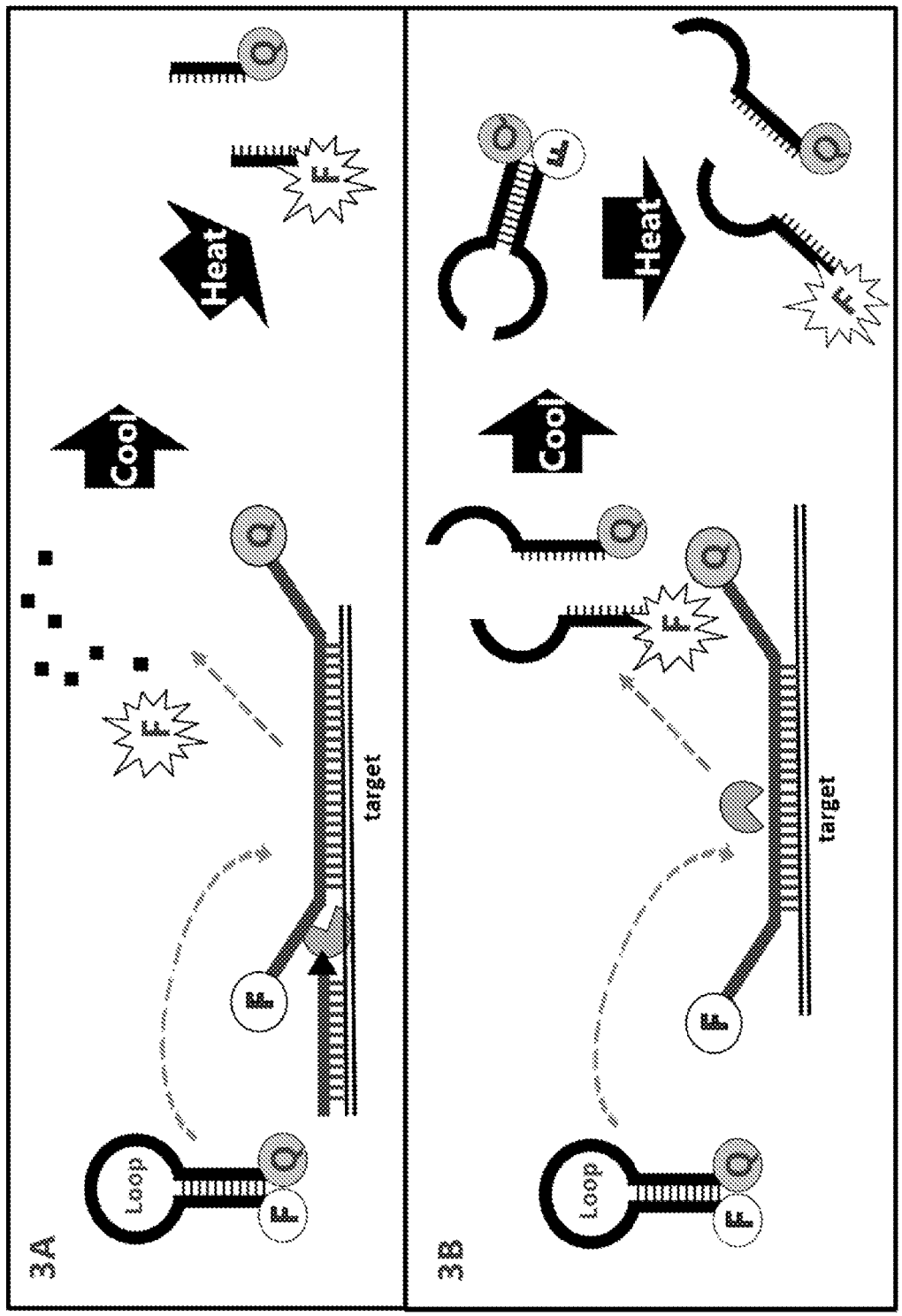
FIG. 3 illustrates exemplary strategies for detection of a target using LOCS oligonucleotides which are specific for a target. The LOCS oligonucleotides contain a stem region, a fluorophore quencher dye pair and a Loop region which comprises a region complementary to the target amplicon. In the scheme illustrated in FIG. 3A, the Loop region of the LOCS oligonucleotides binds to target amplicons during amplification. During extension of primers, the exonuclease activity of the polymerase degrades the Loop region, generating a fluorescent signal in real time, but leaves the stem regions intact. The stein regions are complementary to each other but not to their target. Following amplification, the reaction may be cooled so that the stem of the degraded, open LOCS structure re-anneals. A subsequent melt curve analysis may be performed to measure the temperature at which the stem region derived from the open LOCS melts and generates fluorescence. In the scheme illustrated in FIG. 3B, the Loop region of the LOCS oligonucleotide comprises a region complementary to the target amplicon and further contains a recognition site for a restriction enzyme, for example a nicking enzyme. The Loop region of the LOCS oligonucleotide binds to the target and the nicking enzyme cleaves the Loop region, leaving the target molecule intact. This opens the LOCS and generates a fluorescent signal. The reaction can then be cooled so that the stem of the cleaved, open LOCS structure can re-anneal; and then melt curve analysis can be performed to measure the temperature at which the stem region derived from the open LOCS melts. The strategy may be used to directly detect target sequences or may detect target amplicons when combined with a target amplification method.

Referring now to the exemplary embodiment depicted in FIG. 3 two exemplary strategies are illustrated for detection of a target using LOCS oligonucleotides which have Loop regions which are specific for, and complementary to, a target and/or amplicon Referring now to the embodiment illustrated in FIG. 3A, the LOCS oligonucleotide contains a stem region, a fluorophore quencher dye pair and a Loop region which comprises a region complementary to the target amplicon. During amplification, the Loop region of the LOCS oligonucleotides binds to target amplicons. During extension of primers, the exonuclease activity of the polymerase degrades the Loop region leaving the stem regions intact and generating a fluorescent signal in real time. Following amplification, the reaction may be cooled so that a stem of the degraded, open LOCS structure re-anneals; and then melt curve analysis may be performed to measure the temperature at which the stem region, derived from the degraded open LOCS, melts. One skilled in the art would recognize that the targets could be detected in real time or at the end of the reaction.

In a further exemplary embodiment depicted in FIG. 3B, the LOCS oligonucleotide contains a stem region, a fluorophore/quencher dye pair and a Loop region which comprises a region complementary to the target and which further comprises a recognition site for a restriction enzyme, for example a nicking enzyme. When the Loop region of the LOCS oligonucleotide binds to the target, the nicking enzyme cleaves the Loop strand of the LOCS leaving the target intact and generating a fluorescent signal. The reaction may be cooled so that the intact stem of the cleaved, open LOCS structure re-anneals; and then melt curve analysis may be performed to measure the temperature at which the stem region derived from the cleaved open LOCS melts. One skilled in the art would readily recognize that the target could be directly detected in a reaction without prior amplification. Further, one skilled in the art would recognize that the target amplicons generated by target amplification could be detected in real time or at the end of the reaction. In preferred embodiments, the restriction enzyme used in conjunction with target amplification may be active and thermostable at the reaction temperature or temperatures.

In a further exemplary embodiment, the LOCS oligonucleotide may contain a stem region, a fluorophore/quencher dye pair and a Loop region which may comprise a substrate for a DNAzyme or a ribozyme, for example, a DNAzyme or ribozyme which can only be catalytically active in the presence of a metal ion. Specific DNAzymes and ribozymes are known in the art to require a metal cation cofactor to enable catalytic activity. For example, some DNAzymes and ribozymes can only be catalytically active in the presence of, for example, lead or mercury. Such metals may be present in, for example, in an environmental sample. If a LOCS oligonucleotide contains a loop comprising a substrate for a DNAzyme or ribozyme, which is, for example, lead dependent, then the presence of lead in a sample can result in cleavage of the LOCS and generation of a fluorescent signal. The reaction may be cooled so that the intact stem of the cleaved, open LOCS structure re-anneals; and then melt curve analysis may be performed to measure the temperature at which the stein region derived from the cleaved open LOCS melts. One skilled in the art would readily recognize that multiple DNAzymes and/or ribozymes, each of which is dependent on a specific metal cofactor, could be combined in a single reaction designed to detect multiple targets, for example lead and mercury. Further, one skilled in the art would recognize that the targets could be detected in real time or at the end of the reaction.

Reference to a sequence of nucleotides that is "substantially complementary" to another sequence of nucleotides herein may mean that a first sequence is at least 60%, 65%, 70%, 75%, 80%, 85%, 90%, 95%, 97%, 98% or 99% identical to the complement of a second sequence over a region of 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides.

A sequence of nucleotides that is "complementary" to another sequence of nucleotides herein may mean that a first sequence is 100% identical to the complement of a second sequence over a region of 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides.

Reference to a sequence of nucleotides that is "substantially non-complementary" to another sequence of nucleotides herein may mean that a first sequence is less than 1%, 2%, 3%, 4%, 5%, 10%, 15%, 20%, 25%, 30%, 35%, or 40% identical to the complement of a second sequence over a region of 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides. A sequence of nucleotides that is "non-complementary" to another sequence of nucleotides herein may mean that a first sequence is 0% identical to the complement of a second sequence over a region of 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides.

Non-limiting examples of target nucleic acids (i.e. a polynucleotide), which may be detected using LOCS oligonucleotides could include DNA, methylated DNA, alkylated DNA, complementary DNA (cDNA), RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof (including in mixed polymers of deoxyribonucleotide and ribonucleotide bases).

In some embodiments, the melting temperature ("Tm") of the intact LOCS oligonucleotide is higher than the Tm of the open LOCS structure.

Analyses of Fluorescent Signals

Fluorescent signals generated by dissociation of open LOCS structures can be analysed in any suitable manner to detect, differentiate, and/or quantify target molecules in accordance with the methods of the present invention.

While standard melting curve analyses can be used, various other approaches are disclosed and exemplified herein (see Examples) which can be readily adopted to the analysis of various assay formats.

By way of non-limiting example, measurements of fluorescence signal at a single temperature, or at multiple temperatures, may be obtained at various time points within a reaction suitable for detecting cleavage or degradation of the loop regions of LOCS oligonucleotides. By way of non-limiting examples, these time points may comprise (i) a time point at the initiation of a reaction, and/or (i) a single time point, or multiple time points, during the course of the reaction; and/or (iii) a time point at the conclusion or endpoint of the reaction.

In some embodiments, measurement of fluorescent signal may be obtained at two or more temperatures at each cycle during PCR amplification. Analysis may be performed by comparing levels of fluorescence obtained at a first and/or second temperature and/or at a further temperature.

In other embodiments, measurement of fluorescent signal may be obtained at two or more temperatures at each cycle during PCR, and amplification curves may be plotted for each series of measurement obtained at each temperature. Threshold fluorescence values can be assigned to each amplification plot for each specific temperature and Cq values may be measured as the cycle number where the amplification plots cross the threshold values. In embodiments wherein measurement of fluorescent signal is obtained at two temperatures at each cycle during PCR, the Cq measured using fluorescent signal at the lower temperature may allow direct quantification of the starting concentration of a first target; and the Cq measured using fluorescent signal at the higher temperature may be analysed as exemplified in Example 12, thus allowing quantification of the starting concentration of a second target.

By way of non-limiting example, the post-amplification measurements of fluorescence, relative to a no template control, at two temperatures comprising a first temperature that is at or above the melting temperature of a first open LOCS and below the melting temperature of a second open LOCS; and a second temperature that is at or above the melting temperature of the second open LOCS allows for specific detection of a first and a second cleaved, open LOCS. As demonstrated in Example 15 (Analytical Method A), at a first temperature, cleavage of a first LOCS produces significant fluorescence signal relative to a no template control reaction and crosses a pre-determined threshold. At this first temperature, an intact closed first and second LOCS, and/or a cleaved open second LOCS, do not contribute to production of significant fluorescence signal, due to the higher melting temperatures of the closed first and second LOCS and the open second LOCS, and do not cross a pre-determined threshold. At a second temperature, which is higher than the first temperature, cleavage of the second LOCS produces significant fluorescence signal relative to a no template control and crosses a pre-determined threshold, whereas an intact, closed first and second LOCS and/or a open first LOCS doe not contribute to production of significant fluorescence signal relative to a no template control and does not cross a pre-determined threshold. The detection of each cleaved LOCS reporter indicates the presence of the corresponding target in the sample.

By way of non-limiting example, the post-amplification measurements of fluorescence, relative to a control baseline fluorescence at specific temperature-points, comprising a first temperature that is at or above the melting temperature of a first closed LOCS and below the melting temperature of a second closed LOCS; and a second temperature that is at or above the melting temperature of the second closed LOCS, allows for specific detection of a first and a second cleaved open LOCS.

As demonstrated in Example 15 (Analytical Method B), a control baseline fluorescence can be obtained by measuring fluorescence at or below a temperature wherein none of the open and/or closed LOCS produce significant fluorescence signal (temperature-0). Analysis may be performed by comparing levels of fluorescence obtained at a first and/or second temperature and a temperature-0 and comparing these relative levels of fluorescence relative to a pre-determined threshold. As demonstrated in Example 15, at a first temperature, cleavage of a first LOCS produces significant fluorescence signal relative to signal at a temperature-0 and crosses a pre-determined threshold. At this first temperature, an intact, closed first and second LOCS, and/or a cleaved open second LOCS, do not contribute to production of significant fluorescence signal and the signals do not cross a pre-determined threshold. This is due to the higher melting temperatures of the closed first and second LOCS and the open second LOCS. At a second temperature, which is higher than the first temperature, cleavage of the second LOCS produces significant fluorescence signal relative to signal obtained at a temperature-O and/or relative to a first temperature and the signal crosses a pre-determined threshold. At this second temperature, an intact, closed first and/or second LOCS and an open first LOCS do not contribute to production of significant fluorescence signal relative to signal at a temperature-0 and/or a first temperature and do not cross a pre-determined threshold. The detection of each cleaved LOCS reporter indicates the presence of the corresponding target in the sample.

By way of non-limiting example, the control baseline fluorescence can also be obtained by measuring fluorescence at the first and second temperatures at an additional time point at the initiation of a reaction, for example pre-PCR. At this additional time-point, all the LOCS are intact (closed) and do not produce significant fluorescence signal and would not cross a pre-determined threshold. Analysis may be performed by comparing levels of fluorescence obtained at a first and second temperature at a time point at the initiation of a reaction and levels of fluorescence obtained at a first and second temperature at a time point during and/or after the reaction (e.g. during PCR or post-PCR). As demonstrated in Example 15 (Analytical Method C), at a first temperature and at a post-PCR time-point, cleavage of a first LOCS produces significant fluorescence signal relative to signal of an intact, closed first LOCS measured at a first temperature and at a pre-PCR time-point. This relative signal crosses a pre-determined threshold. At this first temperature, an intact, closed first and second LOCS and/or a cleaved, open second LOCS do not contribute to production of significant fluorescence signal relative to signal obtained pre-PCR due to the higher melting temperatures of the closed first and second LOCS and open second LOCS. At a second temperature, which is higher than the first temperature, and at a post-PCR time-point, cleavage of the second LOCS produces significant fluorescence signal, relative to signal obtained at a second temperature at a pre-PCR time-point. At this second temperature and at a time-point post-PCR, an intact, closed first or second LOCS and/or an open first LOCS do not contribute to production of significant fluorescence signal relative to a pre-PCR time-point at the same second temperature and do not cross a pre-determined threshold. Alternatively, the difference between the relative signal obtained pre- and post-PCR at a second temperature and the relative signal obtained pre- and post-PCR at a first temperature can be are compared to a pre-determined threshold to determine the presence of a cleaved second LOCS; where in the presence of an open second LOCS, the difference value is greater than a pre-determined threshold and in the absence, the difference value is lower than a pre-determined threshold, as demonstrated in Example 15 (Analytical Method C). The detection of each cleaved LOCS reporter indicates the presence of the corresponding target in the sample.

By way of non-limiting example, another alternative method is to measure the height of melt peak in the melt signature, which is equivalent to the dFluorescence/dTemperature (dF/dT) value at the Tm of each cleaved LOCS. However, the usability of this method is not confined for determining the dF/dT value at the Tm of the cleaved LOCS, but also inclusive of a range of temperatures which includes the Tm. The dF/dT value at first or second temperature (A° C.) is equivalent to the gradient of fluorescence level across (A−N)° C. and (A+N)° C. As demonstrated in Example 15 (Analytical Method D), dF/dT value at a first temperature, calculated from fluorescence signals at (a first temperature+N)° C. and (a first temperature−N)° C., is higher than a pre-determined threshold only in the presence of open first LOCS. dF/dT value at a second temperature, which is higher than a first temperature, calculated from fluorescence signals at (a second temperature+N)° C. and (a second temperature−N)° C., is higher than a pre-determined threshold only in the presence of open second LOCS. The detection of each cleaved LOCS reporter indicates the presence of the corresponding target gene in the sample. The dF/dT at first and second temperature can be expressed as a ratio, which is unique for each of the possible combinations of open and LOCS. This information can be used to detect specific open LOCS and therefore a corresponding target, by determining whether the ratio falls into a pre-defined range of values.

In some embodiments, fluorescence signals, or derivatives thereof, at first, second and/or further temperatures are compared relative to a pre-determined threshold wherein signal from a cleaved, open first LOCS crosses a pre-determined threshold at a first temperature and a cleaved, open LOCS crosses a pre-determined threshold at a second temperature and intact, closed first and second LOCS do not cross pre-determined thresholds at first and second temperatures. Therefore, the utility of pre-determined thresholds at first and second temperatures can be used to detect cleaved, open first and second LOCS. The detection of cleaved, open first and second LOCS indicates the presence of a first and second target gene in the sample. In other embodiments, the fluorescence signals, or derivatives thereof, at first, second and/or further temperatures can be expressed as a ratio, wherein there is a unique ratio value for each of the possible combinations of open and/or closed LOCS. These unique ratio values can be used to detect a cleaved, open first and second LOCS and indicates the presence of a first and second target gene in the sample.

In some embodiments, detection, differentiation and/or quantification of first and second targets by use of first and second LOCS in a single fluorescence channel are described. However, one skilled in the art would recognize that the methods are applicable for detection, differentiation and/or quantification of more than two targets as demonstrated in Example 15.

Exemplary Applications of LOCS Oligonucleotides
Detection of Targets During or Following Target Amplification LOCS oligonucleotides of the present invention may be used determine the presence of amplified target nucleic acid sequences. No particular limitation exists in relation to amplification techniques to which the LOCS reporters may be applied. Amplicons generated by various reactions may be detected by LOCS reporters, provided the presence of target amplicons can promote the cleavage or degradation of LOCS reporter to produce open LOCS structures. Non-limiting examples of methods useful in cleaving or degrading Loop regions contained within LOCS structures include cleavage by MNAzymes, DNAzymes, ribozymes, restriction enzymes, endonucleases or degradation by exonucleases including but not limited to the exonuclease activity of a polymerase.

In general, nucleic acid amplification techniques utilise enzymes (e.g. polymerases) to generate copies of a target nucleic acid that is bound specifically by one or more oligonucleotide primers. Non-limiting examples of amplification techniques in which LOCS oligonucleotides may be used include one or more of the polymerase chain reaction (PCR), the reverse transcription polymerase chain reaction (RT-PCR), strand displacement amplification (SDA), helicase dependent amplification (HDA), Recombinase Polymerase Amplification (RPA), loop-mediated isothermal amplification (LAMP), rolling circle amplification (RCA), transcription-mediated amplification (TMA), self-sustained sequence replication (3SR), nucleic acid sequence based amplification (NASBA).

The skilled addressee will readily understand that the applications of LOCS oligonucleotides described above are provided for the purpose of non-limiting exemplification only. The LOCS oligonucleotides disclosed may be used in any primer-based nucleic acid amplification technique and the invention is not so limited to those embodiments specifically described.

Detection of Amplicons Generated Using LOCS Reporters

As discussed above, LOCS reporters of the present invention may be utilised in any polynucleotide amplification technique, non-limiting examples of which include the PCR, RT-PCR, SDA. HDA, RPA, LAMP, RCA, TMA, 3SR, or NASBA.

Amplicons generated by techniques that utilise LOCS reporters which may be may cleaved or degraded using any suitable method known in the art. Non-limiting examples include the use of catalytic nucleic acids, exonucleases (see Example 11), endonucleases (see Example 10), and the like.

An MNAzyme may be utilised to open LOCS reporters by detecting amplicons generated through methods such as PCR, RT-PCR, SDA, HDA, RPA, TMA, LAMP, RCA, 3SR, and NASBA. The MNAzyme may comprise one or more partzyme(s). MNAzymes are multi-component nucleic acid enzymes which are assembled and are only catalytically active in the presence of an assembly facilitator which may be, for example, a target to be detected such as an amplicon generated from a polynucleotide sequence using primers. MNAzymes are composed of multiple part-enzymes, or partzymes, which self-assemble in the presence of one or more assembly facilitators and form active MNAzymes which catalytically modify substrates. The substrate and assembly facilitators (target) are separate nucleic acid molecules. The partzymes have multiple domains including (i) sensor arms which bind to the assembly facilitator (such as a target nucleic acid); (ii) substrate arms which bind the substrate, and (iii) partial catalytic core sequences which, upon assembly, combine to provide a complete catalytic core. MNAzymes can be designed to recognize a broad range of assembly facilitators including, for example, different target nucleic acid sequences. In response to the presence of the assembly facilitator, MNAzymes modify their substrates. This substrate modification can be linked to signal generation and thus MNAzymes can generate an enzymatically amplified output signal. The assembly facilitator may be a target nucleic acid present in a biological or environmental sample (e.g. an amplicon generated from a polynucleotide target using primers). In such cases, the detection of the modification of the substrate by the MNAzyme activity is indicative of the presence of the target. Several MNAzymes capable of cleaving nucleic acid substrates are known in the art. MNAzymes and modified forms thereof are known in the art and disclosed in PCT patent publication numbers WO/2007/041774, WO/2008/040095, WO2008/122084, and related US patent publication numbers 2007-0231810, 2010-0136536, and 2011-0143338 (the contents of each of these documents are incorporated herein by reference in their entirety).

Diagnostic Applications

LOCS oligonucleotides may be used for diagnostic and/or prognostic purposes in accordance with the methods described herein. The diagnostic and/or prognostic methods may be performed ex vivo or in vitro. However, the methods of the present invention need not necessarily be used for diagnostic and/or prognostic purposes, and hence applications that are not diagnostic or prognostic are also contemplated.

In some embodiments, the methods described herein may be used to diagnose infection in a subject. For example, the methods may be used to diagnose infection by bacteria, viruses, fungi/yeast, protists and/or nematodes in the subject. In one embodiment, the virus may be an enterovirus.

The subject may be a bovine, equine, ovine, primate, avian or rodent species. For example, the subject may be a mammal, such as a human, dog, cat, horse, sheep, goat, or cow. The subject may be afflicted with a disease arising from the infection. For example, the subject may have meningitis arising from an enterovirus infection. Accordingly, methods of the present invention may in certain embodiments be used to diagnose meningitis.

The methods of the present invention may be performed on a sample. The sample may be derived from any source. For example, the sample may be obtained from an environmental source, an industrial source, or by chemical synthesis.

It will be understood that a "sample" as contemplated herein includes a sample that is modified from its original state, for example, by purification, dilution or the addition of any other component or components.

The methods of the present invention including, but not limited to diagnostic and/or prognostic methods, may be performed on a biological sample. The biological sample may be taken from a subject. Stored biological samples may also be used. Non-limiting examples of suitable biological samples include whole blood or a component thereof (e.g. blood cells, plasma, serum), urine, stool, saliva, lymph, bile fluid, sputum, tears, cerebrospinal fluid, bronchioalveolar lavage fluid, synovial fluid, semen, ascitic tumour fluid, breast milk and pus.

Kits

The present invention provides kits comprising one or more agents for performing methods of the present invention. Typically, kits for carrying out the methods of the present invention contain all the necessary reagents to carry out the method.

In some embodiments the kits may comprise oligonucleotide components capable of forming an MNAzyme in the presence of an appropriate assembly facilitator (e.g. an amplicon as described herein). For example, the kit may comprise at least a first and second oligonucleotide component comprising a first and second partzyme, and a second container comprising a substrate, wherein self-assembly of the first and second partzymes, and the substrate, into an MNAzyme requires association of an assembly facilitator (e.g. an amplicon) present in a test sample. Accordingly, in such embodiment, the first and second partzymes, and a LOCS oligonucleotide comprising a substrate within the Loop region, may be applied to the test sample in order to determine the presence of one or more target amplicons. In general, the kits comprise at least one LOCS oligonucleotide provided herein.

Typically, the kits of the present invention will also comprise other reagents, wash reagents, enzymes and/or other reagents as required in the performance of the methods of the invention such as PCR or other nucleic acid amplification techniques.

The kits may be fragmented kits or combined kits as defined herein.

Fragmented kits comprise reagents that are housed in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion.

Such kits may also include a container which will accept the test sample, a container which contains the reagents used in the assay, containers which contain wash reagents, and containers which contain a detection reagent.

Combined kits comprise all of the components of a reaction assay in a single container (e.g. in a single box housing each of the desired components).

A kit of the present invention may also include instructions for using the kit components to conduct the appropriate methods. Kits and methods of the invention may be used in conjunction with automated analysis equipment and systems, for example, including but not limited to, real time PCR machines.

For application to amplification, detection, identification or quantitation of different targets, a single kit of the invention may be applicable, or alternatively different kits, for example containing reagents specific for each target, may be required. Methods and kits of the present invention find application in any circumstance in which it is desirable to detect, identify or quantitate any entity.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

EXAMPLES

The present invention will now be further described in greater detail by reference to the following specific examples, which should not be construed as in any way limiting the scope of the invention.

Example 1: Use of LOCS Reporters to Increase Multiplexing Capacity

In the following example, LOCS reporters are used to increase the number of targets that can be detected from a single fluorescence channel. In this example, two LOCS reporters are 5' labelled with a fluorophore (FAM) and 3' labelled with a quencher. The loop regions of the LOCS reporters contain a nucleic acid substrate, and the stem regions contain a series of complementary base-pairs that constrain the LOCS reporter in a stem-loop configuration. In this configuration, the fluorophore and quencher are in close proximity and the fluorescence is quenched in the absence of target.

Oligonucleotides

The oligonucleotides specific to this experiment include; LOCS-1 (SEQ ID NO: 1), LOCS-2 (SEQ ID NO: 2), Partzyme A1 (SEQ ID NO: 3), Partzyme B1 (SEQ ID NO: 4), Partzyme A2 (SEQ ID NO: 5), Partzyme B2 (SEQ ID NO: 6), Forward Primer 1 (SEQ ID NO: 7), Reverse Primer 1 (SEQ ID NO: 8), Forward Primer 2 (SEQ ID NO: 9) and Reverse Primer 2 (SEQ ID NO: 10). The sequences are listed in the Sequence Listing. The oligonucleotides specific for MgPa amplification and detection are LOCS-1, Partzyme A1, Partzyme B1, Forward Primer 1 and Reverse Primer 1. The oligonucleotides specific for TV-Btub amplification and detection are LOCS-2, Partzyme A2, Partzyme B2, Forward Primer 2 and Reverse Primer 2.

Reaction Conditions

Real-time amplification and detection of the target sequence was performed in a total reaction volume of 20 µL using a BioRad® CFX96 thermocycler. The cycling parameters were 95° C. for 2 minutes, 10 touchdown cycles of 95° C. for 5 seconds and 61° C. for 30 seconds (0.5° C.

decrement per cycle) and 40 cycles of 95° C. for 5 seconds and 52° C. for 40 seconds (data collected at the 52° C. step). Melt curve parameters were 0.5° C. increment from 20° C. to 90° C. with a 5 sec hold (data acquisition on hold). All reactions were run in duplicate and contained 40 nM of each forward primer, 200 nM of each reverse primer, 200 nM of each partzyme A, 200 nM of each partzyme B, 200 nM of each LOCS reporter, 2 mM $MgCl_2$ (Bioline) and 1× Sensi-FAST Probe No-ROX Mix (Bioline). The reactions contained either G-Block template (10,000 or 40 copies) homologous to the MgPa and/or TV-Btub genes, or no target (nuclease free $H_2O$ (NF $H_2O$)).

Results

Using an in vitro target amplification method known as PCR, two MNAzymes (MNAzyme 1 and MNAzyme 2) are used to monitor amplification of target nucleic acids in real-time via cleavage of their corresponding LOCS reporters (LOCS-1 and LOCS-2 respectively). MNAzyme 1 was designed to detect sequences homologous to the MgPa gene (*Mycoplasma genitalium*) and to cleave and open LOCS-1; and MNAzyme 2 was designed to detect sequences homologous to the TV-Btub (*Trichomonas vaginalis*) and cleave and open LOCS-2. In this experiment, amplification and detection was performed in single tube, containing all MNAzyme, primer and LOCS oligonucleotides. The presence of either MgPa, or TV-Btub, or both MgPa and TV-Btub (representing a sample with a co-infection), were detected by an increase in signal in the FAM channel.

Figure 4:
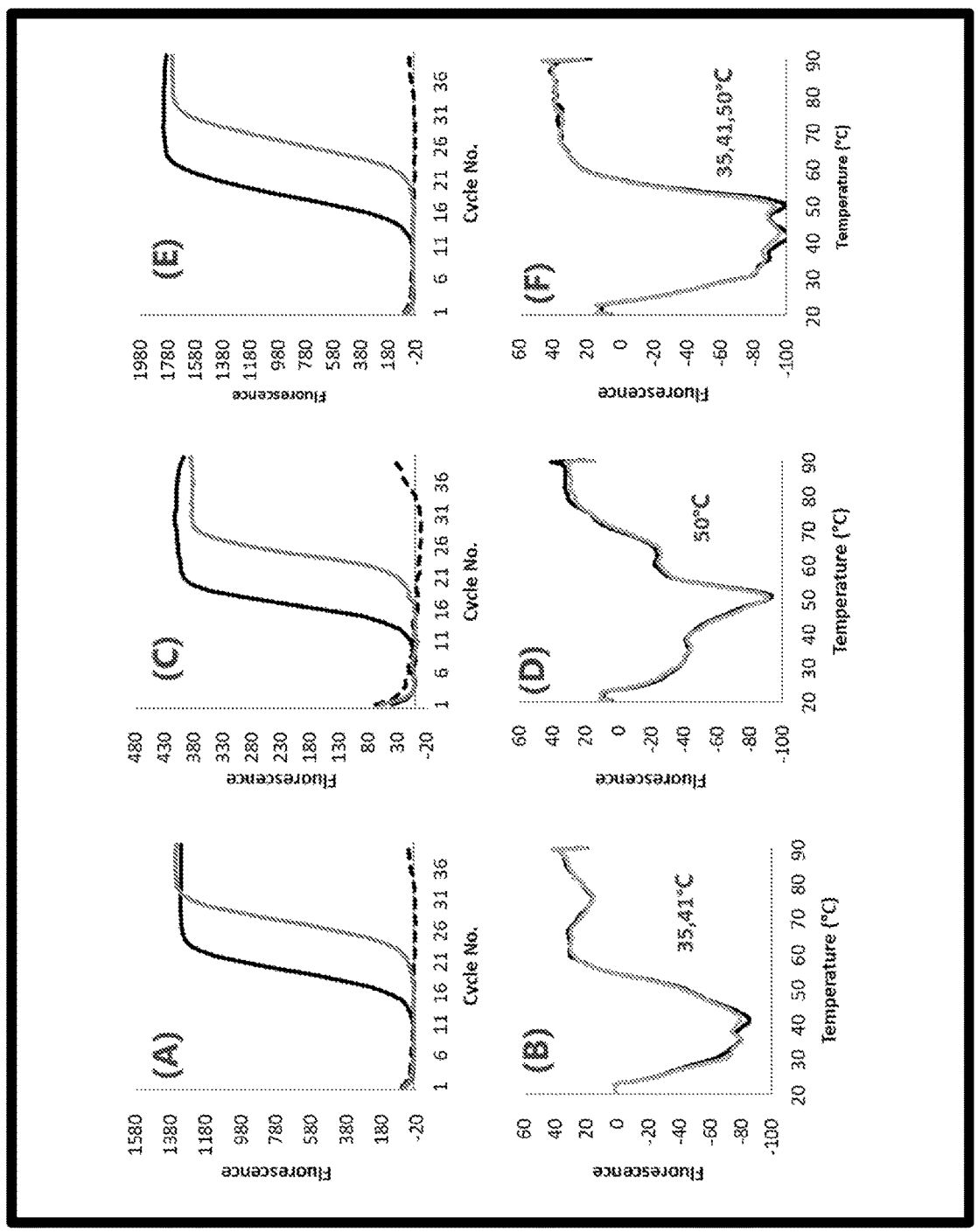
FIG. 4 illustrates the PCR amplification plots obtained from reactions containing 10,000 copies (black line), 40 copies (grey line) or 0 copies (dotted line) of the targets MgPa (FIG. 4A), or TV-Btub (FIG. 4C) or both MgPa and TV-Btub (FIG. 4E). The melt curve signatures obtained post amplification from reactions containing 10,000 copies (black line) and 40 copies (grey line) are shown for the targets MgPa (FIG. 4B), TV-Btub (FIG. 4D) or both MgPa and TV-Btub (FIG. 4F). The melt signatures produced by opening LOCS-1 in the presence of MgPa gene target included peaks at melting temperatures of 35° C. and 41° C.; the melt signatures produced by opening LOCS-2 in the presence of TV-Btub gene target included a peak corresponding to a melting temperature of 50° C.; whilst the melt signatures produced by opening both LOCS-1 and LOCS-2 in the presence of both MgPa and TV-Btub gene targets included three peaks at melting temperatures of 35° C., 41° C. and 50° C. The LOCS melt signature in the presence of MgPa (Tm=35° C. and 41° C.) is distinct from the LOCS melt signature produced in the presence of TV-Btub gene target (Tm=50° C.). Further, the LOCS melt signature in the presence of both MgPa and TV-Btub gene targets (Tm 35° C., 41° C. and 50° C.) is distinct from the aforementioned melt signatures wherein only a single gene target is present, indicating that both targets were detected.

The results shown in FIG. 4 illustrates the respective PCR amplification plots obtained from reactions containing 10,000 copies (black line), 40 copies (grey line) or 0 copies (dotted line) of the targets MgPa (FIG. 4A), TV-Btub (FIG. 4C) or both MgPa and TV-Btub (FIG. 4E). The melt curve signatures obtained post amplification from reactions containing 10,000 copies (black line) and 40 copies (grey line) are shown for the targets MgPa (FIG. 4B), TV-Btub (FIG. 4D) or both MgPa and TV-Btub (FIG. 4F). The results are the averages from duplicate reactions that were plotted using Microsoft Excel (Version 14). The data from this example demonstrates that the LOCS melt signatures produced in the presence of MgPa gene target (Tm=35° C. and 41° C.) are distinct from the LOCS melt signatures produced in the presence of TV-Btub gene target (Tm=50° C.). Further, the LOCS melt signatures in the presence of both MgPa and TV-Btub gene targets are also distinct from the aforementioned melt signatures wherein only a single gene target is present. When both targets were present a melt curve signature (Tm=35° C., 41° C. and 50'C) indicated both targets were detected.

The data from this experiment also demonstrate that the melt signatures of each open LOCS were reproducible for reactions containing high target concentrations (10,000 gene copies) and low target concentrations (40 gene copies). This example demonstrates that two targets, co-amplified in a single well and using a single fluorescent channel, can be distinguished based on their unique LOCS melt signatures. The example provides a simple method useful for detecting multiple targets in a single well using a single fluorescent channel.

The melting temperatures (Tms) of the intact, closed LOCS reporters were designed to be greater than the annealing temperature of the reaction (52'C) so that these LOCS remain sufficiently quenched during the reaction in the absence of target amplification. The Tms of the stem regions were designed to be unique for each LOCS reporter, and this was achieved by modifying the length and nucleotide composition of the complementary regions which form the stem. In this example, the data is consistent with the scenario that cleavage of the loop regions using MNAzymes results in opening of the LOCS allowing separation into two fragments. Due to the large difference in Tm between closed, intact LOCS reporters and open LOCs reporters the open LOCS fragments are not stable enough to sustain duplex formation at the annealing and data acquisition temperature, thus a fluorescence signal is generated.

Real-time monitoring of the two target genes generated fluorescence curves that cross an arbitrary threshold producing a value which can be known as a Ct (cycle threshold). An observed fluorescence curve during the amplification stage indicates that one or both of the target genes are present in a given sample. However, the identity of the specific target cannot be discerned using the amplification curves alone. In this situation, melt curve analysis was performed to determine which LOCS reporter was cleaved and thereby identify the specific gene target(s) present within the sample. Following the amplification stage, samples were exposed to a temperature gradient wherein different melt curve signatures correspond with different universal stems. Due to Tm differences between open and intact LOCS reporters, cleaved LOCS reporter stems will dissociate at lower temperatures compared to un-cleaved closed LOCS. Furthermore, due to different stem lengths and base-pair compositions, the different stems (Stem-1 and Stem-2) within LOCS-1 and LOCS-2 produced unique fluorescence melt curve signatures.

Example 2: Application of the Same LOCS Reporters for the Detection of Various Gene Targets In this example, two LOCS reporters (LOCS-1 and LOCS-2) are used to distinguish a variety of different genetic targets to demonstrate their universality and applicability to analysis of any target of interest. Using PCR amplification, several MNAzymes (MNAzymes 1-6) were used to detect their specific gene targets and cleave their corresponding LOCS reporters (LOCS-1 and LOCS-2). MNAzymes 1, 3 and 4 each have the ability to cleave LOCS-1 in the presence of their corresponding gene targets. MNAzymes 2, 5 and 6 each have the ability to cleave LOCS-2 in the presence of their corresponding gene targets. In this example, the duplex combinations summarized in Table 1 are demonstrated wherein amplification and detection are performed simultaneously in a single tube.

Oligonucleotides

The oligonucleotides specific to this experiment include; LOCS-1 (SEQ ID NO: 1), LOCS-2 (SEQ ID NO: 2), Partzyme A1 (SEQ ID NO: 3), Partzyme B1 (SEQ ID NO: 4), Partzyme A2 (SEQ ID NO: 5), Partzyme B2 (SEQ ID NO: 6), Forward Primer 1 (SEQ ID NO: 7), Reverse Primer 1 (SEQ ID NO: 8), Forward Primer 2 (SEQ ID NO: 9), Reverse Primer 2 (SEQ ID NO: 10), Partzyme A3 (SEQ ID NO: 11), Partzyme B3 (SEQ ID NO: 12), Partzyme A4 (SEQ ID NO: 13), Partzyme B4 (SEQ ID NO: 14), Forward Primer 3 (SEQ ID NO: 15), Reverse Primer 3 (SEQ ID NO: 16), Forward Primer 4 (SEQ ID NO: 17), Reverse Primer 4 (SEQ ID NO: 18), Partzyme A5 (SEQ ID NO: 19), Partzyme B5 (SEQ ID NO: 20), Partzyme A6 (SEQ ID NO: 21), Partzyme B6 (SEQ ID NO: 22), Forward Primer 5 (SEQ ID NO: 23), Reverse Primer 5 (SEQ ID NO: 24), Forward Primer 6 (SEQ TD NO: 25) and Reverse Primer 6 (SEQ ID NO: 26). The sequences are listed in the Sequence Listing.

TABLE 1

| Example 2 reaction components for PCR Mixes A-F | | | |
|---|---|---|---|
| | Mix A | Mix B | Mix C |
| LOCS-1 Reporter (FIG. 5) | MgPa target Partzymes for MNAzyme 1 Forward/Reverse primer set 1 | HMPV target Partzymes for MNAzyme 3 Forward/Reverse primer set 3 | CT-ompA target Partzymes for MNAzyme 4 Forward/Reverse primer set 5 |
| Additional Oligonucleotides in mixes A, B, C | Partzymes for MNAzyme 2 Forward/Reverse primer set 2 LOCS-2 | | |

| Example 2 reaction components for PCR Mixes A-F | | | |
|---|---|---|---|
| | Mix D | Mix E | Mix F |
| LOCS-2 Reporter (FIG. 6) | TV-Btub target MNAzyme 2 Forward/Reverse primer set 2 | VZV target MNAzyme 5 Forward/Reverse primer set 4 | rpoB target MNAzyme 6 Forward/Reverse primer set 6 |
| Additional Oligonucleotides in mixes D, E, F. | Partzymes MNAzyme 1 Forward/Reverse primer set 1 LOCS-1 | | |

Reaction Components and Conditions.

Real-time amplification and detection of the target sequence was performed in a total reaction volume of 20 µL using a BioRad® CFX96 thermocycler. The cycling parameters were 95° C. for 2 minutes, 10 touchdown cycles of 95° C. for 5 seconds and 61° C. for 30 seconds (0.5° C. decrement per cycle) and 40 cycles of 95° C. for 5 seconds and 52° C. for 40 seconds (data collected at the 52° C. step). Melt curve parameters were 0.5° C. increment from 20° C. to 90° C. with a 5 sec hold (data acquisition on hold). All reactions were run as duplex reactions containing the oligonucleotides specified in Table 1. Each reaction contained 40 nM of each forward primer, 200 nM of each reverse primer, 200 nM of each partzyme A, 200 nM of each partzyme B, 200 nM of each LOCS reporter, 2 mM $MgCl_2$ (Bioline) and 1× SensiFAST Probe No-ROX Mix (Bioline). The reactions contained either G-Block template (10,000 or 40 copies) or no target (NF $H_2O$). The results presented in FIGS. 5 and 6 are the averages from duplicates that were plotted using Microsoft Excel (Version 14).

Results

Figure 5:
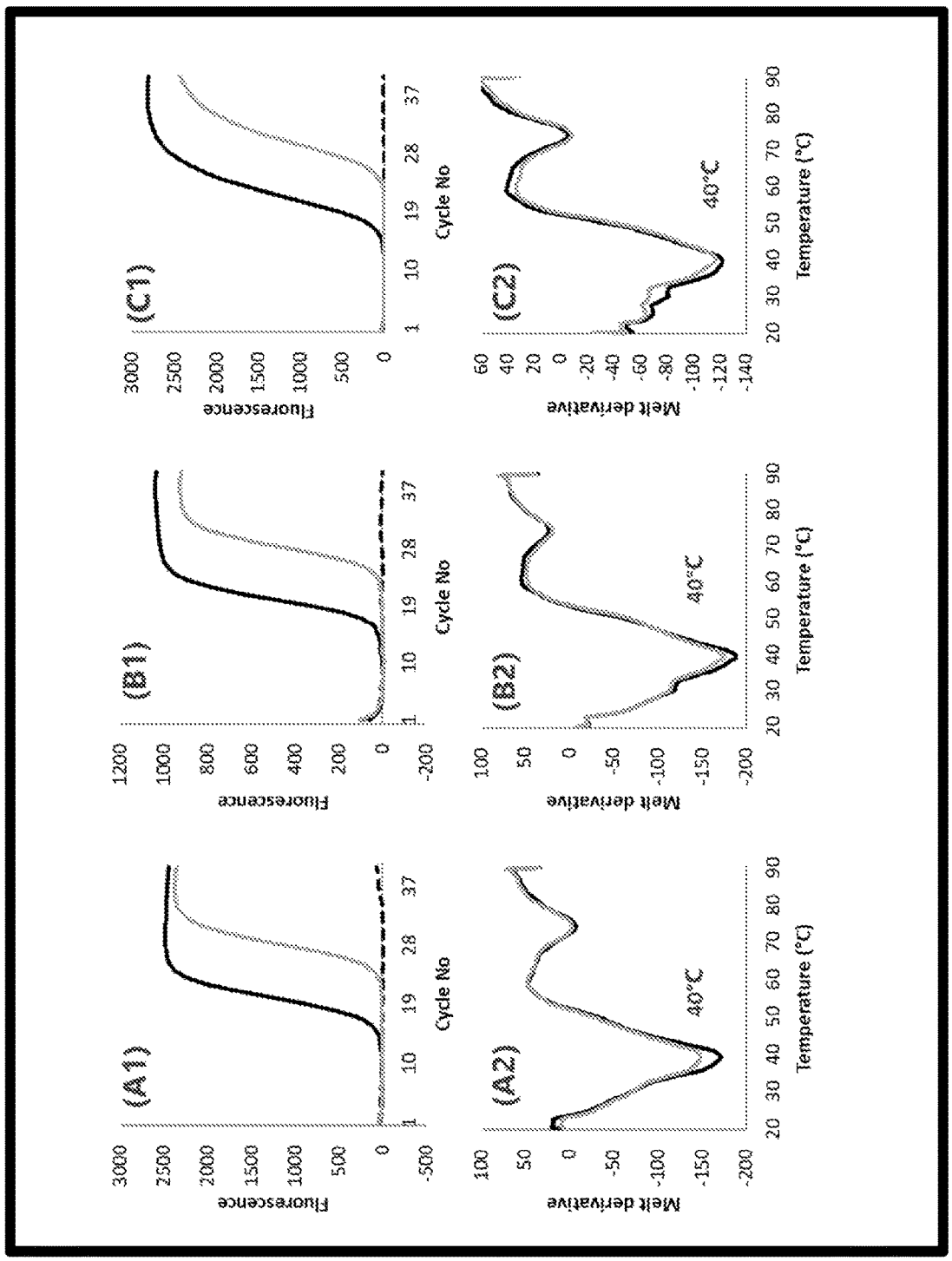
FIG. 5 (top panel) illustrates PCR amplification plots obtained from reactions containing 10,000 copies (black line), 40 copies (grey line) or 0 copies (dotted line) of MgPa (FIG. 5A1), HMPV (FIG. 5B1), and CT-ompA (FIG. 5C1) gene targets. The results shown in the bottom panel are melt curve signatures obtained from reactions containing 10,000 copies (black line) and 40 copies (grey line) of MgPa (FIG. 5A2), HMPV (FIG. 5B2), and CT-ompA (FIG. 5C2) gene targets. The three targets were specifically detected using 3 different MNAzymes; each of which had identical substrate binding arms and differed only by the target binding arms. Each MNAzyme opened the same universal LOCS-1 oligonucleotide comprising a universal substrate and a universal stem. Each target produced a melt curve signature with a peak at 40° C. which corresponds to the Tm of the universal stem.

The results shown in FIG. 5 (top panel) illustrate the PCR amplification plots obtained for reactions containing 10,000 copies (black line), 40 copies (grey line) or 0 copies (dotted line) of MgPa (FIG. 5A1), HMPV (FIG. 5B1), and CT-ompA (FIG. 5C1). The results shown in the bottom panel are melt curve signatures obtained from reactions containing 10,000 copies (black line) and 40 copies (grey line) of MgPa (FIG. 5A2), HMPV (FIG. 5B2) and CT-ompA (FIG. 5C2) gene targets. The three targets were specifically detected with MNAzymes 1, 3, and 5; each of which had target-specific sensor arms but all of which had identical substrate binding arms. Each MNAzyme, once formed in the presence of its target assembly facilitator, was able to bind, cleave and open the same Universal LOCS-1 comprising a first universal substrate and a first universal stem. As such, the presence of each target produced a melting curve with a peak at 40° C. which corresponds to the Tn of the first universal stem.

The results shown in FIG. 6 (top panel) illustrate the PCR amplification plots obtained for reactions containing 10,000 copies (black line), 40 copies (grey line) or 0 copies (dotted line) of the targets TV-Btub (FIG. 6A1), VZV (FIG. 6B1), and rpoB (FIG. 6C1). The results shown in the bottom panel are melt curve signatures obtained from reactions containing 10,000 copies (black line) or 40 copies (grey line) of TV-Btub (FIG. 6A2), VZV (FIG. 6B2), and rpoB (FIG. 6C2) gene targets. The three targets were specifically detected with MNAzymes 2, 4, and 6; each of which had target-specific sensor arms but all of which had identical substrate binding arms. Each MNAzyme, once formed in the presence of its target assembly facilitator, was able to bind, cleave and open the same universal LOCS-2 comprising a second universal substrate and a second universal stem. As such, the presence of each target produced a melting curve with a peak at 50° C. which corresponds to the Tm of the second universal stem.

The data from this example demonstrate that comparable melt signatures are produced using the same universal LOCS reporters for the detection of different target genes. The LOCS melt signatures are demonstrated to be independent of target sequence and can therefore be easily implemented into any assay. This example demonstrates that the LOCS reporters are universal and can be applied for the detection of any desired target gene or transcript.

Example 3: Use of Different Stems to Generate LOCS Reporters with Different Melting Temperatures to Increase Multiplexing Capacity In this example, LOCS reporters comprising different stem compositions are used to in demonstrate the effects of stem length and base-pair composition on the final melt signature. In the current example, four LOCS reporters are 5' labelled with a fluorophore (FAM) and 3' labelled with a quencher. LOCS-1 and LOCS-3 contain identical loop regions containing Substrate 1; however the stem region of LOCS-3 (Stem 3) is longer than the stem region of LOCS-1 (Stem 1) by a single base pair, yielding a structure with a slightly higher predicted Tm in both the intact (closed) and open states. An MNAzyme with target sensor arms capable of directing assembly in the presence of the target assembly facilitator (AF-CT-Cds) and substrate arms capable of binding and cleaving substrate 1 within the Loop of either LOCS-1 or LOCS-3 were used to monitor isothermal signal detection Similarly, LOCS-2 and LOCS-4 contain identical loop regions containing Substrate 2; however the stem region of LOCS-2 (Stem 2) is longer than the stem region of LOCS-4 (Stem 4) by two base pairs, yielding a structure with a higher predicted Tm in both the intact (closed) and open states. An MNAzyme with target sensor arms capable of directing assembly in the presence of the target assembly facilitator (AF-TFRC) and substrate arms capable of binding and cleaving substrate 2 within the Loop of either LOCS-2 or LOCS-4 were used to monitor PCR amplification.

Reaction Components and Conditions

The oligonucleotides specific to this experiment include; LOCS-1 (SEQ ID NO: 1), LOCS-2 (SEQ ID NO: 2), LOCS-3 (SEQ ID NO: 27), LOCS-4 (SEQ ID NO: 28), Partzyme A7 (SEQ ID NO: 29), Partzyme B7 (SEQ ID NO: 30), Partzyme A8 (SEQ ID NO: 31), Partzyme B8 (SEQ ID NO: 32), AF-CT-Cds (SEQ ID NO: 33) and AF-TFRC (SEQ ID NO: 38). The sequences are listed in the Sequence Listing.

Real-time detection of the target sequence was performed in a total reaction volume of 20 µL. Each reaction contains 1×NH4 Buffer (Bioline), 8 mM $MgCl_2$ (Bioline), 200 nM of each Partzyme and 200 nM of LOCS reporter. Reactions either contained target assembly facilitator at final concentrations of 10 nM, or lacked target (no DNA control). Reactions were incubated on a BioRad® CFX96 thermocycler at 52'C with acquisition taking place every 10 seconds for a total of 150 cycles. Next, samples were subject to an increasing temperature gradient of 20° C.-90° C. with a 0.5° C. increment and 5 sec hold time (acquisition at each hold). The results presented in FIG. 7 are the averages from duplicates that were plotted using Microsoft Excel (Version 14).

Results

The results shown in Table 2 and FIG. 7 illustrate the difference in melt curve signatures obtained for closed, intact LOCS reporters (dotted line) present in reactions lacking target, and those consistent with open LOCS reporters (black line) in reactions containing targets which directed the assembly of MNAzymes capable of cleaving and opening specific LOCS reporters.

TABLE 2

Summary of Melting Temperatures (Tms) of intact (closed) and open LOCS Reporters as illustrated in FIG. 7 (Panels A, B, C and D).

| Re-action | LOCS-1 (Panel A) | LOCS-2 (Panel B) | LOCS-3 (Panel C) | LOCS-4 (Panel D) | Comment |
|---|---|---|---|---|---|
| No Target | 65° C. | 77° C. | 66° C. | 67° C. | All LOCS remain closed in the absence of targets. In all cases, as anticipated, the Tm of intact,closed LOCS is higher than the corresponding open LOCS structures. |
| TFRC | | 50° C. | | 32° C. | An MNAzyme with target sensor arms complementary to TFRC assembled in the presence of target and cleaved substrate 2 within either LOCS-2 or LOCS-4. LOCS-2 and LOCS-4 differ only in their stem region. This difference is reflected as a different Tm at which the stems of open LOCS structures melt. |
| CT-Cds | 30° C. | | 36° C. | | An MNAzyme with target sensor arms complementary to CT-CDs assembled in the presence of target and cleaved substrate 1 within either LOCS-1 or LOCS-3. LOCS-1 and LOCS-3 differ only in their stern region. This difference is reflected as a difference in Tm at which the stems of the open LOCS structures melt. |

Further, the data from this example demonstrate the difference in melt signatures obtained when the sequence and or length of the stem regions are varied. The data demonstrate that open LOCS-1 produces melt signatures with a lower Tm (30° C.) compared with those of open LOCS-3 (36° C.). Similarly, open LOCS-4 produces melt signatures with a lower Tm (32° C.) compared with those of open LOCS-2 (50° C.). These results are consistent with the fact that LOCS-1 and LOCS-4 have shorter stems than LOCS-3 and LOCS-2 respectively. Furthermore, each LOCS produces a unique melt signature distinct from the other LOCS reporters. This experiment demonstrates that different melt signatures can be produced by modifying the length and composition of the stem regions. Thus, a suite of LOCS-reporters could be used simultaneously to achieve detection of multiple targets from a single channel. Furthermore, the data generated in this experiment was achieved using isothermal target detection, exemplifying that the LOCS reporters can be used with a range of different biosensing techniques.

Example 4: LOCS Reporter Compatibility Across Several Platforms

In this example, two LOCS reporters are tested for their compatibility across several commonly used PCR platforms. Two MNAzymes (MNAzyme 1 and MNAzyme 2) are used to monitor amplification of target nucleic acids in real-time via cleavage of their corresponding LOCS reporters (LOCS-1 and LOCS-2 respectively). In this example, amplification and detection of two different genes, namely MgPa gene (*Mycoplasma genitalium*) and TV-Btub (*Trichomonas vaginalis*), are performed simultaneously in a single tube, wherein both are able to produce signal in the FAM channel.

Reaction Components and Conditions

The oligonucleotides specific to this experiment include; LOCS-1 (SEQ ID NO: 1), LOCS-2 (SEQ ID NO: 2), Partzyme A1 (SEQ ID NO: 3), Partzyme B1 (SEQ ID NO: 4), Partzyme A2 (SEQ ID NO: 5), Partzyme B2 (SEQ ID NO: 6), Forward Primer 1 (SEQ ID NO: 7), Forward Primer 2 (SEQ ID NO: 8), Reverse Primer 1 (SEQ ID NO: 9) and Reverse Primer 2 (SEQ ID NO: 10). The oligonucleotides specific for MgPa amplification and detection are LOCS-1, Partzyme A1, Partzyme B1, Forward Primer 1 and Reverse Primer 1.

The oligonucleotides specific for TV-Btub amplification and detection are LOCS-2, Partzyme A2, Partzyme B2, Forward Primer 2 Reverse Primer 1 and Reverse Primer 2. The sequences are listed in the Sequence Listing.

The cycling parameters were 95° C. for 2 minutes, 10 touchdown cycles of 95° C. for 5 seconds and 61° C. for 30 seconds (0.5° C. decrement per cycle) and 40 cycles of 95° C. for 5 seconds and 52° C. for 40 seconds (data collected at the 52° C. step). Melt curve parameters on the BioRad® CFX96 thermocycler were 0.5° C. increment from 20° C. to 90° C. with a 5 sec hold (data acquisition on hold). Melt curve parameters on the Lightcycler 480 thermocycler were set to continuous acquisition mode at a ramp rate of 0.02° C. per ranging from 20° C. to 90° C. with a 1 sec hold at each temperature. Melt curve parameters on the ABI 7500 thermocycler were set at a 1% ramp rate from 20° C. to 90° C. with a 5 sec hold (data acquisition on hold). Melt curve parameters on the Xxpress PCR thermocycler were 0.5° C. increment from 30° C. to 90° C. with a 0.5 sec hold (data acquisition on hold). All reactions were run in duplicate and contained 40 nM of each forward primer, 200 nM of each reverse primer, 200 nM of each partzyme A, 200 nM of each partzyme B, 200 nM of each LOCS reporter, 2 mM $MgCl_2$ (Bioline) and 1× SensiFAST Probe No-ROX Mix (Bioline).

Real-time amplification and detection of the target sequence was performed in a total reaction volume of 20 p L, except for reactions mu on the XXpress PCR thermocycler which were performed in a 15 µL volume. The reactions contained either G-Block template (10,000 or 40 copies) or no target (NF H$_2$O). Real-time amplification and detection of the target sequence was performed using a BioRad® CFX96 thermocycler, a Lightcycler 480 thermocycler, an ABI 7500 thermocycler and an XXpress PCR thermocycler.

Results

The results in FIG. 8 and FIG. 9 show the melting curves obtained following amplification of the MgPa and TV-Btub targets respectively when amplification was performed on the BioRad® CFX96 thermocycler (Panel A) or a Lightcycler 480 thermocycler (Panel B), or an ABI 7500 thermocycler (Panel C), or the XXpress PCR thermocycler (Panel D). Both targets were monitored in the FAM channel on all machines. The results illustrated in FIG. 8D and FIG. 9D were obtained using a 3 minute melt curve protocol, thus demonstrating that melt curve distinction using LOCS reporters can be achieved using rapid conditions. The data demonstrates the capacity to generate comparable melt curve signatures obtained across different platforms using two different LOCS reporters. Further, the data demonstrates that capacity to generate comparable melt curve signatures obtained using varied melt curve parameters.

Example 5: LOCS Reporter Compatibility Across Several Fluorescent Channels

In this example, ten LOCS reporters are tested for their compatibility across several commonly used fluorescent channels. Two MNAzymes (MNAzyme 1 and MNAzyme 2) are used to monitor amplification of target nucleic acids in real-time via cleavage of their corresponding LOCS reporter. In this example, the same LOCS reporter sequences are used, however the LOCS are labelled with different fluorophore and quencher pairs. In this example, amplification and detection of two different genes, namely MgPa gene (*Mycoplasma genitalium*) and TV-Btub (*Trichomonas vaginalis*), are performed simultaneously in a single tube, wherein both are able to produce signal in the same channel. Several fluorescent channels were tested including FAM, HEX, Texas Red and Cy5.

Reaction Components and Conditions

The oligonucleotides specific to this experiment include; LOCS-1 (SEQ ID NO: 1), LOCS-2 (SEQ ID NO: 2), Partzyme A1 (SEQ ID NO: 3), Partzyme B1 (SEQ ID NO: 4), Partzyme A2 (SEQ ID NO: 5), Partzyme B2 (SEQ ID NO: 6), Forward Primer 1 (SEQ ID NO: 7), Forward Primer 2 (SEQ ID NO: 8), Reverse Primer 1 (SEQ ID NO: 9), Reverse Primer 2 (SEQ ID NO: 10), LOCS-5 (SEQ ID NO: 35) LOCS-6 (SEQ ID NO: 36), LOCS-7 (SEQ ID NO: 37) LOCS-8 (SEQ ID NO: 38), LOCS-9 (SEQ ID NO: 39) and LOCS-10 (SEQ ID NO: 40). The oligonucleotides specific for MgPa amplification and detection are Partzyme A1, Partzyme B1, Forward Primer 1, Reverse Primer 1 and either LOCS-1, LOCS-5, LOCS-7 or LOCS-9. The oligonucleotides specific for TV-Btub amplification and detection are Partzyme A2, Partzyme B2, Forward Primer 2, Reverse Primer 2 and either LOCS-2, LOCS-6, LOCS-8 or LOCS-10. The sequences are listed in the Sequence Listing. The cycling parameters were 95° C. for 2 minutes, 10 touchdown cycles of 95° C. for 5 seconds and 61° C. for 30 seconds (0.5° C. decrement per cycle) and 40 cycles of 95° C. for 5 seconds and 52° C. for 40 seconds (data collected at the 52° C. step). Melt curve parameters on the BioRad® CFX96 thermocycler were 0.5° C. increment from 20° C. to 90° C. with a 5 sec hold (data acquisition on hold). All reactions were run in duplicate and contained 40 nM of each forward primer, 200 nM of each reverse primer, 200 nM of each partzyme A, 200 nM of each partzyme B, 200 nM of each LOCS reporter, 2 mM MgCl$_2$ (Bioline) and 1× SensiFAST Probe No-ROX Mix (Bioline). Real-time amplification and detection of the target sequence was performed in a total reaction volume of 20 µL using a BioRad® CFX96 thermocycler. The reactions contained either G-Block template (10,000 or 40 copies) or no target (NF H$_2$O).

Results

The results in FIG. 10 show the melting curves obtained following amplification of the MgPa and TV-Btub targets respectively when amplification was performed on the BioRad® CFX96 thermocycler. Both targets were monitored simultaneously in a single fluorescent channel. Results shown in black illustrate melt curves obtained in the presence of MgPa gene and results shown in grey illustrate the melt curve signatures obtained in the presence of TV-Btub targets. The solid lines represent target concentrations of 10,000 copies and the dotted lines represent target concentrations of 40 copies. The results illustrated in FIG. 10A illustrates melt curves obtained using LOCS-1 and LOCS-2 in the FAM channel. The melt curves shown in FIG. 10B were obtained using LOCS-5 and LOCS-6 in the HEX channel. The melt curves shown in FIG. 10C were obtained using LOCS-7 and LOCS-8 in the Texas Red channel and the melt curves shown in FIG. 10D were obtained using LOCS-9 and LOCS-10 in the Cy5 channel. The data demonstrates the capacity to generate comparable melt curve signatures obtained across different fluorescent channels using the same two LOCS stems and substrates, but simply changing the fluorophore-quencher pair.

Example 6: Simultaneous Detection of Three Targets in a Single Fluorescent Channel Using Three LOCS Reporters In the following example, LOCS reporters are used to increase the number of targets that can be detected from a single fluorescence channel. In this example, three LOCS reporters are 5' labelled with a fluorophore (FAM) and 3' labelled with a quencher. The loop regions of the LOCS reporters contain a nucleic acid substrate, and the stem regions contain a series of complementary base-pairs that constrain the LOCS reporter in a loop-stem configuration. In this configuration, the fluorophore and quencher are in close proximity and the fluorescence is quenched in the absence of target.

Oligonucleotides

The oligonucleotides specific to this experiment include; LOCS-1 (SEQ ID NO: 1), LOCS-2 (SEQ ID NO: 2), Partzyme A1 (SEQ ID NO: 3), Partzyme B1 (SEQ ID NO: 4), Partzyme A2 (SEQ ID NO: 5), Partzyme B2 (SEQ ID NO: 6), Forward Primer 1 (SEQ ID NO: 7), Reverse Primer 1 (SEQ ID NO: 8), Forward Primer 2 (SEQ ID NO: 9), Reverse Primer 2 (SEQ ID NO: 10), LOCS-11 (SEQ ID NO: 45), Partzyme A9 (SEQ ID NO: 43), Partzyme B9 (SEQ ID NO: 44), Forward Primer 7 (SEQ ID NO: 41) and Reverse Primer 7 (SEQ ID NO: 42). The sequences are listed in the Sequence Listing. The oligonucleotides specific for MgPa amplification and detection are LOCS-1, Partzyme A1, Partzyme B1, Forward Primer 1 and Reverse Primer 1. The oligonucleotides specific for TV-Btub amplification and detection are LOCS-2, Partzyme A2, Partzyme B2, Forward Primer 2 and Reverse Primer 2. The oligonucleotides specific for CTcry amplification and detection are LOCS-11, Partzyme A9, Partzyme B9, Forward Primer 7 and Reverse Primer 7.

Reaction Conditions

Real-time amplification and detection of the target sequence was performed in a total reaction volume of 20 μL using a BioRad® CFX96 thermocycler. The cycling parameters were 95° C. for 2 minutes, 10 touchdown cycles of 95° C. for 5 seconds and 61° C. for 30 seconds (0.5° C. decrement per cycle) and 35 cycles of 95° C. for 5 seconds and 52° C. for 40 seconds (data collected at the 52° C. step). Melt curve parameters were 0.5° C. increment from 20° C. to 90° C. with a 5 sec hold (data acquisition on hold). All reactions were run in duplicate and contained 40 nM of each forward primer, 200 nM of each reverse primer, 200 nM of each partzyme A, 200 nM of each partzyme B, 200 nM of each LOCS reporter, 2 mM $MgCl_2$ (Bioline) and 1× Sensi-FAST Probe No-ROX Mix (Bioline). The reactions contained either i-Block template (10,000 copies) homologous to the MgPa and/or TV-Btub and/or CTcry genes, or no target (NF $H_2O$).

Results

Using an in vitro target amplification method known as PCR, three MNAzymes (MNAzyme 1, MNAzyme 2 and MNAzyme 9) are used to monitor amplification of target nucleic acids in real-time via cleavage of their corresponding LOCS reporters (LOCS-1, LOCS-2 and LOCS-11 respectively). MNAzyme 1 was designed to detect sequences homologous to the MgPa gene (*Mycoplasma genitalium*) and to cleave and open LOCS-1; MNAzyme 2 was designed to detect sequences homologous to the TV-Btub (*Trichomonas vaginalis*) and cleave and open LOCS-2; and MNAzyme 9 was designed to detect sequences homologous to the CTcry (*Chlamydia trachomatis*) and cleave and open LOCS-11. In this experiment, amplification and detection was performed in single tube, containing all MNAzymes, primers and LOCS oligonucleotides. The presence of either MgPa, TV-Btub, CTcry or various combinations of the three (representing a sample with multiple infections) were detected by an increase in signal in the FAM channel.

The results shown in FIGS. 11 & 12 illustrate the respective melt curve signatures obtained post amplification from reactions containing 10,000 copies of the targets MgPa (FIG. 11A), TV-Btub (FIG. 11B), CTcry (FIG. 11C), both MgPa and TV-Btub (FIG. 11D) both MgPa and CTcry (FIG. 11E), both TV-Btub and CTcry (FIG. 11F), or all three of MgPa, TV-Btub and CTcry (FIG. 12). The results are the averages from duplicate reactions that were plotted using Microsoft Excel (Version 14).

The data from this example, summarized in Table 3, demonstrates that the LOCS melt signatures produced in the presence of MgPa gene target (Tm=39° C. and 66° C.) are distinct from the LOCS melt signatures produced in the presence of TV-Btub (Tm=49° C. and 64° C.) and CTcry (Tm=30° C., 41° C. and 64° C.) gene targets. Further, the LOCS melt signatures in the presence of two or more gene targets are also distinct from the aforementioned melt signatures wherein only a single gene target is present. When MgPa and TV-Btub targets were present within a single reaction, a unique melt curve signature (Tm=39° C., 49° C. and 66° C.) indicated that both targets were detected. Similarly, when MgPa and CTcry or TV-Btub and CTcry were present within a single reaction, unique melt curve signatures ((Tm=31° C., 41° C. and 74° C.) and (Tm=30° C., 41° C., 49° C. and 66° C.) respectively) indicated which two targets were detected. When MgPa, TV-Btub and CTcry targets were all present within a single reaction, a unique melt curve signature (Tm=30° C., 41° C. and 49° C.) indicated all three targets were detected.

TABLE 3

Summary of Melting Temperatures (Tms) of LOCS Reporters in the presence of one, two or three targets as illustrated in FIGS. 11 and 12.

| Figure | Targets Present | Melt Curve Tms (Tms indicative of closed LOCS in italics) |
|---|---|---|
| FIG. 11A | MgPa | 39° C., 66° C., 74° C. |
| FIG. 11B | TV-Btub | 49° C., 64° C. |
| FIG. 11C | CTcry | 30° C., 41° C., 64° C., 74° C. |
| FIG. 11D | MgPa and TV-Btub | 39° C., 49° C., 66° C. |
| FIG. 11E | MgPa and CTcry | 31° C., 41° C., 74° C. |
| FIG. 11F | TV-Btub and Ctory | 30° C., 41° C., 49° C., 64° C. |
| FIG. 12 | MgPa, TV-Btub and CTcry | 30° C., 41° C., 49° C. |

This example demonstrates that three targets, co-amplified in a single well and using a single fluorescent channel, can be distinguished based on their unique LOCS melt signatures. The example provides a simple method useful for detecting multiple targets in a single well using a single fluorescent channel. Due to different stem lengths and base-pair compositions, the different stems (Stem-1, Stem-2 and Stem-3) within LOCS-1, LOCS-2 and LOCS-11 have produced unique fluorescence melt curve signatures.

In this specific example the Tm of open LOCS 1 (one peak at ~39° C. indicative of MgPa) and open LOCS 3 (two peaks at ~30/31° C. and ~41° C. indicative of CTcry) result in a merged peak when both MgPa and CTcry targets are present. None-the-less the reaction containing MgPa, TV-Btub and CTcry (FIG. 12) can be distinguished from that containing only TV-Btub and CTcry (FIG. 11F) by the disappearance of the peak of the Tm of the Open LOCS 1 (~64° C.). While a merged peak is not ideal for the method, alternative stem sequences which produce more clearly discriminated peaks can be readily identified using the stem screening assay described in Example 7.

Example 7: Method for Screening Sequences Suitable for Use as Universal Stems which May be Incorporated into LOCS Reporter Oligonucleotides In the following example, a series of double stranded oligonucleotides (DSOs) were screened for suitability for use as universal stems. These DSOs, which are not connected by loops, were subjected to gradually increasing temperatures, in the presence of SYBR green 1 intercalating dye. This melt curve screening assay can be used to examine various sequence lengths and compositions in order to identify a series DSOs which melt at discreet temperatures and can subsequently be incorporated as universal stems within LOCS reporter oligonucleotides. SYBR green 1 is an intercalating dye that generates a fluorescence signal when it binds to double stranded DNA structures. Upon exposure to an increasing temperature gradient, the two oligonucleotide strands of the DSO dissociate and the fluorescence decreases. The following example demonstrates that the temperature at which the two oligonucleotides dissociate (Tm) can be regulated by varying the stem length and composition. Furthermore, the DSOs were tested at various concentrations to demonstrate how the Tm can be further manipulated by modifying the oligonucleotide concentration.

Oligonucleotides

The oligonucleotides specific to this experiment include; DSO-1A (SEQ ID NO: 56), DSO-1B (SEQ ID NO: 57), DSO-2A (SEQ ID NO: 58), DSO-2B (SEQ ID NO: 59), DSO-3A (SEQ ID NO: 60), DSO-3B (SEQ ID NO: 61). DSO-4A (SEQ ID NO: 62), DSO-4B (SEQ ID NO: 63), DSO-5A (SEQ ID NO: 64), DSO-5B (SEQ ID NO: 65), DSO-6A (SEQ ID NO: 66), DSO-6B (SEQ ID NO: 67), DSO-7A (SEQ ID NO: 68), DSO-7B (SEQ ID NO: 69), DSO-8A (SEQ ID NO: 70) and DSO-8B (SEQ ID NO: 71). The sequences are listed in the Sequence Listing.

Reaction Conditions

Melt Curve analysis was performed in a total reaction volume of 20 µL using a BioRad® CFX96 thermocycler. Melt curve parameters were 0.5° C. increment from 15° C. to 70° C. with a 5 sec hold (data acquisition on hold). All reactions were run in duplicate and contained either 100 nM, 200 nM or 300 nM of DSO-A and DSO-B oligonucleotides, 1 µM of SYBR green I, 8 mM MgCl$_2$(Bioline) and 1x NH4 buffer (Bioline).

Results

The results shown in Table 4 illustrate the melting temperatures (Tms) obtained when DSOs are subject to an increasing temperature gradient. The results are the averages from duplicate reactions that were plotted using Microsoft Excel (Version 14).

This example demonstrates that increasing stem length and GC content results in a higher Tm. Moreover, increasing the oligonucleotide concentration also leads to a slightly higher Tm, with the greatest difference observed when the concentration was increased from 100 nM to 200 nM. The method described in this example can be used as a screening method to better identify alternative stem sequences which produce more clearly discriminated peaks.

TABLE 4

Summary of Tis of DSOs at various concentrations

| Stem # | Sequence | # of nucleotides | Predicted Tm | Experimental Tm & oligo concentrations | | |
|---|---|---|---|---|---|---|
| | | | | 100 nM | 200 nM | 300 nM |
| 1 | 3' GCGTGA 5'<br>5' CGCACT 3' | 6 | 20° C. | 28° C. | 30° C. | 30° C. |
| 2 | 3' GCGTGAA 5'<br>5' CGCACTT 3' | 7 | 22° C. | 30° C. | 30° C. | 30° C. |
| 3 | 3' GCGTGAC 5'<br>5' CGCACTG 3' | 7 | 24° C. | 35° C. | 35° C. | 36° C. |
| 4 | 3' GCGTGACA 5'<br>5' CGCACTGT 3' | 8 | 26° C. | 39° C. | 40° C. | 41° C. |
| 5 | 3' GCGTGACC 5'<br>5' CGCACTGG 3' | 8 | 28° C. | 41° C. | 43° C. | 43° C. |
| 6 | 3' GCGTGACCA 5'<br>5' CGCACTGGT 3' | 9 | 30° C. | 45° C. | 46° C. | 47° C. |
| 7 | 3' GCGTGACCG 5'<br>5' CGCACTGGC 3' | 9 | 32° C. | 47° C. | 50° C. | 51° C. |
| 8 | 3' GCGTGACCGT 5'<br>5' CGCACTGGCA 3' | 10 | 34° C. | 50° C. | 52° C. | 53° C. |

The method can also be used to examine the effects of other components of a reaction mix, including but not limited to salt concentration, Mg concentration, buffer, dNTP concentrations and other additives. A series of DSOs, which when incorporated into LOCS, result in a ladder of well separated Tms could be identified using this screening method. In an alternative format, the DSOs could be labelled with different fluorophore and quencher dye pairs to investigate whether or not different dye combinations can influence the Tm of a specific DSO.

Example 8: Simultaneous Detection of Four Targets in a Single Well Using Two Fluorescent Channels and Four LOCS Reporters Utilising Only Two Stems In the following example, multiple LOCS reporters comprising the same stem composition and connected to different substrates (loops) are combined in a single reaction vessel to demonstrate that the same stem region can be used multiple times to detect and differentiate multiple targets simultaneously in a single reaction. In the current example, two stems (stem-1 and stem-2) are used to differentiate four different targets across two fluorescent channels. In this example, two LOCS reporters are 5' labelled with a FAM fluorophore (LOCS-12 and LOCS-13) and the other two are 5' labelled with a Texas Red fluorophore (LOCS-7 and LOCS-8). All four LOCS reporters are 3' labelled with a quencher. Each of the loop regions of the four LOCS reporters contains a different nucleic acid substrate (Sub1, Sub2, Sub3 and Sub4). Two LOCS reporters, one for each fluorophore, contain Stem-1 (LOCS-7 and LOCS-12) and the other two LOCS reporters contain Stem-2 (LOCS-8 and LOCS-13). The stem regions contain a series of complementary base-pairs that constrain the LOCS reporter in a loop-stem configuration. In this configuration, the fluorophore and quencher are in close proximity and the fluorescence is quenched in the absence of target. Stem-1 has a lower melting temperature than stem-2 and is connected to Loops 1 and 3 for the detection of Targets MgPa and NGopa at a first detection temperature (40° C.) whereas stem-2 has a higher melting temperature and is connected to Loops 2 and 4 for the differentiation of targets TV-Btub and gpd at a second detection temperature (50° C.).

Oligonucleotides

The oligonucleotides specific to this experiment include; LOCS-7 (SEQ ID NO: 37), LOCS-8 (SEQ ID NO: 38), Partzyme A1 (SEQ ID NO: 3), Partzyme B1 (SEQ ID NO: 4), Partzyme A2 (SEQ ID NO: 5), Partzyme B2 (SEQ ID NO: 6), Forward Primer 1 (SEQ ID NO: 7), Reverse Primer 1 (SEQ ID NO: 8), Forward Primer 2 (SEQ ID NO: 9), Reverse Primer 2 (SEQ ID NO: 10), LOCS-12 (SEQ ID NO: 46), LOCS-13 (SEQ ID NO: 47), Partzyme A10 (SEQ ID NO: 48), Partzyme B10 (SEQ ID NO: 49), Partzyme A11 (SEQ ID NO: 50), Partzyme B11 (SEQ ID NO: 51), Forward Primer 8 (SEQ ID NO: 52), Reverse Primer 8 (SEQ ID NO: 53), Forward Primer 9 (SEQ ID NO: 54) and Reverse Primer 9 (SEQ ID NO: 55). The sequences are listed in the Sequence Listing. The oligonucleotides specific for MgPa amplification and detection are LOCS-7, Partzyme A1, Partzyme B1, Forward Primer 1 and Reverse Primer 1. The oligonucleotides specific for TV-Btub amplification and detection are LOCS-8, Partzyme A2, Partzyme B2, Forward Primer 2 and Reverse Primer 2. The oligonucleotides specific for NGopa amplification and detection are LOCS-12, Partzyme A10, Partzyme B10, Forward Primer 8 and Reverse Primer 8. The oligonucleotides specific for gpd amplification and detection are LOCS-13, Partzyme A11, Partzyme B11, Forward Primer 9 and Reverse Primer 9.

Reaction Conditions

Real-time amplification and detection of the target sequence was performed in a total reaction volume of 20 μL using a BioRad® CFX96 thermocycler. The cycling parameters were 95° C. for 2 minutes, 10 touchdown cycles of 95° C. for 5 seconds and 61° C. for 30 seconds (0.5° C. decrement per cycle) and 35 cycles of 95° C. for 5 seconds and 52° C. for 40 seconds (data collected at the 52° C. step). Melt curve parameters were 0.5° C. increment from 20° C. to 90'C with a 5 sec hold (data acquisition on hold). All reactions were run in duplicate and contained 40 nM of each forward primer, 200 nM of each reverse primer, 200 nM of each partzyme A, 200 nM of each partzyme B, 200 nM of each LOCS reporter, 2 mM $MgCl_2$ (Bioline) and 1× SensiFAST Probe No-ROX Mix (Bioline). The reactions contained G-Block template (10,000 copies) homologous to either the MgPa, TV-Btub, NGopa or gpd genes, or contained no target (NF $H_2O$).

Results

Using an in vitro target amplification method known as PCR, four MNAzymes (MNAzyme 1, MNAzyme 2, MNAzyme 10 and MNAzyme 11) are used to monitor amplification of target nucleic acids in real-time via cleavage of their corresponding LOCS reporters (LOCS-7, LOCS-8, LOCS-12 and LOCS-13 respectively). MNAzyme 1 was designed to detect sequences homologous to the MgPa gene (*Mycoplasma genitalium*) and to cleave and open LOCS-7; MNAzyme 2 was designed to detect sequences homologous to the TV-Btub gene (*Trichomonas vaginalis*) and cleave and open LOCS-8; MNAzyme 10 was designed to detect sequences homologous to the NGopa gene (*Neisseria gonorrhoeae*) and cleave and open LOCS-12; and MNAzyme 11 was designed to detect sequences homologous to the gpd gene (Herpes simplex virus type 2) and cleave and open LOCS-13. In this experiment, amplification and detection was performed in single tube, containing all MNAzymes, primers and LOCS oligonucleotides.

The presence of either MgPa or TV-Btub genes was detected by an increase in signal in the Texas Red channel; and the presence of either NGopa or gpd genes were detected by an increase in signal in the FAM channel. The differentiation of MgPa or TV-Btub in the Texas Red channel, and NGopa or gpd in the FAM channel, was determined based on the presence of a unique melt curve signature. The results shown in FIG. 13A illustrate the respective melt curve signatures obtained in the Texas Red channel post amplification from reactions containing either 10,000 copies of MgPa (black line) or TV-Btub (grey line) gene target.

The results shown in FIG. 13B illustrate the respective melt curve signatures obtained in the FAM channel post amplification from reactions containing either 10,000 copies of NGopa (black line) or gpd (grey line) gene target. The results are the averages from duplicate reactions that were plotted using Microsoft Excel (Version 14). The presence of MgPa was determined by both an increase in the Texas Red signal and a unique melt signature in the Texas Red channel (Tm=43° C.). The presence of TV-Btub was determined by both an increase in the Texas Red signal and a unique melt signature in the Texas Red channel (Tm=54° C.). The presence of NGopa was determined by both an increase in the FAM signal and a unique melt signature in the FAM channel (Tm=26° C. and 42° C.). The presence of gpd was determined by both an increase in FAM signal and a unique melt signature in the FAM channel (Tm=49° C.).

This data from this example, as summarized in Table 5, demonstrates that the same universal stem regions can be utilized multiple times in a single reaction by connecting them to different substrates (loops) and detecting them across different fluorescent channels. Furthermore, the data demonstrates that four targets, co-amplified in a single well and monitored using two fluorescent channels, can be distinguished based on their unique LOCS melt temperatures. The example provides a simple method useful for detecting multiple targets in a single well. The use of the same stem sequence for differentiating multiple targets in a single reaction facilitates a straightforward design of highly multiplexed assays and enables the fast and easy adaption of LOCS probes for the detection of any gene target of choice.

TABLE 5

Summary of Melting Temperatures (Tms) of open LOCS Reporters in the presence of one of the four targets listed as illustrated in FIG. 13.

| Gene Target | FAM Channel Tm | Texas Red Channel Tm | FIG. 13 |
|---|---|---|---|
| MgPa | | 43° C. | Panel A (black line) |
| TV-Btub | | 53° C. | Panel A (grey line) |
| NGopa | 26° C., 42° C. | | Panel B (black line) |
| gpd | 49° C. | | Panel B (grey line) |

Example 9—the Same Stem Sequence can be Combined with Different Substrates within LOCS Reporters to Generate Reproducible Melting Temperatures In the following example, three LOCS reporters are used to demonstrate that the same stem can be paired with different loop sequences (substrates), generating comparable melt signatures. In this example, all three LOCS reporters are 5' labelled with a FAM fluorophore and 3' labelled with a quencher. Each of the loop regions of the three LOCS reporters contains a different substrate for a nucleic acid enzyme (an MNAzyme) but all three contain the same stem sequence (Stem-2).

Oligonucleotides

The oligonucleotides specific to this experiment include; Forward primer 10 (SEQ ID NO: 72), Reverse primer 10 (SEQ ID NO: 73), LOCS-2 (SEQ ID NO: 2), LOCS-14 (SEQ ID NO: 78), LOCS-15 (SEQ ID NO: 79), Partzyme A8 (SEQ ID NO: 31), Partzyme B8 (SEQ ID NO: 32), Partzyme A12 (SEQ ID NO: 74), Partzyme B12 (SEQ ID NO: 75), Partzyme A13 (SEQ ID NO: 76) and Partzyme B13 (SEQ ID NO: 77). The sequences are listed in the Sequence Listing. The oligonucleotides specific for amplification of TFRC gene are Forward primer 10 (SEQ ID NO: 72) and Reverse primer 10 (SEQ ID NO: 73). The oligonucleotides specific for detection of TFRC amplicon and cleavage of LOCS-2 are Partzyme A8 (SEQ ID NO: 31) and Partzyme B8 (SEQ ID NO: 32). The oligonucleotides specific for detection of TFRC amplicon and cleavage of LOCS-14 are Partzyme A12 (SEQ ID NO: 74) and Partzyme B12 (SEQ ID NO: 75). The oligonucleotides specific for detection of TFRC amplicon and cleavage of LOCS-15 are Partzyme A13 (SEQ ID NO: 76) and Partzyme B13 (SEQ ID NO: 77).

Reaction Conditions

Real-time amplification and detection of the target sequence was performed in a total reaction volume of 20 μL using a BioRad® CFX96 thermocycler. The cycling parameters were 95° C. for 2 minutes, 10 touchdown cycles of 95° C. for 5 seconds and 61° C. for 30 seconds (0.5° C. decrement per cycle) and 35 cycles of 95° C. for 5 seconds and 52° C. for 40 seconds (data collected at the 52° C. step). Melt curve parameters were 0.5° C. increment from 20° C. to 90° C. with a 5 sec hold (data acquisition on hold). All reactions were run in duplicate and contained 40 nM of each forward primer, 200 nM of each reverse primer, 200 nM of each partzyme A, 200 nM of each partzyme B, 200 nM of each LOCS reporter, 2 mM $MgCl_2$ (Bioline) and 1× SensiFAST Probe No-ROX Mix (Bioline). The reactions contained G-Block template (10,000 copies) homologous to the human transferrin receptor (TFRC) gene, or contained no target (NF $H_2O$).

Results

In this experiment, PCR amplification, signal detection and melt curve differentiation were performed in a single tube, as single-plex reactions. During PCR, three MNAzymes (MNAzyme 8, MNAzyme 12 and MNAzyme 13) were used to monitor amplification of target nucleic acids in real-time via cleavage of their corresponding LOCS reporters (LOCS-2, LOCS-14 and LOCS-15 respectively). All three MNAzymes were designed to detect the same target sequence (TFRC gene), however, each MNAzyme can hybridise and cleave a different substrate sequence (Loop); thus opening a different LOCS reporter.

Results shown in FIG. 14 illustrate the respective melt curve signatures obtained in the FAM channel post PCR amplification from reactions containing either 10,000 copies of TFRC gene target (black line) or no target (grey line). The presence of TFRC gene was demonstrated by the presence of a PCR amplification curve crossing a threshold value (data not shown) and melting peaks at Tms of 49° C., 48° C. and 49° C. (FIGS. 14A, 14B and 14C respectively) correlating to cleaved LOCS-2, LOCS-14 and LOCS-15 respectively. The absence of TFRC gene was determined by the absence of a PCR amplification curve which crossed the threshold value (data not shown) and the presence of a melting peak at a Tm of 74° C., 75° C. and 75° C. correlating to un-cleaved LOCS-2, LOCS-14 and LOCS-15 respectively (FIGS. 14A, 14B and 14C respectively). The results are the averages from duplicate reactions that were plotted using Microsoft Excel (Version 14). The data from this example demonstrates that the same universal stem regions can be utilized with different 0.30 substrates (loops) to generate comparable melt curve signatures. The use of the same stem sequence for engineering LOCS reporters with different substrates facilitates a straightforward design of highly multiplexed assays and enables the fast and easy adaption of LOCS probes for the detection of any gene target of choice.

Example 10—Using Nicking Endonuclease as an Alternative Method for Opening LOCS Reporters In the following example, a nicking endonuclease (Nt. AlwI) is used to demonstrate that comparable melt signatures are produced when the loop portion of LOCS reporters are opened following cleavage by a nicking endonuclease as an alternative method to MNAzyme cleavage. The general strategy is illustrated in FIG. 38. In this example, a dual-labelled LOCS reporter contains a loop region that is complementary to the target sequence and a stem region that is not complementary to the target. Hybridisation of the Loop region of a LOCS reporter with the target completes a nicking endonuclease recognition site, facilitating cleavage of the LOCS reporter by the nicking endonuclease and leaving the target in-tact. Since intramolecular bonds are stronger than intermolecular bonds, the stem regions of the intact LOCS structures will melt at higher temperatures than the stems of the open, cleaved LOCS structures.

Oligonucleotides

The oligonucleotides specific to this experiment include; AF-NE-TV1 (SEQ ID NO: 82), LOCS-16 (SEQ ID NO: 80), AF-NE-R5b (SEQ ID NO: 83), and LOCS-17 (SEQ ID NO: 81). The sequences are listed in the Sequence Listing.

Reaction Conditions

Real-time detection of the target sequence was performed in a total reaction volume of 20 μL using a BioRad® CFX96 thermocycler. Reactions were incubated at a constant temperature of 52° C. with data collected every 20 see for a total of 200 data collections. Melt curve parameters were 0.5° C. increment from 20° C. to 90° C. with a 5 sec hold (data acquisition on hold). All reactions were run in duplicate and contained 5 mM $MgCl_2$ (Ambion), 1×PCR Buffer II (ABI), 4 units of Nt. AlwI (NEB) and 200 nM of LOCS (either LOCS-16 or LOCS-17). The reactions contained either AF-NE-TV1 or AF-NE-R5b (200 nM) or contained no target (NF $H_2O$).

Results

Signal detection and melt curve differentiation were performed in a single tube. Results shown in FIGS. 15A and 15B illustrate the respective melt curve signatures for LOCS-16 and LOCS-17 obtained in the FAM channel from reactions containing either 200 nM of target (black line; AF-NE-TV1 or AF-NE-R5b respectively) or no target (grey line; NF $H_2O$). The results are the averages from duplicate reactions that were plotted using Microsoft Excel (Version 14). The presence of the target AF-NE-TV1 was detected both by a rapid increase in fluorescence over time and by the presence of a melt peak at 29° C. corresponding to cleaved LOCS-16. The absence of the target AF-NE-TV1 was determined by (i) the lack of fluorescence increase over time, (ii) the absence of a melting peak at 29° C. and (iii) the presence of a melting peak at 65° C. corresponding to un-cleaved LOCS-16 (FIG. 15A). The presence of the target AF-NE-R5b was detected both by a rapid increase in fluorescence over time and by the presence of a melt peak at 48° C. corresponding to cleaved LOCS-17. The absence of the target AF-NE-R5b was determined by (i) the lack of fluorescence increase over time, (ii) the absence of a melting peak at 48° C. and (iii) the presence of a melting peak at 76° C. corresponding to un-cleaved LOCS-17 (FIG. 15B).

The data from this example demonstrate that LOCS reporters can be used with alternative target detection methods such as those using nicking endonuclease enzymes. Furthermore, the data also demonstrates that LOCS reporters containing the same stem (Stem-2) produce peaks at the same melting temperature (~50° C.) regardless of the loop degradation mechanism, for example cleavage by either a Nicking enzyme or by an MNAzyme. In the current example, intact and open LOCS reporters containing Stem-2 produced melt peaks at 48° C. and 76° C. respectively. These melt peaks are comparable to the melt peaks generated using Stem-2 with MNAzymes as demonstrated in FIG. 4D.

Although small shifts of 1-2° C. may be observed for LOCS containing the same stem when used in different protocols, for example cleavage of the loop by nicking enzymes versus cleavage of the loop by an MNAzyme, these shifts likely reflect differences in the reaction milieu where concentrations of salt, glycerol or other component can influence the Tm of the stem.

Example 11—Using TaqMan Exonuclease as an Alternative Method for Opening LOCS Reporters In the following example, the TaqMan/Hydrolysis probe-like method is used to demonstrate that comparable melt signatures are produced when the Stem portion of LOCS reporters are opened following exonuclease degradation as an alternative method to MNAzyme cleavage of the loop. The general strategy for this example is illustrated in FIG. 3A. In this example, a dual-labelled LOCS reporter contains a loop region that is complementary to the target sequence and a stem region that is not complementary to the target. During PCR amplification, the Loop region of a LOCS reporter can hybridise with the target and/or amplicon sequence. During the primer extension stage of PCR, the upstream primer is extended into the region where the LOCS reporter is hybridised with the target, the polymerase progressively cleaves the 5' end of the loop region of the LOCS reporter but leaves the stem region intact. Degradation of the Loop region reduces the melting temperature of the LOCS stem as the inter-molecular forces between two LOCS stem fragments are significantly weaker than the intra-molecular forces that occur between them within a closed LOCS molecule.

Oligonucleotides

The oligonucleotides specific to this experiment include; Forward primer 2 (SEQ ID NO: 9), Reverse primer 2 (SEQ ID NO: 10) and LOCS-18 (SEQ ID NO: 84). The sequences are listed in the Sequence Listing.

Reaction Conditions

Real-time amplification and detection of the target sequence was performed in a total reaction volume of 20 μL using a BioRad® CFX96 thermocycler. The cycling parameters were 95° C. for 2 minutes and 50 cycles of 95° C. for 5 seconds and 52° C. for 40 seconds (with data acquisition at the 52° C. step). Melt curve parameters were 0.5° C. increment from 20° C. to 90° C. with a 5 sec hold (data acquisition on hold). All reactions were run in duplicate and contained 400 nM of each primer, 200 nM of LOCS-16, 2 mM $MgCl_2$ (Bioline) and 1× SensiFAST Probe No-ROX Mix (Bioline). The reactions contained synthetic G-Block template (10,000 copies) or contained no target (NF $H_2O$).

Results

In this experiment, PCR amplification, signal detection and melt curve differentiation were performed in a single tube. The presence of the target gene (TV-btub) was detected by the presence of a PCR amplification curve and a melting peak at a Tm of 40° corresponding to degraded, open LOCS-18. The absence of the target gene was determined by the absence of a PCR amplification curve, the absence of a melting peak at a Tm of 40° C. and the presence of a melting peak at a Tm of 61° C., corresponding to un-cleaved, closed LOCS-18. Results shown in FIGS. 16A and 16B illustrate the respective amplification curves and melt curve signatures obtained in the FAM channel from reactions containing either 10,000 copies of gene target (black line) or no target (grey line). The results are the averages from duplicate reactions that were plotted using Microsoft Excel (Version 14).

The data from this example demonstrate that LOCS reporters can be used with alternative target detection methods which use similar mechanisms to TaqMan/Hydrolysis probe, namely where polymerase enzymes with exonuclease activity degrade sequences which hybridize to amplicons. Essentially in this example the LOCS probe consists of a loop portion which serves a similar function as a standard TaqMan probe sequence, however the "TaqMan-like probe sequence" has complementary stem sequences appended to the 5' and 3 of the hybridizing region which are themselves not complementary to the target but which are complementary to each other. Furthermore, the data also demonstrates that LOCS reporters containing the same stem (Stem-1) produce peaks at the same melting temperature regardless of the mechanism for loop breakdown, for example exonuclease degradation versus MNAzyme cleavage. In the current example, closed and open LOCS reporters containing Stem-1 produced melt peaks at 61° C. and 40° C. respectively. These melt peaks are comparable to the melt peaks generated using Stem-1 with MNAzymes as demonstrated in FIGS. 5A2, 5B2 and 5C2. The current method has an advantage compared with other exonuclease-based melt curve methods such as TOCE in that the released labeled probe fragment does not have to subsequently hybridize with the capture probe to detect the presence of the target sequence and the LOCS reporter may be better quenched initially since the fluorophore and quencher are locked in close proximity.

Example 12: Method for Simultaneous Detection and Quantification of Multiple Targets in a Single Fluorescent Channel Using Two Acquisition Temperatures During Amplification The following example demonstrates an approach where LOCS reporters allow simultaneous detection and quantification of multiple targets in a single fluorescent channel by acquiring fluorescence readings at two discrete temperatures in real time during PCR. The strategy eliminates the requirement for melting curve analysis following PCR which was demonstrated in various examples above. Further, this example describes two alternative methods for analysis of data which facilitate quantification of the amount of either target if present in the sample.

In this example, two LOCS reporters comprising different stem lengths, compositions and melting temperatures were used to simultaneously detect, differentiate and quantify two targets X and Y in a single fluorescence channel by measuring fluorescence in real time at two different temperatures ($T_L$ and $T_H$) during each PCR cycle. The assay is designed such that target X is monitored using LOCS-X (cleavable by MNAzyme X only in the presence of target X), and target Y is monitored using LOCS-Y (cleavable by MNAzyme Y only in the presence of Target Y). Further, the assay is designed such that an open LOCS-X has a lower Tm than the open LOCS-Y.

The lower temperature of detection (TL) is selected such that the stem of an open LOCS-X will melt (dissociate) resulting in increased fluorescence, whilst the stem of a closed LOCS-X, and the stems of both the open and closed LOCS-Y, will remain associated and quenched. The higher temperature (Ti) is selected such that the stem of the open LOCS-Y will melt (dissociate) resulting in increased fluorescence whilst the stem of a closed LOCS-Y will remain associated and quenched. Since the stem of LOCS-X has a lower Tm, it will melt (dissociate) at this higher temperature, resulting in increased fluorescence regardless of whether it is in its open or closed conformation; however the fluorescence arising from closed LOCS-X will only contribute to an increased background/baseline.

Two PCR amplification curves can be plotted using fluorescence measurements taken at $T_L$ and at $T_H$ temperatures. Threshold values for determination of the presence of targets X and/or Y are set for both the $T_L$ plot (Threshold X; TX) and for the $T_H$ plot (Threshold Y; TY). The thresholds (TX and TY), and various endpoints where reactions are known to plateau, may be predetermined based on prior experiments, where reactions containing only target X plateau at endpoint EX1 at $T_L$ or at endpoint EX2 at $T_H$; reactions containing only target Y plateau at endpoint EY1 at $T_H$, and reactions containing both Target X and Target Y plateau at endpoint EY2 at $T_H$. Optionally, endpoints EX1, EX2, EY1 and EY2 may be derived from positive controls run in parallel with experimental samples.

With respect to the $T_L$ amplification plot, if PCR produces an amplification curve that crosses TX and plateaus at an endpoint EX1, which exceeds the TX, this result would indicate the presence of cleaved LOCS-X associated with target X. If Target Y were also present, the amplification curve should not be affected since cleaved LOCS-Y does not produce fluorescence at $T_L$. Therefore, the Cq values obtained from an amplification curve crossing TX allow quantification of target X in the sample.

With respect to the $T_H$ amplification plot, if PCR produces an amplification curve that crosses TY and plateaus at either EY1 or EY2, this indicates the presence of target Y. The threshold TY is set above the value EX2, so that the amplification curve from a reaction containing only target X does not cross this threshold. When both targets X and Y are present, cleavage of LOCS-X and LOCS-Y will produce amplification curve which crosses TY and plateaus at EY2 which is greater than EY1, which is associated with cleaved LOCS-Y in the presence of target Y only. Since EX2<TY<EY1<EY2 and EX2≠TY≠EY1≠EY2, the endpoints at which amplification curves plateau can indicate the presence of Target X, Y or both. However, the Cq values obtained from Tt amplification curves crossing TY will be affected by the amount of both target X and Y, and therefore are only semi-quantitative for target Y. Various analytical methods for adjusting of Cq values so as to allow for accurate quantification of the amount of Target Y are described below (Quantification Methods 1 and 2).

Target Y Quantification Method 1 The two amplification curves arising from cleaved species of LOCS-X alone at $T_L$ 39° C. and $T_H$ 72° C. have the same efficiency and Cq but plateaus at different endpoints EX1 and EX2 respectively. Therefore, the fluorescence signal arising from cleaved species of LOCS-X in amplification curve at 72° C. (F-LOCS-$X_{FAF}$) can be extrapolated from the amplification curve at 39° C. by applying a fluorescence adjustment factor (FAF). FAF is the ratio of endpoints EX1 and EX2. The total fluorescence signal in the amplification curve at 72° C. (F-total) arises from the fluorescence signal arising from cleaved species of both LOCS-X (F-LOCS-$X_{FAF}$) and LOCS-Y (F-LOCS-Y). From this, the amplification curve at 72° C. arising from LOCS-Y can be extrapolated by the following:

Since $F$-total=$F$-LOCS-$X_{FAF}$+$F$-LOCS-$Y$, $F$-LOCS-$Y$=$F$-total−$F$-LOCS-$X_{FAF}$ ∴Amplification curve at 72° C. arising from LOCS-Y=Experimental amplification curve at 72° C.−Experimental amplification curve at 39° C.*FAF =Experimental amplification curve at 72° C.−Experimental amplification curve at $$39° C. \cdot \frac{EX2}{EX1}$$

The Cq values obtained from the amplification curve at $T_H$ 72° C. arising from LOCS-Y using TY is fully quantitative for target Y. The formula can be applied whether or not the sample contains target X, Y or both to determine the correct quantification.

Target Y Quantification Method 2

In the presence of both targets X and Y, the experimentally determined Cq values at 72° C. (Cq$_{observed}$) are shifted from the Cq values for the sample containing the same concentration of target Y without target X. The relationship between Cq$_{observed}$ and expected Cq values determined from the standard curve for target Y in the absence of target X at 72° C. (Cq$_{standard\ curve\ target\ Y}$) is described below:

Cq$_{observed}$=Cq$_{standard\ curve\ of\ targert\ Y}$+relative shift in Cq where Cq$_{standard\ curve\ of\ target\ Y}$=$f$(copy number of target $Y$)

and relative shift in Cq=$f$(copy number of target $Y$)

Since both Cq$_{standard\ curve\ of\ target\ Y}$ and relative shift in Cq are both functions of copy number of target Y, the copy number of target Y can be calculated from the experimentally determined Cq value (Cq$_{observed}$). This relative shift in Cq value has a mathematical relationship (logistic) with the natural log of (copy number of target Y/copy number of target X). If the Cq values were determined with the threshold being half of the maximum fluorescence level in the amplification curve measured at 72° C., and the logistic relationship can be expressed as the following formula:

$$y = -L + \frac{2L}{1+e^{-kx}}$$

where y relative shift in Cq, L=maximum possible shift in Cq, k=steepness factor, x=ln(copy number of target Y/copy number of target X); Note copy number of target X is determined from the amplification curves at 39° C.

The incorporation of the shift factor in the Cq value into the standard curve equation for target Y that was determined in the absence of target X enables correction of Cq value in the presence of target X and subsequently leads to correct quantification of target Y. The strategy described above can be adapted to detect any targets, however in this specific example target X is the CTcry gene and target Y is NGopa gene; the accumulation of amplicons from each target was monitored at a low temperature ($T_L$ 39° C.) and a higher temperature ($T_H$ 72° C.) during PCR by fluorescence changes associated with LOCS-X (LOCS-19) and LOCS-Y (LOCS-20); and both LOCS were labelled with the same fluorophore (JOE).

Oligonucleotides

The oligonucleotides specific to this experiment include; LOCS-19, LOCS-20, Partzyme A9, Partzyme B9, Partzyme A10, Partzyme B10, Forward Primer 7, Reverse Primer 7, Forward Primer 8 and Reverse Primer 11. The sequences are listed in the Sequence Listing. The oligonucleotides specific for CTcry amplification and quantification are LOCS-19, Partzyme A9, Partzyme B9, Forward Primer 7 and Reverse Primer 7. The oligonucleotides specific for NGopa amplification and quantification are LOCS-20, Partzyme A10, Partzyme B10, Forward Primer 8 and Reverse Primer 11.

Reaction Conditions

Real-time detection of the target sequence was performed in a total reaction volume of 20 µL using a BioRad® CFX96 thermocycler. The cycling parameters were 95° C. for 2 minutes followed by 10 touchdown cycles of 95° C. for 5 seconds and 61° C. for 30 seconds (0.5° C. decrement per cycle) and 40 cycles of 95° C. for 5 seconds, 52° C. for 40 seconds, 39° C. for 1 sec and 72° C. for 1 sec (data collected at both the 39° C. and 72° C. steps). Each reaction contained 40 nM of each forward primer, 200 nM of each reverse primer, 200 nM of each Partzyme, 100 nM of LOCS-19 reporter, 200 nM of LOCS-20 reporter and 1× PlexMastermix (Bioline). The reactions contained either no target (NF $H_2O$), synthetic G-Block X (20,000, 4,000, 800, 160 or 32 copies), synthetic G-Block of NGopa gene (20,000, 4,000, 800, 160 or 32 copies), various concentrations of synthetic G-Block of CTcry gene (20,000, 4,000, 800, 160 or 32 copies) in a background of synthetic G-Block of CTcry gene (20,000, 4,000, 800, 160 or 32 copies) or various concentrations of synthetic G-Block of NGopa gene (20,000, 4,000, 800, 160 or 32 copies) in a background of synthetic G-Block of CTcry gene (20,000, 4,000, 800, 160 or 32 copies).

Results

During PCR, two MNAzymes (MNAzyme 9 and MNAzyme 10) are used to monitor amplification of target nucleic acids in real-time via cleavage of their corresponding LOCS reporters (LOCS-19 and LOCS-20 respectively). MNAzyme 9 was designed to detect sequences homologous to CTcry for detection of *Chlamydia trachomatis* and to cleave and open LOCS-19. MNAzyme 10 was designed to detect sequences homologous to NGopa for detection of *Neisseria gonorrhoeae* and to cleave and open LOCS-20.

The results shown in FIGS. 17A and 17B illustrate the comparative amplification curves obtained in the JOE channel from reactions containing either 20,000 copies of CTcry or NGopa or 20,000 copies of both gene targets, measured at 39° C. and 72° C. respectively. The results are plotted as the averages from duplicate reactions. At 39° C., samples containing 20,000 copies of CTcry template (solid black line) show amplification curves with fluorescence levels that exceed TX (black horizontal line denoted as TX) and reach an EX1 (black horizontal line denoted as EX1). At 39° C., samples containing 20,000 copies of both CTcry and NGopa templates (solid grey line) show amplification curves with fluorescence levels that exceed TX and reach EX1, whereas samples that do not contain CTcry template (dotted black line) do not exceed TX and do not reach EX1. Therefore, the amplification curve at 39° C. plateauing at EX1 confirms the presence of CTcry in the sample. The graph shows the samples containing 20,000 copies of CTcry only (solid black line) and 20,000 copies of both CTcry and NGopa (solid grey line) have similar Cq values. Since the Cq values at 39° C. are unaffected by the presence of NGopa, it can be used for quantification of the CTcry in the sample. The results for quantification of CTcry in the samples of all combinations of 0, 32, 160, 800, 4,000 and 20,000 copies of CTcry and 0, 32, 160, 800, 4,000 and 20,000 copies of NGopa gene targets is summarised in Table 6. NULL refers to where there is no Cq value determined at 39° C. and therefore there is no CTcry present in the sample.

TABLE 6

Copy number determination of CTcry for samples containing varying copynumbers of CTery and NGopa

| | Sample with | | | | | |
|---|---|---|---|---|---|---|
| | 20000 copies of CTcry | 4000 copies of CTcry | 800 copies of CTcry | 160 copies of CTcry | 32 copies of CTcry | 0 copies of CTcry |
| With 20000 copies of NGopa | 18339 | 3537 | 734 | 141 | 29 | NULL |
| With 4000 copies of NGopa | 19234 | 3480 | 688 | 139 | 31 | NULL |
| With 800 copies of NGopa | 18686 | 3747 | 717 | 134 | 25 | NULL |
| With 160 copies of NGopa | 18534 | 3453 | 740 | 147 | 44 | NULL |
| With 32 copies of NGopa | 19697 | 3491 | 778 | 152 | 33 | NULL |
| With 0 copies of NGopa | 24028 | 3601 | 693 | 140 | 39 | NULL |

FIG. 17B shows amplification curves at 72° C. for samples containing 20,000 copies of NGopa template (dotted black line) with fluorescence levels that exceed TY (black horizontal line denoted as TY) and plateau at EY1 (black horizontal line denoted as EY1). At 72° C., samples containing 20,000 copies of both CTcry and NGopa (solid grey line) show amplification curves with fluorescence levels that exceed TY and plateau at EY2 (black horizontal line denoted as EY2), whereas samples that do not contain target NGopa template (solid black line) do not exceed TY and do not reach EY1 and EY2, but only plateaus at endpoint EX2 (black horizontal line denoted as endpoint EX2). Therefore, the amplification curve at 72° C. plateauing at EX2 confirms the presence of target CTcry, but not NGopa in the sample; plateauing at EY1 confirms the presence of NGopa, but not CTcry in the sample; plateauing at EY2 confirms the presence of both CTcry and NGopa in the sample.

At 72° C. the Cq value of samples containing 20,000 copies of both CTcry and NGopa (solid grey line) is not the same as the Cq value of the samples containing 20,000 copies of NGopa template only (dotted black line). The presence of CTcry in the sample may shift the Cq value for NGopa at 72° C. by up to approximately −4.77 in this example. Therefore, use of Cq values at 72° C. without normalisation determines the concentration of NGopa within 2.77 times or less than the expected value, assuming 100% efficiency in PCR amplification. The analysis of the amplification at 72° C. of the samples of all combinations of 0, 32, 160, 800, 4,000 and 20,000 copies of CTcry and 0, 32, 160, 800, 4,000 and 20,000 copies of NGopa gene targets without any normalisations is summarised in Table 7 for Cq values and Table 8 for the quantification of NGopa. NULL is where there is no Cq value determined at 72° C. and therefore there is no NGopa present in the sample. The results show that the methodology without normalisation is fully quantitative for CTcry and semi-quantitative for NGopa.

TABLE 7

Determination of Cq values of amplification curves at 72° C.
for samples containing varying copy numbers of
CTery and NGopa genes without normalisation

| | Sample with | | | | | |
|---|---|---|---|---|---|---|
| | 20000 copies of CTcry | 4000 copies of CTery | 800 copies of CTcry | 160 copies of CTery | 32 copies of CTcry | 0 copies of CTcry |
| With 20000 copies of NGopa | 17.82 | 19.12 | 20.31 | 22.06 | 23.91 | NULL |
| With 4000 copies of NGopa | 18.73 | 20,32 | 21.32 | 22.63 | 24,61 | NULL |
| With 800 copies of NGopa | 19.29 | 21.32 | 22.73 | 23.93 | 24.65 | NULL |
| With 160 copies of NGopa | 19,47 | 21.79 | 23.71 | 25.15 | 25.91 | NULL |
| With 32 copies of NGopa | 19.68 | 22.14 | 24.12 | 25.88 | 27.40 | NULL |
| With 0 copies of NGopa | 19.54 | 22.09 | 24.43 | 26.83 | 28.37 | NULL |

TABLE 8

Copy number determination for NGopa gene
for samples containing varying copy numbers
of CTcry and NGopa genes without normalisation

| | Sample with | | | | | |
|---|---|---|---|---|---|---|
| | 20000 copies of CTery | 4000 copies of CTery | 800 copies of CTery | 160 copies of CTery | 32 copies of CTery | 0 copies of CTery |
| With 20000 copies of NGopa | 82075 | 32256 | 13675 | 3893 | 1033 | NULL |
| With 4000 copies of NGopa | 42621 | 13623 | 6620 | 2586 | 621 | NULL |
| With 800 copies of NGopa | 28592 | 6628 | 2416 | 1018 | 607 | NULL |
| With 160 copies of NGopa | 25142 | 4746 | 1187 | 423 | 244 | NULL |
| With 32 copies of NGopa | 21551 | 3690 | 887 | 250 | 84 | NULL |
| With 0 copies of NGopa | 23865 | 3820 | 712 | 126 | 42 | NULL |

The results shown in FIG. 18 illustrate the comparative amplification curves obtained in the JOE channel from reactions containing all possible combinations of 0, 32 and 20,000 copies of CTcry and 0, 32 and 20,000 copies of NGopa gene targets, measured at 39° C. and 72° C. respectively. The results are plotted as the averages from duplicate reactions. The samples presented in the graphs contains the specified amount of NGopa on the left-hand side of the graphs. The samples that contain 20,000 copies of CTcry are presented in dotted black line, the samples that contain 32 copies of CTcry are presented in solid grey line and the samples that contain 0 copies of CTcry are presented in solid black line. From the non-normalised amplification curves taken at 72° C. in FIGS. 18B and 18E, it is observed that the presence of CTcry in the sample shifts the Cq values. Results were further analysed using Quantification method 1. Subtracting the amplification curve at 39° C. multiplied by the FAF from the amplification curve at 72° C. (since F-LOCS-Y=F-total-F-LOCS-$X_{FAF}$) produces extrapolated amplification curves that correspond to the fluorescence signal from cleaved species of LOCS-20 without contribution from the cleaved LOCS-19 (FIGS. 18C and 18F). All extrapolated amplification curves at 72° C. displays similar Cq values where the same number of NGopa templates are present without regards to the amount of CTcry in the sample. FIG. 18I displays that the extrapolated amplification curves at 72° C. do not show any significant amplification where samples do not contain any NGopa templates. The effect of normalisation with subtraction with F-LOCS-$X_{FAF}$ signals is further demonstrated in Table 9 (F-LOCS-$X_{FAF}$ normalised Cq values) and Table 10 (quantification of NGopa after F-LOCS-$X_{FAF}$ normalisation), which are the analysis of the amplification at 72° C. of the samples of all combinations of 0, 32, 160, 800, 4,000 and 20,000 copies of CTcry and 0, 32, 160, 800, 4,000 and 20,000 copies of NGopa gene targets after normalising by subtraction with F-LOCS-$X_{FAF}$ signals. NULL is where there is no Cq value determined at 72° C. and therefore there is no target Y present in the sample.

TABLE 9

Determination of Cq values of amplification curves at 72° C.
for samples containing varying copy numbers of CTery and
NGopa genes after normalisation with FAF

| | Sample with | | | | | |
|---|---|---|---|---|---|---|
| | 20000 copies of CTcry | 4000 copies of CTcry | 800 copies of CTcry | 160 copies of CTcry | 32 copies of CTcry | 0 copies of CTcry |
| With 20000 copies of NGopa | 19.69 | 22.44 | 24.57 | 26.71 | 28.77 | NULL |
| With 4000 copies of NGopa | 19.41 | 22.20 | 24.30 | 26.57 | 29.02 | NULL |
| With 800 copies of NGopa | 19.46 | 22.05 | 24.59 | 26.91 | 28.17 | NULL |
| With 160 copies of NGopa | 19.48 | 21.98 | 24.43 | 26.89 | 28.29 | NULL |
| With 32 copies of NGopa | 19.68 | 22.15 | 24.33 | 26.98 | 29.16 | NULL |
| With 0 copies of NGopa | 19.56 | 22.11 | 24.46 | 26.86 | 28.39 | NULL |

TABLE 10

Copy number determination for NGopa for samples containing varying copy numbers of CTery and NGopa genes after normalisation with FΔF

|  | Sample with | | | | | |
| --- | --- | --- | --- | --- | --- | --- |
|  | 20000 copies of CTcry | 4000 copies of CTcry | 800 copies of CTcry | 160 copies of CTcry | 32 copies of CTcry | 0 copies of CTcry |
| With 20000 copies of NGopa | 21368 | 2958 | 642 | 138 | 31 | NULL |
| With 4000 copies of NGopa | 26256 | 3532 | 779 | 152 | 26 | NULL |
| With 800 copies of NGopa | 25209 | 3920 | 634 | 119 | 48 | NULL |
| With 160 copies of NGopa | 24887 | 4136 | 710 | 121 | 44 | NULL |
| With 32 copies of NGopa | 21643 | 3641 | 762 | 113 | 24 | NULL |
| With 0 copies of NGopa | 23457 | 3770 | 694 | 123 | 41 | NULL |

For the amplification curves from the data acquired at 72° C., the Cq values for the samples containing both CTcry and NGopa are shifted relative to the sample containing NGopa only. Results were further analysed using Quantification method 2. FIG. 19 displays the logistic regression of the natural log of (copy number of NGopa/copy number of CTcry) plotted against the relative shift in Cq, where the Cq threshold is set at the half of the maximum fluorescence level in the amplification curve, governed by the following formula:

$$\text{relative shift in } Cq = -1.865 + \frac{3.730}{1 + e^{-0.7712 \frac{\ln \text{ copy number of } NGopa}{\ln \text{ copy number of } CTcry}}}$$

The above formula can be incorporated into the standard curve equation of NGopa determined in the absence of CTcry at 72° C. as the following:

$$Cq_{observed} = Cq_{\text{standard of curve of } NGova} + \text{relative shift in } Cq =$$

$$-1.415 \ln \text{ copy number of } NGopa + 32.343 -$$

$$1.865 + \frac{3.730}{1 + e^{-0.7712 \frac{\ln \text{ copy number of } NGopa}{\ln \text{ copy number of } CTcry}}}$$

As the copy number of CTcry is determined from the data acquired at 39° C., the in formula above can be used to determine the copy number of NGopa in a sample from the experimental Cq ($Cq_{observed}$) at 72° C. with a mathematical solvation program. Table 11 shows the observed Cq at 72° C. with the relative shift factors in Cq calculated for the samples of all combinations of 0, 32, 160, 800, 4,000 and 20,000 copies of CTcry and 0, 32, 160, 800, 4,000 and 20,000 copies of NGopa gene targets, presented as an average of duplicates. Table 12 displays the determination of copy number using the Cq values normalised with relative shift factor for the same samples.

TABLE 11

Experimental Cq values of amplification curves at 72° C. for samples containing varying copy numbers of CTery and NGopa and the relative shift factors

|  | Sample with | | | | | |
| --- | --- | --- | --- | --- | --- | --- |
|  | 20000 copies of CTcry | 4000 copies of CTery | 800 copies of CTery | 160 copies of CTery | 32 copies of CTery | 0 copies of CTery |
| With 20000 copies of NGopa | 18.21−0.29 | 19.49+0.96 | 21.19+1.54 | 23.10+1.76 | 25.33+1.83 | NULL |
| With 4000 copies of NGopa | 19.20−1.22 | 20.63−0.20 | 21.94+0.99 | 23.43+1.52 | 25.65+1.77 | NULL |
| With 800 copies of NGopa | 19.71−1.64 | 21.63−1.21 | 23.14−0.12 | 24.32+1.03 | 25.58+1.48 | NULL |
| With 160 copies of NGopa | 19.89−1.80 | 22.09−1.64 | 24.12−1.14 | 25.53+0.01 | 26.37+0.79 | NULL |
| With 32 copies of NGopa | 19.84−1.85 | 22.30−1.79 | 24.34−1.67 | 26.18−0.94 | 27.78+0.02 | NULL |
| With 0 copies of NGopa | 18.15−NULL | 20.67−NULL | 23.06−NULL | 25.28−NULL | 27.24−NULL | NULL |

TABLE 12

Copy number determination for NGopa for samples containing varying copy numbers of CTery and NGopa after normalisation with relative shift factor

|  | Sample with | | | | | |
| --- | --- | --- | --- | --- | --- | --- |
|  | 20000 copies of CTcry | 4000 copies of CTery | 800 copies of CTcry | 160 copies of CTcry | 32 copies of CTcry | 0 copies of CTcry |
| With 20000 copies of NGopa | 26656 | 4457 | 890 | 197 | 39 | NULL |
| With 4000 copies of NGopa | 25410 | 4529 | 771 | 186 | 32 | NULL |

TABLE 12-continued

Copy number determination for NGopa for
samples containing varying copy numbers of CTery
and NGopa after normalisation with relative shift factor

| | Sample with | | | | | |
|---|---|---|---|---|---|---|
| | 20000 copies of CTcry | 4000 copies of CTcry | 800 copies of CTcry | 160 copies of CTcry | 32 copies of CTcry | 0 copies of CTcry |
| With 800 copies of NGopa | 23927 | 4564 | 727 | 139 | 42 | NULL |
| With 160 copies of NGopa | 23676 | 4466 | 744 | 122 | 39 | NULL |
| With 32 copies of NGopa | 25356 | 4285 | 932 | 151 | 25 | NULL |
| With 0 copies of NGopa | 22558 | 3819 | 704 | 147 | 37 | NULL |

Example 13: Simultaneous Detection of Six Targets in Two Fluorescent Channels Using Six LOCS Reporters In the following example, LOCS reporters are used to increase the number of targets that can be detected across two fluorescence channels. In this example, three targets are detected in each of the two fluorescent channels. In this example, all six LOCS reporters are 5' labelled with a fluorophore (JOE or Atto101) and 3' labelled with a quencher (3IABkFQ or 3IAbRQSp respectively). The loop regions of the LOCS reporters each contain a different nucleic acid substrate, and the stem regions contain a series of complementary base-pairs that constrain the LOCS reporter in a loop-stem configuration. In this configuration, the fluorophore and quencher are in close proximity and the fluorescence is quenched in the absence of target.

Oligonucleotides

The oligonucleotides specific to this experiment include; LOCS-21 (SEQ ID NO: 88), LOCS-22 (SEQ ID NO: 89), LOCS-23 (SEQ ID NO: 90), LOCS-24 (SEQ ID NO: 91), LOCS-25 (SEQ ID NO: 92), LOCS-26 (SEQ ID NO: 93), Partzyme A14 (SEQ ID NO: 94), Partzyme B14 (SEQ ID NO: 95), Partzyme A15 (SEQ ID NO: 96), Partzyme B15 (SEQ ID NO: 97), Partzyme A16 (SEQ ID NO: 98), Partzyme B16 (SEQ ID NO: 99), Partzyme A17 (SEQ ID NO: 100), Partzyme B17 (SEQ ID NO: 101), Partzyme A18 (SEQ ID NO: 102), Partzyme B18 (SEQ ID NO: 103), Partzyme A19 (SEQ ID NO: 104), Partzyme B19 (SEQ ID NO: 105), Forward Primer 12 (SEQ ID NO: 106), Reverse Primer 12 (SEQ ID NO: 107), Forward Primer 9 (SEQ ID NO: 54), Reverse Primer 9 (SEQ ID NO: 55), Forward Primer 13 (SEQ ID NO: 108), Reverse Primer 13 (SEQ ID NO: 109), Forward Primer 14 (SEQ ID NO: 110), Reverse Primer 2 (SEQ ID NO: 10), Forward Primer 1 (SEQ ID NO: 7), Reverse Primer 1 (SEQ ID NO: 8), Forward Primer 15 (SEQ ID NO: 111), Reverse Primer 15 (SEQ ID NO: 112). The sequences are listed in the Sequence Listing. The oligonucleotides specific for gpd amplification and detection are LOCS-21, Partzyme A14, Partzyme B14, Forward Primer 12 and Reverse Primer 12. The oligonucleotides specific for gpd3 amplification and detection are LOCS-22, Partzyme A15, Partzyme B15, Forward Primer 9 and Reverse Primer 12. The oligonucleotides specific for porA amplification and detection are LOCS-23, Partzyme A16, Partzyme B16, Forward Primer 13 and Reverse Primer 13. The oligonucleotides specific for TV-Btub amplification and detection are LOCS-24, Partzyme A17, Partzyme B17, Forward Primer 14 and Reverse Primer 2. The oligonucleotides specific for MgPa amplification and detection are LOCS-25, Partzyme A18, Partzyme B18, Forward Primer 1 and Reverse Primer 1. The oligonucleotides specific for LGV amplification and detection are LOCS-26, Partzyme A19, Partzyme B19, Forward Primer 15 and Reverse Primer 15.

Reaction Conditions

Real-time amplification and detection of the target sequence was performed in a total reaction volume of 20 µL using a BioRad® CFX96 thermocycler. The cycling parameters were 40° C. for one second, 70° C. for one second, 85° C. for one second, 95° C. for 2 minutes, 10 touchdown cycles of 95° C. for 5 seconds and 61° C. for 30 seconds (0.5° C. decrement per cycle) and 40 cycles of 95° C. for 5 seconds, 52° C. for 40 seconds and 65° C. for 1 second (data collected at the 65° C. step), followed by 40° C. for one second, 70° C. for one second and 85° C. for one second. Melt curve parameters were 0.5° C. increment from 20° C. to 95° C. with a 5 sec hold (data acquisition on hold). All reactions were run in duplicate and contained 40 nM of each forward primer, 200 nM of each reverse primer, 200 nM of each partzyme A, 200 nM of each partzyme B, 200 nM each of LOCS-21, LOCS-22, LOCS-24 and LOCS-25 and 150 nM each of LOCS-23 and LOCS-26, 8 mM MgCl$_2$ (Bioline), 0.2 mM dNTPs (Bioline), 2 units MyTaq polymerase (Bioline) and 1× NH4 Buffer (Bioline). The reactions contained either G-Block template (10,000 copies) homologous to the gpd and/or gpd3 and/or porA or TV-Btub and/or MgPa and/or LGV genes, or no target (NF H$_2$O).

Results

Using an in vitro target amplification method known as PCR, six MNAzymes (MNAzyme 14, MNAzyme 15, MNAzyme 16, MNAzyme 17, MNAzyme 18 and MNAzyme 19) are used to monitor amplification of target nucleic acids in real-time via cleavage of their corresponding LOCS reporters (LOCS-21, LOCS-22, LOCS-23, LOCS-24, LOCS-25 and LOCS-26 respectively). Presence of any or all targets for each channel (JOE and Texas Red) was determined by an increase in fluorescence in the amplification phase of the PCR (data not shown); this was followed by discernment of individual targets based on unique LOCS melt signatures. MNAzyme 14 was designed to detect sequences homologous to the gpd gene and to cleave and open LOCS-21; MNAzyme 15 was designed to detect sequences homologous to the gpd3 gene and to cleave and open LOCS-22; MNAzyme 16 was designed to detect sequences homologous to the porA gene and to cleave and open LOCS-23; MNAzyme 17 was designed to detect sequences homologous to the TV-Btub gene and cleave and open LOCS-24; MNAzyme 18 was designed to detect sequences homologous to the MgPa gene and to cleave and open LOCS-25; and MNAzyme 19 was designed to detect sequences homologous to the LGV gene and cleave and open LOCS-26. In this experiment, amplification and detection was performed in a single tube, containing all MNAzymes, primers and LOCS oligonucleotides. The presence of either gpd, gpd3, porA, TV-Btub, MgPa, LGV genes or various combinations of the six genes (representing a sample with multiple infections) were detected by an increase in signal in either or both the JOE and Texas Red channels (data not shown).

The results shown in FIGS. 20-22 illustrate the respective melt curve signatures obtained post amplification from reactions containing 10,000 copies of the targets gpd (FIG. 20A), gpd3 (FIG. 20B), porA (FIG. 20C), both gpd and gpd3 (FIG. 20D), both gpd and porA (FIG. 20E), both gpd3 and porA (FIG. 20F), or all three of gpd, gpd3 and porA (FIG. 22A), TV-Btub (FIG. 21A), MgPa (FIG. 21B), LGV (FIG. 21C), both TV-Btub and MgPa (FIG. 21D) both TV-Btub and LGV (FIG. 21E), both MgPa and LGV (FIG. 21F), or all three of TV-Btub, MgPa and LGV (FIG. 22B). The results are the averages from duplicate reactions that were plotted using Microsoft Excel (Version 14).

The data from this example, summarized in Table 13, demonstrates that the LOCS melt signature produced in the presence of gpd gene target (Tm=53° C., 68° C. and 85° C.) is distinct from the LOCS melt signature produced in the presence of gpd3 (Tm=30° C., 43° C. 77° C. and 85° C.) and porA (Tm=68° C. and 77° C.) gene targets. This example demonstrates that simultaneous detection of TV-Btub, MgPa and/or LGV gene targets can be achieved in a second channel in addition to the detection of gpd, gpd3 and/or porA. The LOCS melt signature produced in the presence of TV-Btub gene target (Tm=30° C., 42° C., 66° C. and 82° C.) is distinct from the LOCS melt signatures produced in the presence of MgPa (53° C., 66° C. and 82° C.) and LGV (Tm=68° C.) gene targets. Further, the LOCS melt signatures in the presence of two or more gene targets reading from a single channel are also distinct from the aforementioned melt signatures wherein only a single gene target is present. In the JOE channel, when gpd and gpd3 gene targets were present in a single reaction, a unique LOCS melt signature (Tm=30° C., 43° C. 53° C. and 85° C.) indicated that both targets were detected. Similarly, when gpd and porA or gpd3 and porA were present in a single reaction, unique melt curve signatures (Tm=53° C. and 68° C. and Tm=30° C., 43° C., 68° C. and 77° C., respectively) indicated specifically which two targets were detected. Likewise, in the Texas Red channel, LOCS melt signatures were unique for each combination of targets: TV-Btub and MgPa (Tm=30° C., 42° C., 53° C. and 82° C.), TV-Btub and LGV (Tm=30° C., 42° C. and 68° C.) or MgPa and LGV (Tm=53° C. and 68° C.). When gpd, gpd3 and porA gene targets were all present within a single reaction, a unique LOCS melt signature (Tm=30° C., 43° C., 53° C. and 68° C.) within the JOE channel indicated all three targets were detected. Likewise, in the Texas Red channel, the presence of TV-Btub, MgPa and LGV targets in a single yielded a unique LOCS melt signature (Tm=30° C., 42° C., 53° C. and 68° C.).

TABLE 13

Summary of Melting Temperatures (Tms) of LOCS Reporters in the presence of one, two or three targets as illustrated in FIGS. 20, 21 and 22.

| Figure | Gene Targets Present | Detection Channel | Melt Curve Tms (Tms indicative of closed LOCS in italics) |
|---|---|---|---|
| 20A | gpd | HEX | 53° C., 68° C. and 85° C. |
| 20B | gpd3 | | 30° C., 43° C., 77° C. and 85° C. |
| 20C | porA | | 68° C. and 77° C. |
| 20D | gpd and gpd3 | | 30° C., 43° C., 53° C. and 85° C. |
| 20E | gpd and porA | | 53° C. and 68° C. |
| 20F | gpd3 and porA | | 30° C., 43° C., 68° C. and 77° C. |
| 21A | TV-Btub | Texas Red | 30° C., 42° C., 66° C. and 82° C. |
| 21B | MgPa | | 53° C., 66° C. and 82° C. |
| 21C | LGV | | 68° C. |
| 21D | TV-Btub and MgPa | | 30° C., 42° C., 53° C. and 82° C. |
| 21E | TV-Btub and LGV | | 30° C., 42° C. and 68° C. |
| 21F | MgPa and LGV | | 53° C. and 68° C. |
| 22A | gpd, gpd3 and porA | HEX | 30° C., 43° C., 53° C. and 68° C. |
| 22B | TV-Btub, MgPa and LGV | Texas Red | 30° C., 42° C., 53° C. and 68° C. |

This example demonstrates that six targets, co-amplified in a single well and using two fluorescent channels (three targets detected in each channel), can be distinguished based on their unique LOCS melt signatures. The example provides a simple method for detecting multiple targets in a single well using only two fluorescent channels. Due to different stem lengths and base-pair compositions, the different stems (Stem-5, Stem-6, Stem-7, Stem-8, Stem-9 and Stem-10) within LOCS-21, LOCS-22, LOCS-23, LOCS-24, LOCS-25 and LOCS-26 have produced unique fluorescence melt curve signatures.

Example 14: Simultaneous Detection and Discrimination of Ten Targets in a Single Well Using Five Fluorescent Channels and Ten LOCS Reporters In the following example, LOCS reporters are used to increase the number of targets that can be simultaneously detected in a single well using five fluorescent channels by increasing the number of targets that can be detected within each channel. In this example, two targets are detected in each of the five fluorescent channels. In this example, all ten LOCS reporters are 5' labelled with a fluorophore (FAM, JOE, AttoRhol01, Cy5 or Cy5.5) and 3' labelled with a quencher (either 3IABkFQ or 3IAbRQSp). The loop regions of the LOCS reporters contain a nucleic acid substrate, and the stem regions contain a series of complementary base-pairs that constrain the LOCS reporter in a loop-stem configuration. In this configuration, the fluorophore and quencher are in close proximity and the fluorescence is quenched in the absence of target.

Oligonucleotides

The oligonucleotides specific to this experiment include; LOCS-10 (SEQ ID NO: 40), LOCS-15 (SEQ ID NO: 79), LOCS-21 (SEQ ID NO: 88), LOCS-22 (SEQ ID NO: 89), LOCS-24 (SEQ ID NO: 91), LOCS-27 (SEQ ID NO: 113), LOCS-28 (SEQ ID NO: 114), LOCS-29 (SEQ ID NO: 115), LOCS-30 (SEQ ID NO: 116), LOCS-31 (SEQ ID NO: 117), Partzyme A9 (SEQ ID NO: 43), Partzyme B9 (SEQ ID NO: 44), Partzyme A10 (SEQ ID NO: 48), Partzyme B10 (SEQ ID NO: 49), Partzyme A14 (SEQ ID NO: 94), Partzyme B14 (SEQ ID NO: 95), Partzyme AIS (SEQ ID NO: 97), Partzyme B15 (SEQ ID NO: 98), Partzyme A16 (SEQ ID NO: 98), Partzyme B16 (SEQ ID NO: 99), Partzyme A17 (SEQ ID NO: 100), Partzyme B17 (SEQ ID NO: 101), Partzyme A18 (SEQ ID NO: 102), Partzyme B18 (SEQ ID NO: 103), Partzyme A19 (SEQ ID NO: 104), Partzyme B19 (SEQ ID NO: 105), Partzyme A20 (SEQ ID NO: 118), Partzyme B20 (SEQ ID NO: 119), Partzyme A21 (SEQ ID NO: 120), Partzyme B21 (SEQ ID NO: 121), Forward Primer 1 (SEQ ID NO: 7), Reverse Primer 1 (SEQ ID NO: 8), Reverse Primer 2 (SEQ ID NO: 10), Forward Primer 7 (SEQ ID NO: 41), Reverse Primer 7 (SEQ ID NO: 42), Forward Primer 8 (SEQ ID NO: 52), Forward Primer 9 (SEQ ID NO: 54), Reverse Primer 9 (SEQ ID NO: 55), Forward Primer 10 (SEQ ID NO: 72), Reverse Primer 10 (SEQ ID NO: 73), Reverse Primer 11 (SEQ ID NO: 85), Forward Primer 12 (SEQ ID NO: 106), Reverse Primer 12 (SEQ ID NO: 107), Forward Primer 13 (SEQ ID NO: 108), Reverse Primer 13 (SEQ ID NO: 109), Forward Primer 14 (SEQ ID NO: 110), Forward Primer 15 (SEQ ID NO: 111), Reverse Primer 15 (SEQ ID NO: 112), Forward Primer 16 (SEQ ID NO: 122) and Reverse Primer 16 (SEQ ID NO: 123). The sequences are listed in the Sequence Listing.

The oligonucleotides specific for CTcry amplification and detection are LOCS-29, Partzyme A9, Partzyme B9, Forward Primer 7 and Reverse Primer 7. The oligonucleotides specific for NGopa amplification and detection are LOCS- 15, Partzyme A10, Partzyme B10, Forward Primer 8 and Reverse Primer 11. The oligonucleotides specific for gpd amplification and detection are LOCS-21, Partzyme A14, Partzyme B14, Forward Primer 12 and Reverse Primer 12. The oligonucleotides specific for gpd3 amplification and detection are LOCS-22, Partzyme A15, Partzyme B15, Forward Primer 9 and Reverse Primer 9. The oligonucleotides specific for porA amplification and detection are LOCS-27, Partzyme A16, Partzyme B16, Forward Primer 13 and Reverse Primer 13. The oligonucleotides specific for TV-Btub amplification and detection are LOCS-24, Partzyme A17, Partzyme B17, Forward Primer 14 and Reverse Primer 2. The oligonucleotides specific for MgPa amplification and detection are LOCS-28, Partzyme A18, Partzyme B18, Forward Primer 1 and Reverse Primer 1. The oligonucleotides specific for LGV amplification and detection are LOCS-10, Partzyme A19, Partzyme B19, Forward Primer 15 and Reverse Primer 15. The oligonucleotides specific for polA amplification and detection are LOCS-30, Partzyme A20, Partzyme B20, Forward Primer 16 and Reverse Primer 16. The oligonucleotides specific for TFRC amplification and detection are LOCS-31, Partzyme A21, Partzyme B21, Forward Primer 10 and Reverse Primer 10.

Reaction Conditions

Real-time amplification and detection of the target sequence was performed in a total reaction volume of 20 µL using a BioRad® CFX96 thermocycler. The cycling parameters were 31° C. for one second, 42° C. for one second, 53° C. for one second, 60° C. for one second, 95° C. for 2 minutes, 10 touchdown cycles of 95° C. for 5 seconds and 61° C. for 30 seconds (0.5° C. decrement per cycle) and 40 cycles of 95° C. for 5 seconds and 52° C. for 40 seconds and 65° C. for 5 seconds (data collected at the 65° C. step), followed by 31° C. for one second, 42° C. for one second, 53° C. for one second and 60° C. for one second. Melt curve parameters were 0.5° C. increment from 20° C. to 95° C. with a 5 sec hold (data acquisition on hold). All reactions were run in duplicate and contained 40 nM of each forward primer, 200 nM of each reverse primer, 200 nM of each partzyme A, 200 nM of each partzyme B, 200 nM each of LOCS-10, LOCS-15, LOCS-21, LOCS-22, LOCS-24, LOCS-27, LOCS-29, and LOCS-31 reporters and 150 nM each of LOCS-28 and LOCS-30, 8 mM MgCl$_2$ (Bioline), 0.2 mM dNTPs (Bioline), 2 units MyTaq polymerase (Bioline) and 1×NH4 Buffer (Bioline). The reactions contained either G-Block template (10,000 copies) homologous to the NGopa and/or porA, gpd and/or gpd3, TV-Btub and/or MgPa, CTcry and/or LGV or polA genes or no target (NF H$_2$O). All reactions contained a background of 10,000 copies of human genomic DNA containing the TFRC gene target which serves as an endogenous control. The detection of TFRC gene was monitored in every reaction as an internal control by an increase in fluorescence in the Cy5.5 channel (data not shown).

Results

Using an in vitro target amplification method known as PCR, ten MNAzymes (MNAzyme 9, MNAzyme 10 and MNAzymes 14-21) are used to monitor amplification of target nucleic acids in real-time via cleavage of their corresponding LOCS reporters (LOCS-29, LOCS-15, LOCS-21, LOCS-22, LOCS-27, LOCS-24, LOCS-28, LOCS-10, LOCS-30 and LOCS-31 respectively). Presence of one or both targets within each channel (FAM, HEX, Texas Red, Cy5 and Cy5.5) was determined by an increase in fluorescence in the amplification phase of the PCR followed by discernment of individual targets using LOCS melt signatures.

MNAzyme 10 was designed to detect sequences homologous to the NGopa gene and to cleave and open LOCS-15; MNAzyme 16 was designed to detect sequences homologous to the porA gene and to cleave and open LOCS-27; MNAzyme 14 was designed to detect sequences homologous to the gpd gene and to cleave and open LOCS-21; MNAzyme 15 was designed to detect sequences homologous to the gpd3 gene and to cleave and open LOCS-22; MNAzyme 17 was designed to detect sequences homologous to the TV-Btub and cleave and open LOCS-24; MNAzyme 18 was designed to detect sequences homologous to the MgPa gene and to cleave and open LOCS-28; MNAzyme 9 was designed to detect sequences homologous to the CTcry gene and to cleave and open LOCS-29; MNAzyme 19 was designed to detect sequences homologous to the LGV pmpH gene and cleave and open LOCS-10, MNAzyme 20 was designed to detect sequences homologous to the polA gene and cleave and open LOCS-30 and MNAzyme 21 was designed to detect the human TFRC gene and cleave and open LOCS-31.

In this experiment, amplification and detection was performed in a single tube, containing all partzymes for all MNAzymes, all primers and all LOCS oligonucleotides. The presence of any of NGopa, porA, gpd, gpd3, TV-Btub, MgPa, CTcry, LGV, polA, TFRC, or various combinations of these ten gene targets (representing a sample with multiple infections), were detected by an increase in signal in either the FAM, HEX, Texas Red, Cy5 or Cy5.5 channels (data not shown).

The results shown in FIG. 23 illustrate the respective melt curve signatures obtained post amplification from reactions containing 10,000 copies of the targets NGopa (FIG. 23A), porA (FIG. 23B), both NGopa and porA (FIG. 23C), gpd (FIG. 23D), gpd3 (FIG. 23E), both gpd and gpd3 (FIG. 23F), TV-Btub (FIG. 23G), MgPa (FIG. 23H), both TV-Btub and MgPa (FIG. 23I), CTcry (FIG. 23J), LGV (FIG. 23K), both CTcry and LGV (FIG. 23L), polA (FIG. 23M) or TFRC (FIG. 23N). The results are the averages from duplicate reactions that were plotted using Microsoft Excel (Version 14). The data from this example, summarized in Table 14, demonstrates that the LOCS melt signature produced in the presence of a single target is distinct from the LOCS melt signature produced by the presence of a second target fluorescing in the same channel. Additionally, the LOCS melt signature produced by the presence of both targets within a single channel is distinct from the LOCS melt signature produced by either of the two single targets detected at the specific wavelength. This result is consistent across all five channels in this example. In the FAM channel, the LOCS melt signatures produced in the presence of NGopa (Tm=53° C.), porA (Tm=30° C. and 76° C.) and both NGopa and porA (Tm=30° C. and 53° C.) gene targets were all distinct. In the HEX channel, the LOCS melt signatures produced in the presence of gpd (53° C. and 70° C.), gpd3 (30° C., 43° C. and 76° C.) and both gpd and gpd3 (30° C., 43° C. and 53° C.) gene targets were all distinct. In the Texas Red channel, the LOCS melt signatures produced in the presence of TV-Btub (31° C., 41° C., 59° C. and 83° C.), MgPa (63° C.) and both TV-Btub and MgPa (31° C., 41° C. and 63° C.) gene targets were all distinct. In the Cy5 channel, the LOCS melt signatures produced in the presence of CTcry (61° C. and 79° C.), LGV (47° C. and 80° C.) and both CTcry and LGV (47° C. and 61° C.) gene targets were all distinct. In this example, human genomic DNA (TFRC)

is detected in Cy5.5 channel in all reactions, thereby serving as an endogenous control. Consequently, the reaction detecting polA simultaneously detects TFRC, which is demonstrated in the LOCS melt signature by two peaks (39° C. and 59° C.) corresponding to TFRC and polA gene targets, respectively. In the Cy5.5 channel, the LOCS melt signatures produced in the presence of polA and TFRC (39° C. and 59° C.) is distinct from the LOCS melt signature produced by the presence of TFRC (39° C. and 80° C.) alone, providing differentiation between reactions containing polA (polA and TFRC melt signatures) and reactions lacking polA (TFRC LOCS melt signature only).

TABLE 14

Summary of Melting Temperatures (Tms) of LOCS Reporters in the presence of one or two targets as illustrated in FIG. 23.

| Figure | Targets Present | Channel | Melt Curve Tms (Tms indicative of closed LOCS in italics) |
|---|---|---|---|
| FIG. 23A | NGopa | FAM | 53° C. |
| FIG. 23B | porA | FAM | 30° C. and 76° C. |
| FIG. 23C | NGopa and porA | FAM | 30° C. and 53° C. |
| FIG. 23D | gpd | HEX | 53° C. and 70° C. |
| FIG. 23E | gpd3 | HEX | 30° C., 43° C. and 76° C. |
| FIG. 23F | gpd and gpd3 | HEX | 30° C., 43° C. and 53° C. |
| FIG. 23G | TV-Btub | Texas Red | 31° C., 41° C., 59° C. and 83° C. |
| FIG. 23H | MgPa | Texas Red | 63° C. |
| FIG. 23I | TV-Btub and MgPa | Texas Red | 31° C., 41° C. and 63° C. |
| FIG. 23J | CTcry | Cy5 | 61° C. and 79° C. |
| FIG. 23K | LGV | Cy5 | 47° C. and 80° C. |
| FIG. 23L | CTcry and LGV | Cy5 | 47° C. and 61° C. |
| FIG. 23M | polA and TFRC | Cy5.5 | 39° C. and 59° C. |
| FIG. 23N | TFRC | Cy5.5 | 39° C. and 80° C. |

This example demonstrates that ten gene targets, co-amplified in a single well and using five fluorescent channels (two targets detected in each well), can be distinguished based on their unique LOCS melt signatures. The example provides a simple method for detecting multiple targets in a single well using five fluorescent channels thereby doubling the multiplex capacity of a single PCR machine.

Example 15: Methods for Single Channel, Single Well Multiplexing by Measuring Fluorescence at Defined Temperature-Points The following example provides alterative protocols for detecting and discriminating multiple targets at a single wavelength without the requirement for full melt curve analysis over a broad range of temperatures, as previously exemplified in Examples 1 to 6. In the present example, several methods of detecting and identifying three targets at a single wavelength are demonstrated through using modified LOCS protocols coupled with a choice of analytical strategies. Targets X, Y and Z can be detected using three LOCS reporters X, Y and Z, all of which can be labelled with the same fluorophore. Each of the three LOCS reporters comprise different stem regions with different melting temperatures where the Tm of LOCS-X<Tm of LOCS-Y<Tm of LOCS-Z. In addition, each of the LOCS reporters contain a different loop region comprising a substrate specific for the MNAzymes X, Y or Z respectively. MNAzymes X, Y or Z are designed to recognize and detect Targets X, Y and Z respectively and cleave LOCS reporters X, Y and Z respectively. A limited number of fluorescence measurements (total of six or less) can be obtained before and/or after PCR amplification of the targets. Various methods of analysis can utilise measurements taken at specific temperatures and time points. These are summarized in Table 15.

TABLE 15

Summary of analytical protocols allowing specific detection of three cleaved LOCS in a single channel using measurement of Relative Fluorescence Units (RFU) collected at specific temperature-points

| Analytical Protocol | Acquisition temperature ($T_X < T_Y < T_Z$) | Criteria for determining target/cleaved LOCS in the sample |
|---|---|---|
| A RFU measured post-PCR | $T_{Xa}$ | RFU at temperature $T_{Xa}$ for cleaved LOCS-X > Threshold FXa |
|  | $T_{Ya}$ | RFU at temperature $T_{Ya}$ for cleaved LOCS-Y > Threshold FYa |
|  | $T_{Za}$ | RFU at temperature $T_{Za}$ for cleaved LOCS-Z > Threshold FZa RFU may optionally be normalised relative to no template control |
| B RFU measured post-PCR | $T_{Ob}$ $T_{Xb}$ | RFU at temperature $T_{Xb}$ – RFU at temperature $T_{Ob}$ for cleaved LOCS-X > Threshold FXb |
|  | $T_{Yb}$ | RFU at temperature $T_{Yb}$ – RFU at temperature $T_{Xb}$ for cleaved LOCS-Y > Threshold FYb |
|  | $T_{Zb}$ | RFU at temperature $T_{Zb}$ – RFU at temperature $T_{Yb}$ for cleaved LOCS-Z > Threshold FZb Temperature $T_{Ob}$ < Temperature $T_{Xb}$ |
| C RFU measured pre- and post-PCR | $T_{Xc}$ | Post-PCR RFU at temperature $T_{Xc}$ – Pre-PCR RFU at temperature $T_{Xc}$ for cleaved LOCS-X > Threshold FXc |
|  | $T_{Yc}$ | Post-PCR RFU at temperature $T_{Yc}$ – Pre-PCR RFU at temperature $T_{Yc}$ for cleaved LOCS-Y > Threshold FYc |
|  | $T_{Zc}$ | Post-PCR RFU at temperature $T_{Zc}$ – Pre-PCR RFU at temperature $T_{Zc}$ for cleaved LOCS-Z > Threshold FZc |
| D RFU measured post-PCR | $T_{Xd}$ – N; $T_{Xd}$ + N | RFU at temperature ($T_{Xd}$ + N) – RFU at temperature ($T_{Xd}$ – N) for cleaved LOCS-X > Threshold FXd |
|  | $T_{Yd}$ – N; $T_{Yd}$ + N | R.FU at temperature ($T_{Yd}$ + N) – RFU at temperature ($T_{Yd}$ – N) for cleaved LOCS-Y > Threshold FYd |
|  | $T_{Zd}$ – N; $T_{Zd}$ + N | RFU at temperature ($T_{Zd}$ + N) – RFU at temperature ($T_{Za}$ – N) for cleaved LOCS-Z > Threshold FZd |

The strategies described outlined in this example can be adapted to detect any targets, however in this specific example target X is the TFRC gene, target Y is rpoB gene and target Z is pss gene, detected by probes LOCS-X (LOCS-22), LOCS-Y (LOCS-21) and LOCS-Z (LOCS-23) respectively, that were labelled with the same fluorophore (JOE). The various detection temperatures used are $T_{Xa}$=40.5° C.; $T_{Xb}$=56.5° C.; $T_{Xc}$=78.5° C.; $T_{Ob}$=32° C.; $T_{Xb}$=40.5° C.; $T_{Yb}$=56.5° C.; $T_{Zb}$=65.5° C.; $T_{Xc}$=39.5° C.; $T_{Yc}$=56.5° C.; $T_{Zc}$=65.5° C.; $T_{Xd}$=40° C.; $T_{Yd}$=51° C.; and $T_{Zd}$=65° C. Further, in the following analysis a value of N=0.5° C. was assigned.

Analytical Protocol A1

At a first specific temperature $T_{Xa}$ cleavage of LOCS-X produces significant fluorescence signal, relative to a no template control, and this will exceed a threshold $F_{Xa}$. At the same temperature the presence of the cleaved LOCS-Y and/or LOCS-Z does not contribute to production of significant fluorescence signal due to the higher Tm of the stems of these LOCS and consequently the fluorescence level, relative to a no template control, stays below threshold $F_{Xa}$. The post-amplification measurement of fluorescence at temperature $T_{Xa}$ allows for a specific detection of the cleaved LOCS-X.

At a second specific temperature $T_{Ya}$, which is higher than the temperature $T_{Xa}$, the cleaved LOCS-Y produces a relative fluorescence signal which is significantly greater than a threshold $F_{Ya}$. At temperature $T_{Ya}$, the relative fluorescence signal produced by the cleaved LOCS-X and/or LOCS-Z will be significantly less than the threshold $F_{Ya}$. Therefore, the post-amplification measurement of fluorescence at temperature $T_Y a$ allows for a specific detection of the cleaved LOCS-Y.

At a third specific temperature $T_{Za}$, which is higher than temperatures $T_{Xa}$ and $T_{Ya}$, the cleaved LOCS-Z produces a relative fluorescence signal significantly greater than a threshold $F_{Za}$. At temperature $T_{Za}$, the relative fluorescence signal produced by the cleaved LOCS-X and/or LOCS-Y is significantly less than the threshold $F_{Za}$. Therefore, the post-amplification measurement of fluorescence at temperature $T_{Za}$ allows for a specific detection of the cleaved LOCS-Z. The detection of each cleaved LOCS reporter indicates the presence of the corresponding target in the sample.

Analytical Protocol A2

Instead of using the threshold values, an algorithm can be used to determine the cleaved LOCS species when one or more LOCS species are cleaved in a sample. This algorithm uses the ratio of the fluorescence levels, relative to that of a no template control, measured at each of the three detection temperatures (temperatures $T_{Xa}$, $T_{Ya}$ and $T_{Za}$). The ratio of the relative fluorescence levels measured at the above mentioned three temperatures is unique for each of the possible combinations of cleaved LOCS species and functions as a fingerprint, indicating the presence of the corresponding target gene/s in the sample. The algorithm comprises a series of seven logical tests; one logical test is assigned for each possible combination of cleaved and un-cleaved LOCS to determine the presence of one or more cleaved LOCS species. The possible combinations are (X only), (Y only), (Z only). (X & Y only), (X & Z only), (Y & Z only) or (X, Y & Z). For a sample to be determined positive for a specific combination of targets, it needs to be determined TRUE for a specific logical test. A logical test determines if (1) the ratio of fluorescence signal measured at the three different temperatures falls within a pre-defined range of values, and (2) the fluorescence signal is significantly greater than a no template control. A sample can be determined TRUE for a maximum of one set of logical tests which indicates the specific combination of cleaved species of LOCS-X, LOCS-Y and LOCS-Z and therefore identifying the presence of the corresponding target/s. If a sample is determined FALSE to all logical test, then the sample will be determined negative and does not contain any cleaved species of LOCS, indicating the sample does not contain any of the three targets.

Analytical Protocol B1

At a first specific temperature $T_{0b}$, none of the cleaved species of LOCS-X, LOCS-Y or LOCS-Z produces fluorescence signal that is significantly higher than that of a no template control. At a second specific temperature $T_{Xb}$, which is higher than $T_{0b}$, the cleaved LOCS-X produces significant fluorescence signal whereas the cleaved LOCS-Y and/or LOCS-Z do not contribute to production of significant fluorescence signal due to the higher Tm of the stems of theses LOCS. The difference between post-amplification fluorescence signals at temperatures $T_{0a}$ and $T_{Xb}$ is higher than threshold FXb in the presence of cleaved LOCS-X and lower in the absence of cleaved LOCS-X, and therefore this allows for a specific detection of the cleave LOCS-X. At a third specific temperature $T_{Yb}$, which is higher than $T_{Xb}$, the cleaved LOCS-Y produces significant fluorescence signal. On the other hand, the cleaved LOCS-Z does not contribute to production of significant fluorescence signal at temperature $T_{Yb}$, due to the higher Tm of its stem. The cleaved LOCS-X does not further contribute to increased production of significant fluorescence at temperature $T_{Yb}$ in comparison to temperature $T_{Xb}$. The difference between post-amplification fluorescence signals at temperatures $T_{Xb}$ and $T_{Yb}$ is higher than threshold FYb in the presence of cleaved LOCS-Y and lower in the absence of cleaved LOCS-Y, and therefore this allows for a specific detection of the cleaved LOCS-Y. At a forth specific temperature $T_{Zb}$, which is higher than $T_{Yb}$, the cleaved LOCS-Z produces significant fluorescence signal. The cleaved LOCS-X and/or LOCS-Y does not further contribute to increased production of significant fluorescence at temperature $T_{Zb}$. The difference between post-amplification fluorescence signals at temperatures $T_{Yb}$ and $T_{Zb}$ is higher than threshold FZb in the presence of cleaved LOCS-Z and lower in the absence of cleaved LOCS-Z, and therefore this allows for a specific detection of the cleaved LOCS-Z.

The calculations mentioned above are described using the following formulae:

For determination of the presence of cleaved LOCS-X,

If post-amplification fluorescence level at temperature $T_{Xb}$-post-amplification fluorescence level at temperature $T_{0b}$>threshold FXb, then LOCS-X is present in the sample.

For determination of the presence of cleaved LOCS-Y,

If post-amplification fluorescence level at temperature $T_{Yb}$-post-amplification fluorescence level at temperature $T_{Xb}$>threshold FYb, then LOCS-Y is present in the sample.

For determination of the presence of cleaved LOCS-Z,

If post-amplification fluorescence level at temperature $T_{Zb}$-post-amplification fluorescence level at temperature $T_{Yb}$>threshold FZb, then LOCS-Z is present in the sample.

The detection of each cleaved LOCS reporter indicates the presence of the corresponding target gene in the sample.

Analytical Protocol B2

Instead of using the threshold values, an algorithm can alternatively be used to determine the cleaved LOCS species when one or more LOCS species are cleaved in a sample using the ratio of the values calculated from the differences between the post-amplification fluorescence levels measured at $T_{0b}$, $T_{Xb}$, $T_{Yb}$ and $T_{Zb}$. The ratio of the values (a) (post-amplification fluorescence level at temperature $T_{Xb}$—post-amplification fluorescence level at temperature $T_{0b}$), (b) (post-amplification fluorescence level at temperature $T_{Yb}$—post-amplification fluorescence level at temperature $T_{Xb}$) and (c) (post-amplification fluorescence level at temperature $T_{Zb}$—post-amplification fluorescence level at temperature $T_{Yc}$) is unique for each of the possible combinations of cleaved LOCS species and functions as a fingerprint that indicates the presence of the corresponding target is in the sample. The algorithm comprises a series of eight logical tests; one logical test is assigned for each possible combination of cleaved and un-cleaved LOCS to determine the presence of one or more cleaved LOCS species. The possible combinations are (no target). (X only), (Y only), (Z only), (X & Y only), (X & Z only), (Y & Z only) or (X, Y & Z). For a sample to be determined positive for a specific combination of targets, it needs to be determined TRUE for a logical test. A logical test determines if the ratio of the differences between the three above-mentioned values is within a pre-defined range of values. A sample can be determined TRUE for a maximum of one logical test, which indicates the specific combination of cleaved species of LOCS-X, LOCS-Y and LOCS-Z, and indicative of the presence of the corresponding target/s or when determined TRUE for the (no target) logical test this indicates absence of, any target/s Analytical Protocol C1

The post-amplification detection of cleaved LOCS species at a defined temperature can also be determined using the information obtained from the differences between pre- and post-amplification fluorescence measurements at specific temperatures. This method is an alternative to determining the relative post-amplification fluorescence level to the no template control or to a reference temperature ($T_{Ob}$) as described above in Protocols A and B, respectively. At a first specific temperature $T_{Xc}$, the cleaved LOCS-X produces significant fluorescence signal, and the difference between pre- and post-amplification measurement of fluorescence at temperature $T_{Xc}$ is higher than threshold FXc. On the other hand, the presence of the cleaved LOCS-Y and/or LOCS-Z does not lead to production of significant fluorescence signal at temperature $T_{Xc}$ due to the higher Tm of the stem, and the difference between pre- and post-amplification measurement of fluorescence at temperature $T_{Xc}$ is below threshold FXc. Therefore, the pre- and post-amplification measurements of fluorescence at temperature $T_{Xc}$ allow for a specific detection of the cleaved species of LOCS-X. The incremental fluorescence signal produced by cleaved LOCS-Y at a second temperature $T_{Yc}$ over temperature $T_{Xc}$ (where $T_{Yc} > T_{Xc}$) is significantly higher than threshold FYc. On the other hand, the incremental fluorescence signal produced by cleaved LOCS-X and/or LOCS-Z at temperature TY over temperature $T_{Xc}$ is significantly less than threshold FYc. The incremental fluorescence signal at temperature $T_{Yc}$ over temperature $T_{Xc}$ is determined from calculating the difference of the difference between pre- and post-amplification fluorescence level at temperature $T_{Yc}$ and the difference between pre- and post-amplification fluorescence level at temperature $T_{Xc}$. Therefore, the information from pre- and post-amplification measurements of fluorescence level at temperature $T_{Xc}$ and $T_{Yc}$ allow for a specific detection of the cleaved LOCS-Y. The incremental fluorescence signal produced by cleaved LOCS-Z at a third temperature $T_{Zc}$ over temperature $T_{Yc}$ (where $T_{Zc} > T_{Yc}$) is significantly higher than threshold FZc. On the other hand, the incremental fluorescence signal produced by cleaved LOCS-X and/or LOCS-Y at temperature $T_{Zc}$ over temperature $T_{Yc}$ is significantly less than threshold FZc. The incremental fluorescence signal at temperature $T_{Zc}$ over temperature $T_{Yc}$ is determined from calculating the difference of the difference between pre- and post-amplification fluorescence level at temperature $T_{Yc}$ and the difference between pre- and post-amplification fluorescence level at temperature $T_{Xc}$. Therefore, the information from pre- and post-amplification measurements of fluorescence level at temperature $T_{Yc}$ and $T_{Zc}$ allow for a specific detection of the cleaved LOCS-Z. The calculations mentioned above are described in the following:

For determination of the presence of LOCS-X,

If post-amplification fluorescence level at temperature $T_{Xc}$–pre-amplification fluorescence level at temperature $T_{Xc}$>threshold FXc, then LOCS-X is present in the sample.

For determination of the presence of LOCS-Y,

If (post-amplification fluorescence level at temperature $T_{Yc}$–pre-amplification fluorescence level at temperature $T_{Yc}$)–(post-amplification fluorescence level at temperature $T_{Xc}$–pre-amplification fluorescence level at temperature $T_{Xc}$) >threshold FYc, then LOCS-Y is present in the sample.

For determination of the presence of LOCS-Z,

If (post-amplification fluorescence level at temperature $T_{Zc}$–pre-amplification fluorescence level at temperature $T_{Zc}$)–(post-amplification fluorescence level at temperature $T_{Yc}$–pre-amplification fluorescence level at temperature $T_{Yc}$)>threshold FZc, then LOCS-Z is present in the sample.

The detection of each cleaved LOCS reporter indicates the presence of the corresponding target in the sample. This method requires six fluorescence measurements.

Analytical Protocol C2

Instead of using the threshold values, an algorithm can be used to determine the cleaved LOCS species when one or more LOCS species are cleaved in a sample using the ratio of the values calculated from the differences between the pre- and post-amplification fluorescence levels measured at each of the three detection temperatures $T_{Xc}$, $T_{Yc}$ and $T_{Zc}$. The ratio of the values (i) post-amplification fluorescence level at temperature $T_{Xc}$—pre-amplification fluorescence level at temperature $T_{Xc}$, (ii) (post-amplification fluorescence level at temperature $T_{Yc}$—pre-amplification fluorescence level at temperature $T_{Yc}$)—(post-amplification fluorescence level at temperature $T_{Xc}$—pre-amplification fluorescence level at temperature $T_{Xc}$) and (iii) (post-amplification fluorescence level at temperature $T_{Zc}$—pre-amplification fluorescence level at temperature $T_{Zc}$)—(post-amplification fluorescence level at temperature $T_{Yc}$—pre-amplification fluorescence level at temperature $T_{Yc}$) is unique for each of the possible combinations of cleaved and un-cleaved LOCS species and can function as a fingerprint that indicates the presence of the corresponding target gene/s in the sample. The algorithm comprises a series of eight logical tests; one logical test is assigned for each possible combination of cleaved and un-cleaved LOCS to determine the presence of one or more cleaved LOCS species. The possible combinations are (no target), (X only), (Y only), (Z only), (X & Y only), (X & Z only), (Y & Z only) or (X, Y & Z). For a sample to be determined positive for a specific combination of targets, it needs to be determined TRUE for a logical test. A logical test determines if the ratio of the differences between the values (i), (ii) and (iii) is within a pre-defined range of values. A sample can be determined TRUE for a maximum of one logical test, which indicates the specific combination of cleaved species of LOCS-X, LOCS-Y and LOCS-Z, and therefore the contain the corresponding target Is or, does not contain any targets when determined TRUE for the (no target) logical test.

Analytical Protocol D1

Another alternative method is to measure the height of melt peak in the melt signature, which is equivalent to the dFluorescence/dTemperature value at the Tm of each cleaved LOCS. However, the usability of this method is not confined for determining the dFluorescence/dTemperature value at the Tm of the cleaved LOCS, but also inclusive of a range of temperatures which includes the Tm. The dFluorescence/dTemperature value at the specific temperature A° C. is equivalent to the gradient of fluorescence level across (A–N)° C. and (A+N° C.) Mathematically, it can be expressed as the following formula:

For $f$ (Temperature)=Fluorescence, $$f'(A° \text{ C.}) = \frac{\text{Fluorescence}_{A+N° C.} - \text{Fluorescence}_{A-N° C.}}{(A+N)-(A-N)}$$
$$= \frac{\text{Fluorescence}_{A+N° C.} - \text{Fluorescence}_{A-N° C.}}{2N}$$

As seen in the above formula, the calculation of the dFluorescence/dTemperature value at A° C. requires two measurements of fluorescence at the temperatures (A–N)° C. and (A+N° C.) For a triplex, three dFluorescence/dTemperature values are required and, therefore, six post-amplification fluorescence measurements are required. In the presence of the cleaved species of LOCS-X, the dFluorescence/dTemperature value at the temperature $T_{Xd}$ is greater than the threshold FXd, but in the absence of the cleaved species of LOCS-X, the dFluorescence/dTemperature value the temperature $T_{Xd}$ is less than the threshold FXd. In the presence of the cleaved species of LOCS-Y, the dFluorescence/dTemperature value at the temperature $T_{Yd}$ is greater than the threshold $F_{Yd}$, but in the absence of the cleaved species of LOCS-Y, the dFluorescence/dTemperature value at the temperature $T_{Yd}$ is less than the threshold FYd. In the presence of the cleaved species of LOCS-Z, the dFluorescence/dTemperature value at the temperature $T_{Zd}$ is greater than the threshold FZd, but in the absence of the cleaved species of LOCS-Z, the dFluorescence/dTemperature value at the temperature $T_{Zd}$ is less than the threshold FZd. The detection of each cleaved LOCS reporter indicates the presence of the corresponding target gene in the sample.

Analytical Protocol D2

Instead of using the threshold values, an algorithm can be used to determine the cleaved LOCS species when one or more LOCS species are cleaved in a sample using the ratio of the dFluorescence/dTemperature values at the three detection temperatures $T_{Xd}$, $T_{Yd}$ and $T_{Zd}$. The ratio of the dFluorescence/dTemperature values at the above-mentioned three temperatures is unique for each of the possible combinations of cleaved LOCS species and functions as a fingerprint that indicates the presence of the corresponding target/s in the sample. The algorithm comprises a series of eight logical tests; one logical test is assigned for each possible combination of cleaved and un-cleaved LOCS to determine the presence of one or more cleaved LOCS species. The possible combinations are (no target), (X only), (Y only), (Z only), (X & Y only), (X & Z only), (Y & Z only) or (X, Y & Z). For a sample to be determined positive for a specific combination of targets, it needs to be determined TRUE for a logical test. A logical test determines if the ratio of the dFluorescence/dTemperature values at the above-mentioned three temperatures is within a pre-defined range of values. A sample can be determined TRUE for a maximum of one logical test, which indicates the specific combination of cleaved species of LOCS-X, LOCS-Y and LOCS-Z, and therefore the corresponding target /s, or determined to not contain any targets when determined TRUE for the (no target) logical test.

Oligonucleotides

The oligonucleotides specific to this experiment include: LOCS-22 (SEQ ID 89), LOCS-21 (SEQ ID 88), LOCS-23 (SEQ ID 90), Partzyme A22 (SEQ ID 124), Partzyme B22 (SEQ ID 125), Partzyme A23 (SEQ ID 126), Partzyme B23 (SEQ ID 127), Partzyme A24 (SEQ ID 130), Partzyme B24 (SEQ ID 131), Forward primer 10 (SEQ ID 72), Reverse primer 10 (SEQ ID 73), Forward primer 6 (SEQ TD 25), Reverse primer 6 (SEQ ID 26), Forward primer 17 (SEQ ID 128) and Reverse primer 17 (SEQ ID 129). The sequences are listed in the Sequence Listing. The oligonucleotides specific for amplification and detection of TFRC gene are LOCS-22, Partzyme A22, Partzyme B22, Forward Primer 10 and Reverse Primer 10. The oligonucleotides specific for amplification and detection of rpoB gene are LOCS-21, Partzyme A23, Partzyme B23, Forward Primer 6 and Reverse Primer 6. The oligonucleotides specific for amplification and detection of pss gene are LOCS-23, Partzyme A24, Partzyme B24, Forward Primer 17 and Reverse Primer 17.

Reaction Conditions

Real-time detection of the target sequence was performed in a total reaction volume of 20 µL using a BioRad® CFX96 thermocycler. The cycling parameters were 39.5° C. for 30 seconds with data acquisition, 56.5° C. for 30 seconds with data acquisition, 65.5° C. for 30 seconds with data acquisition, 95° C. for 2 minutes 10 touchdown cycles of 95° C. for 5 seconds and 61° C. for 30 seconds (0.5° C. decrement per cycle) and 40 cycles of 95° C. for 5 seconds and 52° C. for 40 seconds (data collected at the 52'C step), followed by 39.5° C. for 30 seconds with data acquisition, 40.5° C. for 30 seconds with data acquisition, 50.5° C. for 30 seconds with data acquisition, 51.5° C. for 30 seconds with data acquisition, 56.5° C. for 30 seconds with data acquisition, 64.5° C. for 30 seconds with data acquisition, 65.5° C. for 30 seconds with data acquisition and 78.5° C. for 30 seconds with data acquisition. Each reaction contained 40 nM of each forward primer, 200 nM of each reverse primer, 200 nM of each Partzyme, 80 nM of LOCS-22 reporter, 210 nM of LOCS-21 reporter, 300 nM of LOCS-23 reporter, 2 mM $MgCl_2$ (Bioline) and 1× Sensi-FAST Probe No-ROX Mix (Bioline). The reactions contained either genomic DNA or synthetic G-Block template of target genes (10,000 copies per target gene in NF $H_2O$) or no target (NF $H_2O$).

Results

During PCR, three MNAzymes (MNAzyme 22, MNAzyme 23 and MNAzyme 24) are used to monitor amplification of target nucleic acids in real-time via cleavage of their corresponding LOCS reporters (LOCS-22, LOCS-21 and LOCS-23 respectively). MNAzyme 22 was designed to detect TFRC gene (*Homo sapiens*) sequences and to cleave LOCS-22. MNAzyme 23 was designed to detect rpoB gene (*Klebsiella pneumoniae*) sequences and to cleave LOCS-21. MNAzyme 24 was designed to detect pss gene (*Streptococcus pneumoniae*) sequences and to cleave LOCS-23. The presence of either target gene TFRC, rpoB or pss was detected by fluorescence signal in the JOE channel measured at several temperatures, at pre- or post-amplification stage of PCR cycles.

The results shown in FIG. 24 illustrate the comparative post-amplification fluorescence levels obtained in the JOE channel from reactions containing 10,000 copies of TFRC, rpoB, pss or all combinations of two or more gene targets, measured at 40.5° C., 56.5° C. and 78.5° C. The results are the averages of the fluorescence level from triplicate reactions subtracted by the average from triplicate reactions of the no template control. At 40.5° C., the samples containing TFRC has higher fluorescence level (relative to no template control) than the threshold FXa but not the samples containing no TFRC. At 56.5° C., the samples containing rpoB has higher fluorescence level (relative to no template control) than the threshold FYa but not the samples containing no rpoB. At 78.5° C., the samples containing pss has higher fluorescence level (relative to no template control) than the threshold FZa but not the samples containing no pss.

Table 16 shows the outcomes obtained after subjecting post-amplification fluorescence level (measured at 40.5° C., 56.5° C. and 78.5° C. from each of the samples containing 10,000 copies of TFRC, rpoB, pss or all combinations of two or more gene targets) to seven logical tests. Each of the seven logical tests comprises three criteria (second row of Table 16), that determines whether the sample contains (TFRC only), (rpoB only), (pss only), (TFRC & rpoB only), (TFRC & pss only), (rpoB & pss only) or (TFRC, rpoB & pss). The first two criteria determine if the ratio between two fluorescence levels measured at different temperatures (40.5° C., 56.5° C. or 78.5° C.) subtracted by the average fluorescence level from no template control at the same temperatures is either greater or less than a pre-defined value or falls between a pre-defined range. The final criterion determines if the fluorescence signal observed is significantly higher than that of no template control. Each sample is deemed TRUE to a logical test only if it is TRUE to all three criteria of the logical test. The experiment was performed using eight types of samples in duplicates, which are all combinations of either 0 or 10000 copies of the three target templates (no template control has 0 copy of all three templates). All tested samples were determined TRUE for a maximum of one logical test while remaining FALSE for all other logical tests and correctly determined the presence of the target gene. The no template control samples remained FALSE for all logical tests.

TABLE 16

Results obtained using Protocol A2

| Sample type | Does the sample contain X and no Y or Z? (X only) F at 40.5° C. > 70%*F at 56.5° C. AND F at 40.5° C. > F at 78.5° C. AND F at 40.5° C. > 200 | Does the sample contain Y and no X or Z? (Y only) F at 56.5° C. > 200%*F at 40.5° C. AND F at 56.5° C. > 400%*F at 78.5° C. AND F at 56.5° C. > 200 | Does the sample contain Z and no X or Y? (Z only) F at 78.5° C. > 400%*F at 40.5° C. AND F at 78.5° C. > 400%*F at 56.5° C. AND F at 78.5° C. > 200 | Does the sample contain X and Y and no Z? (X & Y only) F at 40.5° C. > 80%*F at 78.5° C. AND F at 56.5° C. > 150%*F at 40.5° C. AND F at 40.5° C. > 200 | Does the sample contain X and Z and no Y? (X & Z only) F at 40.5° C. > 60%*F at 56.5° C. AND F at 78.5° C. > 150%*F at 56.5° C. AND F at 40.5° C. > 200 | Does the sample contain Y and Z and no X? (Y & Z only) F at 56.5° C. > 400%*F at 40.5° C. AND F at 78.5° C. > 400%*F at 40.5° C. AND F at 56.5° C. > 200 | Does the sample contain X, Y and Z? (X, Y & Z) F at 40.5° C. > 30%*F at 56.5° C. AND F at 120% 78.5° C. > F at 56.5° C. > 80%*F at 78.5° C. AND F at 40.5° C. > 200 |
|---|---|---|---|---|---|---|---|
| X #1 | TRUE | FALSE | FALSE | FALSE | FALSE | FALSE | FALSE |
| X #2 | TRUE | FALSE | FALSE | FALSE | FALSE | FALSE | FALSE |
| X #3 | TRUE | FALSE | FALSE | FALSE | FALSE | FALSE | FALSE |
| Y #1 | FALSE | TRUE | FALSE | FALSE | FALSE | FALSE | FALSE |
| Y #2 | FALSE | TRUE | FALSE | FALSE | FALSE | FALSE | FALSE |
| Y #3 | FALSE | TRUE | FALSE | FALSE | FALSE | FALSE | FALSE |
| Z #1 | FALSE | FALSE | TRUE | FALSE | FALSE | FALSE | FALSE |
| Z #2 | FALSE | FALSE | TRUE | FALSE | FALSE | FALSE | FALSE |
| Z #3 | FALSE | FALSE | TRUE | FALSE | FALSE | FALSE | FALSE |
| X + Y #1 | FALSE | FALSE | FALSE | TRUE | FALSE | FALSE | FALSE |
| X + Y #2 | FALSE | FALSE | FALSE | TRUE | FALSE | FALSE | FALSE |
| X + Y #3 | FALSE | FALSE | FALSE | TRUE | FALSE | FALSE | FALSE |
| X + Z #1 | FALSE | FALSE | FALSE | FALSE | TRUE | FALSE | FALSE |
| X + Z #2 | FALSE | FALSE | FALSE | FALSE | TRUE | FALSE | FALSE |
| X + Z #3 | FALSE | FALSE | FALSE | FALSE | TRUE | FALSE | FALSE |
| Y + Z #1 | FALSE | FALSE | FALSE | FALSE | FALSE | TRUE | FALSE |
| Y + Z #2 | FALSE | FALSE | FALSE | FALSE | FALSE | TRUE | FALSE |
| Y + Z #3 | FALSE | FALSE | FALSE | FALSE | FALSE | TRUE | FALSE |
| X + Y + Z #1 | FALSE | FALSE | FALSE | FALSE | FALSE | FALSE | TRUE |
| X + Y + Z #2 | FALSE | FALSE | FALSE | FALSE | FALSE | FALSE | TRUE |
| X + Y + Z #3 | FALSE | FALSE | FALSE | FALSE | FALSE | FALSE | TRUE |
| NTC #1 | FALSE | FALSE | FALSE | FALSE | FALSE | FALSE | FALSE |
| NTC #2 | FALSE | FALSE | FALSE | FALSE | FALSE | FALSE | FALSE |
| NTC #3 | FALSE | FALSE | FALSE | FALSE | FALSE | FALSE | FALSE |

FIG. 25 shows the comparison of the average of differential post-amplification fluorescence measurements taken at 32° C., 40.5° C., 56.5° C. and 65.5° C. in the JOE channel from triplicate reactions containing 10,000 copies of TFRC, rpoB, pss or all combinations of two or more gene targets. The difference between the fluorescence levels measured at 32° C. and 40.5° C., denoted as (a), were larger than the threshold FXb only in the samples containing TFRC. The difference between the fluorescence levels measured at 40.5° C. and 56.5° C., denoted as (b), were larger than the threshold FYb only in the samples containing rpoB. The difference between the fluorescence levels measured at 56.5° C. and 65.5° C., denoted as (c), were larger than the threshold FZb only in the samples containing pss.

Table 17 shows the outcomes obtained after subjecting the differential post-amplification fluorescence values between 32° C., 40.5° C., 56.5° C. and 65.5° C. from each of the samples containing 10,000 copies of TFRC, rpoB, pss or all combinations of two or more gene targets to eight logical tests. These differential values were calculated as the differences of the fluorescence levels measured at 32° C. and 39.5° C.; 40.5° C. and 56.5° C.; and 56.5° C. and 65.5° C. Each of the eight logical tests comprise two criteria (second row of Table 17) that determines whether the sample contains (no target), (TFRC only), (rpoB only), (pss only), (TFRC & rpoB only), (TFRC & pss only), (rpoB & pss only) or (TFRC, rpoB & pss). The two criteria determine if the ratio between two differential fluorescence values is either greater or less than a pre-defined value or falls between a pre-defined range. All tested samples were determined TRUE only for one logical test while remaining FALSE for all other logical tests and correctly determined the presence of the target gene.

The results shown in FIG. 26 illustrate the comparison of the values obtained from pre- and post-amplification fluorescence measurements at 39.5° C., 56.5° C. and 65.5° C. in the JOE channel from reactions containing 10,000 copies of TFRC, rpoB, pss or all combinations of two or more gene targets. The results are the averages of triplicate reactions for the values (i) post-amplification fluorescence level at 39.5° C.—pre-amplification fluorescence level at 39.5° C., (ii) (post-amplification fluorescence level at 56.5° C.—pre-amplification fluorescence level at 56.5° C.)—(post-amplification fluorescence level at 39.5° C.—pre-amplification fluorescence level at temperature 39.5° C.) and (iii) (post-amplification fluorescence level at if) temperature 65.5° C.—pre-amplification fluorescence level at temperature 65.5° C.)—(post-amplification fluorescence level at temperature 56.5° C.—pre-amplification fluorescence level at temperature 56.5° C.). For the samples containing TFRC,

TABLE 17

Results obtained using Protocol B2

| Sample type | Does the sample contain X and no Y or Z? (X only) 250%*(F at 40.5° C. - F at 32° C.) < (F at 56.5° C. - F at 40.5° C.) < 350%*(F at 40.5° C. - F at 32° C.) AND 150%*(F at 65.5° C. - F at 56.5° C.) < (F at 56.5° C. - F at 40.5° C.) < 250%*(F at 65.5° C.. - F at 56.5° C.) | Does the sample contain Y and no X or Z? (Y only) (F at 40.5° C. - F at 32° C.) < 10%*(F at 56.5° C. - F at 40.5° C.) AND 150%*(F at 65.5° C. - F at 56.5° C.) < (F at 56.5° C. - F at 40.5° C.) < 350%*(F at 65.5° C. - F at 56.5° C.) | Does the sample contain Z and no X or Y? (Z only) (F at 40.5° C. - F at 32° C.) < 10%*(F at 56.5° C. - F at 40.5° C.) < 10%*(F at 65.5° C. - F at 56.5° C.) AND (F at 65.5° C. - F at 56.5° C.) > 175%*(F at 56.5° C. - F at 39.5° C.) | Does the sample contain X and Y and no Z? (X & Y only) 125%*(F at 40.5° C. - F at 32° C.) < (F at 65.5° C. - F at 56.5° C.) < 225%*(F at 40.5° C. - F at 32° C.) AND (F at 56.5° C. - F at 39.5° C.) >250%*(F at 65.5° C. - F at 56.5° C.) | Does the sample contain X and Z and no Y? (X & Z only) (F at 40.5° C. - F at 32° C.) > 10%*(F at 65.5° C. - F at 56.5° C.) < (F at 40.5° C. - F at 32° C.) > 10%*(F at 56.5° C. - F at 39.5° C.) < 65.5° C. - F at 56.5° C.) | Does the sample contain Y and Z and no X? (Y & Z only) (F at 40.5° C. - F at 32° C.) < 10%*(F at 56.5° C. - F at 40.5° C.) AND 50%*(F at 56.5° C. - F at 39.5° C.) < (F at 65.5° C. - F at 56.5° C.) < 85%*(F at 56.5° C. - F at 39.5° C.) | Does the sample contain X, Y and Z? (X, Y & Z) (F at 40.5° C. - F at 32° C.) > 10%*(F at 65.5° C. - F at 56.5° C.) AND 50%*(F at 56.5° C. - F at 39.5° C.) < (F at 65.5° C. - F at 56.5° C.) < 85%*(F at 56.5° C. - F at 39.5° C.) | Does the sample NOT contain X, Y or Z? (no target) (F at 40.5° C. - F at 32° C.) < 10%*(F at 65.5° C. - F at 56.5° C.) AND 85%*(F at 39.5° C.) < (F at 65.5° C. - F at 56.5° C.) < 125%*(F at 56.5° C. - F at 39.5° C.) |
|---|---|---|---|---|---|---|---|---|
| X #1 | TRUE | FALSE | FALSE | FALSE | FALSE | FALSE | FALSE | FALSE |
| X #2 | TRUE | FALSE | FALSE | FALSE | FALSE | FALSE | FALSE | FALSE |
| X #3 | TRUE | FALSE | FALSE | FALSE | FALSE | FALSE | FALSE | FALSE |
| Y #1 | FALSE | TRUE | FALSE | FALSE | FALSE | FALSE | FALSE | FALSE |
| Y #2 | FALSE | TRUE | FALSE | FALSE | FALSE | FALSE | FALSE | FALSE |
| Y #3 | FALSE | TRUE | FALSE | FALSE | FALSE | FALSE | FALSE | FALSE |
| Z #1 | FALSE | FALSE | TRUE | FALSE | FALSE | FALSE | FALSE | FALSE |
| Z #2 | FALSE | FALSE | TRUE | FALSE | FALSE | FALSE | FALSE | FALSE |
| Z #3 | FALSE | FALSE | TRUE | FALSE | FALSE | FALSE | FALSE | FALSE |
| X + Y #1 | FALSE | FALSE | FALSE | TRUE | FALSE | FALSE | FALSE | FALSE |
| X + Y #2 | FALSE | FALSE | FALSE | TRUE | FALSE | FALSE | FALSE | FALSE |
| X + Y #3 | FALSE | FALSE | FALSE | TRUE | FALSE | FALSE | FALSE | FALSE |
| X + Z #1 | FALSE | FALSE | FALSE | FALSE | TRUE | FALSE | FALSE | FALSE |
| X + Z #2 | FALSE | FALSE | FALSE | FALSE | TRUE | FALSE | FALSE | FALSE |
| X + Z #3 | FALSE | FALSE | FALSE | FALSE | TRUE | FALSE | FALSE | FALSE |
| Y + Z #1 | FALSE | FALSE | FALSE | FALSE | FALSE | TRUE | FALSE | FALSE |
| Y + Z #2 | FALSE | FALSE | FALSE | FALSE | FALSE | TRUE | FALSE | FALSE |
| Y + Z #3 | FALSE | FALSE | FALSE | FALSE | PALSE | TRUE | FALSE | FALSE |
| X + Y + Z #1 | FALSE | FALSE | FALSE | FALSE | FALSE | FALSE | TRUE | FALSE |
| X + Y + Z #2 | FALSE | FALSE | FALSE | FALSE | FALSE | FALSE | TRUE | FALSE |
| X + Y + Z #3 | FALSE | FALSE | FALSE | FALSE | FALSE | FALSE | TRUE | FALSE |
| NTC #1 | FALSE | FALSE | FALSE | FALSE | FALSE | FALSE | FALSE | TRUE |
| NTC #2 | FALSE | FALSE | FALSE | FALSE | FALSE | FALSE | FALSE | TRUE |
| NTC #3 | FALSE | FALSE | FALSE | FALSE | FALSE | FALSE | FALSE | TRUE | the normalised fluorescence values (i) are larger than the threshold FXc but not the samples containing no TFRC. For the samples containing rpoB, the normalised fluorescence values (ii) are larger than the threshold FYc but not the samples containing no rpoB For the samples containing pss is either greater or less than a pre-defined value or falls between a pre-defined range. All tested samples were determined TRUE for one logical test only while remaining FALSE for all other logical tests and correctly determined the presence of the target gene.

TABLE 18

Results obtained using Protocol C2

| Sample type | Does the sample contain X and no Y or Z? (X only) ΔF at 39.5° C. > 150%*(ΔF a: 56.5° C. - ΔF at 39.5° C.) AND (ΔF at 65.5° C. - ΔF at 56.5° C.) < 20%*(ΔF at 56.5° C. - ΔF at 39.5° C.) | Does the sample contain Y and no X or Z? (Y only) (ΔF at 56.5° C. - ΔF at 39.5° C.) > 175%*ΔF at 39.5° C. AND (ΔF at 56.5° C. - ΔF at 39.5° C.) > 300%*(ΔF at 65.5° C. - ΔF at 56.5° C.) | Does the sample contain Z and no X or Y? (Z only) (ΔF at 55.5° C. - ΔF at 56.5° C.) > 175%*ΔF at 39.5° C. AND (ΔF at 65.5° C. - ΔF at 56.5° C.) > 175%*(ΔF at 56.5° C. - ΔF at 39.5° C.) | Does the sample contain X and Y and no Z? (X & Y only) (ΔF at 39.5° C.) > ΔF at 39.5° C. AND (ΔF at 65.5° C. - ΔF at 56.5° C.) < 15%*(ΔF at 56.5° C. - ΔF at 39.5° C.) | Does the sample contain X and Z and no Y? (X & Z only) ΔF at 39.5° C. > 175%*(ΔF at 56.5° C. - ΔF at 39.5° C.) AND 250%*(ΔF at 56.5° C. - ΔF at 39.5° C.) > 200%*ΔF at 39.5° C. > (ΔF at 65.5° C. - ΔF at 56.5° C.) > 125%*(ΔF at 56.5° C. - ΔF at 39.5° C.) | Does the sample contain Y and Z and no X? (Y & Z only) (ΔF at 56.5° C. - ΔF at 39.5° C.) > 200%*ΔF at 39.5° C. > AND (ΔF at 65.5° C. - ΔF at 56.5° C.) > 200%*ΔF at 39.5° C. | Does the sample contain X, Y and Z? (X, Y & Z) 200%*ΔF at 39.5° C. > (ΔF at 56.5° C. - ΔF at 39.5° C.) > 125%*ΔF at 39.5° C. AND (ΔF at 65.5° C. - ΔF at 56.5° C.) > 80%*ΔF at 39.5° C. | Does the sample NOT contain X, Y or Z? (no target) ΔF at 39.5° C. > 150%*(ΔF at 56.5° C. - ΔF at 39.5° C.) AND (ΔF at 65.5° C. - ΔF at 55.5° C.) < ΔF at 39.5° C. < 300%*(ΔF at 65.5° C. - ΔF at 56.5° C.) |
|---|---|---|---|---|---|---|---|---|
| X #1 | TRUE | FALSE | FALSE | FALSE | FALSE | FALSE | FALSE | FALSE |
| X #2 | TRUE | FALSE | FALSE | FALSE | FALSE | FALSE | FALSE | FALSE |
| X #3 | TRUE | FALSE | FALSE | FALSE | FALSE | FALSE | FALSE | FALSE |
| Y #1 | FALSE | TRUE | FALSE | FALSE | FALSE | FALSE | FALSE | FALSE |
| Y #2 | FALSE | TRUE | FALSE | FALSE | FALSE | FALSE | FALSE | FALSE |
| Y #3 | FALSE | TRUE | PALSE | EALSE | FALSE | FALSE | FALSE | FALSE |
| Z #1 | FALSE | FALSE | TRUE | FALSE | FALSE | FALSE | FALSE | FALSE |
| Z #2 | FALSE | FALSE | TRUE | FALSE | FALSE | FALSE | FALSE | FALSE |
| Z #3 | FALSE | FALSE | TRUE | FALSE | FALSE | FALSE | FALSE | FALSE |
| X + Y #1 | FALSE | FALSE | FALSE | TRUE | FALSE | FALSE | FALSE | FALSE |
| X + Y #2 | FALSE | FALSE | FALSE | TRUE | FALSE | PALSE | FALSE | FALSE |
| X + Y #3 | FALSE | FALSE | FALSE | TRUE | FALSE | FALSE | FALSE | FALSE |
| X + Z #1 | FALSE | FALSE | FALSE | FALSE | TRUE | FALSE | FALSE | FALSE |
| X + Z #2 | FALSE | FALSE | FALSE | FALSE | TRUE | FALSE | FALSE | FALSE |
| X + Z #3 | FALSE | FALSE | FALSE | FALSE | TRUE | FALSE | FALSE | FALSE |
| Y + Z #1 | FALSE | FALSE | FALSE | FALSE | FALSE | TRUE | FALSE | FALSE |
| Y + Z #2 | FALSE | FALSE | FALSE | FALSE | FALSE | TRUE | FALSE | FALSE |
| Y + Z #3 | FALSE | FALSE | FALSE | FALSE | FALSE | TRUE | FALSE | FALSE |
| X + Y + Z #1 | FALSE | FALSE | FALSE | FALSE | FALSE | PALSE | TRUE | FALSE |
| X + Y + Z #2 | FALSE | FALSE | FALSE | FALSE | FALSE | FALSE | TRUE | FALSE |
| X + Y + Z #3 | FALSE | FALSE | FALSE | FALSE | FALSE | FALSE | TRUE | FALSE |
| NTC #1 | FALSE | FALSE | FALSE | FALSE | FALSE | FALSE | FALSE | TRUE |
| NTC #2 | FALSE | FALSE | FALSE | FALSE | FALSE | FALSE | FALSE | TRUE |
| NTC #3 | FALSE | FALSE | FALSE | FALSE | FALSE | FALSE | FALSE | TRUE | the normalised fluorescence values (iii) are larger than the threshold FZc but not the samples containing no pss.

Table 18 shows the outcomes obtained after subjecting the above-mentioned values (i), (ii) and (iii) to eight logical tests. Each of the eight logical tests comprise two criteria (second row of Table 18), that determines whether the sample contains (no target). (TFRC only), (rpoB only), (pss only), (TFRC & rpoB only), (TFRC & pss only), (rpoB & pss only) or (TFRC, rpoB & pss). Each of the two criteria determine if the ratio between two of values (i), (ii) and (iii)

FIG. 27 shows the comparative the average post-amplification dFluorescence/dTemperature values obtained in the JOE channel from triplicate reactions containing 10,000 copies of TFRC, rpoB, pss or all combinations of two or more gene targets at 37° C., 50° C. and 65° C. These values were calculated from the post-amplification fluorescence measurements taken at 36.5° C., 37.5° C., 49.5° C., 50.5° C., 64.5° C. and 65.5° C. The dFluorescence/dTemperature value at 37° C. were larger than the threshold FXd only in the samples containing TFRC. The dFluorescence/dTemperature value at 50° C. were larger than the threshold FYd only in the samples containing rpoB. The dFluorescence/dTemperature 11 value at 65° C. were larger than the threshold FZd only in the samples containing pss.

ratio between two dFluorescence/dTemperature values is either greater or less than a pre-defined value or falls between a pre-defined range. All tested samples were determined TRUE only for one logical test while remaining FALSE for all other logical tests and correctly determined the presence of the target gene.

TABLE 19

Results obtained using Protocol D2

| Sample type | Does the sample contain X and no Y or Z? (X only) dF/dT at 40° C. > 80% *dF/dT at 51° C. AND dF/dT at 40° C. > 80% *d/F/dT at 65° C. | Does the sample contain Y and no X or Z? (Y only) dF/dT at 51° C. > 400% *dF/dT at 40° C. AND dF/dT at 51° C. > 175% *d/F/dT at 65° C. | Does the sample contain Z and no X or Y? (Z only) dF/dT at 65° C. > 600% *dF/dT at 40° C. AND dF/dT at 65° C. > 300% *d/F/dT at 51° C. | Does the sample contain X and Y and no Z? (X & Y only) dF/dT at 40° C. > 65° C. AND dF/dT at 51° C. > 200% *d/F/dT at 65° C. | Does the sample contain X and Z and no Y? (X & Z only) dF/dT at 40° C. > 50% *dF/dT at 51° C. AND dF/dT at 65° C. > 200% *d/F/dT at 51° C. | Does the sample contain Y and Z and no X? (Y & Z only) dF/dT at 51° C. > 400% *dF/dT at 40° C. 70% *dF/dT at 65° C. < dF/dT at 51° C. < 225% dF/dT at 65° C. | Does the sample contain X, Y and Z? (X, Y & Z) 125% *dF/dT at 40° C. < dF/dT at 51° C. < 225% *dF/dT at 40° C. AND 125% *dF/dT at 40° C. < dF/dT at 65° C. < 225% *dF/dT at 40° C. | Does the sample NOT contain X, Y or Z? (no target) dF/GT at 51° C. > 200% *dF/dT at 40° C. AND 150% *d/F/dT at 51° C. < dF/dT at 65° C. < 200% *dF/dT at 51° C. |
|---|---|---|---|---|---|---|---|---|
| X #1 | TRUE | FALSE | FALSE | FALSE | FALSE | FALSE | FALSE | FALSE |
| X #2 | TRUE | FALSE | FALSE | FALSE | FALSE | FALSE | FALSE | FALSE |
| X #3 | TRUE | FALSE | FALSE | FALSE | FALSE | FALSE | FALSE | FALSE |
| Y #1 | FALSE | TRUE | FALSE | FALSE | FALSE | FALSE | FALSE | FALSE |
| Y #2 | FALSE | TRUE | FALSE | FALSE | FALSE | FALSE | FALSE | FALSE |
| Y #3 | FALSE | TRUE | FALSE | FALSE | FALSE | FALSE | FALSE | PALSE |
| Z #1 | FALSE | FALSE | TRUE | FALSE | FALSE | FALSE | FALSE | PALSE |
| Z #2 | FALSE | FALSE | TRUE | FALSE | FALSE | FALSE | FALSE | FALSE |
| Z #3 | FALSE | FALSE | TRUE | FALSE | FALSE | FALSE | FALSE | FALSE |
| X + Y #1 | FALSE | FALSE | FALSE | TRUE | FALSE | PALSE | FALSE | FALSE |
| X + Y #2 | FALSE | FALSE | FALSE | TRUE | FALSE | FALSE | FALSE | FALSE |
| X + Y #3 | FALSE | FALSE | FALSE | TRUE | FALSE | FALSE | FALSE | FALSE |
| X + Z #1 | FALSE | FALSE | FALSE | FALSE | TRUE | FALSE | FALSE | FALSE |
| X + Z #2 | FALSE | FALSE | FALSE | FALSE | TRUE | FALSE | FALSE | FALSE |
| X + Z #3 | FALSE | FALSE | FALSE | FALSE | TRUE | FALSE | FALSE | FALSE |
| Y + Z #1 | FALSE | FALSE | FALSE | FALSE | FALSE | TRUE | FALSE | FALSE |
| Y + Z #2 | FALSE | FALSE | FALSE | FALSE | FALSE | TRUE | FALSE | FALSE |
| Y + Z #3 | FALSE | FALSE | FALSE | FALSE | FALSE | TRUE | FALSE | FALSE |
| X + Y + Z #1 | FALSE | FALSE | FALSE | FALSE | FALSE | FALSE | TRUE | FALSE |
| X + Y + Z #2 | FALSE | FALSE | FALSE | FALSE | FALSE | FALSE | TRUE | FALSE |
| X + Y + Z #3 | FALSE | FALSE | FALSE | FALSE | FALSE | FALSE | TRUE | FALSE |
| NTC #1 | FALSE | FALSE | FALSE | FALSE | FALSE | FALSE | FALSE | TRUE |
| NTC #2 | FALSE | FALSE | FALSE | FALSE | FALSE | FALSE | FALSE | TRUE |
| NTC #3 | FALSE | FALSE | FALSE | FALSE | FALSE | FALSE | FALSE | TRUE |

Table 19 shows the outcomes obtained after subjecting dFluorescence/dTemperature values at 37° C., 50° C. and 65.5° C. from each of the samples containing 10,000 copies of TFRC, rpoB, pss or all combinations of two or more gene targets to eight logical tests. These values were calculated from the post-amplification fluorescence measurements taken at 36.5° C., 37.5° C., 49.5° C., 50.5° C., 64.5° C. and 65.5° C. Each of the eight logical tests comprise two criteria (second row of Table 19) that determines whether the sample contains (no target), (TFRC only), (rpoB only), (pss only), (TFRC & rpoB only), (TFRC & pss only), (rpoB & pss only) or (TFRC, rpoB & pss). The two criteria determine if the

| SEQUENCES USED IN EXAMPLES 1-15 | | | |
|---|---|---|---|
| SEQ ID NO | Designation | Target | Sequence |
| 1 | LOCS-1 | Universal | FAM/TATGCCGACTTTTTCGACG TCCCguCCTCTACCGCTTT TCTCGGCATA/3IABkFQ |
| 2 | LOCS-2 | Universal | FAM/CGCACTGGCTTTTATCACG CCTCguCTCCTCCCAGTTTT GCCAGTGCG/3IABkFQ |

SEQUENCES USED IN EXAMPLES 1-15

| SEQ ID NO | Designation | Target | Sequence |
|---|---|---|---|
| 3 | Partzyme A1 | MgPa | ATCAGAAGGTATGATAACAACGGACAACGAGGGACGTCGA/3Phos/ |
| 4 | Partzyme B1 | MgPa | CGGTAGAGGAGGCTAGCTTAGAGCTTTATATGATATTAACTTAG/3Phos/ |
| 5 | Partzyme A2 | TV-Btub | AAGCTCACAACACCAACATACGACAACGAGAGGCGTGAT/3Phos/ |
| 6 | Partzyme B2 | TV-Btub | CTGGGAGGAGAGGCTAGCTGCGATCTTAACCACCTTGTTTC/3Phos/ |
| 7 | Forward Primer 1 | MgPa | GTTGAGAAATACCTTGATGGTCAGCAAAAC |
| 8 | Reverse Primer 1 | MgPa | ACCCCTITGCACCGTTGAGG |
| 9 | Forward Primer 2 | TV-Btub | CGAAGCTCTTTATGATATTTGCTTCC |
| 10 | Reverse Primer 2 | TV-Btub | AACATGTTGTTCCGGACATAACCAT |
| 11 | Partzyme A3 | HMPV | CAGAGGCCTTCAGCACCAGAACAACGAGGGACGTCGA/3Phos/ |
| 12 | Partzyme B3 | HMPV | CGGTAGAGGAGGCTAGCTCACACCTATAATTTTATTATGTGTAGGTGC/3Phos/ |
| 13 | Partzyme A4 | CT-ompA | TTGCACCACTTGGTGTGACGACAACGAGGGACGTCGA/3Phos/ |
| 14 | Partzyme B4 | CT-ompA | CGGTAGAGGAGGCTAGCTCTATCAGCATGCGTGTGGGTT/3Phos/ |
| 15 | Forward Primer 3 | HMPV | ACAATGGTAACTTTGCTTAAGGAATCATCAGG |
| 16 | Reverse Primer 3 | HMPV | TCAACTTCAAGTCTCTAGTCCCACTTCTATTGTTGA |
| 17 | Forward Primer 4 | CT-ompA | TTTCGGCGGAGATCCTTGCGATCC |
| 18 | Reverse Primer 4 | CT-ompA | CGAAAACAAAGTCACCGTAGTAACC |
| 19 | Partzyme A5 | VZV | CAACAGTTCTACAAGTTTGCGGACAACGAGAGGCGTGAT/3Phos/ |
| 20 | Partzyme B5 | VZV | CTGGGAGGAGAGGCTAGCTGCATAATCGTTAATAAATTGACAG/3Phos/ |
| 21 | Partzyme A6 | rpoB | TACCTGTCTGCTATCGAAGAACAACGAGAGGCGIGAT/3Phos/ |
| 22 | Partzyme B6 | rpoB | CTGGGAGGAGAGGCTAGCTGGCAACTACGTTATCGCTCA/3Phos/ |
| 23 | Forward Primer 5 | VZV | CTAACGGTGTCGTCATATAACAAC |
| 24 | Reverse Primer 5 | VZV | CAGAAGGTTTTAATGAAGGGAGTCG |
| 25 | Forward Primer 6 | rpoB | CAACGGTGTGGTTACTGACG |
| 26 | Reverse Primer 6 | rpoB | TCTACGAAGTGGCCGTTTTC |
| 27 | LOCS-3 | Universal | FAM/CTATGCCGACTTTTTCGACGTCCCguCCTCTACCGCTTTTCTCGGCATAG/3TABkFQ/ |
| 28 | LOCS-4 | Universal | FAM/CACTGGCTTTTATCACGCCTCguCTCCTCCCAGTTTTGCCAGTG/3IABkBQ/ |
| 29 | Partzyme A7 | CT-Cds | TGCTCGAAGCACGTGCGGACAACGAGGGACGTCGA/3Phos/ |
| 30 | Partzyme B7 | CT-Cds | GCGGTAGAGGAGGCTAGCTGGTTATCTTAAAAGGGATTG/3Phos/ |
| 31 | Partzyme A8 | TFRC | GGAATATGGAAGGAGACTGTCACAACGAGAGGCGTGAT/3Phos/ |
| 32 | Partzyme B8 | TFRC | CTGGGAGGAGAGGCTAGCTCCTCTGACTGGAAAACAGACT/3Phos/ |
| 33 | AF-CT-Cds | CT-Cds | ACTACAAGCTGCAATCCCTTTTAAGATAACCCCGCACGTGCTTCGAGCAACCGCTGTGACGGAGTACAAACGCCTAGGGTGCTCAGACTCCG |
| 34 | AF-TFRC | TFRC | AGTCTGTTTTCCAGTCAGAGGGACAGTCTCCTTCCATATTCC |
| 35 | LOCS-5 | Universal | /56JOEN/TATGCCGACTTTTTCGACGTCCCguCCTCTACCGCTTTTCTCGGCATA/3IABkFQ/ |
| 36 | LOCS-6 | Universal | /56JOEN/CGCACTGGCTTTTATCACGCCCTCguCTCCTCCCAGTTTTGCCAGTGCG/3IBkFQ/ |
| 37 | LOCS-7 | Universal | /5TexRd-XN/TATGCCGACTTTTTCGACGTCCCguCCTCTACCGCTTTTCTCGGCATA/3IAbRQSp/ |
| 38 | LOCS-8 | Universal | /5TexRd-XN/CGCACTGGCTTTTATCACGCCTCguCTCCTCCCAGTTTTGCCAGTGCG/3IAbRQSp/ |
| 39 | LOCS-9 | Universal | /5Cy5/TATGCCGACTTTTTCGACGTCCCguCCTCTACCGCTTTTCTCGGCATA/3IAbRQSp/ |
| 40 | LOCS-10 | CTcry | /5Cy5/CGCACTGGCTTTTATCACGCCTCguCTCCTCCCAGTTTTGCCAGTGCG/3IAbRQSp/ |
| 41 | Forward Primer 7 | CTcry | AATATCATCTTTGCGGTTGCGTGTCC |
| 42 | Reverse Primer 7 | CTcry | GCTGTGACGGAGTACAAACGCC |
| 43 | Partzyme A9 | CTcry | TCCTGTGACCTTCATTATGTCGACAACGAGAGGAAACCTT/3Phos/ |
| 44 | Partzyme B9 | CTcry | TGCCCAGGGAGGCTAGCTGAGTCTGAGCACCCTAGGC/3Phos/ |
| 45 | LOCS-11 | Universal | /56-FAM/TATGGCCTATTTTTAAGGTTTCCTCguCCCTGGGCATTTTATAGGCCATA/3IABkFQ/ |
| 46 | LOCS-12 | Universal | /56-FAM/TATGCCGACTTTTCTCGACCCTCguCCCTCGTCCTTTTCTCGGCATA/3IABkFQ/ |
| 47 | LOCS-13 | Universal | /56-FAM/CGCACTGGCTTTTACCGCACCTGguCCCCAGCTGTTTTGCCAGTGCG/3IABkFQ/ |
| 48 | Partzyme A10 | NGopa | CGAACCCGATATAATCCGCACAACGAGAGGGTCGAG/3Phos/ |
| 49 | Partzyme B10 | NGopa | GGACGAGGGAGGCTAGCTCCTTCAACATCAGTGAAAATC/3Phos/ |
| 50 | Partzyme A11 | gpd | AGACCCCTCGCTTAAGATGGACAACGAGAGGTGCGGT/3Phos/ |
| 51 | Partzyme B11 | gpd | GAGCTGGGGAGGCTAGCTCCGATCCCAATCGATTTCGC/3Phos/ |
| 52 | Forward Primer 8 | NGopa | GTGTTGAAACACCGCCCGG |
| 53 | Reverse Primer 8 | NGopa | CGGGCTCCTTATTCGGTTTGACC |
| 54 | Forward Primer 9 | gpd | CTACCAAATACGCCTTAGCAGACC |
| 55 | Reverse Primer 9 | gpd | CAGGCTGAATGTGGTAAACACGCTTC |
| 56 | DSO-1A | Universal | TTTTAGTGCG |
| 57 | DSO-1B | Universal | CGCACTTTTT |
| 58 | DSO-2A | Universal | TTTTAAGTGCG |
| 59 | DSO-2B | Universal | CGCACTTTTT |
| 60 | DSO-3A | Universal | TTTTCAGTGCG |
| 61 | DSO-3B | Universal | CGCACTGTTTT |
| 62 | DSO-4A | Universal | TTTTACAGTGCG |
| 63 | DSO-4B | Universal | CGCACTGTTTTT |
| 64 | DSO-5A | Universal | TTTTCCAGTGCG |
| 65 | DSO-5B | Universal | CGCACTGGTTTT |
| 66 | DSO-6A | Universal | TTTTACCAGTGCG |
| 67 | DSO-6B | Universal | CGCACTGGTTTTT |
| 68 | DSO-7A | Universal | TTTTGCCAGTGCG |
| 69 | DSO-7B | Universal | CGCACTGGCTTTT |
| 70 | DSO-8A | Universal | TTTTTGCCAGTGCG |
| 71 | DSO-8B | Universal | CGCACTGGCATTTT |
| 72 | Forward Primer 10 | TFRC | GCTAAAACAATAACTCAGAACTTACG |
| 73 | Reverse Primer 10 | TFRC | CAGCTTTCTGAGGTTACCATCCTA |

SEQUENCES USED IN EXAMPLES 1-15

| SEQ ID NO | Designation | Target | Sequence |
|---|---|---|---|
| 74 | Partzyme A12 | TFRC | GGAATATGGAAGGAGACTGTCACAACGAGGGACGTCGA/3Phos/ |
| 75 | Partzyme B12 | TFRC | GCGGTAGAGGAGGCTAGCTCCTCTGACTGGAAAACAGACT/3Phos/ |
| 76 | Partzyme A13 | TFRC | GGAATATGGAAGGAGACTGTCACAACGAGAGGGTCGAG/3Phos/ |
| 77 | Partzyme B13 | TFRC | GGACGAGGGAGGCTAGCTCCTCTGACTGGAAAACAGACT/3Phos/ |
| 78 | LOCS-14 | Universal | /56-FAM/CGCACTGGCTTTTTCGACGTCCCrGrOCCTCTACCGCTTTTGCCAGTGCG/3IABkFQ/ |
| 79 | LOCS-15 | Universal | /56-FAM/CGCACTGGCTTTTTCTCGACCCTCguCCCTCGTCCTTTTGCCAGTGCG/3IABkFQ/ |
| 80 | LOCS-16 | TV-btub | /56-FAM/TATGCCGACTTTTCACGGCGTGGATCGCAAGCAGCTTTTCTCGGCATA/3IABkFQ/ |
| 81 | LOCS-17 | CTcry | /56-FAM/CGCACTGGCTTTTATAAGAGGATCGATACATAAGACGAGTTTTGCCAGTGCG/3IABkFQ/ |
| 82 | AF-NE-TV1 | TV-btub | GCTGCTTGCGATCCACGCCGTG/3Phos/ |
| 83 | AF-NE-R5b | CTcry | CTCGTCTTATGTATCGATCCTCTTAT/3Phos/ |
| 84 | LOCS-18 | TV-btub | /FAM/TATGCCGACTTTTCACCAACATACGGCGATCTTAACTTTTCTCGGCATA/3IABkFQ/ |
| 85 | Reverse Primer 11 | NGopa | GCTCCTTATTCGGTTTGACCGG |
| 86 | LOCS-19 | Universal | /56JOEN/CGTGCAGTTTTAAGGTTTCCTCguCCCTGGGCATTTTCTGCACG/3IABkFQ/ |
| 87 | LOCS-20 | Universal | /56JOEN/AACGACAATGGCCTTTTCTCGACCTCguCCCTCGTCCTTTTGGCCATTGTCGTT/3IABkFQ/ |
| 88 | LOCS-21 | Universal | /56JOEN/TCGGGTAGCTTTTTTCT/CGACCCguCTCCACGCCATTTTAAGCTACCCGA/3IABkFQ |
| 89 | LOCS-22 | Universal | /56JOEN/ACAGTGCATTTTCCTAGTCCTCguCCTCACGTCCTTTTGCACTGT/3IABkFQ/ |
| 90 | LOCS-23 | Universal | /56JOEN/GCGTGACCGGTCCTTTTACCGCACCTCguCCCCAGCTCTTTTGGACCGGTCACGC/3IABkFQ/ |
| 91 | LOCS-24 | Universal | /5RHO101N/TCAAGGACTTTTTCCTCTCCCguCCCCTTCAACTTTTGTCCTTGA/3IAbRQS/ |
| 92 | LOCS-25 | Universal | /5RHO101N/TCTACGCCACTTTTACCGCCCTCguCCCGTGAACTTTTGTGGCGTAGA/3IAbRQSp/ |
| 93 | LOCS-26 | Universal | /5RHO101N/GCTGTCGATCCGTTATTTTATCACGCCTCguCTCCTCCCAGTTTTAACGGATCGACAGC/3IAbRQSp/ |
| 94 | Partzyme A14 | gpd | CCGATCATCAGTTATCCTTAAGACAACGAGGGGTCGAG/Phos/ |
| 95 | Partzyme B14 | gpd | TGGCGTGGAGAGGCTAGCTGTCTCTTTTGTGTGGTGCGTT/Phos/ |
| 96 | Partzyme A15 | gpd3 | AGACCCCTCGCTTAAGATGGACAACGAGAGGACTAGG/Phos/ |
| 97 | Partzyme B15 | gpd3 | GACGTGAGGGGCTAGCTCCGATCCCAATCGATTTCGC/3Phos/ |
| 98 | Partzyme A16 | porA | AAGTCCGCCTATACGCCTGACAACGAGAGGTGCGGT/3Phos/ |
| 99 | Partzyme B16 | porA | AGCTGGGGAGGCTAGCTCTACTTTCACGCTGGAAAGTA/3Phos/ |
| 100 | Partzyme A17 | TV-btub | CCGTACACTCAAGCTCACAACACAACGAGGGGAGAGGA/3Phos/ |
| 101 | Partzyme B17 | TV-btub | TTGAAGGGGAGGCTAGCTCAACATACGGCGATCTTAACCAC/3Phos/ |
| 102 | Partzyme A18 | MgPa | ATCAGAAGGTATGATAACAACGGACAACGAGAGGGCGGTT/3Phos/ |
| 103 | Partzyme B18 | MgPa | GGTTCACGGGAGGCTAGCTTAGAGCTTTATATGATATTAACTTAG/3Phos/ |
| 104 | Partzyme A19 | LGV | CCGAGCATCACTAACTGTTGACAACGAGAGGCGTGAT/3Phos/ |
| 105 | Partzyme B19 | LGV | TGGGAGGAGAGGCTAGCTGAGCAGGCGGAGTTGATGAT/3Phos/ |
| 106 | Forward Primer 12 | gpd | CTAACAGCGCGAACGACCAAC-TAC |
| 107 | Reverse Primer 12 | gpd | CAGCCCCCATACCGGAACGC |
| 108 | Forward Primer 13 | porA | AGCATTCAATTTGTTCCGAGTC |
| 109 | Reverse Primer 13 | porA | CAACAGCCGGAACTGGTTTCAT |
| 110 | Forward Primer 14 | Btub | TGCATTGATAACGAAGCTCTTTTATGATATTTGC |
| 111 | Forward Primer 15 | LGV | TACAGAAAAAATAGACCCTTTCC |
| 112 | Reverse Primer 15 | LGV | GTATTCTCCTTTATCTACTGTGC |
| 113 | LOCS-27 | Universal | /56-FAM/TATGCCGACTTTTACCGCACCTCguCCCCAGCTCTTTTCTCGGCATA/3IABkFQ/ |
| 114 | LOCS-28 | Universal | /5RHO101N/TCTACGCCACCAGTTTTACCGCCCTCguCCCGTGAACTTTTCTGGTGGCGTAGA/3IABRQSp/ |
| 115 | LOCS-29 | Universal | /5Cy5/CACGGTCTAGAGCTCTTTTAAGGTTTCCTCguCCCTGGGCATTTTGAGCTCTAGACCGTG/3IAbRQSp/ |
| 116 | LOCS-30 | Universal | /5Cy55/AACGACAATGGCCTTTTTCGACGTCCCguCCTCTACCGCTTTTGGCCATTGTCGTT/3IAbRQSp/ |
| 117 | LOCS-31 | Universal | /5Cy55/CGCACTGGCTTTTCCACGGTCCguCCTCCTGTACCTTTTGCCAGTGCG/3IAbRQSp/ |
| 118 | Partzyme A20 | polA | TTGAAGTCGGAGTTGAAGACGAACAACGAGGGACGTCGA/3Phos/ |
| 119 | Partzyme B20 | polA | CGGTAGAGGAGGCTAGCTGTGCTGTGTCTGGCGCCATA/3Phos/ |
| 120 | Partzyme A21 | TFRC | GGAATATGGAAGGAGACTGTCACAACGAGGGACCGTGG/3Phos/ |
| 121 | Partzyme B21 | TFRC | GGTACAGGAGGAGGCTAGCTCCTCTGACTGGAAAACAGACT/3Phos/ |
| 122 | Forward Primer 16 | polA | AGGGCTAGTACACCGGAGG |
| 123 | Reverse Primer 16 | polA | CCTAAGATCTCTATTTTCTATAGG |
| 124 | Partzyme A22 | TFRC | GGAATATGGAAGGAGACTGTCACAACGAGAGGACTAGG/3Phos/ |
| 125 | Partzyme B22 | TFRC | GACGTGAGGAGGCTAGCTCCTCTGACTGGAAAACAGACT/3Phos/ |
| 126 | Partzyme A23 | rpoB | TACCTGTCTGCTATCGAAGAACAACGAGGGGTCGAG/3Phos/ |
| 127 | Partzyme B23 | rpoB | TGGCGTGGAGAGGCTAGCTGGCAACTACGTTATCGCTCA/3Phos/ |
| 128 | Forward Primer 17 | pss | CTAAGTAGCCACCATAAGATGCC |
| 129 | Reverse Primer 17 | pss | CAGTTCCTTTATATCAGGTGTCCTT |
| 130 | Partzyme A24 | pss | AGATGCCAAATCGAGAAGGACAACGAGAGGTGCGGT/3Phos/ |
| 131 | Partzyme B24 | pss | GAGCTGGGGAGGCTAGCTGCCACACAAAGAGCTCCTA/3Phos/ |

The invention claimed is:

1. A method for determining the presence or absence of first and second targets in a sample, the method comprising:
   (a) preparing a reaction mixture by contacting the sample or a derivative thereof putatively comprising the first and/or second targets or amplicons thereof with:
   first and second closed stem-loop oligonucleotides, wherein each of the closed stem-loop oligonucleotides comprise a double-stranded stem portion of hybridised nucleotides, connected to a closed single-stranded loop portion of unhybridised nucleotides, a fluorophore being connected to one strand of the double-stranded portion and a quencher to the other strand, wherein:
   the number of hybridised nucleotides and/or the sequence of hybridised nucleotides in the stem portion of the first and second closed stem-loop oligonucleotide differs, and
   enzymes capable of cleaving or degrading the single-stranded loop portion of the first and second closed stem-loop oligonucleotides only when in contact with the first or second target or an amplicon of the first or second target;
   (b) treating the reaction mixture:
   under conditions suitable for the enzymes to induce cleavage or degradation of the loop portion of the first and second closed stem-loop oligonucleotides if the first and second targets are present in the reaction mixture to thereby produce first and second open stem-loop oligonucleotides;
   at a first temperature at or above which strands of the double-stranded stem portion of the first open stem-loop oligonucleotide disassociate to thereby facilitate spatial separation of the fluorophore and quencher molecules of the stem portion of the first open stem-loop oligonucleotide and provide a first detectable fluorescent signal, and
   at a second temperature at or above which strands of the double-stranded stem portion of the second open stem-loop oligonucleotide disassociate to thereby facilitate spatial separation of the fluorophore and quencher molecules of the stem portion of the second open stem-loop oligonucleotide and provide a second detectable fluorescent signal;
   wherein:
   the first temperature is lower than the second temperature, and
   the fluorophore of the first open stem-loop oligonucleotide and the fluorophore of the second open stem-loop oligonucleotide emit in the same colour region of the visible spectrum; and
   (c) detecting levels of said first and second fluorescent signals at one or more temperatures comprising or consisting of a temperature equal to or above the second temperature, to thereby determine the presence or absence of said targets in the sample.

2. The method of claim 1, wherein:
   (i) the enzymes comprise multi-component nucleic acid enzymes (MNAzymes), and said treating of the reaction mixture comprises treating the reaction mixture under conditions suitable for:
   binding of sensor arms of a first multi-component nucleic acid enzyme (MNAzyme) to the first target or amplicon thereof and hybridisation of substrate arms of said first MNAzyme to the loop portion of the first closed stem-loop oligonucleotide, to thereby facilitate said cleavage of the loop portion of the first closed stem-loop oligonucleotide by the first MNAzyme forming the first open stem-loop oligonucleotide; or
   (ii) the first target is an analyte, protein, compound or molecule;
   the enzymes comprise an enzyme with an aptamer capable of binding to the first target; and
   binding of the first target to the aptamer is capable of rendering the enzymes with an aptamer catalytically active.

3. The method of claim 2, wherein the first target is a nucleic acid sequence or amplicon thereof capable of hybridising to the sensor arms of the first MNAzyme to thereby facilitate assembly of the first MNAzyme.

4. The method of claim 1, wherein the enzymes comprise restriction endonucleases, and said treating of the reaction mixture comprises:
   treating the reaction mixture under conditions suitable for hybridisation of a first target or amplicon thereof to the loop portion of the first closed stem-loop oligonucleotide to form a double-stranded sequence for a first restriction endonuclease to associate with and thereby facilitate said cleavage of the loop portion of the first closed stem-loop oligonucleotide forming the first open stem-loop oligonucleotide.

5. The method of claim 1, wherein the enzymes comprise exonuclease activity, and said treating of the reaction mixture comprises:
   treating the reaction mixture under conditions suitable for:
   hybridisation of a first target or amplicon thereof to the loop portion of the first closed stem-loop oligonucleotide to form a first double-stranded sequence comprising the first target or amplicon thereof,
   hybridisation of a first primer oligonucleotide to the first target or amplicon thereof to form a second double-stranded sequence located upstream (5') relative to the first double-stranded sequence comprising the first target or amplicon thereof
   association of a first enzyme comprising exonuclease activity with a loop portion of the first closed stem-loop oligonucleotide at or adjacent to a terminus of the first primer oligonucleotide, and
   catalytic activity of the first enzyme comprising exonuclease activity to thereby facilitate degradation of the loop portion of the first double-stranded sequence comprising the first target or amplicon and formation of the first open stem-loop oligonucleotide.

6. The method of claim 1, wherein the enzymes comprise exonuclease activity, and said treating of the reaction mixture comprises:
  treating the reaction mixture under conditions suitable for:
    hybridisation of a first target or amplicon thereof to the loop portion of the first closed stem-loop oligonucleotide to form a first double-stranded sequence comprising the first target or amplicon thereof,
    association of a first enzyme comprising exonuclease activity with the first double-stranded sequence comprising the first target or amplicon thereof, and
    catalytic activity of the first enzyme comprising exonuclease activity to thereby facilitate degradation of the loop portion of the first double-stranded sequence comprising the first target or amplicon and formation of the first open stem-loop oligonucleotide.

7. The method of claim 1, wherein the enzymes comprise DNAzymes and/or ribozymes requiring a first co-factor for catalytic activity, and said treating of the reaction mixture comprises treating the reaction mixture under conditions suitable for:
  binding of a said first cofactor to the DNAzyme and/or binding of a said first cofactor to the ribozyme to render the DNAzyme and/or ribozyme catalytically active,
  hybridisation of DNAzyme and/or ribozyme to the loop portion of a first closed stem-loop oligonucleotide,
  catalytic activity of the DNAzyme and/or ribozyme to thereby facilitate cleavage of the loop portion of the first closed stem-loop oligonucleotide and formation of the first open stem-loop oligonucleotide,
wherein:
  the first target is the first co-factor.

8. The method of claim 2, wherein said treating further comprises treating the reaction mixture under conditions suitable for:
  binding of the sensor arms of a second MNAzyme to a second target or amplicon thereof and hybridisation of substrate arms of said second MNAzyme to the loop portion of the second closed stem-loop oligonucleotide, to thereby facilitate said cleavage of the loop portion of the second closed stem-loop oligonucleotide by the second MNAzyme forming the second open stem-loop oligonucleotide.

9. The method of claim 8, wherein:
  (i) the second target is a nucleic acid sequence or amplicon thereof capable of hybridising to the sensor arms of the second MNAzyme to thereby facilitate assembly of the second MNAzyme; or
  (ii) the second target is an analyte, protein, compound or molecule;
  the enzymes comprise an enzymes with an aptamer capable of binding to the second target; and
  binding of the second target to the aptamer is capable of rendering the enzymes with an aptamer catalytically active.

10. The method of claim 1, wherein:
  (i) said enzymes do not induce cleavage or degradation of any said target or amplicon thereof; and/or
  (ii) further comprising determining the presence or absence of a third target or amplicon thereof in a sample by:
  (d) contacting the reaction mixture comprising the sample or a derivative thereof with:
    a third closed stem-loop oligonucleotide, wherein the third closed stem-loop oligonucleotide comprises a double-stranded stem portion of hybridised nucleotides connected to a closed single-stranded loop portion of unhybridised nucleotides, wherein:
    the number of hybridised nucleotides and/or the sequence of hybridised nucleotides in the stem portion of the third closed stem-loop oligonucleotide differs from that of the stem portions of the first and second closed stem-loop oligonucleotide;
    the double-stranded stem portion comprises a fluorophore molecule connected to one strand and a quencher molecule connected to an opposing strand; and
    enzymes capable of cleaving or degrading the single-stranded loop portion of the third closed stem-loop oligonucleotide only when in contact with the target or amplicon thereof;
  (e) treating the reaction mixture:
    under conditions suitable for the enzymes to induce cleavage or degradation of the loop portion of the third closed stem-loop oligonucleotide to thereby produce a third open stem-loop oligonucleotide;
    at a third temperature at or above which strands of the double-stranded stem portion of the third open stem-loop oligonucleotide disassociate to thereby facilitate spatial separation of the fluorophore and quencher molecules of the stem portion of the third open stem-loop oligonucleotide and provide a third detectable fluorescent signal;
  wherein:
    the third temperature is higher than the first and second temperatures, and
  (f) detecting levels of said first, second and third fluorescent signals at one or more temperatures comprising or consisting of a temperature equal to or above the third temperature, to thereby determine the presence or absence of said targets in the sample.

11. The method of claim 1, further comprising determining the presence or absence of a third target or amplicon thereof in a sample by:
  (d) contacting the reaction mixture comprising the sample or a derivative thereof with:
    a third closed stem-loop oligonucleotide, wherein the third closed stem-loop oligonucleotide comprises a double-stranded stem portion of hybridised nucleotides connected to a closed single-stranded loop portion of unhybridised nucleotides, wherein:
    the number of hybridised nucleotides and/or the sequence of hybridised nucleotides in the stem portion of the third closed stem-loop oligonucleotide is the same as that of the stem portions of the first or second closed stem-loop oligonucleotide;
    the double-stranded stem portion comprises a fluorophore molecule connected to one strand and a quencher molecule connected to an opposing strand, wherein the fluorophore molecule connected to the third open stem-loop oligonucleotide emits in a different colour region of the visible spectrum than the fluorophore of the first and/or second closed stem-loop oligonucleotides; and
    enzymes capable of cleaving or degrading the single-stranded loop portion of the third closed stem-loop oligonucleotide only when in contact with the target or amplicon thereof;
  (e) treating the reaction mixture:
    under conditions suitable for the enzymes to induce cleavage or degradation of the loop portion of the third closed stem-loop oligonucleotide to thereby produce a third open stem-loop oligonucleotide;

at a third temperature at which strands of the double-stranded stem portion of the third open stem-loop oligonucleotide disassociate to thereby facilitate spatial separation of the fluorophore and quencher molecules of the stem portion of the third open stem-loop oligonucleotide and provide a third detectable fluorescent signal (f) detecting levels of said first, second and third fluorescent signals at one or more temperatures comprising or consisting of a temperature equal to or above the third temperature, to thereby determine the presence or absence of said targets in the sample.

12. The method of claim 10, wherein the method comprises step (ii) and treating the reaction mixture under conditions suitable for any one or more of:

binding of sensor arms of a third MNAzyme to the third target or amplicon thereof and hybridisation of substrate arms of said third MNAzyme to the loop portion of the third closed stem-loop oligonucleotide, to thereby facilitate said cleavage of the loop portion of the third closed stem-loop oligonucleotide by the third MNAzyme forming the third open stem-loop oligonucleotide;

hybridisation of the third target or amplicon thereof to the loop portion of the third closed stem-loop oligonucleotide to form a double-stranded sequence for a third restriction endonuclease to associate with the double-stranded sequence and thereby facilitate said cleavage of the loop portion of the third closed stem-loop oligonucleotide forming the third open stem-loop oligonucleotide;

hybridisation of a third target or amplicon thereof to the loop portion of the third closed stem-loop oligonucleotide to form a third double-stranded sequence comprising the third target or amplicon thereof, hybridisation of a third primer oligonucleotide to the third target or amplicon thereof to form a third double-stranded sequence located upstream (5') relative to the third double-stranded sequence comprising the third target or amplicon thereof, association of a third enzyme comprising exonuclease activity with a loop portion of the third closed stem-loop oligonucleotide at or adjacent to a terminus of the third primer oligonucleotide, and catalytic activity of the third enzyme comprising exonuclease activity to thereby facilitate degradation of the loop portion of the third double-stranded sequence comprising the third target or amplicon and formation of the third open stem-loop oligonucleotide;

hybridisation of a third target or amplicon thereof to the loop portion of the third closed stem-loop oligonucleotide to form a third double-stranded sequence comprising the third target or amplicon thereof, association of a third enzyme comprising exonuclease activity with the third double-stranded sequence comprising the third target or amplicon thereof, and catalytic activity of the third enzyme comprising exonuclease activity to thereby facilitate degradation of the loop portion of the third double-stranded sequence comprising the third target or amplicon and formation of the third open stem-loop oligonucleotide;

binding of a third cofactor to a DNAzyme and/or binding of a third cofactor to a ribozyme to render the DNAzyme and/or ribozyme catalytically active, hybridisation of DNAzyme and/or ribozyme to the loop portion of a third closed stem-loop oligonucleotide, catalytic activity of the DNAzyme and/or ribozyme to thereby facilitate cleavage of the loop portion of the third closed stem-loop oligonucleotide and formation of the third open stem-loop oligonucleotide, wherein:

the third target is the third co-factor.

13. The method of claim 12, wherein:

(i) the third target is a nucleic acid sequence or amplicon thereof capable of hybridising to the sensor arms of the third MNAzyme to thereby facilitate assembly of the third MNAzyme; or (ii) the target is an analyte, protein, compound or molecule;

the enzymes comprise an enzymes with an aptamer capable of binding to the third target; and binding of the third target to the aptamer is capable of rendering the enzymes with an aptamer catalytically active; or (iii) the target is an analyte, protein, compound or molecule;

the enzymes comprise an enzymes with an aptamer capable of binding to the third target;

binding of the third target to the aptamer is capable of rendering the enzymes with an aptamer catalytically active; and the enzyme with an aptamer comprise any one or more of: an apta-DNAzyme, an aptaribozymes, and an apta-MNAzymes.

14. The method of claim 10, wherein:

(a)

the number of hybridised nucleotides and/or the sequence of hybridised nucleotides in the stem portion of the third closed stem-loop oligonucleotide differs from that of the stem portions of the first and second closed stem-loop oligonucleotides;

the third temperature differs from the first and second temperatures; and the fluorophore of the third closed and open stem-loop oligonucleotides emits in the same colour region of the visible spectrum as the fluorophores of the first and second closed and open stem-loop oligonucleotides; or (b)

the fluorophore of the first closed and open stem-loop oligonucleotides emits in the same colour region of the visible spectrum as the fluorophore of the second closed and open stem-loop oligonucleotides; and the fluorophore of the third closed and open stem-loop oligonucleotides emits in a different colour region of the visible spectrum than the fluorophore of the first and second closed and open stem-loop oligonucleotides.

15. The method of claim 1, wherein:

(i) said determining the presence or absence of the first and second targets comprises a melt curve analysis using said first and second fluorescent signals; and/or (ii) part (c) comprises detecting levels of said first and second fluorescent signals during and/or upon completion of a nucleic acid amplification reaction.

16. The method of claim 1, wherein part (c) comprises detecting levels of said first and second fluorescent signals at:

a temperature equal to or above the second temperature; and a temperature equal to or above the first temperature and below the second temperature.

17. The method of claim 16 further comprising generating a first target positive control fluorescent signal:
(i) using a known concentration of the first target and/or a known concentration the first closed stem-loop oligonucleotide; and/or
(ii) by repeating said method on a separate control sample comprising said first target.

18. The method of claim 17, wherein:
(i) the control sample comprising the first target comprises a known concentration of the first target; and/or
(ii) the control sample comprising the first target further comprises said second target; and/or
(iii) the method further comprises normalising said first fluorescent signal and/or said second fluorescent signal using the first target positive control fluorescent signal.

19. The method of claim 15, further comprising:
(a) generating a second target positive control fluorescent signal by repeating said method on a separate control sample comprising said second target; or
(b) generating a combined positive control fluorescent signal by repeating said method on a separate control sample comprising said first and said second targets; or
(c) generating a combined positive control fluorescent signal by repeating said method on a separate control sample comprising said first and said second targets, wherein the combined control sample comprises a known concentration of the first target and/or a known concentration of the second target; or
(d) normalising said first fluorescent signal and/or said second fluorescent signal using any said positive control fluorescent signal.

20. The method of claim 15, further comprising generating a negative control fluorescent signal by repeating steps (a), (b) and (c) on a negative control sample in place of the sample, wherein the negative control sample does not contain:
(i) said first target; or
(ii) said second target; or
(iii) said first target or said second target; and
further comprising normalising said first fluorescent signal and/or said second fluorescent signal using said negative control fluorescent signal.

21. The method of claim 15, further comprising comparing said first and/or second fluorescent signals to a threshold value wherein:
the threshold value is generated using fluorescent signals derived from a series of control samples tested according to steps (a), (b) and (c) in place of the sample, the series of control samples comprising any one or more of:
(i) a no template control and the first target
(ii) a no template control and the second target
(iii) a no template control, the first target, and the second target
to thereby determine said presence or absence of the first and second targets in the sample.

22. The method of claim 4, wherein said treating further comprises treating the reaction mixture under conditions suitable for:
hybridisation of a second target or amplicon thereof to the loop portion of the second closed stem-loop oligonucleotide to form a double-stranded sequence for a second restriction endonuclease to associate with the double-stranded sequence and thereby facilitate said cleavage of the loop portion of the second closed stem-loop oligonucleotide forming the second open stem-loop oligonucleotide.

23. The method of claim 5, wherein said treating further comprises treating the reaction mixture under conditions suitable for:
hybridisation of a second target or amplicon thereof to the loop portion of the second closed stem-loop oligonucleotide to form a second double-stranded sequence comprising the second target or amplicon thereof,
hybridisation of a second primer oligonucleotide to the second target or amplicon thereof to form a second double-stranded sequence located upstream (5') relative to the second double-stranded sequence comprising the second target or amplicon thereof,
association of a second enzyme comprising exonuclease activity with a loop portion of the second closed stem-loop oligonucleotide at or adjacent to a terminus of the second primer oligonucleotide, and
catalytic activity of the second enzyme comprising exonuclease activity to thereby facilitate degradation of the loop portion of the second double-stranded sequence comprising the second target or amplicon and formation of the second open stem-loop oligonucleotide.

24. The method of claim 6, wherein said treating further comprises treating the reaction mixture under conditions suitable for:
hybridisation of a second target or amplicon thereof to the loop portion of the second closed stem-loop oligonucleotide to form a second double-stranded sequence comprising the second target or amplicon thereof,
association of a second enzyme comprising exonuclease activity with the second double-stranded sequence comprising the second target or amplicon thereof, and
catalytic activity of the second enzyme comprising exonuclease activity to thereby facilitate degradation of the loop portion of the second double-stranded sequence comprising the second target or amplicon and formation of the second open stem-loop oligonucleotide.

25. The method of claim 7, wherein said treating further comprises treating the reaction mixture under conditions suitable for:
binding of a second cofactor to a DNAzyme and/or binding of a second cofactor to a ribozyme to render the DNAzyme and/or ribozyme catalytically active,
hybridisation of the DNAzyme and/or ribozyme to the loop portion of the second closed stem-loop oligonucleotide,
catalytic activity of the DNAzyme and/or ribozyme to thereby facilitate cleavage of the loop portion of the second closed stem-loop oligonucleotide and formation of the second open stem-loop oligonucleotide,
wherein:
the second target is the second co-factor.

* * * * *

UNITED STATES PATENT AND TRADEMARK OFFICE
CERTIFICATE OF CORRECTION

PATENT NO. : 12,163,182 B2
APPLICATION NO. : 17/266951
DATED : December 10, 2024
INVENTOR(S) : Nicole Jane Hasick et al.

Page 1 of 1

It is certified that error appears in the above-identified patent and that said Letters Patent is hereby corrected as shown below:

In the Claims

In Column 150, Line 31, Claim 2, delete "enzymes" and insert -- enzyme --, therefor.

In Column 151, Line 53, Claim 9, delete "enzymes" and insert -- enzyme --, therefor.

In Column 151, Line 56, Claim 9, delete "enzymes" and insert -- enzyme --, therefor.

In Column 154, Line 15, Claim 13, delete "enzymes" and insert -- enzyme --, therefor.

In Column 154, Line 18, Claim 13, delete "enzymes" and insert -- enzyme --, therefor.

In Column 154, Line 22, Claim 13, delete "enzymes" and insert -- enzyme --, therefor.

In Column 154, Line 28, Claim 13, delete "aptaribozymes," and insert -- apta-ribozyme --, therefor.

In Column 154, Line 29, Claim 13, delete "MNAzymes." and insert -- MNAzyme. --, therefor.

Signed and Sealed this
Eighteenth Day of March, 2025

Coke Morgan Stewart
*Acting Director of the United States Patent and Trademark Office*